(12) United States Patent
Bumcrot et al.

(10) Patent No.: US 12,145,963 B2
(45) Date of Patent: Nov. 19, 2024

(54) PHENOTHIAZINE DERIVATIVES AND USES THEREOF

(71) Applicant: Camp4 Therapeutics Corporation, Cambridge, MA (US)

(72) Inventors: David A. Bumcrot, Belmont, MA (US); Alfica Sehgal, Belmont, MA (US); Donald L. Hertzog, Cambridge, MA (US)

(73) Assignee: Camp4 Therapeutics Corporation, Cambridge, MA (US)

( * ) Notice: Subject to any disclaimer, the term of this patent is extended or adjusted under 35 U.S.C. 154(b) by 23 days.

(21) Appl. No.: 18/056,008

(22) Filed: Nov. 16, 2022

(65) Prior Publication Data
US 2023/0257410 A1    Aug. 17, 2023

Related U.S. Application Data

(63) Continuation of application No. 16/640,482, filed as application No. PCT/US2019/026158 on Apr. 5, 2019, now Pat. No. 11,542,290.

(60) Provisional application No. 62/653,741, filed on Apr. 6, 2018, provisional application No. 62/653,752, filed on Apr. 6, 2018.

(51) Int. Cl.
*C07D 417/06* (2006.01)
*C07D 279/28* (2006.01)
*C07H 7/06* (2006.01)

(52) U.S. Cl.
CPC ............. *C07H 7/06* (2013.01); *C07D 279/28* (2013.01); *C07D 417/06* (2013.01)

(58) Field of Classification Search
CPC ............................ C07D 417/06; C07D 471/10
See application file for complete search history.

(56) References Cited

U.S. PATENT DOCUMENTS

| | | | | |
|---|---|---|---|---|
| 2,860,138 | A | * | 11/1958 | Sherlock ............. C07D 417/06 544/45 |
| 2,921,069 | A | | 1/1960 | Ullyot |
| 3,240,779 | A | | 3/1966 | Jacob et al. |
| 3,882,109 | A | | 5/1975 | Soudijn et al. |
| 4,139,632 | A | | 2/1979 | Hirose et al. |

(Continued)

FOREIGN PATENT DOCUMENTS

| | | |
|---|---|---|
| BE | 666965 | 1/1966 |
| CN | 104829554 A | 8/2015 |

(Continued)

OTHER PUBLICATIONS

Jackson et al., "Identification of Phase-I and Phase-II Metabolites of Fluphenazine in Rat Bile" Drug Metabolism and Disposition vol. 19 No. 1 pp. 188-193 (Year: 1991).*

(Continued)

*Primary Examiner* — Eric Olson
(74) *Attorney, Agent, or Firm* — Foley Hoag LLP; David P. J. Halstead

(57) ABSTRACT

The present invention provides phenothiazine compounds, processes for their preparation, pharmaceutical compositions comprising the compounds, and the use of the compounds or the compositions in the treatment of various diseases or conditions, for example ribosomal disorders and ribosomopathies, e.g. Diamond Blackfan anemia (DBA).

1 Claim, 1 Drawing Sheet

(56) References Cited

U.S. PATENT DOCUMENTS

| | | | |
|---|---|---|---|
| 4,514,395 | A | 4/1985 | Hirose et al. |
| 7,981,885 | B2 | 7/2011 | Roth et al. |
| 11,542,290 | B2 * | 1/2023 | Bumcrot .............. C07D 417/06 |
| 2012/0035161 | A1 | 2/2012 | Roth et al. |
| 2015/0265627 | A1 | 9/2015 | Zon et al. |
| 2021/0061837 | A1 | 3/2021 | Bumcrot et al. |
| 2023/0257410 | A1 | 8/2023 | Bumcrot et al. |

FOREIGN PATENT DOCUMENTS

| | | |
|---|---|---|
| EP | 0414422 A2 | 2/1991 |
| FR | 1297717 A | 9/1962 |
| GB | 1000686 A | 8/1965 |
| JP | S42-024589 B | 11/1967 |
| JP | S48-021939 B1 | 7/1973 |
| JP | S48-021941 B1 | 7/1973 |
| JP | S48-021942 B1 | 7/1973 |
| JP | H04-224589 A | 8/1992 |
| KR | 10-2016-0038175 A | 4/2016 |
| PL | 211760 B1 | 6/2012 |
| WO | WO-2008/027521 A1 | 3/2008 |
| WO | WO-2013/138101 A2 | 9/2013 |
| WO | WO-2018/013761 A1 | 1/2018 |
| WO | WO-2018/226230 A1 | 12/2018 |
| WO | WO-2019/195789 A1 | 10/2019 |

OTHER PUBLICATIONS

Uechi et al., "Zebrafish Models of Diamond-Blackfan Anemia: A Tool for Understanding the Disease Pathogenesis and Drug Discovery" Pharmaceuticals vol. 12 p. 151, doi:10.3390/ph12040151 (Year: 2019).*

Farley-Barnes et al., "Ribosomopathies: Old Concepts, New Controversies" Trends in Genetics vol. 35 No. 10 pp. 754-767 DOI 10.1016/j.tig.2019.07.004 (Year: 2019).*

Mills et al., "Ribosomopathies: There's strength in numbers" Science vol. 358, 608 pp. 1-8, DOI 10.1126/science.aan2755 (Year: 2017).*

Anonymous, "The Use of Trifluoperazine in Transfusion Dependent DBA (DBA)." ClinicalTrials.gov. May 29, 2019.

Chaudhari et al., "Pharmaceutical Excipients: A review" International Journal of Advances in Pharmacy, Biology and Chemistry vol. 1(1) pp. 21-34 (Year: 2012).

Chemcats file; CAS Registry No. 100167-49-5; STN entry date: Feb. 8, 1986; chemical name: 10H-Phenothiazine, 10-[3-(1-piperidinyl)propyl]-2-(trifluoromethyl)-, hydrochloride.

Chemcats file; CAS Registry No. 1217472-45-1; STN entry date: Apr. 8, 2010; chemical name: 4-Piperidinol, 1-[3-[2-(trifluoromethyl)-10H-phenothiazin-10-yl]propyl]-, hydrochloride (1:2).

Chemcats file; CAS Registry No. 1217473-27-2; STN entry date: Apr. 8, 2010; chemical name: 10H-Phenothiazine, 10-[3-(1-piperidinyl)propyl]-2-(trifluoromethyl)-, hydrochloride (1:2).

Chemcats file; CAS Registry No. 1977-91-9; STN entry date: Nov. 16, 1984; chemical name: 10H-Phenothiazine, 10-[3-(1-piperidinyl)propyl]-2-(trifluoromethyl)-.

Chemcats file; CAS Registry No. 3834-22-8; STN entry date: Nov. 16, 1984; chemical name: 10H-Phenothiazine, 10-[3-(1-piperidinyl)propyl]-2-(trifluoromethyl)-, hydrochloride (1:1).

Chemcats file; CAS Registry No. 806-78-0; STN entry date: Nov. 16, 1984; chemical name: 4-Piperidinol, 1-[3-[2-(trifluoromethyl)-10H-phenothiazin-10-yl]propyl]-.

English CAS abstract of H42-24589, downloaded form STN (Year: 1942).

English machine translation of H42-24589, translated by Google (Year: 1942).

Gasiorowski et al., "Antimutagenic Activity of New Analogues of Fluphenazine," Cellular & Molecular Biology Letters 8:927-942 (2003).

Hirata et al., "Potential CNS Antitumor Agents—Phenothiazines I:Nitrogen Mustard Derivatives," Journal of Pharmaceutical Sciences 6(11):1699-1701 (1976).

Huber, J. "Investigation of Novel Drugs to Rescue Ribosomal Protein Deficiencies." Austrian Marshall Plan Foundation, submitted on Mar. 31, 2017, p. 72.

International Search Report for international application No. PCT/US2019/026158 dated Sep. 3, 2019 (4 pages).

Jaszcyszyn et al., "New Fluphenazine Analogues as Inhibitors of P-Glycoprotein in Human Lymphocyte Cultures," Wspolczesna Onkol 16(4):332-337 (2012).

Macari et al., "Calmodulin Inhibition Rescues DBA Models with Ribosomal Protein Deficiency through Reduction of RSK Signaling." Blood (2016) 128 (22): 332. (Abstract only).

Macari et al., "Calmodulin Inhibition Rescues the Effects of Ribosomal Protein Deficiency in in Vitro and In Vivo Diamond Blackfan Anemia Models." Blood(2015) 126 (23): 672. (Abstract only).

McKeon, Jr. et al., "Antagonism of Intravenous Histamine in the Guinea Pig by Piperidyl-Alkyl-Trifluoromethylphenothiazines and Trifluoperazine," Arch. Int. Pharmacodyn 168 (1) pp. 55-63 (1967).

McKeon, Jr., W.B., "Antagonism of Intravenous Histamine in the Guinea Pig by Piperidyl-Alkylphenothiazines and Chlorpromazine," Arch. Int. Pharmacodyn. 145:3-4 (1963).

Nagai et al., Studies on Psychotrophic Agents I. Synthesis of 3,8-Disubstituted-1-oxa-3,8-diazaspiro[4,5]decan-2,4-dione Derivatives Chem. Pharm. Bull. 24(6)1179-1188 (1976).

Partial European Search Report for EP Application No. 19781957.6 dated Dec. 22, 2021.

Pubchem-CID: 68149971 Creation Date: Nov. 30, 2012, pp. 1-6.

Pubchem-CID:54605270 Creation Date: Dec. 19, 2011, pp. 1-5.

Shetty et al., "Syntheiss of Deuterium-Labeled Fluphenazine," J. of Pharmaceutical Sciences 73(1):87-90 (1984).

Sobczak et al., "New Fluphenazine Analogue with Antimutagenic and Anti-multidrug Resistance Activity-Degradation Profile and Stability-Indicating Method," Med. Chem. Res., 26:2443-2451 (2017).

STN Chemical Structure Search Results dated Mar. 19, 2019 (194 pages).

Supplementary European Search Report for EP Application No. 19781957.6 dated May 9, 2022.

Written Opinion of the International Searching authority for international application No. PCT/US2019/026158 dated Sep. 3, 2019 (7 pages).

Zyta et al., "Synthesis, Pro-Apoptotic Activity and 2D-Qsar Studies of New Analoges of Fluphenazine," Acta Poloniae Pharmaceutica—Drug Research 71(1):49-58 (2014).

* cited by examiner

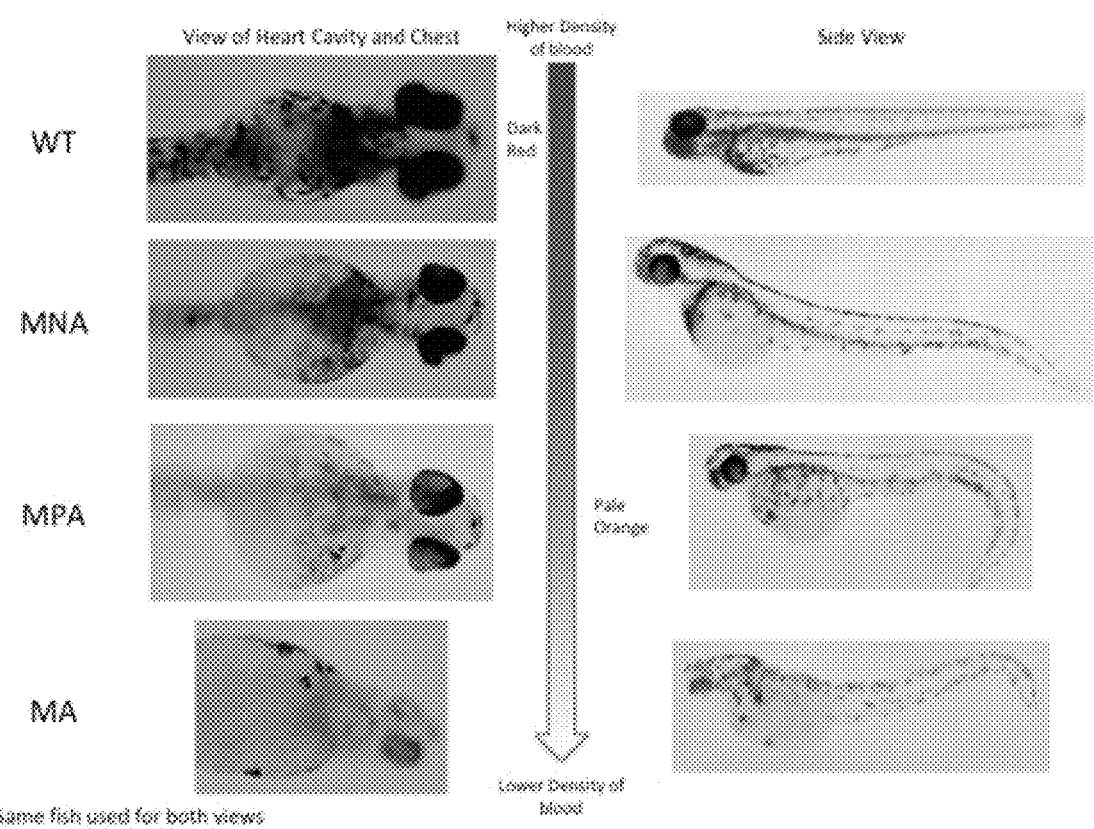

PHENOTHIAZINE DERIVATIVES AND USES THEREOF

CROSS-REFERENCE TO RELATED APPLICATIONS

This application is a continuation of U.S. application Ser. No. 16/640,482, filed Feb. 20, 2022, which is a national stage filing under U.S.C. § 371 of International Application No. PCT/US19/26158, filed Apr. 5, 2019, which claims priority to and the benefits of U.S. Provisional Patent Application Ser. No. 62/653,741, filed Apr. 6, 2018, and U.S. Provisional Patent Application Ser. No. 62/653,752, filed Apr. 6, 2018, each of which is incorporated herein by reference in its entirety.

FIELD OF THE INVENTION

The invention relates generally to novel phenothiazine compounds, processes for their preparation, pharmaceutical compositions comprising the compounds, and the use of such compounds and/or compositions in the treatment of various diseases or conditions, for example ribosomal disorders and ribosomopathies.

BACKGROUND OF THE INVENTION

Mutations in ribosomal protein (RP) genes or transcription factor GATA1 can result in the loss of erythrocyte progenitor cells and cause severe anemia. This is seen in patients with Diamond-Blackfan anemia (DBA), a rare blood disorder that is almost exclusively linked to RP gene haploinsufficiency. DBA, also known as Blackfan-Diamond anemia or inherited erythroblastopenia, affects approximately seven per million live births and is usually diagnosed during the first year of life (Vlachos et al., Br J Haematol. 2008 September; 142(6): 859-876). Classic diagnostic criteria are: (1) macrocytic, normochromic, anemia; (2) reticulocytopenia; (3) bone marrow erythroid hypoplasia; and (4) early onset of anemia (90% present before age one year) (Alter et al., N Engl J Med. 1976; 295(26):1437-43).

In DBA patients, erythrocyte precursors do not mature sufficiently leading to congenital erythroid aplasia, developmental defects and increased risk of myelodysplastic syndrome or acute myeloid leukemia. Affected individuals may have physical abnormalities, such as craniofacial malformations, thumb or upper limb abnormalities, cleft palate, as well as defects of the genitalia, urinary tract, eyes and heart. In some cases, low birth weight and short stature are sometimes observed. DBA patients are also at a modest risk of developing leukemia and other malignancies.

The current treatment options for DBA includes corticosteroids, blood transfusion, and bone marrow transplantation (Vlachos et al., Bone Marrow Transplant. 2001; 27(4):381-86). Approximately 80% of DBA patients respond to an initial course of corticosteroids. However, the efficacy of corticosteroids can wane over time in many patients. These patients and the 20% who do not respond initially to such therapy must be maintained on a chronic blood transfusion with iron chelation (Vlachos et al., Blood 2010; 116(19): 3715-3723). Chronic transfusions are known to cause iron overload in various organs including the liver, heart, and endocrine system. Other therapies such as interleukin-3 (Bastion et al., Blood. 1994; 83(2):617-8), high dose corticosteroids, cyclosporine, anti-thymocyte globulin, immunoglobulin (reviewed in Vlachos et al., Br J Haematol 2008; 142(6):859-76), and metoclopramide (Abkowitz et al., Blood. 2002; 100:2687-2691; Leblanc et al., Blood. 2007; 109:2266-2267), are either of unproved benefit and/or seem to benefit relatively few people. Pharmacological doses of Erythropoietin (EPO) are also ineffective. Bone marrow transplantation is the sole cure for the hematologic manifestation of DBA-related anemia, but is usually only considered in corticosteroid-resistant persons because of substantial morbidity and mortality. Typically, only transplants from human leukocyte antigen (HLA)-identical sibling were considered. For many patients, the lack of a suitable donor excludes bone marrow transplantation as a therapeutic option.

Consequently, there is a dire need to develop novel, effective, and targeted therapies for DBA and other associated ribosomal disorders or ribosomopathies. In particular, improved methods for treatment of DBA with small-molecule drugs are strongly desired.

SUMMARY OF THE INVENTION

The present invention provides novel phenothiazine compounds, processes for their preparation, pharmaceutical compositions comprising the compounds, and the use of such compounds and/or compositions in the treatment of various diseases or conditions, for example ribosomal disorders and/or ribosomopathies.

In one aspect, the present invention provides a compound of formula (I):

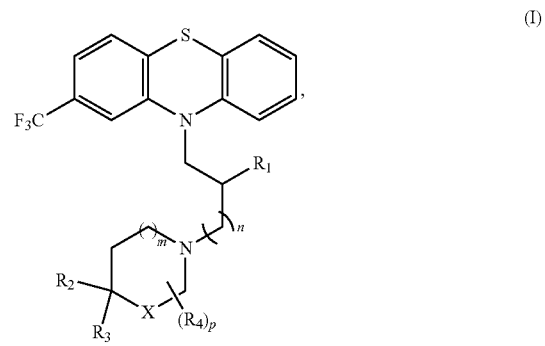

(I)

or a pharmaceutically acceptable salt thereof, wherein the variables are as defined herein.

In another aspect, the present invention provides a pharmaceutical composition comprising a compound of formula (Ia):

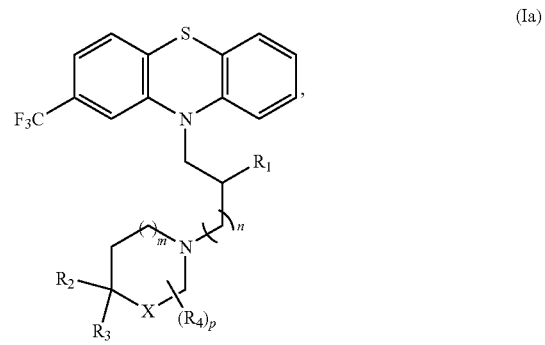

(Ia)

or a pharmaceutically acceptable salt thereof, wherein the variables are as provided herein, and a pharmaceutically acceptable excipient.

In another aspect, the present invention provides a compound of formula (II):

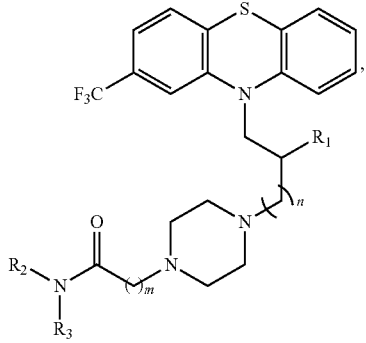

(II)

or a pharmaceutically acceptable salt thereof, wherein the variables are as defined herein.

In another aspect, the present invention provides a compound of formula (III):

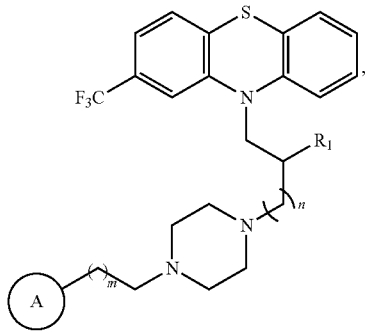

(III)

or a pharmaceutically acceptable salt thereof, wherein the variables are as defined herein.

In some embodiments, the compound is a compound of formula (IIIa):

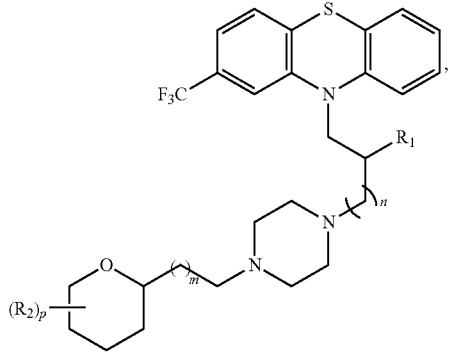

(IIIa)

or a pharmaceutically acceptable salt thereof, wherein the variables are as defined herein.

In another aspect, the present invention provides a compound of formula (IV):

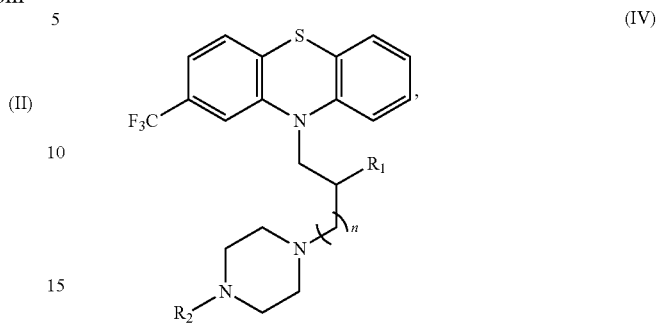

(IV)

or a pharmaceutically acceptable salt thereof, wherein the variables are as defined herein.

In another aspect, the present invention provides a compound of formula (V):

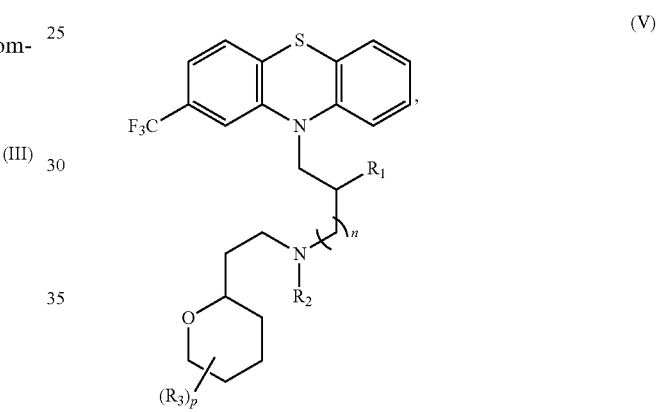

(V)

or a pharmaceutically acceptable salt thereof, wherein the variables are as defined herein.

In some embodiments, provided herein is a phenothiazine compound having a structure selected from any one of those listed in Table 1.

In another aspect, the present invention provides a pharmaceutical composition comprising a compound disclosed herein (e.g., a compound of formula (Ia), (II), (III), (IIIa), (IV), or (V)) and a pharmaceutically acceptable excipient.

In another aspect, the present invention provides a method of using a disclosed compound (e.g., a compound of formula (I), (Ia), (II), (III), (IIIa), (IV), or (V)), wherein the compound binds to Calmodulin and inhibit Calmodulin activity.

In some embodiments, the compound may bind to Calmodulin with a half maximal inhibitory concentration (IC50) of about 1-100 nM.

In some embodiments, the compound may have lower permeability cross blood-brain barrier when compared to trifluoperazine (TFP).

In some embodiments, the compound is a p-glycoprotein substrate.

In another aspect, the present invention provides a method of treating a ribosomal disorder or ribosomopathy in a subject in need thereof, comprising administering to the subject a therapeutically effective amount of a compound disclosed herein (e.g., a phenothiazine compound selected from any one of those listed in Table 1, a compound of formula (I), (Ia), (II), (III), (IIIa), (IV), or (V)), or a compound of formula (VI):

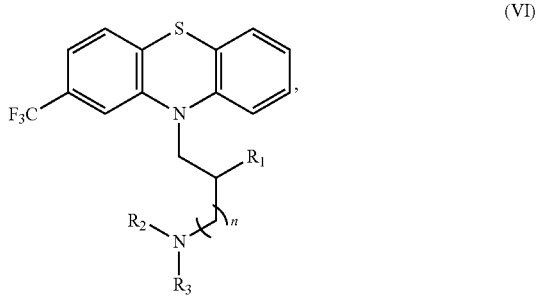

or a pharmaceutically acceptable salt thereof, wherein the variables are as defined herein.

Also provided herein is a method of treating a ribosomal disorder or ribosomopathy in a subject in need thereof, comprising administering to the subject an effective amount of a disclosed pharmaceutical composition (e.g., a pharmaceutical composition comprising a compound of formula (I), (Ia), (II), (III), (IIIa), (IV), (V), or (VI)).

In some embodiments, the ribosomal disorder is Diamond Blackfan Anemia (DBA). The ribosomal disorder may be DBA1, DBA2, DBA3, DBA4, DBA5, DBA6, DBA7, DBA8, DBA9, DBA10, DBA11, DBA12, DBA13, DBA14, DBA15, DBA16, or DBA17.

In some embodiments, the subject may have at least one mutation in ribosomal protein 19 (RPS19). In other embodiments, the subject may have at least one mutation in one or more ribosomal proteins selected from the group consisting of RPS19, RPS24, RPS17, RPL35A, RPL5, RPL11, RPS7, RPS10, RPS26, RPL26, RPL15, RPS29, TSR2, RPS28, RPL27, and RPS27.

In some embodiment, the method may further comprises administering a second therapeutic agent or regimen selected from the group consisting of: corticosteroids, blood transfusions, bone marrow transplantation, and other calmodulin inhibitors. The other calmodulin inhibitors may be one or more compounds selected from the group consisting of: A-3, W-7, A-7, W-5, CGS-9343B, trifluoperazine, fluphenazine, and perphenazine.

In some embodiments, the phenothiazine compound increases the number of CD71+ erythroid cells in the subject.

In some embodiments, the phenothiazine compound increases hemoglobin levels in the subject.

In some embodiments, the phenothiazine compound decreases the levels of p21 in CD34+ cells present in an erythroid cell population of the subject.

In some embodiments, the ribosomal disorder or ribosomopathy is myelodysplasia. In some embodiments, the myelodysplasia is 5q-myelodysplasia. In some embodiments, the subject has a mutation in RPSL4 or decrease in RPSL4 expression.

In some embodiments, the ribosomal disorder or ribosomopathy is Shwachman-Diamond syndrome. In some embodiments, the subject has a mutation in SBDS.

In some embodiments, the ribosomal disorder or ribosomopathy is Treacher-Collins Syndrome. In some embodiments, the subject has a mutation in the TCOF1 gene.

In some embodiments, the compound may be administered orally to the subject.

In some embodiments, the compound does not cross blood-brain barrier.

In some embodiments, the compound does not cause dyskinesia or extrapyramidal effects in the subject.

In another aspect, the present invention procides a method of inhibiting Calmodulin to treat a disease or disorder in a subject in need thereof, the method comprising administering to the subject a therapeutically effective amount of a disclosed phenothiazine compound (e.g., a compound of formula (I), (Ia), (II), (III), (IIIa), (IV), (V), or (VI)).

In some embodiments, the compound is selected from the group consisting of:

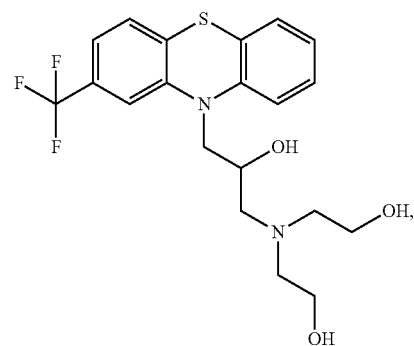

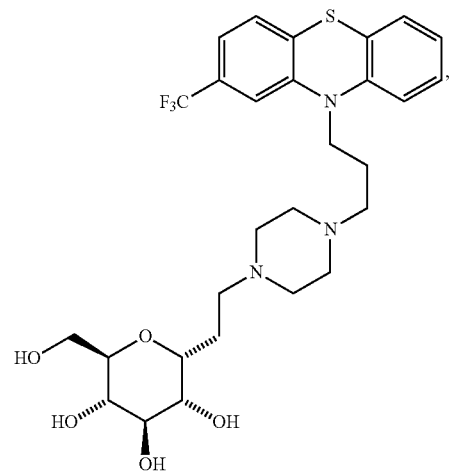

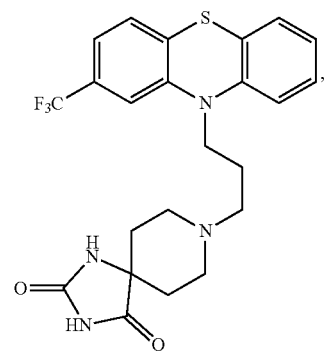 [SMILES: O=C1NC(=O)C2(CCN(CCCN3c4ccccc4Sc4ccc(C(F)(F)F)cc43)CC2)N1]

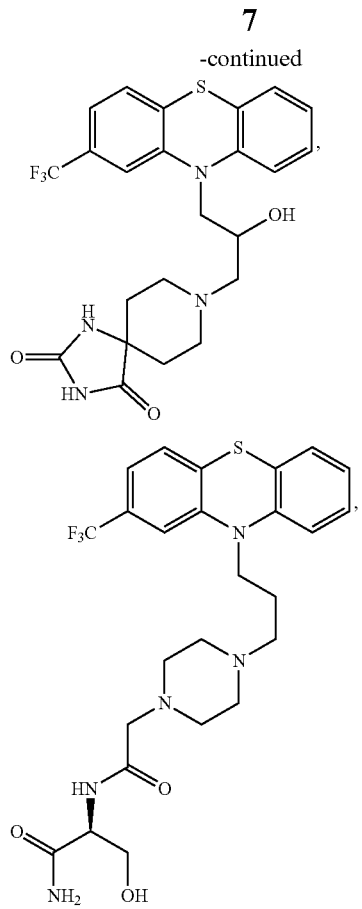

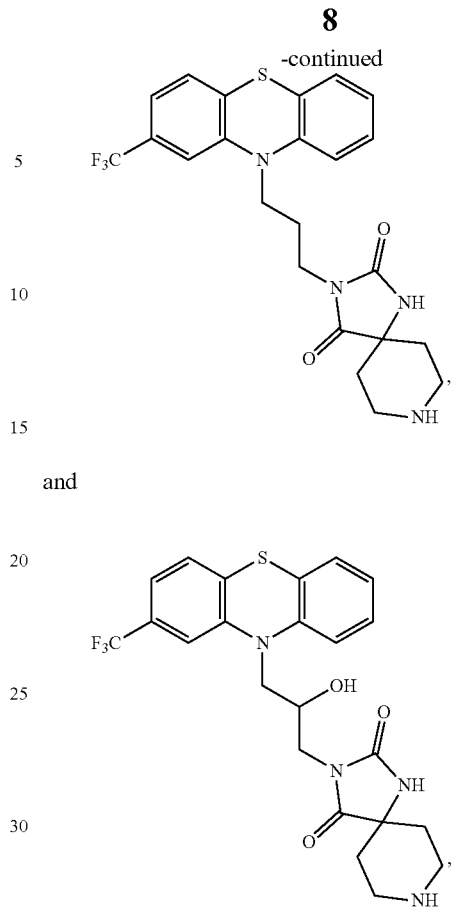

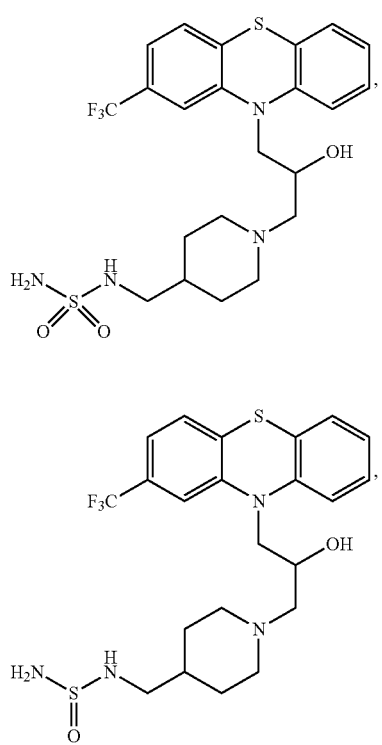

or a pharmaceutically acceptable salt thereof.

Further provided herein, in part, is a method for preparing a phenothiazine compound having a structure selected from any one of those listed in Table 1.

BRIEF DESCRIPTION OF THE DRAWINGS

FIG. 1 shows images of zebrafish embryos with phenotypes of rps29 mutation in tail development and anemia. From top to bottom, the first row shows an embryo of WT (wild type) group, where the tail stays straight, and the blood is dark red due to high density of red blood cells. The second row shows an embryo of MNA (mutant not anemic) group, where there is a noticeable downward bend in the tail. The majority of the blood is dark red due to high density of red blood cells, but there are some low density areas that appear pale orange (roughly 75% dark red/25% pale orange). The third row shows an embryo of MPA (mutant partial anemic), where there is a tail bend, and the majority of the blood is pale orange due to low density of blood cells and there are small clusters of dark red blood (typically under 25% dark red). The fourth row shows an embryo of MA (mutant anemic) group, which also has a tail bend and no blood or very small speckles of pale orange blood.

DETAILED DESCRIPTION OF THE INVENTION

I. Introduction

Calmodulin inhibitors and calcium channel blockers were identified in an in vivo chemical screen in a zebrafish model of DBA to screen for compound that rescue DBA phenotype (Taylor et al., Blood 2012 120:512; U.S. Pat. No. 9,827,252; the contents of which are hereby incorporated by reference in their entirety). Dr. Leonard Zon and colleagues demonstrated that calmodulin inhibition in rps29 (ribosomal protein S29)-defective embryos rescues the morphological, endothelial and hemoglobin phenotypes. Interstingly, several structurally distinct calmodulin inhibitors successfully rescued the endothelial defect in rps29-defective embryos. These include members of the phenothiazine family such as trifluoperazine (TFP), fluphenazine, perphenazine. The effect of phenothiazine compounds, particularly TFP, on rescuing DBA phenotype was confirmed in subsequent in vitro and in vivo studies published by the same group (Macari et al., Blood 2015 126:672; Macari et al., Blood 2016 128:332; the contents of which are hereby incorporated by reference in their entirety).

Phenothiazine compounds (e.g., trifluoperazine (TFP), fluphenazine, perphenazine, and chlorpromazine) inhibit the activity of calmodulin through a selective calcium-dependent binding to calmodulin. Although phenothiazines are FDA-approved antipsychotics, their long-term use is associated with dyskinesia and extrapyramidal effects (Kennedy et al., BrJ Psychiatry 1971; 118:509-518, the content of which is hereby incorporated by reference in its entirety), making them risky to use in children. The extrapyramidal reactions have been seen in patients receiving phenothiazines and are apparently mediated via blockade of central dopaminergic receptors involved in motor function. Therefore, safer compound that is peripherally restrained and/or have low dopamine receptor activity is desired.

The present invention provides, among other things, novel phenothiazine compounds that overcome the above-mentioned limitations of existing phenothiazines, particularly TFP. Methods for using such compounds to treat and/or prevent DBA and other ribosomal disorders and/or ribosomopathies are also provided.

Ribosomal Disorders and Ribosomopathies

Ribosomes are small organelles found in all cells which are responsible for the production of proteins. In eukaryotes, they are composed of four ribosomal RNA (rRNA) molecules and 79-80 ribosomal proteins which are assembled into a large and a small subunit. Numerous enzymes, transcription regulators, chaperones, nuclear export protein, and more, are involved in the process of making ribosomes.

As used herein, the term "ribosomal protein" (RP) refers to any of the intracellular ribonucleoprotein particles involved in protein synthesis. They consist of reversibly dissociable units and are found either bound to cell membranes or free in the cytoplasm. They may occur singly or in clusters, also known as polyribosomes or polysomes, which are ribosomes linked by mRNA and are actively engaged in protein synthesis. Ribonucleoproteins (RNPs) are important in protein synthesis; they consist of two, one large (L) and one small (S), reversibly dissociable units (also called 60S and 40S subunits in eukaryotes, and 50S and 30S in bacteria). The term includes any of the proteins that, in conjunction with rRNA, make up the ribosomal subunits involved in the cellular process of translation. The term encompasses proteins of the small (S) subunit and the large (L) subunit of the ribosomes. Due to the high conservation of both the RNA and protein moieties of ribosomes and of the ribosome biogenesis machinery from yeast and bacteria, a large part of the knowledge about these organic molecules has come from the study of E. coli ribosomes, and also applies to humans. In the small (30S) subunit of E. coli ribosomes, the proteins denoted S4, S7, S8, 515, 517, S20 bind independently to 16S rRNA. After assembly of these primary binding proteins, S5, S6, S9, S12, S13, S16, S18, and S19 bind to the growing ribosome. These proteins also potentiate the addition of S2, S3, S10, S11, S14, and 521. Protein binding to helical junctions is important for initiating the correct tertiary fold of RNA and to organize the overall structure. Nearly all the proteins contain one or more globular domains. Moreover, nearly all contain long extensions that can contact the RNA in far-reaching regions. Additional stabilization results from the proteins' basic residues, as these neutralize the charge repulsion of the RNA backbone. Protein-protein interactions also exist to hold structure together by electrostatic and hydrogen bonding interactions. Theoretical investigations pointed to correlated effects of protein-binding onto binding affinities during the assembly process.

As used herein, the term "ribosomopathy" refer to any disease or malfunction of ribosomes. A disease or malfunction of ribosomes may include (a) disease of ribosomal biogenesis proteins, (b) disease of small nucleolar ribonuceloproteins, and (c) diseases of ribosomal proteins. See, Freed et al., Mol. Biosyst. 2010; 6(3); 481-493, which is hereby incorporated by reference in its entirety. Diseases of ribosomal biogenesis proteins may include, but are not limited to, Treachers Collins syndrome (TCS), male infertility due to a mutation in UTP14c, native American indian childhood cirrhosis (NAIC), Bowen-Conradi syndrome (BCS), alopecia neurological defect and endocrinopathy syndrome (ANE syndrome), shwachman-dimaond syndrome (SDS), candidate gene for primary open angle glaucoma (POAG), and modifier of neurofibromatosis type I (NF1). Diseases of small nucleolar ribonuceloproteins may include, but are not limited to, Anauxetic dysplasia (AD), cartilage-hair dysplasia (or metaphyseal chondrodysplaia, McKusick type; CCH), metaphyseal dysplasia without hypotrichosis (MDWH), Dyskeratosis congenita (or Zinzzer-Engman-Cole syndrome), Hoyeraal-Hreidarsson syndrome (where some cases are severe variants of Dyskeratosis congenita), and Prader-Willi syndrome (PWS).

As used herein, diseases of ribosomal proteins are also termed "ribosomal disorders" or "ribosomal protein disorders." They may include a disease due to mutation in a ribosomal protein, or a disease due to a decreased level, or partial loss of function, of a ribosomal protein, or alternatively, a disease due to an increased level of a ribosomal protein, as compared to a normal healthy control subject. Such disorders include genetic diseases of ribosomal proteins, including but not limited to, Diamond-Blackfan anemia (DBA), myelodysplasia (e.g., 5q-myelodysplastic syndrome (5q-MDS)), Shwachman-Diamond Syndrome (SDS), and Treacher-Collins Syndrome (TCS).

Diamond-Blackfan Anemia (DBA)

DBA is a congenital erythroid aplasia that usually develops during the neonatal period. DBA is characterized by low red blood cell counts (anemia) with decreased erythroid progenitors in the bone marrow. In DBA patients, levels of other blood components such as platelets and the white blood cells are normal. This is in contrast to Shwachman-Diamond syndrome, in which the bone marrow defect results primarily in low neutrophil counts (neutropenia), and Fanconi anemia, where all types of blood cells are affected (pancytopenia).

Ribosomal protein mutations have been implicated in the pathophysiology of DBA. The first gene, mutated in approximately 25% of DBA patients, was identified as RPS19 (ribosomal protein S19) (Gustavsson et al., Nat Genet. 1997 August; 16(4):368-71; Draptchinskaia et al., Nat Genet. 1999 February;21(2):169-75). Sequencing of patient samples has identified mutations of either large (60s)

or small (40s) subunit ribosomal proteins in over 50% of patients (Vlachos et al., Br J Haematol. 2008 September; 142(6): 859-876). Identified genes include but are not limited to RPS19, RPL5, RPS10, RPL11, RPL35A, RPS7, RPS17, RPS24, RPL26, RPS26 and GATA1 genes, and most recently RPS29 (Mirabello et al., Blood. 2014 Jul. 3; 124 (1):24-32). Some mutations of unknown significance are reported in other ribosomal protein genes (Doherty et al., Am J Hum Genet 2010; 86(2):222-8). Patients are heterozygous for these mutations, always maintaining a wildtype copy of the affected RP gene. However, approximately 30% of people with DBA have no detectable RP mutation. Some phenotype/genotype correlations are known, relating to congenital abnormalities (Gazda et al., Am J Hum Genet. 2008; 83(6):769-80; Quarello et al., Haematologica. 2010; 95(2): 206-13).

Diamond-Blackfan anemia-1 (DBA1, OMIM #105650) is caused by heterozygous mutations in the RPS19 gene on chromosome 19q13. Other forms of DBA include DBA2 (OMIM #606129), caused by mutations on chromosome 8p23-p22; DBA3 (OMIM #610629), caused by mutation in the RPS24 gene on 10q22; DBA4 (OMIM #612527), caused by mutation in the RPS17 gene on 15q; DBA5 (OMIM #612528), caused by mutation in the RPL35A gene on 3q29; DBA6 (OMIM #612561), caused by mutation in the RPL5 gene on 1p22.1; DBA7 (OMIM #612562), caused by mutation in the RPL11 gene on 1p36; DBA8 (OMIM #612563), caused by mutation in the RPS7 gene on 2p25; DBA9 (OMIM #613308), caused by mutation in the RPS10 gene on 6p; DBA10 (OMIM #613309), caused by mutation in the RPS26 gene on 12q; DBA11 (OMIM #614900), caused by mutation in the RPL26 gene on 17p13; DBA12 (OMIM #615550), caused by mutation in the RPL15 gene on 3p24; DBA13 (OMIM #615909), caused by mutation in the RPS29 gene on 14q; DBA14 (OMIM #300946), caused by mutation in the TSR2 gene on Xp11; DBA15 (OMIM #606164), caused by mutation in the RPS28 gene on 19p13; DBA16 (OMIM #617408), caused by mutation in the RPL27 gene on chromosome 17q21; and DBA17 (OMIM #617409), caused by mutation in the RPS27 gene on chromosome 1q21.

Mutations in ribosomal proteins impact ribosomal protein function, leading to ribosomal insufficiency and increased stress. Impaired ribosome biogenesis has been linked to p53 induction and cell-cycle arrest. Ribosomal protein knockdown leads to an increase of free ribosomal proteins. Some ribosomal proteins, including RPL11, RPL5, and RPL13, bind to MDM2 and block MDM2-mediated p53 ubiquitination and degradation (Lindstram et al, Cell Cycle 6:4, 434-437, 15 Feb. 2007; Fumagalli et al, Nat Cell Biol. 2009 April; 11(4):501-8). Other ribosomal proteins may activate p53 by different mechanisms. For example, RPL26 has been found to increase the translation rate of p53 mRNA by binding to its 5' untranslated region (Tagaki et al., Cell. 2005 Oct. 7; 123(1):49-63).

p53 activation plays an important role in DBA pathogenesis, as well as in other diseases where ribosomal and related genes are mutated, termed "ribosomopathies" herein. In patients with 5q-myelodysplastic syndrome, where one copy of RPS14 is lost (Ebert et al., Nature. 2008 Jan. 17; 451 (7176):335-9), induction of p53 and up-regulation of the p53 pathway was observed (Pellagatti et al., Blood. 2010 Apr. 1; 115(13):2721-3). p53 activation is also a common feature in bone marrow failure disorders, such as Fanconi Anemia (Ceccaldi et al., Cell Stem Cell. 2012 Jul. 6; 11(1):36-49). In human CD34+ cells, RPS19 knockdown leads to p53 activation (Ebert et al., Blood. 2005 Jun. 15; 105(12):4620-6; Flygare et al., Blood. 2005 Jun. 15; 105(12):4627-34), with increased accumulation in erythroid cells. Differentiation defects can be rescued by p53 inhibition (Dutt et al., Blood. 2011 Mar. 3; 117(9):2567-76). Mouse models of RPS19 mutation or knockdown have hematopoietic defects that can be rescued by p53 mutation (McGowan et al., Nat Genet. 2008 August; 40(8):963-70; Jaako et al., Blood. 2011 Dec. 1; 118(23):6087-96). Rps19 has been targeted by morpholino in zebrafish embryos, and the hematopoietic defects in rpl 11 mutant zebrafish are rescued by p53 knockdown (Danilova et al., Blood. 2008 Dec. 15; 112(13):5228-37; Torihara et al., Br J Haematol. 2011 March;152(5):648-54; Danilova et al., Blood 2011; 118:3439).

A zebrafish mutant in rps29, a ribosomal protein in the small subunit, has been previously characterized (Taylor et al., Blood 2010 116:1170; Taylor et al., Exp Hematol. 2012 March;40(3):228-237.e5, the contents of which are hereby incorporated by reference in their entirety). Rps29−/− embryos have hematopoietic and endothelial defects, including morphological defects in the head, as well as decreased hematopoietic stem cells, hemoglobin, and staining of endothelial markers. Consistent with other models of DBA, knockdown of p53 near completely rescues the rps29 mutant phenotype. Rps29−/− embryos also have defects in arterial specification, leading to decreased hematopoietic stem cells (HSCs) and decreased flk1 expression in the intersegmental vessels at 24 hours post fertilization. Primitive erythropoiesis is affected, as rps29−/− embryos have less hemoglobin. These embryos have increased apoptosis, particularly in the head, and die by five days post fertilization. p53 pathways are activated in the embryo, and p53 mutation rescues all hematopoietic and apoptotic phenotypes.

Myelodysplasia

Myelodysplasia or myelodysplastic syndromes (MDS) are a group of hematological disorders related to the body's inability to produce enough normal blood cells. In MDS patients, the immature blood cells in the bone marrow do not mature and instead they die in the bone marrow or just after entering the bloodstream. MDS can affect the production of any, and sometimes all, types of blood cells including red blood cells, platelets, and white blood cells (cytopenias). Over time, there are more immature, defective cells than healthy ones. As a result, patients with MDS often have anemia (low red blood cell count or reduced hemoglobin) which can cause fatigue and shortness of breath, neutropenia (low neutrophil count) which can cause increased susceptibility to infection, and/or thrombocytopenia (low platelet count) which can cause bleeding and easy bruising with no apparent cause.

Marrow cell disturbances in MDS patients range from mild to very severe. In some cases, patients with MDS often develop severe anemia and require frequent blood transfusions. In most cases, the disease worsens and the patient develops cytopenias caused by progressive bone marrow failure. In about 30% of patients with MDS, the disease progresses into acute myelogenous leukemia (AML), usually within months to a few years.

MDS most often affect adults between the age of 60 and 75 years. MDS in children is rare. Males are slightly more commonly affected than females. Previous treatment with chemotherapy or radiation is a key factor in the onset of MDS. Exposure to certain chemicals (e.g., tobacco smoke, pesticides, benzene) and heavy metals (e.g., lead, mercury) can increase the risk of myelodysplastic syndromes. Some inherited disorders can also lead to MDS, including Fanconi anemia, Shwachman-Diamond syndrome, Diamond-Blackfan anemia, and Familial platelet disorder.

5q-myelodysplasia, also known as Del 5q, 5q-syndrome, chromosome 5q deletion syndrome, or chromosome 5q monosomy, is a rare form of MDS. It is caused by deletion of a region of DNA in the long arm (q arm, band 5q31.1) of human chromosome 5. Most people with 5q-myelodysplasia are missing a fragment of about 1.5 million base pairs. 5q-myelodysplasia is characterized by severe anemia, frequent thrombocytosis, typical dysmegakaryopoiesis and favorable outcome. Unlike other MDS, 5q-myelodysplasia is found predominantly in females of advanced age.

The commonly deleted region of DNA in 5q-myelodysplasia contains 40 genes, including RPS14, MIR145 and MIR146 loci. Loss of the RPS14 gene leads to the problems with red blood cell development characteristic of 5q-myelodysplasia, and loss of the MIR145 and MIR146 loci contributes to the platelet abnormalities and megakaryocyte dysplasia associated with the 5q-myelodysplasia. Ebert et al. (Nature. 2008 Jan. 17; 451(7176):335-9, the content of which is hereby incorporated by reference in its entirety) demonstrated that impaired function of the ribosomal subunit protein RPS14 recapitulated the characteristic phenotype of the 5q-myelodysplasia in normal CD34+ human hematopoietic progenitor cells. In addition, over expression of RPS14 rescued the disease phenotype in patient-derived bone marrow cells.

Subjects with 5q-myelodysplasia can be treated with Lenalidomide (REVLIMID®) (Bennett et al., N Engl J Med. 2006 Oct. 5; 355(14):1456-65; Raza et al., Blood. 2008 Jan. 1; 111(1):86-93). One of the side effects of Lenalidomide treatment may be low blood cell counts initially leading the individual to utilize supportive care. Supportive care includes red blood cell transfusion, antibiotics, and Iron chelation therapy. For younger people, bone marrow transplantation is an option and is the only known cure for MDS.

Shwachman-Diamond syndrome

Shwachman-Diamond syndrome (SDS) or Shwachman-Bodian-Diamond syndrome is a rare genetic disorder that that affects many parts of the body, particularly the pancreas, bone marrow, and skeletal system. Shwachman-Diamond syndrome is inherited in an autosomal recessive pattern. Most cases of SDS are caused by mutations in the SBDS gene, which lies on the long arm of chromosome 7 at cytogenetic position 7911. The protein encoded by SBDS is thought to play a role in RNA processing and ribosome biogenesis, although the exact mechanism of how SBDS mutations lead to the major signs and symptoms of Shwachman-Diamond syndrome is still unclear. Typical symptoms of Shwachman-Diamond syndrome include exocrine pancreatic insufficiency, decreased muscle tone, low blood neutrophil count (neutropenia), anemia, and abnormal bone development affecting the rib cage and/or bones in the arms and/or legs (metaphyseal dysostosis).

Diagnosis of Shwachman-Diamond syndrome can be made based on clinical findings, including pancreatic dysfunction and characteristic hematologic abnormalities. Genetic testing may be used to confirm the diagnosis. SBDS gene mutations are known to cause about 90% of cases of Shwachman-Diamond syndrome. The remaining 10% cases have unknown genetic cause, and hence genetic testing is not an option for these cases.

There is no cure for Shwachman-Diamond syndrome. Treatment usually include oral pancreatic enzyme replacement, vitamin supplementation, blood and/or platelet transfusion, administration of granulocyte-colony stimulating factor (G-CSF), and/or hematopoietic stem cell transplantation.

Treacher-Collins Syndrome (TCS)

Treacher-Collins syndrome (TCS) is a rare genetic condition that affects the development of the bones and tissues of the face. Most cases (78%-93%) of Treacher-Collins syndrome are caused by mutations in the TCOF1 gene. TCOF1 is found on the 5th chromosome in the 5q32 region and encodes a nucleolar protein named treacle. Treacle is involved in ribosomal DNA gene transcription and the loss of treacle reduces the production of rRNA. A small percentage (~8%) of Treacher-Collins syndrome cases have been linked to mutations in the POLR1C or POLR1D genes. In other cases where none of these mutations are present, the cause for this disease is unclear. The severity of this condition may vary from generation to generation and from person to person. Symptoms of Treacher-Collins syndrome include at least one of, but are not limited to: abnormal or almost completely missing outer part of the ears, hearing loss, very small jaw (micrognathia), very large mouth, defect in the lower eyelid (coloboma), scalp hair that reaches to the cheeks, cleft palate. Accordingly, a subject with Treacher-Collins syndrome may have one or more craniofacial deformities. Affected individuals generally have a normal intelligence.

Diagnosis of Treacher-Collins syndrome can be made based on clinical symptoms, X-ray findings, and genetic testing. Individuals with Treacher-Collins syndrome may present a variety of problems, including: (a) Abnormal eye shape, (b) Flat cheekbones, (c) Clefts in the face, (d) Small jaw, (e) Low-set ears, (f) Abnormally formed ears, (g) Abnormal ear canal, (h) Hearing loss, (i) Defects in the eye (coloboma that extends into the lower lid), and (j) Decreased eyelashes on the lower eyelid. A few X-ray techniques (such as orthopantomogram, lateral cephalometric radiograph, and occipitomental radiographs) are used to aid the diagnosis of TCS. Genetic tests can help identify genetic mutations linked to this condition as described above. However, a number of other diseases have similar characteristics, which make it sometimes difficult to diagnose TCS. The OMENS classification was developed as a comprehensive and stage-based approach to differentiate the diseases. This acronym describes five distinct dysmorphic manifestations, namely orbital asymmetry, mandibular hypoplasia, auricular deformity, nerve development, and soft-tissue disease.

There is no cure for Treacher-Collins syndrome. Symptoms may be managed with reconstructive surgery, hearing aids, speech therapy, and other assistive devices.

Calmodulin Inhibitors and Calcium Channel Blockers

Calmodulin (CaM), is an acidic protein considered to be the universal calcium sensor. Intracellular calcium levels are mediated by CaM thus controlling a myriad of physiological responses such as cell proliferation, endocytosis, cellular adhesion, protein turn over and smooth muscle contraction.

The term "calmodulin inhibitor" as used herein, is broadly defined as an agent or molecule that inhibits the activity or expression of calmodulin. Calmodulin inhibitors can be of synthetic or biological origins. They can be organic, or inorganic molecules, or peptides, antibodies or antisense RNA that inhibit calmodulin. Inhibitors of calmodulin of the present invention are chemical entities or molecules that can inhibit expression of calmodulin and/or biological activity of calmodulin, as disclosed herein, for example, compounds of trifluoperazine (TFP), fluphenazine, perphenazine, and naphthalenesulfonamides such as A-3, A-7, W-5, and W-7, and enantiomers, prodrugs, derivatives, and pharmaceutically acceptable salts thereof, which are discussed further below. In the context of this invention, it is of note that the term "calmodulin inhibitor" is used as a synonym for "calmodulin antagonist."

Another group of compounds that may affect calmodulin function are calcium channel blockers. These include calcium blockers and chelators that control calcium channel activity, i.e., channels actuated by the depolarization of cell membranes thereby allowing calcium ions to flow into the cells. Such compounds inhibit the release of calcium ions from intracellular calcium storage thereby blocking signaling through the CaMKII pathway. Exemplary calcium blockers include, but are not limited to, 1,4-dihydropyridine derivatives such as isradipine, nifedipine, nicardipine, nilu-dipine, nimodipine, nisoldipine, nitrendipine, milbadipine, dazodipine, and ferodipine; N-methyl-N-homoveratrilamine derivatives such as verapamil, gallopamil, and tiapamil; benzothiazepine derivatives such as diltiazem; piperazine derivatives such as cinnarizine, lidoflazine, and flunarizine; diphenylpropiramine derivatives such as prenylamine, terodiline, and phendiline; bepridil; and perhexyline. Exemplary calcium chelators include, e.g., BAPTA tetrasodium salt, 5,5'-Dibromo-BAPTA tetrasodium salt, BAPTA/AM, 5,5'-Difluoro-BAPTA/AM, EDTA tetrasodium salt (Ethylenediamine tetraacetic acid), EGTA (Ethylenebis(oxyethylenenitrilo)tetraacetic acid), EGTA/AM, MAPTAM, and TPEN.

Calmodulin inhibitors and calcium channel blockers were identified in an in vivo chemical screen in zebrafish to screen for compound that rescue rps29−/− embryos with morphological defects (Taylor et al., Blood 2012 120:512; U.S. Pat. No. 9,827,252; the contents of which are hereby incorporated by reference in its entirety). Calmodulin inhibition in rps29 mutant embryos rescues the morphological, endothelial and hemoglobin phenotypes, including the flk1 expression defect. Calcium channel blockers and an inhibitor of calmodulin dependent phosphodiesterase type 1 (PDE1) also rescued the flk1 defect in the chemical screen. Treatment with a calmodulin inhibitor A-3 improved the morphology of the apoptotic embryo head. A-3 is known to interact with a host of calmodulin-dependent enzymes and can bind to other proteins in the cell, including p21. W-7, another calmodulin inhibitor related to A-3, rescued the endothelial defect in the rps29 mutant. Additionally, W-5 rescued vascular defects, and A-7 rescued vascular defects. Both W-7 and A-3 rescued hemoglobin levels in the zebrafish embryo. In an in vitro model of primary blood derived CD34+ hematopoietic stem and progenitor cells, which had rps19 knockdown by siRNA, A-3 also rescued rps19 knockdown and decreased p53 and p21 levels or nuclear localization. A-3, A-7, W-5, and W-7 belong to the napthalenesulfonamide family of compounds. Interstingly, several structurally distinct calmodulin inhibitors successfully rescued the endothelial defect in rps29−/− embryos. These include CGS-9343B and members of the phenothiazine family such as trifluoperazine (TFP), fluphenazine, and perphenazine.

Trifluoperazine (TFP) is a phenothiazine derivative which is mainly used in the management of schizophrenia and also acts as a calmodulin inhibitor. Following the demonstration of TFP's potential efficacy in the zebrafish screen, it has been shown that TFP relieved the erythroid differentiation block in normal human CD34+ cells transduced with small hairpin ribonucleic acid (shRNA) against RPS19 and in primary CD34+ bone marrow cells from patients with DBA with RPS19 and RPS29 mutations (Macari et al., Blood 2015 126:672, the content of which is hereby incorporated by reference in its entirety). Injection of TFP in a DBA murine model significantly increased red blood cell number and hemoglobin levels and reduced p53 activity in the bone marrow (Macari et al., Blood 2015 126:672; Macari et al., Blood 2016 128:332; the contents of which are hereby incorporated by reference in its entirety). The effect of TFP was specific to RP deficiency and had no effect on erythroid differentiation or p53 activity in WT cells or mice. In vitro kinase profiling of over 100 kinases revealed that TFP and other CaM inhibitors identified from the screen inhibited the activity of p70 ribosomal S6 kinase (p70S6K) and multiple members of p90 ribosomal S6 kinase (RSK) family. Although the mechanism of TFP's inhibition of p53 activity is not well understood, experiments suggest that RP deficiency increases RSK phosphorylation and CaM inhibitors decrease signaling downstream of RSK, which leads to a reduction of p53 activity and rescues the phenotypes of multiple in vitro and in vivo models of DBA (Macari et al., Blood 2016 128:332; the content of which is hereby incorporated by reference in its entirety).

II. Compounds, Compositions and Methods of the Invention

Phenothiazine Compounds and Compositions

In one aspect, the present invention provides novel phenothiazine compounds.

In some embodiments, phenothiazine compounds of the present invention may be analogs and/or derivatives of trifluoperazine. Trifluoperazine (TFP) is a typical antipsychotic of the phenothiazine chemical class. It belongs to the piperazine class of phenothiazines. It has the chemical name of 10-[3-(4-methylpiperazin-1-yl)propyl]-2-(trifluoromethyl)phenothiazine (also known as brand names ESKAZINYL™, ESKAZINE™, FLUROPER AZINE™ JATRONEURAL™, MODALINA™, NOVO-TRIFLUZINE™, STELAZINE™, SYNKLOR™ TERFLUZINE™, TRIFLUOPERAZ™, TRIFTAZIN™). Trifluoperazine is also known as Trifluoperazin, Trifluoperazina, Trifluoperazine Dihydrochloride, Trifluoperazine HCl, Trifluoperazine Hydrochloride, Trifluoromethylperazine, Trifluoroperazine, Trifluoroperazine Dihydrochloride, Trifluoroperazine Hydrochloride, Trifluperazine, Trifluroperizine, Triphthazine Dihydrochloride, or Tryptazine Dihydrochloride. Trifluoperazine has central antiadrenergic, antidopaminergic, and minimal anticholinergic effects. It exerts its antipsychotic effect by blocking postsynaptic mesolimbic dopaminergic D1 and D2 receptors in the brain, thereby relieving or minimizing the symptoms of schizophrenia such as delusions, hallucinations, and disorganized thought and speech. TFP may be synthesized by methods disclosed in U.S. Pat. No. 2,921,069, the content of which is incorporated herein in its entirety by reference. TFP is typically administered orally, e.g., by way of a tablet, in 1 mg-20 mg unit doses.

Provided herein, in part, is a compound of formula (I):

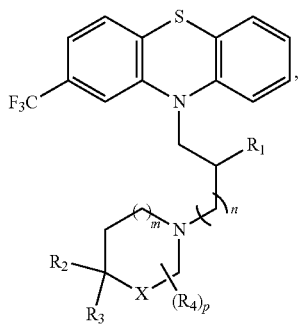

(I)

or a pharmaceutically acceptable salt thereof, wherein
$R_1$ is selected from the group consisting of hydrogen, —OH, and $C_{1-6}$alkoxy;
(a) $R_2$ is $C_{1-6}$alkylene-$NR_5R_6$ and $R_3$ is hydrogen or $C_{1-6}$alkyl; (b) $R_2$ is —OH and $R_3$ is —$CO_2H$, or (c) $R_2$ and $R_3$ are taken together with the carbon to which $R_2$ and $R_3$ are attached to form a 3-7 membered heterocyclylene, wherein the heterocyclylene may be optionally substituted with one or more oxo or $C_{1-6}$alkyl and have one or more heteroatoms, wherein each of the heteroatoms is nitrogen;
each $R_4$ is independently selected from the group consisting of $C_{1-6}$alkyl, oxo, and halogen;
X is $NR_7$ or $CH_2$, wherein the hydrogen(s) of $CH_2$ may be substituted with $R_4$;
$R_5$ is selected from the group consisting of $S(O)_2NR_aR_b$, $S(O)_2C_{1-6}$alkyl, $C(O)NRaR_b$, $C(O)C_{1-6}$alkyl, and $C(O)O-C_{1-6}$alkyl;
$R_6$, $R_7$, $R_a$, and $R_b$ are each independently hydrogen or $C_{1-6}$alkyl;
n is 1 or 2;
m is 0 or 1;
p is selected from the group consisting of 0, 1, 2, 3, and 4, wherein the compound is not

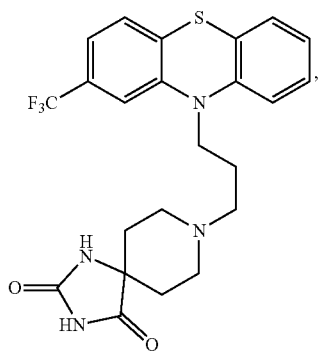

or a pharmaceutically acceptable salt thereof.
In some embodiments, $R_1$ is hydrogen.
In some embodiments, $R_1$ is OH.
In some embodiments, $R_2$ is $C_{1-6}$alkylene-$NR_5R_6$ and $R_3$ is hydrogen.
In some embodiments, $R_2$ and $R_3$ are taken together with the carbon to which $R_2$ and $R_3$ are attached to form a 3-7 membered heterocyclylene, wherein the heterocyclylene may be optionally substituted with one or more oxo or $C_{1-6}$alkyl, and have one or more heteroatoms, wherein each of the heteroatoms is nitrogen.

In some embodiments, each $R_4$ is oxo.
In some embodiments, X is $NR_7$.
In some embodiments, X is $CH_2$.
In some embodiments, $R_5$ is —$S(O)_2NR_aR_b$.
In some embodiments, $R_5$ is —$S(O)_2C_{1-6}$alkyl.
In some embodiments, $R_5$ is —$C(O)NR_aR_b$.
In some embodiments, $R_6$ is hydrogen.
In some embodiments, $R_7$ is hydrogen.
In some embodiments, $R_a$ and $R_b$ are hydrogen.
In some embodiments, p is 0.
In some embodiments, p is 2.
In some embodiments, n is 1.
In some embodiments, m is 0.
In some embodiments, m is 1.

In some embodiments, the compound is selected from the group consisting of:

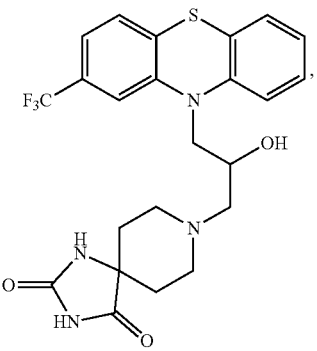

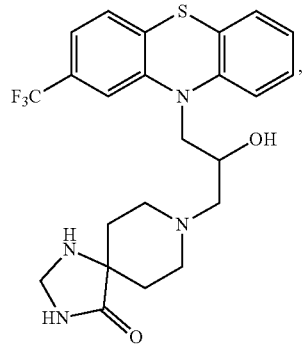

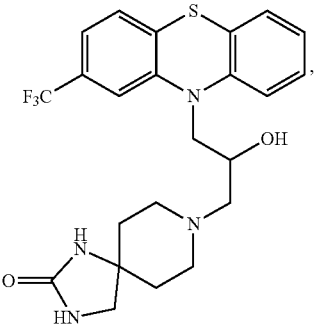

-continued

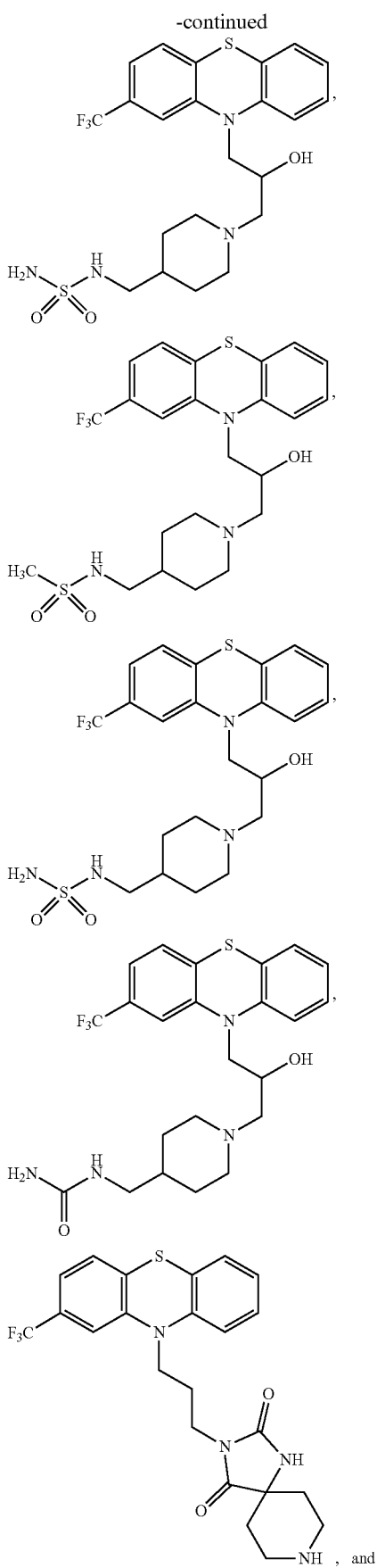

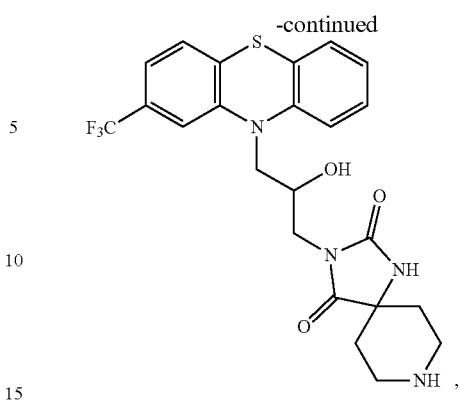

or a pharmaceutically acceptable salt thereof.

Also provided herein is a pharmaceutical composition comprising a compound of formula (Ia):

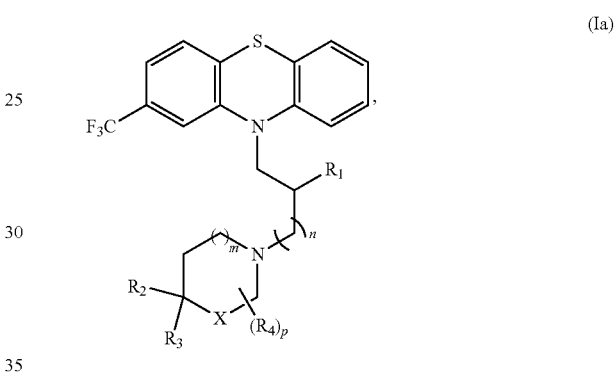

(Ia)

or a pharmaceutically acceptable salt thereof, wherein
  $R_1$ is selected from the group consisting of hydrogen, —OH, and $C_{1-6}$alkoxy;
  (a) $R_2$ is $C_{1-6}$alkylene-$NR_5R_6$ and $R_3$ is hydrogen or $C_{1-6}$alkyl; (b) $R_2$ is —OH and $R_3$ is —$CO_2H$, or (c) $R_2$ and $R_3$ are taken together with the carbon to which $R_2$ and $R_3$ are attached to form a 3-7 membered heterocyclylene, wherein the heterocyclylene may be optionally substituted with one or more oxo or $C_{1-6}$alkyl and have one or more heteroatoms, wherein each of the heteroatoms is nitrogen;
  each $R_4$ is selected from the group consisting of $C_{1-6}$alkyl, oxo, and halogen;
  X is $NR_7$ or $CH_2$, wherein the hydrogen(s) of $CH_2$ may be substituted with $R_4$;
  $R_5$ is selected from the group consisting of $S(O)_2NR_aR_b$, $S(O)_2C_{1-6}$alkyl, $C(O)NR_aR_b$, $C(O)C_{1-6}$alkyl, and $C(O)O$—$C_{1-6}$alkyl;
  $R_6$, $R_7$, $R_a$, and $R_b$ are each independently hydrogen or $C_{1-6}$alkyl;
  n is 1 or 2;
  m is 0 or 1; and
  p is selected from the group consisting of 0, 1, 2, 3, and 4;
and a pharmaceutically acceptable excipient.

In some embodiments of formula (Ia), $R_1$ is hydrogen.
In some embodiments of formula (Ia), $R_1$ is OH.
In some embodiments of formula (Ia), $R_2$ is $C_{1-6}$alkylene-$NR_5R_6$ and $R_3$ is hydrogen.
In some embodiments of formula (Ia), $R_2$ and $R_3$ are taken together with the carbon to which $R_2$ and $R_3$ are attached to form a 3-7 membered heterocyclylene. wherein the heterocyclylene may be optionally substituted with one or more oxo or $C_{1-6}$alkyl and have one or more heteroatoms, wherein each of the heteroatoms is nitrogen.

In some embodiments of formula (Ia), each $R_4$ is oxo.

In some embodiments of formula (Ia), X is $NR_7$.

In some embodiments of formula (Ia), X is $CH_2$.

In some embodiments of formula (Ia), $R_5$ is —$S(O)_2NR_aR_b$.

In some embodiments of formula (Ia), $R_5$ is —$S(O)_2C_{1-6}$alkyl.

In some embodiments of formula (Ia), $R_5$ is —$C(O)NR_aR_b$.

In some embodiments of formula (Ia), $R_6$ is hydrogen.

In some embodiments of formula (Ia), $R_7$ is hydrogen.

In some embodiments of formula (Ia), $R_a$ and $R_b$ are hydrogen.

In some embodiments of formula (Ia), p is 0.

In some embodiments of formula (Ia), p is 2.

In some embodiments of formula (Ia), n is 1.

In some embodiments of formula (Ia), m is 1.

In some embodiments of formula (Ia), m is 2.

In some embodiments of formula (Ia), the compound is selected from the group consisting of:

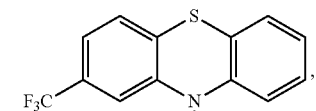,

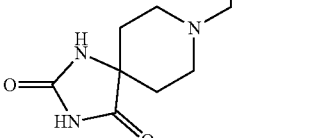,

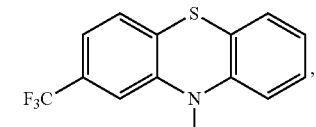,

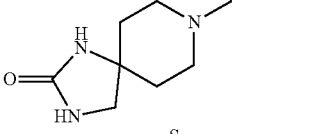,

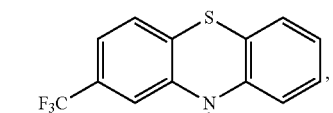,

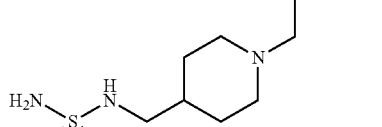,

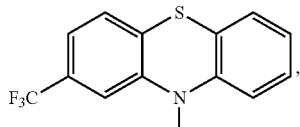,

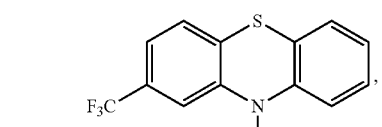,

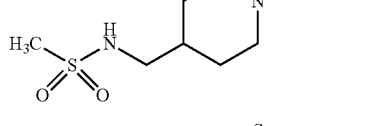,

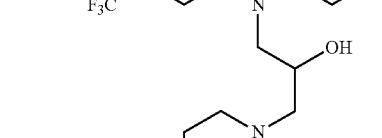,

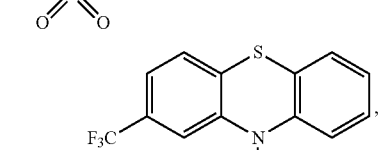,

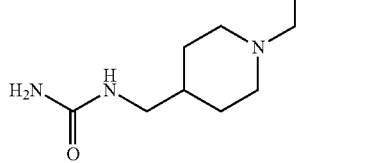,

23

-continued

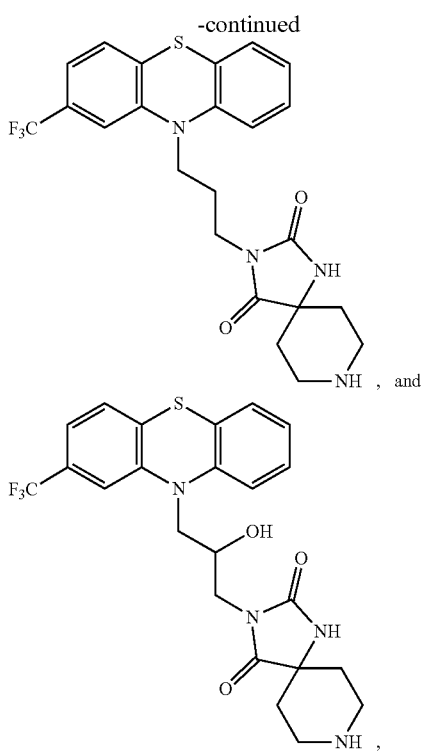

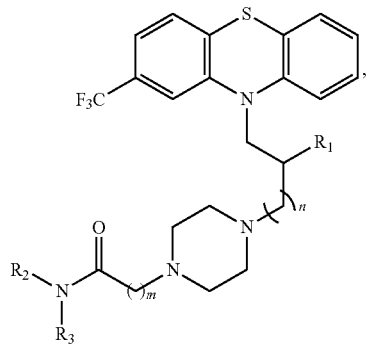

or a pharmaceutically acceptable salt thereof.

In another aspect, the present invention provides a compound of formula (II):

(II)

[structure of formula II]

or a pharmaceutically acceptable salt thereof, wherein
$R_1$ is selected from the group consisting of hydrogen, —OH, and $C_{1-6}$alkoxy;
$R_2$ is $C_{1-6}$alkyl substituted with one or more substituents each independently selected from the group consisting of —OH, $C_{1-6}$alkoxy, —C(O)NR$_a$R$_b$, —C(O)R$_c$, —C(O)OR$_a$, S(O)$_2$C$_{1-6}$alkyl, and S(O)$_2$NR$_a$R$_b$;
$R_3$ is hydrogen or $C_{1-6}$alky;
$R_a$, $R_b$, $R_c$, and $R_d$ are each independently hydrogen or $C_{1-6}$alkyl;
n is 1 or 2; and
m is selected from the group consisting of 1, 2, or 3.

In some embodiments of formula (II), $R_1$ is hydrogen.
In some embodiments of formula (II), $R_1$ is OH.
In some embodiments of formula (II), $R_2$ is $C_{1-6}$alkyl substituted with —OH.
In some embodiments of formula (II), $R_2$ is $C_{1-6}$alkyl substituted with —C(O)NR$_a$R$_b$.

24

In some embodiments of formula (11), $R_2$ is $C_{1-6}$alkyl substituted with —OH and —C(O)NR$_a$R$_b$.
In some embodiments of formula (II), $R_3$ is hydrogen.
In some embodiments of formula (II), n is 1.
In some embodiments of formula (II), m is 1.
In some embodiments of formula (II), the compound is selected from the group consisting of:

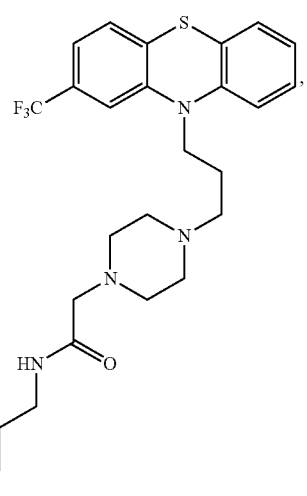

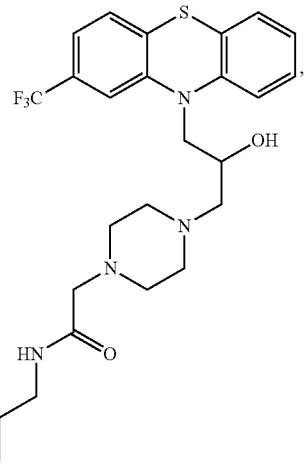

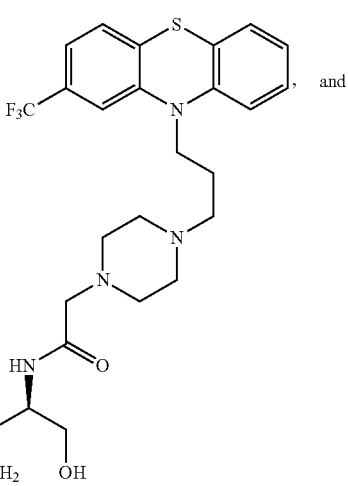

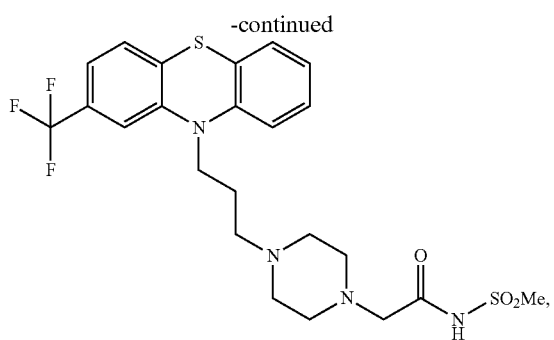

or a pharmaceutically acceptable salt thereof.

In another aspect, the present invention provides a compound of formula (III):

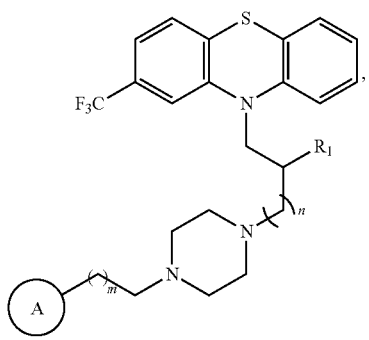

(III)

or a pharmaceutically acceptable salt thereof, wherein
$R_1$ is selected from the group consisting of hydrogen, —OH, and $C_{1-6}$alkoxy;
n is 1 or 2;
m is selected from the group consisting of 1, 2, or 3; and

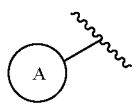

is a monosaccharide or disaccharide.

In some embodiments of formula (III)

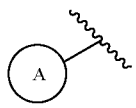

is a monosaccharide.

In some embodiments of formula (III), the compound is a compound of formula (IIIa):

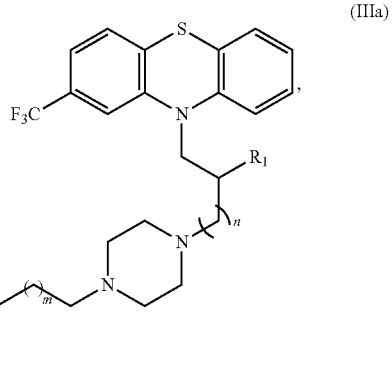

(IIIa)

or a pharmaceutically acceptable salt thereof, wherein
each $R_2$ is independently selected from the group consisting of $C_{1-6}$alky, $C_{1-6}$alkylene-$OR_3$, —$OR_4$, and —$NR_5R_6$;
$R_3$ and $R_4$ are each independently selected from the group consisting of hydrogen, $C_{1-6}$alkyl, $C_{2-6}$alkenyl, $C_{2-6}$alkynyl, phenyl, benzyl, and $C_{3-7}$cycloalkyl;
$R_5$ and $R_6$ are each independently hydrogen or $C_{1-6}$alkyl;
p is selected from the group consisting of 0, 1, 2, 3, and 4; and
$R_1$, n, and m are as defined above.

In some embodiments of formula (III) or (IIIa), $R_1$ is hydrogen.

In some embodiments of formula (III) or (IIIa), $R_1$ is —OH.

In some embodiments of formula (III) or (IIIa), each $R_2$ is independently $C_{1-6}$alkylene-OH or —OH.

In some embodiments of formula (III) or (IIIa), each $R_2$ is independently $CH_2$—OH or OH.

In some embodiments of formula (III) or (IIIa), n is 1.

In some embodiments of formula (III) or (IIIa), m is 1.

In some embodiments of formula (III) or (IIIa), p is 4.

In some embodiments of formula (III) or (IIIa), the compound is

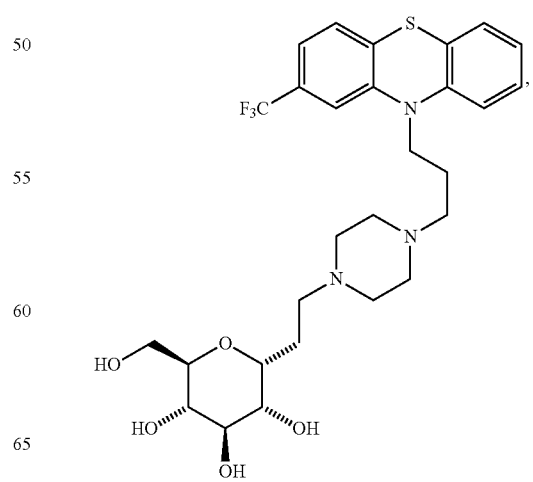

[Structure: phenothiazine with F₃C substituent, N-CH₂-CH(OH)-CH₂-piperazine-CH₂CH₂-(tetrahydropyran with HO, HO, OH, OH substituents)]

or a pharmaceutically acceptable salt thereof.

In another aspect, the present invention provides a compound of formula (IV):

(IV)

[Structure of formula (IV): phenothiazine with F₃C substituent, N-CH₂-CH(R₁)-(CH₂)ₙ-piperazine-N-R₂]

or a pharmaceutically acceptable salt thereof, wherein
- $R_1$ is selected from the group consisting of hydrogen, —OH, and $C_{1-6}$alkoxy;
- $R_2$ is $C_{1-6}$alkyl substituted with one or more $R_3$;
- each $R_3$ is independently selected from the group consisting of —(O—CH$_2$CH$_2$)$_m$—OR$_4$, —OH, —C(O)OR$_5$, $C_{1-6}$alkoxy optionally substituted with C(O)OR$_5$;
- each $R_4$ is independently selected from the group consisting of hydrogen, $C_{1-6}$alkyl, 3-7 membered cycloalkyl, and $C_{1-6}$alkylene-(3-7 membered cycloalkyl);
- each $R_5$ is independently hydrogen or $C_{1-6}$alkyl;
- n is 1 or 2; and
- m is an integer selected from 1 to 10, wherein the compound is not

[Structure: phenothiazine with CF₃ substituent, N-(CH₂)₃-piperazine-CH₂CH₂-OH]

or a pharmaceutically acceptable salt thereof.

In some embodiments of formula (IV), $R_1$ is hydrogen.
In some embodiments of formula (IV), $R_1$ is —OH.
In some embodiments of formula (IV), each $R_3$ is —(O—CH$_2$CH$_2$)$_m$—OR$_4$.
In some embodiments of formula (IV), each $R_3$ is OH.
In some embodiments of formula (IV), each $R_3$ is —C(O)OH.
In some embodiments of formula (IV), each $R_3$ is $C_{1-6}$alkylene-(3-7 membered cycloalkyl).
In some embodiments of formula (IV), each $R_4$ is $C_{1-6}$alkyl.
In some embodiments of formula (IV), each $R_4$ is —CH$_3$.
In some embodiments of formula (IV), each $R_5$ is hydrogen.
In some embodiments of formula (IV), n is 1.
In some embodiments of formula (IV), m is 2.
In some embodiments of formula (IV), the compound is selected from the group consisting of:

[Structure: phenothiazine with CF₃, N-(CH₂)₃-piperazine-CH₂-CO₂H]

[Structure: phenothiazine with CF₃, N-(CH₂)₃-piperazine-CH₂CH₂-O-CH₂CH₂-O-CH₂CH₂-OH]

[Structure: phenothiazine with CF₃, N-CH₂-CH(OH)-CH₂-piperazine-CH₂CH₂-O-CH₂CH₂-O-CH₂CH₂-OH]

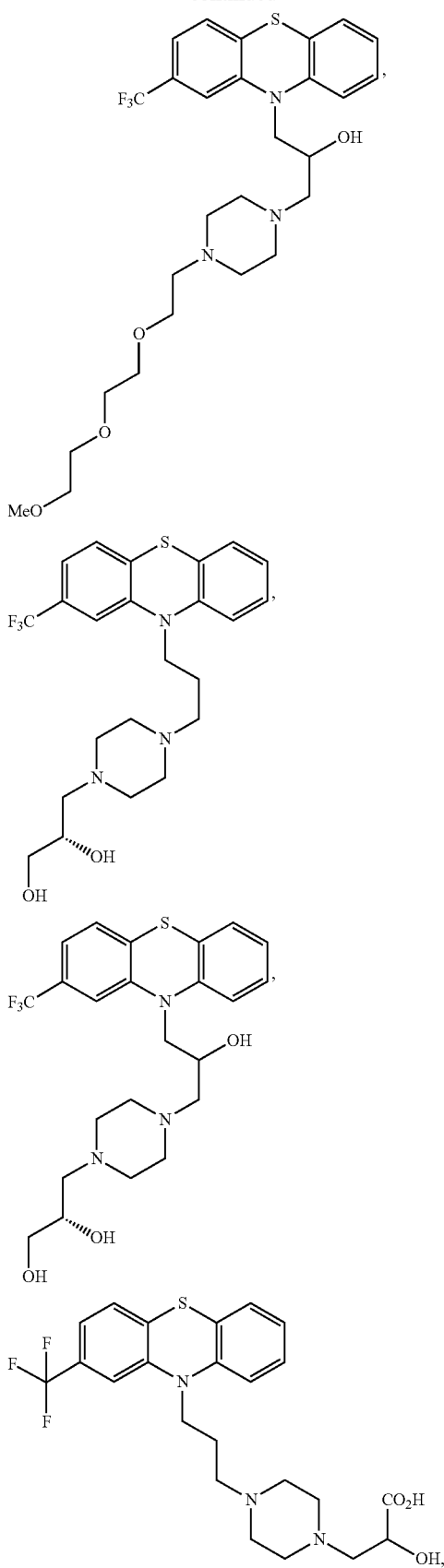
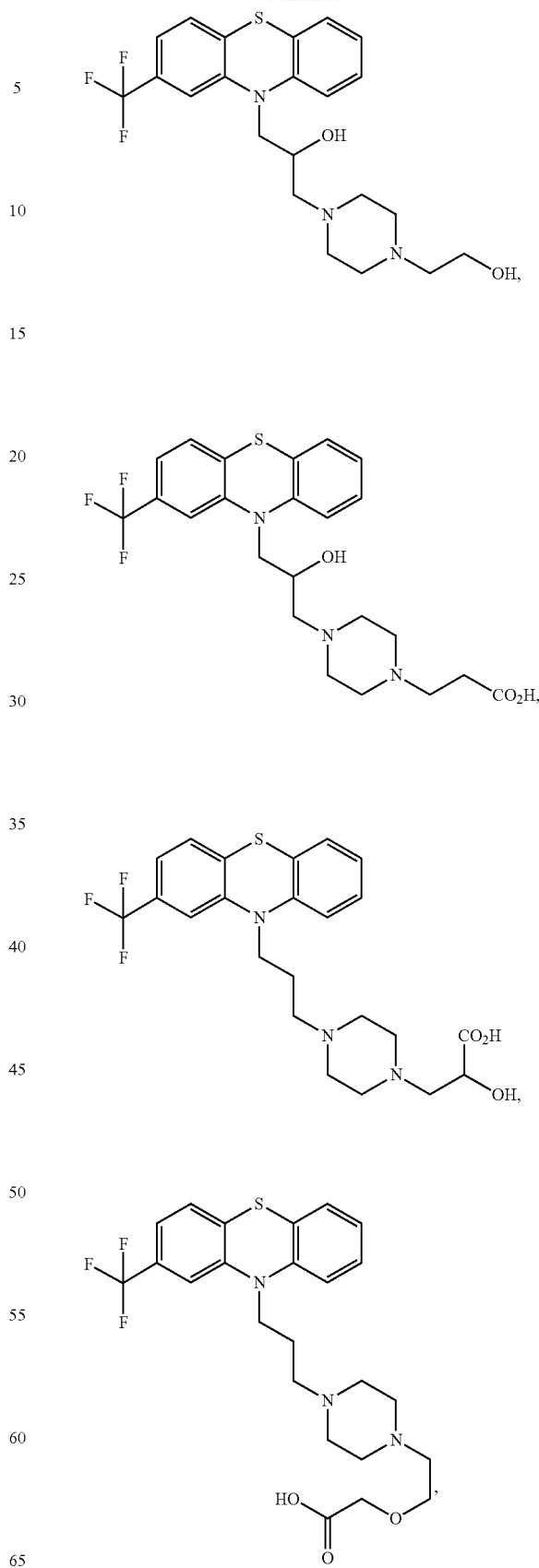

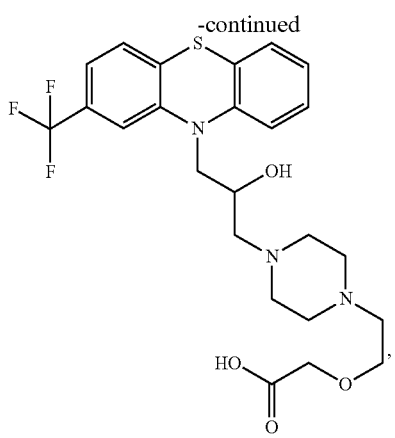

or a pharmaceutically acceptable salt thereof.

In another aspect, the present invention provides a compound of formula (V):

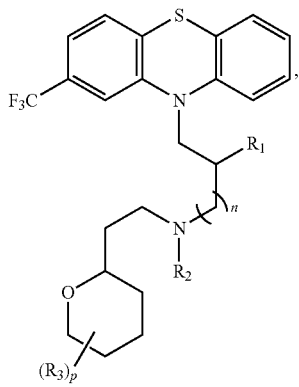

or a pharmaceutically acceptable salt thereof, wherein

R₁ is selected from the group consisting of hydrogen, —OH, and $C_{1-6}$alkoxy;

R₂ is selected from the group consisting of hydrogen and $C_{1-6}$alky;

each R₃ is independently selected from the group consisting of $C_{1-6}$alky, $C_{1-6}$alkylene-OH, —OH, $C_{1-6}$alkoxy, and $C_{1-6}$alkylene-$C_{1-6}$alkoxy;

n is 1 or 2; and p is selected from the group consisting of 0, 1, 2, 3, and 4.

In some embodiments of formula (V), R₁ is hydrogen.
In some embodiments of formula (V), R₁ is —OH.
In some embodiments of formula (V), R₂ is hydrogen.
In some embodiments of formula (V), R₂ is methyl.
In some embodiments of formula (V), each R₃ is independently $C_{1-6}$alkylene-OH or —OH.
In some embodiments of formula (V), each R₃ is independently CH₂—OH or OH.
In some embodiments of formula (V), n is 1.
In some embodiments of formula (V), n is 2.
In some embodiments of formula (V), p is 4.

In some embodiments of formula (V), the compound is selected from the group consisting of:

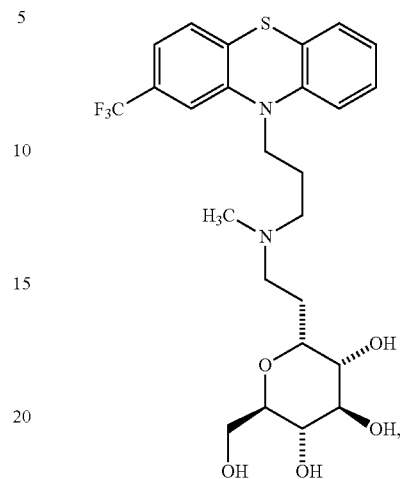

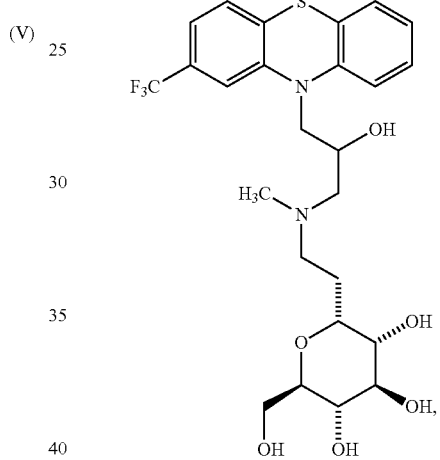

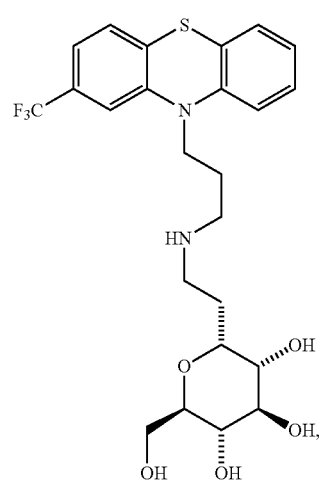

and

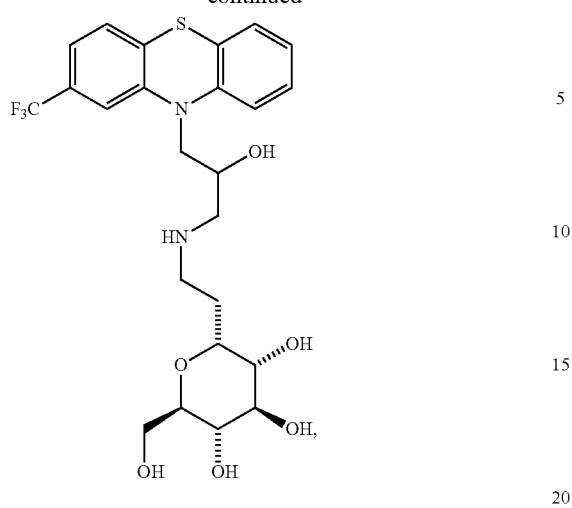
or a pharmaceutically acceptable salt thereof.
In some embodiments, phenothiazine compounds of the present invention include those having any one of the structures listed in Table 1.
TABLE 1
Structure of phenothiazine compounds
| Compound No. | Structure |
|---|---|
| MT-001 | 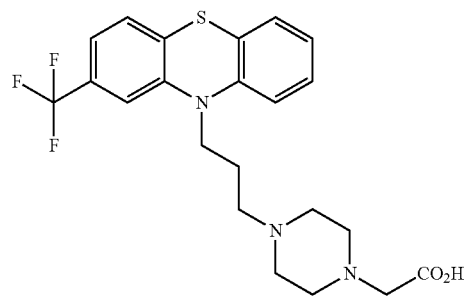 [SMILES: O=C(O)CN1CCN(CCCN2c3ccccc3Sc3ccc(C(F)(F)F)cc32)CC1] |
| MT-002 | 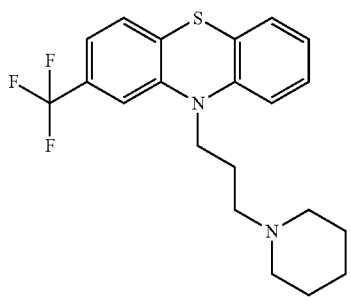 [SMILES: FC(F)(F)c1ccc2c(c1)N(CCCN1CCCCC1)c1ccccc1S2] |

TABLE 1-continued

Structure of phenothiazine compounds

| Compound No. | Structure |
|---|---|
| MT-003 | 10-[3-(4-hydroxypiperidin-1-yl)propyl]-2-(trifluoromethyl)-10H-phenothiazine |
| MT-004 | 1-{3-[2-(trifluoromethyl)-10H-phenothiazin-10-yl]propyl}-4-hydroxypiperidine-4-carboxylic acid |
| MT-005 | 2,2'-({3-[2-(trifluoromethyl)-10H-phenothiazin-10-yl]propyl}azanediyl)bis(ethan-1-ol) |
| MT-006 | 2-hydroxy-3-(4-{3-[2-(trifluoromethyl)-10H-phenothiazin-10-yl]propyl}piperazin-1-yl)propanoic acid |
| MT-007 | 2-(2-{[4-{3-[2-(trifluoromethyl)-10H-phenothiazin-10-yl]propyl}piperazin-1-yl]ethoxy}ethoxy)ethan-1-ol |

TABLE 1-continued
Structure of phenothiazine compounds
| Compound No. | Structure |
|---|---|
| MT-008 | 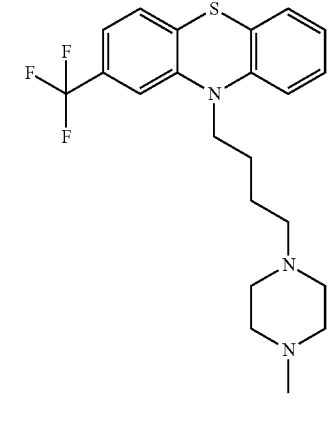 [SMILES: CN1CCN(CCCCN2c3ccccc3Sc3ccc(C(F)(F)F)cc32)CC1] |
| MT-009 | 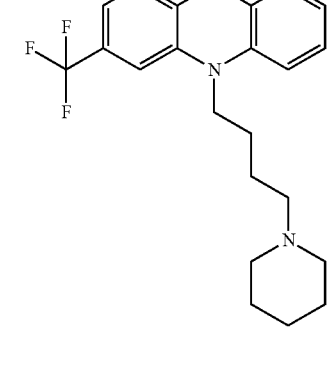 |
| MT-010 | 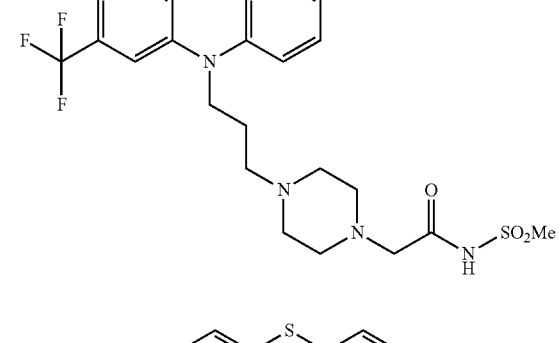 |
| MT-011 | 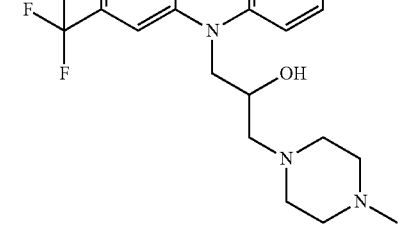 |

TABLE 1-continued

Structure of phenothiazine compounds

| Compound No. | Structure |
|---|---|
| MT-012 | 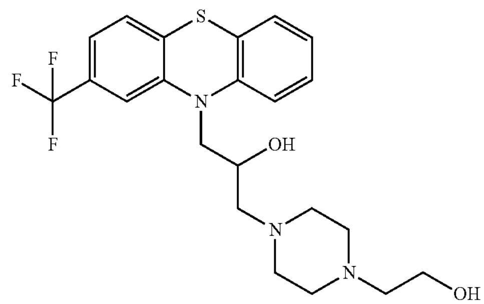 [SMILES: OCCN1CCN(CC(O)CN2c3ccccc3Sc3ccc(C(F)(F)F)cc32)CC1] |
| MT-013 | 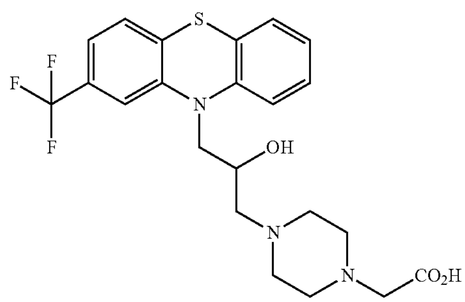 [SMILES: O=C(O)CN1CCN(CC(O)CN2c3ccccc3Sc3ccc(C(F)(F)F)cc32)CC1] |
| MT-014 | 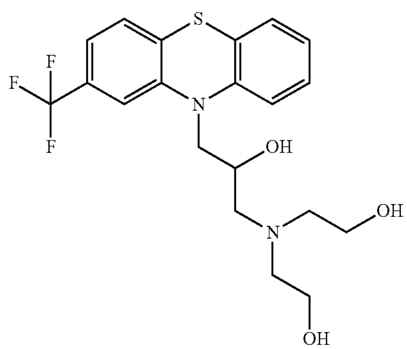 [SMILES: OCCN(CCO)CC(O)CN1c2ccccc2Sc2ccc(C(F)(F)F)cc21] |
| MT-015 | 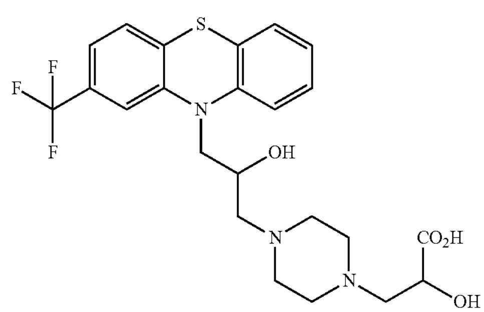 [SMILES: O=C(O)C(O)CN1CCN(CC(O)CN2c3ccccc3Sc3ccc(C(F)(F)F)cc32)CC1] |
| MT-016 | 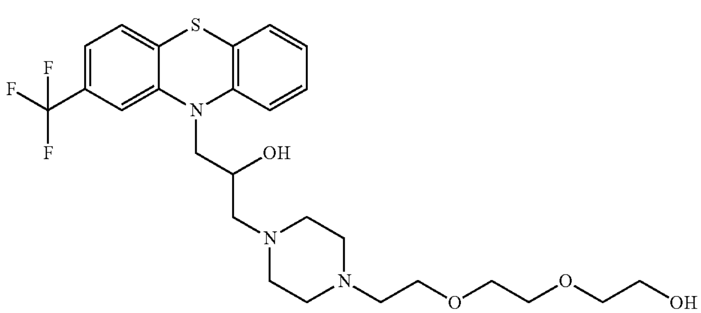 [SMILES: OCCOCCOCCN1CCN(CC(O)CN2c3ccccc3Sc3ccc(C(F)(F)F)cc32)CC1] |

TABLE 1-continued

Structure of phenothiazine compounds

| Compound No. | Structure |
|---|---|
| MT-017 | 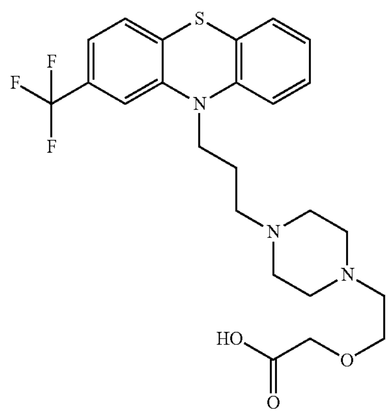 [SMILES: O=C(O)COCCN1CCN(CCCN2c3ccccc3Sc3ccc(C(F)(F)F)cc32)CC1] |
| MT-018 | 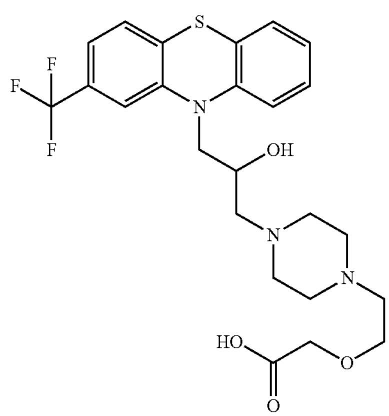 [SMILES: O=C(O)COCCN1CCN(CC(O)CN2c3ccccc3Sc3ccc(C(F)(F)F)cc32)CC1] |
| MT-019 | 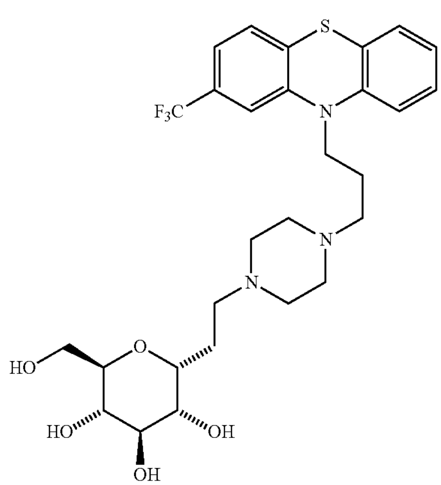 [SMILES: OC[C@H]1O[C@H](CCN2CCN(CCCN3c4ccccc4Sc4ccc(C(F)(F)F)cc43)CC2)[C@H](O)[C@@H](O)[C@@H]1O] |

TABLE 1-continued
Structure of phenothiazine compounds
| Compound No. | Structure |
|---|---|
| MT-020 | 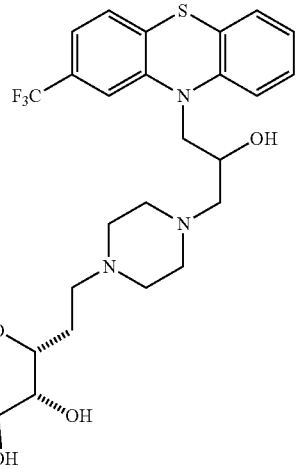 |
| MT-021 | 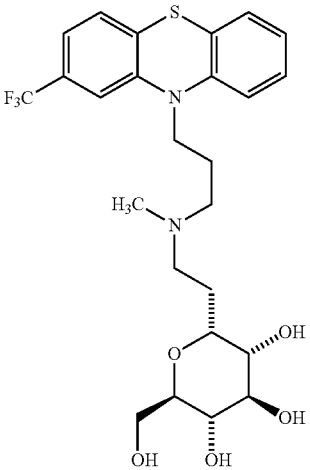 [SMILES: CN(CCCN1c2ccccc2Sc2ccc(C(F)(F)F)cc21)CC[C@H]1O[C@H](CO)[C@@H](O)[C@H](O)[C@H]1O] |
| MT-022 | 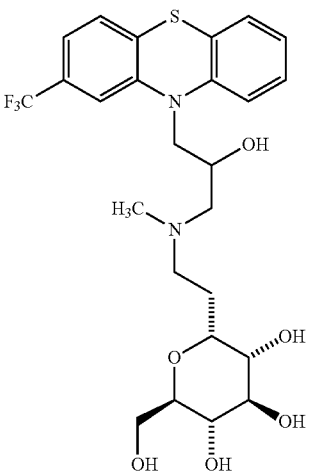 [SMILES: CN(CC[C@H]1O[C@H](CO)[C@@H](O)[C@H](O)[C@H]1O)CC(O)CN1c2ccccc2Sc2ccc(C(F)(F)F)cc21] |

TABLE 1-continued
| Structure of phenothiazine compounds | |
|---|---|
| Compound No. | Structure |
| MT-023 | 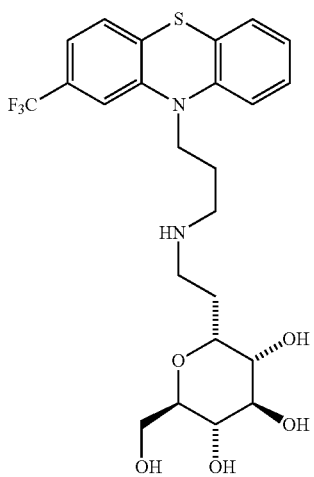 [SMILES: OC[C@H]1O[C@H](CCNCCCN2c3ccccc3Sc3ccc(C(F)(F)F)cc32)[C@H](O)[C@@H](O)[C@@H]1O] |
| MT-024 | 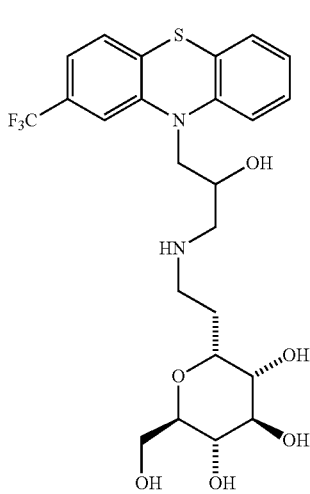 [SMILES: OC[C@H]1O[C@H](CCNCC(O)CN2c3ccccc3Sc3ccc(C(F)(F)F)cc32)[C@H](O)[C@@H](O)[C@@H]1O] |
| MT-025 | 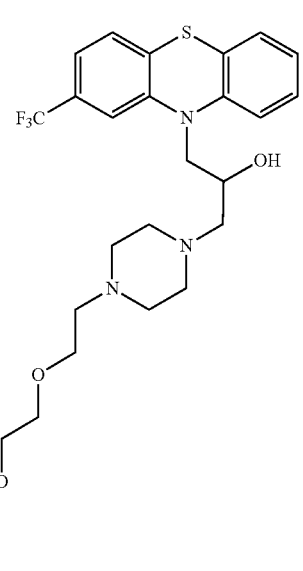 |

TABLE 1-continued
Structure of phenothiazine compounds
| Compound No. | Structure |
|---|---|
| MT-026 | 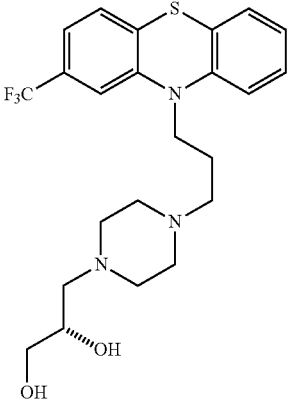 [SMILES: OC[C@@H](O)CN1CCN(CCCN2c3ccccc3Sc3ccc(C(F)(F)F)cc32)CC1] |
| MT-027 | 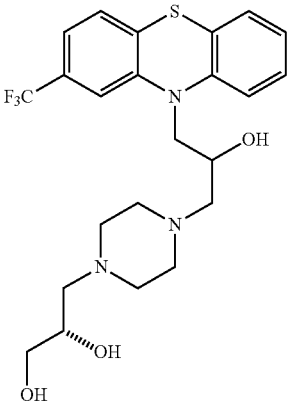 [SMILES: OC[C@@H](O)CN1CCN(CC(O)CN2c3ccccc3Sc3ccc(C(F)(F)F)cc32)CC1] |
| MT-028 | 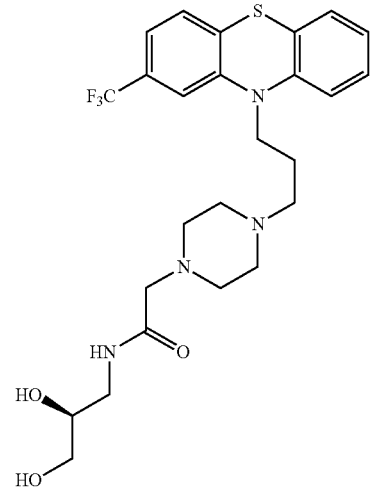 [SMILES: O=C(CN1CCN(CCCN2c3ccccc3Sc3ccc(C(F)(F)F)cc32)CC1)NC[C@H](O)CO] |

TABLE 1-continued
| Structure of phenothiazine compounds | |
|---|---|
| Compound No. | Structure |
| MT-029 | 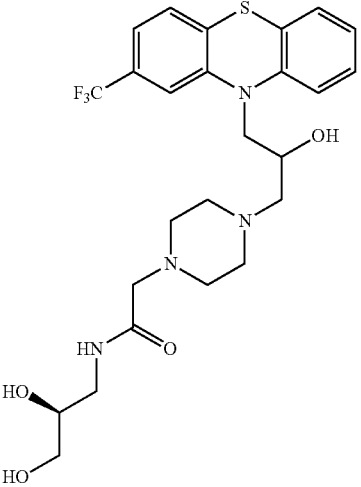 [SMILES: O=C(CN1CCN(CC(O)CN2c3ccccc3Sc3ccc(C(F)(F)F)cc32)CC1)NC[C@H](O)CO] |
| MT-030 | 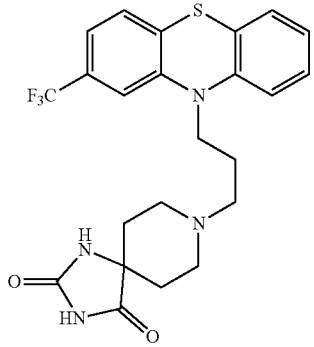 [SMILES: O=C1NC(=O)C2(CCN(CCCN3c4ccccc4Sc4ccc(C(F)(F)F)cc43)CC2)N1] |
| MT-030a | |
| MT-031 | 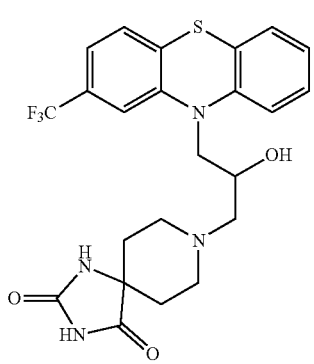 [SMILES: O=C1NC(=O)C2(CCN(CC(O)CN3c4ccccc4Sc4ccc(C(F)(F)F)cc43)CC2)N1] |
| MT-031a | |

TABLE 1-continued
Structure of phenothiazine compounds
| Compound No. | Structure |
|---|---|
| MT-032 | 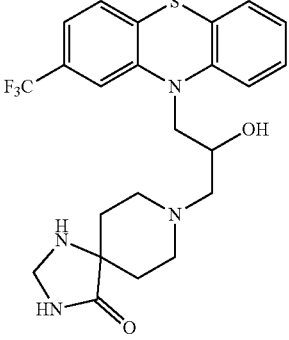 |
| MT-033 | 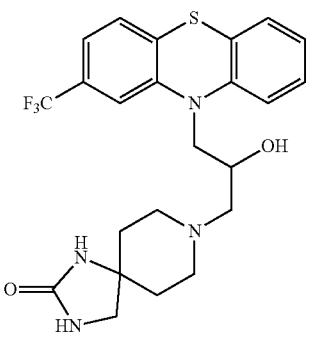 [SMILES: O=C1NCC2(CCN(CC(O)CN3c4ccccc4Sc4ccc(C(F)(F)F)cc43)CC2)N1] |
| MT-034 | 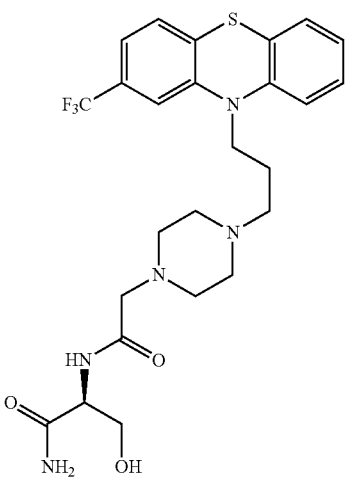 [SMILES: NC(=O)[C@H](CO)NC(=O)CN1CCN(CCCN2c3ccccc3Sc3ccc(C(F)(F)F)cc32)CC1] |
| MT-035 | 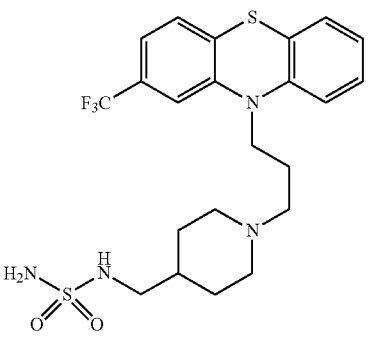 [SMILES: NS(=O)(=O)NCC1CCN(CCCN2c3ccccc3Sc3ccc(C(F)(F)F)cc32)CC1] |

TABLE 1-continued

Structure of phenothiazine compounds

| Compound No. | Structure |
|---|---|
| MT-036 | [Phenothiazine with CF₃ substituent, N-CH₂-CH(OH)-CH₂-piperidine-CH₂-NH-S(=O)₂-CH₃] |
| MT-037 | [Phenothiazine with CF₃ substituent, N-CH₂-CH(OH)-CH₂-piperidine-CH₂-NH-S(=O)₂-NH₂] |
| MT-038 | [Phenothiazine with CF₃ substituent, N-CH₂-CH(OH)-CH₂-piperidine-CH₂-NH-C(=O)-NH₂] |

In some embodiments, the phenothiazine compounds of the present invention may be analogs and/or derivatives of Fluphenazine. Fluphenazine is another antipsychotic drug of the phenothiazine chemical class. Chemically, it is classified as a piperazinyl phenothiazine. It is typically used for the treatment of psychoses such as schizophrenia, manic phases of bipolar disorder, agitation, and dementia. Fluphenazine, also known as 4-[3-[2-(trifluoromethyl)phenothiazin-10-yl] propyl]-1-piperazineethanol, may be synthesized by any of the methods described already for the preparation of trifluoperazine and related antipsychotics, including those disclosed in U.S. Pat. No. 3,058,979 (1962), 3,394,131 (1963), 2,766,235 (1956) and 3,194,733 (1965) and GB Patents 833474 and 829246 (1960), the content of which are incorporated herein in their entirety by reference. Derivatives and salts of fluphenazine include, but are not limited to, Fluphenazine decanoate (Brand names: Modecate, Prolixin Decanoate, Dapotum D, Anatensol, Fludecate, Sinqualone Deconoate); Fluphenazine enanthate (Brand Names: Dapotum Injektion, Flunanthate, Moditen Enanthate Injection, Sinqualone Enanthate), Fluphenazine hydrochloride (Brand names: Prolixin, Permitil, Dapotum, Lyogen, Moditen, Omca, Sediten, Selecten, Sevinol, Sinqualone, Trancin), and flucate. Fluphenazine is often administered as an oral liquid or tablets (e.g., unit does of about 1 mg, 2.5 mg, 5 mg, 10 mg), or as an injectable form (including a short-acting and long-acting form). Fluphenazine has an incomplete oral bioavailability of 40% to 50% due to extensive first pass metabolization in the liver. The half life of fluphenazine is between 15 to 30 hours.

In some embodiments, the phenothiazine compounds of the present invention may be analogs and/or derivatives of perphenazine. Perphenazine, also known as 4-[3-(2-Chloro-10H-phenothiazin-10-yl)propyl]-1-piperazineethanol, is a piperazinyl phenothiazine and a antipsychotic drug. Perphenazine is approximately 5-times as potent as chlorpromazine, thus perphenazine is considered a medium-potency antipsychotic. Perphenazine is marketed in the US under the brand names TRILAFON™ (single drug) and ETRAFON™/TRIAVAIL™ (contains fixed dosages of amitriptyline), and in Europe as DECENTAN™. Preparation of perphenazine is described in U.S. Pat. Nos. 2,766,235 and 2,860,138, the content of which are incorporated herein in their entity by reference. Perphenazine may be administered orally, e.g., via are tablets (e.g., with 2, 4, 8, 16 mg unit doses) or as liquid concentrate (e.g., 4 mg/ml unit dose). Perphenazine has an oral bioavailability of approximately 40% and a half-life of 8 to 12 hours (up to 20 hours), and is usually given in 2 or 3 divided doses each day.

In some embodiments, the phenothiazine compounds of the present invention may be analogs and/or derivatives of chlorpromazine. Chlorpromazine, [3-(2-Chloro-phenothiazin-10-yl)-propyl]-dimethyl-amine, was discovered in 1950 and was the first antipsychotic. Chlorpromazine is classified as a low-potency typical antipsychotic and is primarily used to treat psychotic disorders such as schizophrenia. Chlorpromazine is marketed under the trade names THORAZINE™, LARGACTIL™, HIBERNAL™, and MEGAPHEN™. It can be administrered orally, by injection into a muscle, or into a vein.

In some embodiments, the phenothiazine compounds of the present invention may be analogs and/or derivatives of other phenothiazines such as promazine, desipramine, or promethazine.

In various embodiments, phenothiazine compounds as disclosed herein include all stereoisomers, geometric isomers, tautomers, and isotopes of the structures depicted. In some embodiments, phenothiazine compounds as disclosed herein also include prodrugs and pharmaceutically acceptable salts thereof.

All phenothiazine compounds as disclosed herein are provided herein for illustrative purpose and disclose a particular isomer. However, all stereoisomers, such as enantiomers and diastereomers, are intended unless otherwise indicated. As used herein, the term "isomer" refers to a compound having the same molecular formula but differing in structure. Isomers which differ only in configuration and/or conformation are referred to as "stereoisomers."

The term "enantiomer" is used to describe one of a pair of molecular isomers which are mirror images of each other and are non-superimposable. The designations may appear as a prefix or as a suffix; they may or may not be separated from the isomer by a hyphen; they may or may not be hyphenated; and they may or may not be surrounded by parentheses. The designations "(+)" and "(−)" are employed to designate the sign of rotation of plane-polarized light by the compound, with (−) meaning that the compound is levorotatory (rotates to the left), and (+) meaning that the compound is dextrorotatory (rotates to the right). Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions). Enantiomers generally have identical physical properties, such as melting points and boiling points, and also have identical spectroscopic properties. Enantiomers can differ from each other with respect to their interaction with plane-polarized light and with respect to biological activity.

The term "diastereomer" is used to describe one of a pair of molecular isomers which are not mirror images of each other and are non-superimposable. Diastereomers have two or more stereocenters. They can have different physical properties and reactivity. For example, they may have different melting points and boiling points and different densities.

Phenothiazine compounds of the present invention (e.g., a compound of formula (I), (Ia), (II), (III), (IIIa), (IV), (V), or (VI)) that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Phenothiazine compounds of the present invention (e.g., a compound of formula (I), (Ia), (II), (III), (IIIa), (IV), (V), or (VI)) also include tautomeric forms. Tautomeric forms result from the swapping of a single bond with an adjacent double bond and the relocation of a proton. Tautomeric forms include prototropic tautomers which are isomeric protonation states having the same empirical formula and total charge. Examples of prototropic tautomers include ketone-enol pairs, amide-imidic acid pairs, lactam-lactim pairs, amide-imidic acid pairs, enamine-imine pairs, enamine-enamine pairs, nitroso-oxime pairs, ketene-ynol pairs, annular forms where a proton can occupy two or more positions of a heterocyclic system, such as, 1H— and 3H-imidazole, 1H—, 2H— and 4H— 1,2,4-triazole, 1H— and 2H-isoindole, and 1H— and 2H-pyrazole, and ring-chain tautomers where the proton relocation is accompanied by a change from an open structure to a ring, such as the open chain and cyclic hemiacetal (typically pyranose or furanose forms) of many sugars. Tautomeric forms can be in equilibrium or sterically locked into one form by appropriate substitution.

Phenothiazine compounds of the present invention (e.g., a compound of formula (I), (Ia), (II), (III), (IIIa), (IV), (V), or (VI)) also include all of the isotopes of the atoms occurring in the intermediate or final compounds. "Isotopes" refer to atoms having the same atomic number but different mass numbers resulting from a different number of neutrons in the nuclei. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; F may be in any isotopic form, including $^{18}$F and $^{19}$F; and the like.

In some embodiments, phenothiazine compounds of the present invention (e.g., a compound of formula (I), (Ia), (II), (III), (IIIa), (IV), (V), or (VI)) also include prodrugs of such compounds. As used herein, a "prodrug" refers to a compound that can be converted to a functionally active compound via some chemical or physiological process. A prodrug may be converted into the active drug by various mechanisms, including enzymatic processes and metabolic hydrolysis. In some cases, a prodrug is a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. Prodrugs can be useful because, in some situations, they can improve how a drug is absorbed, distributed, metabolized, and excreted. For example, a prodrug may be bioavailable by oral administration whereas the active compound itself is poorly absorbed from the gastrointestinal tract. The prodrug may also have improved solubility in pharmaceutical compositions compared to the active drug. A prodrug may be less toxic than the active compound. A prodrug may have better tissue compatibility or suitable for delayed release in an organism compared to the active compound. The term "prodrug" is also meant to include any covalently bonded carriers, which release the active compound in vivo when administered to a subject. Prodrugs of an active compound may be prepared by modifying functional group(s) present in the active compound in a way such that the modifications can be cleaved, either in routine manipulation or in vivo, to yield the active compound. For example, prodrugs may include compounds wherein a hydroxy, amino or mercapto group is bonded to any group that, upon entering the body, cleaves to form a free hydroxy, free amino or free mercapto group, respectively.

Examples of prodrugs include, but are not limited to, acetate, formate and benzoate derivatives of an alcohol or acetamide, formamide and benzamide derivatives of an amine functional group in the active compound and the like. See Harper, Drug Latentiation in Jucker, ed. Progress in Drug Research 4:221-294 (1962); Gangwar et al. Pro-drug, molecular structure and percutaneous delivery, Des. Biopharm. Prop. Prodrugs Analogs, [Symp.] Meeting Date 1976, 409-21. (1977); Morozowich et al., Application of Physical Organic Principles to Prodrug Design in E. B. Roche ed. Design of Biopharmaceutical Properties through Prodrugs and Analogs, APHA Acad. Pharm. Sci. 40 (1977); Bundgaard, Bioreversible derivatization of drugs—principle and applicability to improve the therapeutic effects of drugs, Arch. Pharm. Chemi 86(1): 1-39 (1979); Farquhar D et al., Biologically Reversible Phosphate-Protective Groups, Pharm. Sci., 72(3): 324-325 (1983); Bundgaard H. ed. Design of Prodrugs, Elsevier (1985); Fleisher et al. Design of prodrugs for improved gastrointestinal absorption by intestinal enzyme targeting, Methods Enzymol. 112 (Drug Enzyme Targeting, Pt. A): 360-81, (1985); Stella et al. Prodrugs. Do they have advantages in clinical practice?, Drugs 29(5): 455-73 (1985); Bundgaard H. Improved drug delivery by the prodrug approach, Controlled Drug Delivery 17: 179-96 (1987); E. B. Roche, ed. Bioreversible Carriers in Drug in Drug Design, Theory and Application, APHA Acad. Pharm. Sci. (1987); Waller et al. Prodrugs, Br. J. Clin. Pharmac. 28: 497-507 (1989); Balant et al., Prodrugs for the improvement of drug absorption via different routes of administration, Eur. J. Drug Metab. Pharmacokinet., 15(2): 143-53 (1990); Freeman S et al., Bioreversible Protection for the Phospho Group: Chemical Stability and Bioactivation of Di(4-acetoxy-benzyl) Methylphosphonate with Carboxyesterase, Chem. Soc, Chem. Commun., 875-877 (1991); Bundgaard H. Prodrugs as a means to improve the delivery of peptide drugs, Adv. Drug Delivery Rev. 8(1): 1-38 (1992); Nathwani and Wood, Penicillins: a current review of their clinical pharmacology and therapeutic use, Drugs 45(6): 866-94 (1993); Fleisher et al. Improved oral drug delivery: solubility limitations overcome by the use of prodrugs, Adv. Drug Delivery Rev. 19(2): 115-130 (1996); Friis and Bundgaard, Prodrugs of phosphates and phosphonates: Novel lipophilic alphaacyloxyalkyl ester derivatives of phosphate- or phosphonate containing drugs masking the negative charges of these groups, Eur. J. Pharm. Sci. 4: 49-59 (1996); Gaignault et al., Designing Prodrugs and Bioprecursors I. Carrier Prodrugs, Pract. Med. Chem. 671-696 (1996); Sinhababu and Thakker, Prodrugs of anticancer agents, Adv. Drug Delivery Rev. 19(2): 241-273 (1996); Taylor, Improved passive oral drug delivery via prodrugs, Adv. Drug Delivery Rev., 19(2): 131-148 (1996); Browne, Fosphenytoin (Cerebyx), Clin. Neuropharmacol. 20(1): 1-12 (1997); Pauletti et al., Improvement in peptide bioavailability: Peptidomimetics and Prodrug Strategies, Adv. Drug. Delivery Rev. 27:235-256 (1997); Valentino and Borchardt, Prodrug strategies to enhance the intestinal absorption of peptides, Drug Discovery Today 2(4): 148-155 (1997); Mizen et al., The Use of Esters as Prodrugs for Oral Delivery of beta-Lactam antibiotics, Pharm Biotechnol. 11:345-365 (1998); Balimane and Sinko, Involvement of multiple transporters in the oral absorption of nucleoside analogues, Adv. Drug Delivery Rev., 39(1-3): 183-209 (1999); Tan et al., Development and optimization of anti-HIV nucleoside analogs and prodrugs: A review of their cellular pharmacology, structure-activity relationships and pharmacokinetics, Adv. Drug Delivery Rev. 39(1-3): 117-151 (1999); Wang et al., Prodrug approaches to the improved delivery of peptide drug, Curr. Pharm. Design. 5(4):265-287 (1999); Wiebe and Knaus, Concepts for the design of anti-HIV nucleoside prodrugs for treating cephalic HIV infection, Adv. Drug Delivery Rev.: 39(1-3):63-80 (1999); Lambert, Rationale and applications of lipids as prodrug carriers, Eur. J. Pharm. Sci., 11 Suppl. 2:S15-27 (2000); Asgharnejad, Improving Oral Drug Transport, in Transport Processes in Pharmaceutical Systems, G. L. Amidon, P. I. Lee and E. M. Topp, Eds., Marcell Dekker, p. 185-218 (2000); Han et al., Targeted prodrug design to optimize drug delivery, AAPS PharmSci., 2(1): E6 (2000); Sadzuka, Effective prodrug liposome and conversion to active metabolite, Curr. Drug Metab., 1(1): 31-48 (2000), the contents of all of which are herein incorporated by reference in their entirety.

Phenothiazine compounds of the present invention (e.g., a compound of formula (I), (Ia), (II), (III), (IIIa), (IV), (V), or (VI)) also include pharmaceutically acceptable salts thereof. As used herein, the term "pharmaceutically acceptable salt" refers to derivatives of the disclosed compounds wherein the parent compound is modified by converting an existing acid or base moiety to its salt form (e.g., by reacting the free base group with a suitable organic acid). These salts may be prepared in situ in the administration vehicle or the dosage form during manufacturing process, or by separately reacting a phenothiazine compound in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., Pharmaceutical Salts, Pharm. Sci. 66:1-19 (1977), the content of which is herein incorporated by reference in its entirety.

Methods of Preparing a Phenothiazine Compound

In another aspect, a method of preparing a phenothiazine compound disclosed herein (e.g., a compound of formula (I), (Ia), (II), (III), (IIIa), (IV), (V), or (VI)) is provided. In some embodiments, provided herein is a method of preparing a phenothiazine compound having a structure selected from any one of those listed in Table 1.

Exemplary methods for preparing compounds described herein are illustrated in the following synthetic schemes. These schemes are given for the purpose of illustrating the invention, and should not be regarded in any manner as limiting the scope or the spirit of the invention.

The synthetic route illustrated in Scheme 1 depicts an exemplary procedure for preparing phenothiazine compounds C and D. In the first step, compound A is reacted with alkylbromochloride to form intermediate B. Intermediate B is further functionalized to form alkylene-amino substituted phenothiazine compounds C and alkylene-piperazine substituted phenothiazine compounds D.

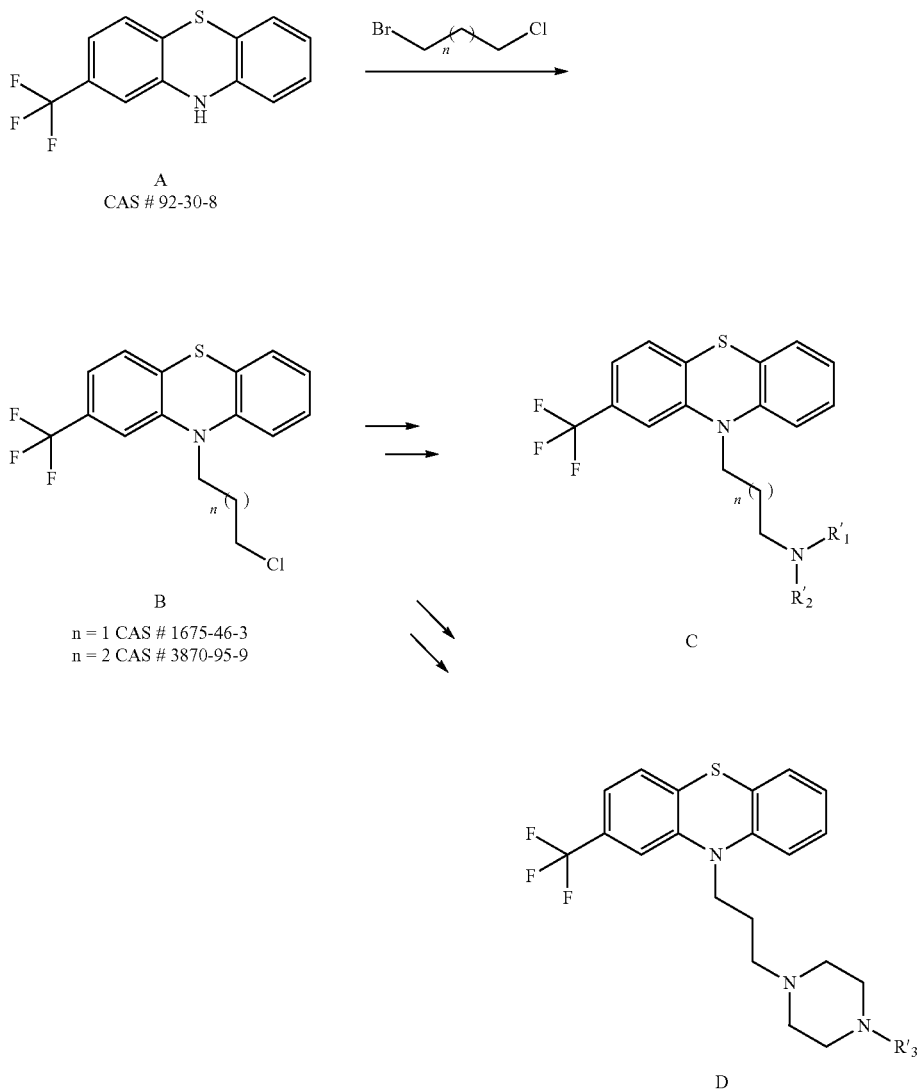

examples of the variables
R′₁ = hydrogen, alkyl (optionally substituted)
R′₂ = alkyl optionally substituted with e.g., a glucose etc
R′₃ = alkyl optionally substitued with e.g., amide, glucose, PEG, etc The synthetic route illustrated in Scheme 2 depicts an exemplary procedure for preparing hydroxylated phenothiazine compounds F-H. In the first step, compound A is reacted with 2-(bromomethyl)oxirane to form epoxide intermediate E. Intermediate E is further functionalized to form hydroxy alkylene-piperazine substituted phenothiazine compounds F, hydroxy alkylene-piperidine substituted phenothiazine compounds G, and hydroxy alkylene-amine substituted phenothiazine compounds H.

SCHEME 2

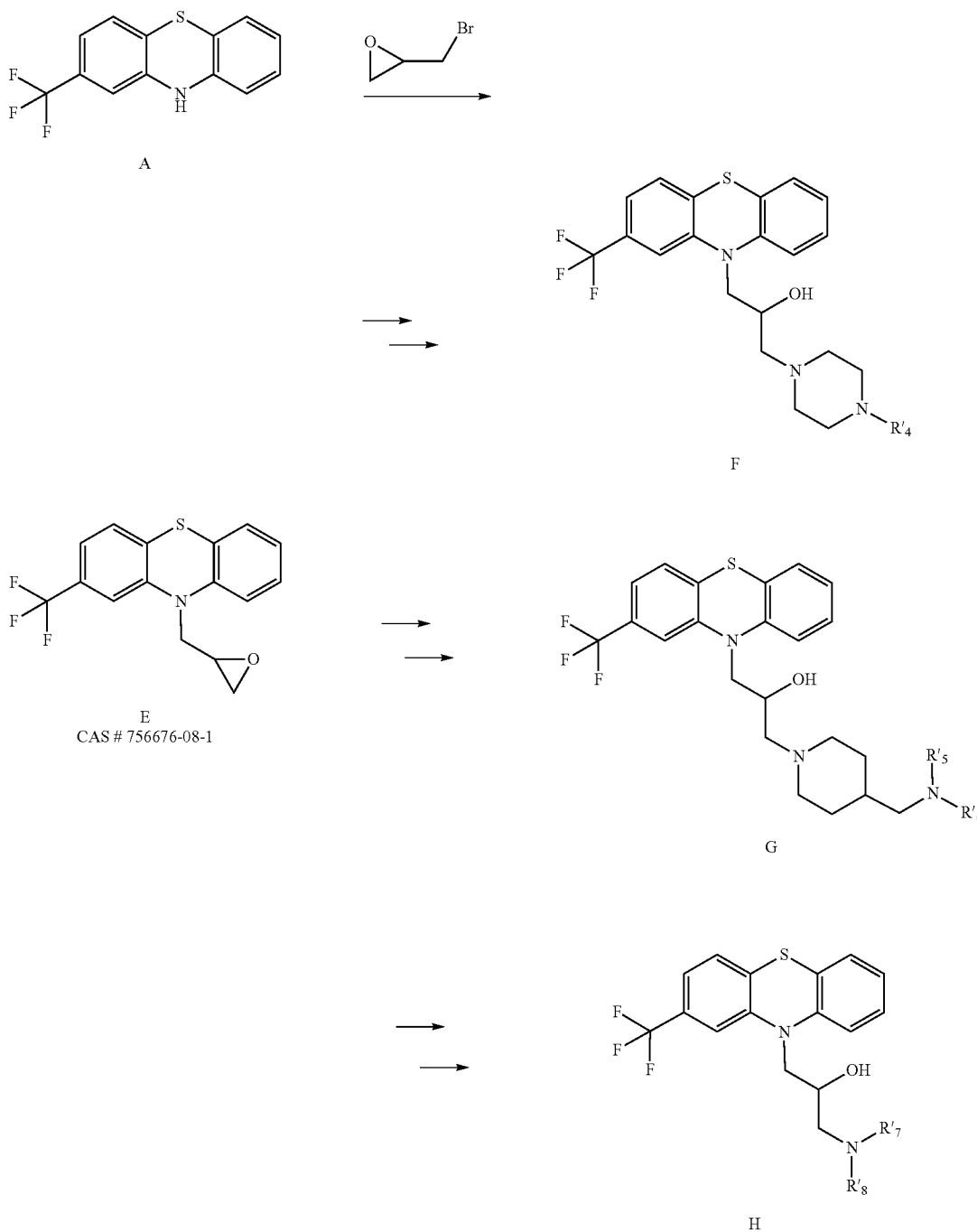

examples of the variables
R'₄ = alkyl optionally substituted with e.g., amide, glucose, PEG, etc
R'₅ = S(O)₂-amine, S(O)₂-alkyl, amide, ketone, and ester
R'₆ = hydrogen or alkyl
R'₇ = hydrogen, alkyl (optionally substituted)
R'₈ = alkyl optionally substituted with e.g., a glucose etc Properties of Phenothiazine Compounds In some embodiments, phenothiazine compounds of the present invention (e.g., a compound of formula (I), (Ia), (II), (III), (IIIa), (IV), (V), or (VI)) are capable of binding to calmodulin. Binding to calmodulin may be characterized using techniques known in the art, such as fluorescence resonance energy transfer-based assays (Sharma et al., Bioconjugate Chem., 2005, 16 (5), pp 1257-1263), and competition-based fluorescence polarization (FP) assays (Dagher et al., Biochim Biophys Acta. 2006 November;

1763(11):1250-5; Arai et al., Anal Biochem. 2010 Oct. 15; 405(2):147-52; Audran et al., Biochim Biophys Acta. 1833 (2013) 1720-1731, the content of which are herein incorporated by reference in their entirety). For example, in the competition-based FP assays, binding affinity may be determined by measuring the competitive binding activity of a compound to a fluorescent probe that is known to bind to CaM with high affinity. Half maximal inhibitory concentration ($IC_{50}$), defined as the concentration of compound that gives 50% binding inhibition, can be calculated to evaluate binding affinity.

In some embodiments, a phenothiazine compound described herein (e.g., a compound of formula (I), (Ia), (II), (III), (IIIa), (IV), (V), or (VI)) binds to calmodulin with an $IC_{50}$ of about 0.1 nM to 100 nM. In some embodiments, a phenothiazine compound binds to calmodulin with an $IC_{50}$ of about 0.1 nM, about 0.5 nM, about 1 nM, about 5 nM, about 10 nM, about 30 nM, about 50 nM, about 70 nM, about 100 nM, from about 0.1 to about 1 nM, from about 0.1 to about 10 nM, from about 0.5 nM to about 20 nM, from about 1 nM to 100 nM, from about 1 to about 50 nM, from about 5 nM to about 100 nM, from about 10 nM to about 100 nM, from about 50 nM to about 100 nM, or above 100 nM In one aspect, the present invention provides a method of using a disclosed phenothiazine compound, wherein the compound binds to Calmodulin and inhibit Calmodulin activity.

In some embodiments, phenothiazine compounds of the present invention (e.g., a compound of formula (I), (Ia), (II), (III), (IIIa), (IV), (V), or (VI)) inhibit the activity or expression of calmodulin. The inhibition of calmodulin by a phenothiazine compound as disclosed herein (e.g., a compound of formula (I), (Ia), (II), (III), (IIIa), (IV), (V), or (VI)), or an analogue or derivative thereof, can be assessed by one of ordinary skill in the art using assays well known in the art. A number of assays are available for measuring calmodulin activity of certain compounds, for example, those described in Agre et al., Association between human erythrocyte calmodulin and the cytoplasmic surface of human erythrocyte membrane, J Biol Chem. 1983 May 25;258(10):6258-65; Itoh et al., The binding of the calcium channel blocker, bepridil, to calmodulin, Biochem Pharmacol. 1986; 35(2):217-20; Kahn et al., Calmodulin regulates L-selectin adhesion molecule expression and function through a protease-dependent mechanism, Cell. 1998 Mar. 20; 92(6):809-18; Roberson et al., Gonadotropin-releasing hormone induction of extracellular-signal regulated kinase is blocked by inhibition of calmodulin, Mol Endocrinol. 2005 September;19(9):2412-23; and U.S. Pat. No. 9,827,252, the content of which are hereby incorporated by reference in their entirety. More details on useful assays and techniques are given below.

For example, inhibition of calmodulin may be determined in the following in vitro assay (according to Itoh et al., Biochem. Pharm. 1986; 35:217-220), which measures the calmodulin-dependent activation of myosin light chain kinase (MLCK). Activated MLCK phosphorylates chicken gizzard myosin light chain. The rate of myosin light chain phosphorylation is reduced when calmodulin is inhibited. To test this, the following experiment may be carried out. A reaction mixture (0.2 ml) containing 20 mM Tris-HCl pH 7.5, 0.05 mM [γ-32P] ATP (1 μCi/assay tube), 5 mM $MgCl_2$, 10 μM myosin light chain, 24 nM calmodulin, 0.1 mM $CaCl_2$), and 0.1 μg/ml MLCK (specific activity: 4.5 moles/min/mg) is incubated at 30° C. for 4 min. The reaction is terminated by addition of 1 ml of 20% trichloroacetic acid, followed by addition of 0.1 ml of bovine serum albumin (1 mg/ml) to the reaction mixture. The sample is then centrifuged for 10 min, and the pellet is resuspended in 5% trichloroacetic acid. The final pellet is dissolved in 2 ml of 1 N NaOH and the radioactivity is measured in a liquid scintillation counter. Trypsin-treated MLCK may be prepared as described in Itoh et al., J Pharmacol. Exp. Ther. 1984, 230, p737. The reaction is initiated by the addition of the ATP and is carried out in the presence of the potential inhibitors or in the presence of their control solvent. Different concentrations of the compounds may be tested and the concentration of the compound which results in 50% decrease of kinase activity is the $IC_{50}$ concentration.

In some embodiments, a method to assay a compound, e.g., a phenothiazine compound as disclosed herein (e.g., a compound of formula (I), (Ia), (II), (III), (IIIa), (IV), (V), or (VI)), for inhibition of calmodulin is a standard assay assessing cAMP levels as described in Inagaki et al., Napthalenesulfonamides as Calmodulin Antagonists and Protein Kinase Inhibitors, Mol Pharmacol. 1986; 29(6):577-81, the content of which is hereby incorporated by reference in its entirety. Alternatively, commercially available kits to measure cAMP levels can be used, for example, those available from Sigma, Cell Signaling Technologies, eEnzyme, Biovision and the like.

An alternative method to assay a compound, e.g., a phenothiazine compound as disclosed herein (e.g., a compound of formula (I), (Ia), (II), (III), (IIIa), (IV), (V), or (VI)), for inhibition of calmodulin may be the method as modified from Roberson et al., 2005 September;19(9):2412-23. This assay measures the inhibition of Gonadotropin-releasing hormone (GnRH) induced ERK phosphorylation in a gonadotrope cell model, αT3-1. αT3-1 cells are serum-starved for 2 hours and pretreated with increasing concentrations of the test compounds or their control solvent for 30 min. GnRH is then added and allowed to incubate for 60 min. Whole cell lysates are prepared and resolved by SDS-PAGE. Western blot analysis is used to determine the phosphorylation status of ERKs using a phospho-specific antibody (Cell Signaling Technologies). As a control, total ERK2 is also determined using an ERK specific antibody (Santa Cruz Biotech). Western blot fluorescence of phospho-ERK and total ERK2 is quantified. The ratio of phospho-ERK/total ERK2 is plotted against the concentrations of the test compound. The estimated concentration, at which a 50% reduction of ERK phosphorylation (relative to total ERK2) occurs, can be used as the $IC_{50}$ value for this compound.

In some embodiments, the ability of phenothiazine compounds of the present invention to inhibit calmodulin may be assessed by the test systems described in the Examples of U.S. Pat. No. 9,827,252, the content of which is hereby incorporated by reference in its entirety. Phenothiazine compounds may be assessed for their ability to rescue at least one of the morphological, hematopoietic or endothelial defects in the Rps29−/− zebrafish embryo and/or prevent p53 function and nuclear accumulation in A549 lung cancer cell line that have had RPS19 knocked down by siRNA, or reduce p21 levels or increase erythroid markers in CD34+ cells that have had RPS19 knocked down by siRNA, as compared to a reference condition without treatment with such compound.

Accordingly, the person skilled in the art is readily to determine by means and methods known in the art and described herein whether a given compound is a calmodulin inhibitor/antagonist.

In some embodiments, a phenothiazine compound as disclosed herein (e.g., a compound of formula (I), (Ia), (II), (III), (IIIa), (IV), (V), or (VI)) may inhibit or decrease the activity of calmodulin by at least about 10%, relative to the activity level in the absence of the phenothiazine compound, e.g., at least about 15%, at least about 20%, at least about 30%, at least about 40%, at least about 50%, at least about 60%, at least about 70%, at least about 80%, at least about 90%, 95%, 99% or even 100%.

The expression of calmodulin includes the amount of mRNA transcribed from a gene, e.g. CALM1 that encodes calmodulin, and/or the amount of calmodulin proteins that is obtained by translation of mRNA transcribed from a gene, e.g. CALM1. For example, a phenothiazine compound as disclosed herein (e.g., a compound of formula (I), (Ia), (II), (III), (IIIa), (IV), (V), or (VI)) may inhibit expression of calmodulin, detected at either the mRNA level or protein level, by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of the phenothiazine compound.

Additionally, ability of a phenothiazine compound to inhibit calmodulin may also be assessed by measuring a decrease in or an inhibition of biological activity of calmodulin (e.g., ability to activate myosin light chain kinase or induce GnRH-dependent ERK phosphorylation) as compared to a negative control, e.g. the experimental condition in the absence of the phenothiazine compound. Accordingly, a phenothiazine compound as disclosed herein (e.g., a compound of formula (I), (Ia), (II), (III), (IIIa), (IV), (V), or (VI)) can inhibit biological activity of calmodulin, by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of the phenothiazine compound.

In some embodiments, a phenothiazine compound of the present invention (e.g., a compound of formula (I), (Ia), (II), (III), (IIIa), (IV), (V), or (VI)) has low or no blood-brain barrier (BBB) permeability. In some embodiments, such a compound has a normal intestinal absorption. As a result, such a compound is retained in bloodstream of the subject after administration, where it can exert its action. Many membrane permeability assays are available for studying drug transport, including, but not limited to, Caco-2, MDCK, and PAMPA-BBB permeability assays. One of ordinary skill in the art may test a phenothiazine compound in any or a combination of these assays and predict brain uptake and/or oral absorption of the compound based on the results of the assays.

For example, the Caco-2 permeability assay provides a measure of the permeability of a test compound across the intestinal barrier and its potential for interactions with drug transporters (e.g., P-glycoprotein). Caco-2 is a human adenocarcinoma cell line and has been widely used as intestinal drug absorption in vitro model. The Caco-2 cells have characteristics that resemble intestinal epithelial cells such as the formation of a polarized monolayer, well-defined brush border on the apical surface and intercellular tight junctions. The method for performing a Caco-2 permeability assay is well-established in the art, for example, as described in Artursson and Karlsson et al., Biochem Biophys Res Commun. 1991 Mar. 29; 175(3):880-5; Wang et al., Mass Spectrom 2000, 35, 71-76; and reviewed in van Breemen and Li, Expert Opin Drug Metab Toxicol. 2005 August; 1(2):175-85, the content of each of which is hereby incorporated by reference in its entirety. A version of this assay is also detailed in the Examples. Alternatively, commercially available Caco-2-based assays may be used, including, for example, those provided by Sigma-Aldrich or Cyprotex.

The MDCK-MDR1 permeability assay may be used for evaluating a compound, e.g., a phenothiazine compound as described herein, for its permeability across the blood-brain barrier. MDCK-MDR1 cells originate from transfection of Madin Darby canine kidney (MDCK) cells with the MDR1 gene, the gene encoding for the efflux protein, P-glycoprotein. Thus, this assay is a useful for the identification and characterization of P-gp substrates and inhibitors. The MDCK-MDR1 assay may be performed according to the method described in Wang et al., International Journal of Pharmaceutics 288 (2005) 349-359, the content of which is hereby incorporated by reference in its entirety. A version of this assay is also detailed in the Examples. Alternatively, commercially available MDCK-MDR1 assays can be used, including, for example, those provided by Cyprotex or Creative Bioarray.

As a further alternative, a modified Parallel Artificial Membrane Permeability Assay (PAMPA), using porcine brain lipids, may be used to evaluate the BBB penetration of a phenothiazine compound. The PAMPA-BBB procedure may be carried out according to Di et al., European Journal of Medicinal Chemistry 38 (2003) 223-232. For example, a test compound may be disssolved in DMSO to make a stock solution at 5 mg/mL. A secondary stock solution (final concentration 25 mg/mL) is prepared by further diluting the stock solutions in a Universal buffer (pION Inc, Woburn, MA) at pH 7.4. 200 μL of the secondary stock solution is added to the donor wells. The filter membrane is coated with porcine brain lipids in dodecane and the acceptor well is filled with 200 mL of pH 7.4 buffer. The acceptor filter plate is placed on top of the donor plate such that the aqueous donor with test compound (bottom), artificial lipid membrane (middle) and the aqueous acceptor (top) form a "sandwich." The "sandwich" is left undisturbed for 18 hours to allow for the test compound to diffuse from the donor well through the lipid membrane and into the acceptor well. The concentration of compound in the acceptor, the donor, and the reference wells can be determined using a UV plate reader and the "effective permeability" (Pe) of the compound can be calculated. The compound may be classified by comparing their Pe values (in $10^{-6}$ cm/s) to a reference standard: a) Pe>4.0: high BBB permeation; b) Pe<2.0: low BBB permeation; or c) Pe from 4.0 to 2.0: BBB permeation uncertain.

In some embodiments, phenothiazine compounds of the present invention (e.g., a compound of formula (I), (Ia), (II), (III), (IIIa), (IV), (V), or (VI)) can reduce the activities of p53 and/or a p53 downstream signaling molecule (e.g., p21) in cells where p53 and/or a p53 downstream signaling molecule (e.g., p21) are activated. As described above, activities of p53 and/or a p53 downstream signaling molecule (e.g., p21) are induced when mutations are present in one or more ribomsomal or related genes, such as RPS19 or RPS29.

In some embodiments, phenothiazine compounds of the present invention (e.g., a compound of formula (I), (Ia), (II), (III), (IIIa), (IV), (V), or (VI)) may rescue one or more phenotypes (e.g., morphological, hematopoietic or endothelial defects) in a subject with a ribomosomal disorder or ribosomopathy. Assays that may be used to evaluate the phenothiazine compounds for such properties include those described in the Examples of U.S. Pat. No. 9,827,252, the content of which is hereby incorporated by reference in its entirety, for example, the ability to rescue at least one of the morphological, hematopoietic or endothelial defects in the rps29 −/− zebrafish embryo and/or prevent p53 function and nuclear accumulation in A549 lung cancer cell line that have had RPS19 knocked down by siRNA, or reduce p21 levels or increase erythroid markers in CD34+ cells that have had RPS19 knocked down by siRNA.

Methods of Using Phenothiazine Compounds

In one aspect, the present invention provides methods for using phenothiazine compounds as disclosed herein (e.g., a compound of formula (I), (Ia), (II), (III), (IIIa), (IV), (V), or (VI)) for treating various disease and disorders associated with ribosomal proteins or ribosomopathies (e.g., DBA).

Provided herein, in part, is a method of using a phenothiazine compound as disclosed herein (e.g., a compound of formula (I), (Ia), (II), (III), (IIIa), (IV), (V), or (VI)) for treating a disease or disorder where calmodulin inhibition is useful for the treatment.

In some embodiments, a phenothiazine compound (e.g., a compound of formula (I), (Ia), (II), (III), (IIIa), (IV), (V), or (VI)) may be administered to a subject who has one or more mutations in one or more ribosomal proteins (e.g., RPS19), or have a decreased level of one or more ribosomal proteins (e.g., RPS19).

In some embodiments, a phenothiazine compound as disclosed herein (e.g., a compound of formula (I), (Ia), (II), (III), (IIIa), (IV), (V), or (VI)) may be used in a method of treating a subject with a ribosomal disorder such as Diamond-Blackfan Anemia (DBA). There are a variety of types of Diamond Blackfan anemeia, for example, DBA1, DBA2, DBA3, DBA4, DBA5, DBA6, DBA7, DBA8, DBA9, DBA10, DBA11, DBA12, DBA13, DBA14, DBA15, DBA16, or DBA17.

Diagnosis of DBA is typically made through a blood count and a bone marrow biopsy. A diagnosis of DBA is made on the basis of anemia, low reticulocyte (immature red blood cells) counts, and diminished erythroid precursors in bone marrow. Features that support a diagnosis of DBA include the presence of congenital abnormalities, macrocytosis, elevated fetal hemoglobin, and elevated adenosine deaminase levels in red blood cells. Most patients are diagnosed in the first two years of life. However, some mildly affected individuals only receive attention after a more severely affected family member is identified.

In some cases, genetic testing may be conducted to aid in diagnosis of DBA. Genetic testing is conducted through a blood test, which typically analyzes the white blood cells. Therefore, even if a DBA patient has recently had a red blood cell transfusion, the patient's blood still contains the patient's own white blood cell, which can be tested. Approximately 65% of DBA patients have a single mutation in a gene encoding a ribosomal protein (e.g., RPS19, RPL5, RPL11, RPL35a, RPS26, RPS24, RPS17, RPS7, and RPS10). About 20-25% of DBA patients may be identified with a genetic test for mutations in the RPS19 gene. Approximately 10-25% of DBA cases have a family history of disease, and most pedigrees suggest an autosomal dominant mode of inheritance.

Accordingly, in some embodiments, the phenothiazine compounds as disclosed herein (e.g., a compound of formula (I), (Ia), (II), (III), (IIIa), (IV), (V), or (VI)) may be used in a method of treating a subject that has a mutation in ribosomal protein 19 (RPS19). The phenotype of DBA patients indicates a hematological stem cell defect specifically affecting the erythroid progenitor population. The RPS19 protein is involved in the production of ribosomes. Disease features may be related to the nature of RPS19 mutations. The disease is characterized by dominant inheritance, and therefore arises due to a partial loss of RPS19 protein function.

In other embodiments, the phenothiazine compounds as disclosed herein (e.g., a compound of formula (I), (Ia), (II), (III), (IIIa), (IV), (V), or (VI)) may be used in a method of treating a subject with a mutation in ribosomal protein from at least one of, but not limited to RPS19, RPS24, RPS17, RPL35A, RPL5, RPL11, RPS7, RPS10, RPS26, RPL26, RPL15, RPS29, TSR2, RPS28, RPL27, and RPS27. For example, a mutation or variant in RPS19 causes DBA1, and a mutation or variant in RPS24 causes DBA3, a mutation or variant in RPS17 causes DBA4, a mutation or variant in RPS34A causes DBA5, a mutation or variant in RPL5 causes DBA6, a mutation or variant in RPL11 causes DBA7, a mutation or variant in RPS7 causes DBA8, a mutation or variant in RPS10 causes DBA9, a mutation or variant in RPS26 causes DBA10, a mutation or variant in RPL26 causes DBA11, a mutation or variant in RPL15 causes DBA12, a mutation or variant in RPS29 causes DBA13, a mutation or variant in TSR2 causes DBA14, a mutation or variant in RPS28 causes DBA15, a mutation or variant in RPL27 causes DBA16, and a mutation or variant in RPS27 causes DBA17.

In some embodiments, a subject with a ribosomal disorder has a mutation in one or more ribosomal proteins selected from the group consisting of: RPL2A, RPL2B, RPL3, RPL4A, RPL4B, RPL7A, RPL7B, RPL10, RPL11, RPL16A, RPL17A, RPL17B, RPL18A, RPL18B, RPL19A, RPL19, RPL25, RPL29, RPL31A, RPL31B, RPL36A, RPL40A, RPS1A, RPS6A, RPS6B, RPS14A, RPS15, RPS19, RPS23B, RPS25A, RPS26B, RPS29, RPS29B, RPS31, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, and RPLP2.

In some embodiments, the method further comprises administering the phenothiazine compounds of the present invention (e.g., a compound of formula (I), (Ia), (II), (III), (IIIa), (IV), (V), or (VI)) in combination with another therapeutic agent to treat a subject with a ribosomal protein disorder, selected from the group consisting of: corticosteroids, blood transfusions and bone marrow transplants and other treatments known to persons of ordinary skill in the art. Corticosteroids can be used to treat anemia in DBA. Blood transfusions can also be used to treat severe anemia in DBA. Periods of remission may occur, during which transfusions and steroid treatments are not required. Bone marrow transplantation (BMT) can cure hematological aspects of DBA, although adverse events in transfusion patients can occur (Diamond Blackfan Anemia Foundation; Pospisilova D et al., (2007). Successful treatment of a Diamond-Blackfan anemia patient with amino acid leucine, Haematologica 92 (5): e66).

In some embodiments, phenothiazine compounds of the present invention (e.g., a compound of formula (I), (Ia), (II), (III), (IIIa), (IV), (V), or (VI)) may be used in combination with existing calmodulin inhibitors and/or calcium channel blockers, including those described herein, to treat a subject with ribosomal protein disorder. For example, a phenothiazine compound of the present invention may be used in combination with a naphthalenesulfonamide compound such as A-3, A-7, W-5, and W-7 to treat a ribosomal protein disorder.

In some embodiments, a phenothiazine compound (e.g., a compound of formula (I), (Ia), (II), (III), (IIIa), (IV), (V), or (VI)) administered to the subject increases the number of CD71+ erythroid cells in the subject and/or increases hemoglobin levels in the subject.

In one embodiment, DBA is treated or prevented by the methods and compositions of the present invention with a phenothiazine compound as disclosed herein (e.g., a compound of formula (I), (Ia), (II), (III), (IIIa), (IV), (V), or (VI)).

In another embodiment, phenothiazine compounds as disclosed herein (e.g., a compound of formula (I), (Ia), (II), (III), (IIIa), (IV), (V), or (VI)) can be used in a method of treating a subject with a ribosomal disorder such as myelodysplasia, for example, but not limited to 5q-myelodysplasia.

In some embodiments, the methods and phenothiazine compounds as disclosed herein (e.g., a compound of formula (I), (Ia), (II), (III), (IIIa), (IV), (V), or (VI)) can be used to treat a subject with a ribosomopathy such as Shwachman-Diamond syndrome, for example, where the subject has a mutation in Sbds. In some embodiments, a subject with Shwachman-Diamond syndrome has one or more symptoms selected from pancreatic insufficiency, bone marrow dysfunction, skeletal deformities.

In another embodiment, phenothiazine compounds as disclosed herein (e.g., a compound of formula (I), (Ia), (II), (III), (IIIa), (IV), (V), or (VI)) can be used in a method of treating a subject with a ribosomopathy such as Treacher-Collins Syndrome, for example, where the subject has a mutation in the TCOF1 gene.

In some embodiments, prophylactic treatments using phenothiazine compounds as disclosed herein (e.g., a compound of formula (I), (Ia), (II), (III), (IIIa), (IV), (V), or (VI)) for prevention of ribosomal disorders or ribosomopathies also fall within the scope of this invention. For example, subjects known to have a mutation in a ribosomal gene or alternatively, low expression levels of a specific ribosomal protein, can be subjected to such prophylactic treatment to prevent or delay the onset of one or more symptoms associated with the mutation in the ribosomal gene, and/or decreased levels in the ribosomal protein. In some embodiments, prophylactic treatment may be administered to subjects who had received prior treatment of a disease associated with a ribosomal protein disorder. For example, for subjects who have received corticosteroids or blood transfusions for the treatment of DBA and/or other previous treatment to stabilize their DBA can be prophylactically treated with a phenothiazine compound as disclosed herein (e.g., a compound of formula (I), (Ia), (II), (III), (IIIa), (IV), (V), or (VI)). The prophylactic treatment comprising the phenothiazine compounds as disclosed herein may completely or partially prevent a disease or the onset of one or more symptoms of a ribosomal protein disorder or ribosomopathy.

In another aspect, the present invention provides a method of treating a ribosomal disorder or ribosomopathy in a subject in need thereof, comprising administering to the subject a therapeutically effective amount of a compound provided in the present disclosure (e.g., a compound of formula (I), (II), (III), (IV), or (V)), or a compound of formula (VI):

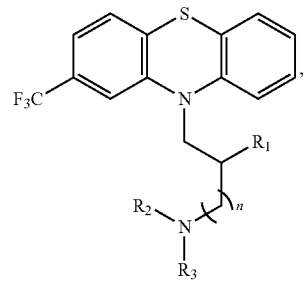
(VI)

or a pharmaceutically acceptable salt thereof, wherein
$R_1$ is selected from the group consisting of hydrogen, —OH, and $C_{1-6}$alkoxy;
n is 1 or 2;
(a) $R_2$ and $R_3$ are taken together with the nitrogen to which $R_2$ and $R_3$ are attached to form:

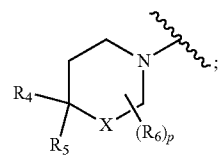

(b) $R_2$ and $R_3$ are taken together with the nitrogen to which $R_2$ and $R_3$ are attached to form:

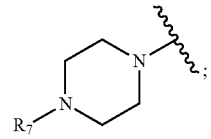

or
(c) $R_2$ is hydrogen or $C_{1-6}$alkyl optionally substituted with —OH or $C_{1-6}$alkoxy, and $R_3$

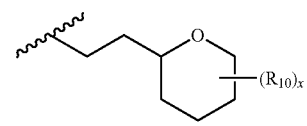

is or $C_{1-6}$alkyl substituted with —OH or $C_{1-6}$alkoxy;
wherein
$R_4$ is selected from the group consisting of hydrogen, —OH, and $C_{1-6}$alkylene-$NR_aR_b$, and $R_5$ is selected from the group consisting of hydrogen, $C_{1-6}$alkyl, and $CO_2H$; or
$R_4$ and $R_5$ are taken together with the carbon to which $R_4$ and $R_5$ are attached to form a 3-7 membered heterocyclylene; wherein the heterocyclylene may be optionally substituted with one or more oxo or $C_{1-6}$alkyl, and has one or more heteroatoms, wherein each of the heteroatoms is nitrogen;
$R_a$ is selected from the group consisting of $S(O)_2NR_cR_d$, $S(O)_2C_{1-6}$alkyl, $C(O)NR_cR_d$, $C(O)C_{1-6}$alkyl, and $C(O)O—C_{1-6}$alkyl, $R_b$, $R_c$, and $R_d$ are each independently hydrogen or $C_{1-6}$alkyl;

R$_6$ is selected from the group consisting of C$_{1-6}$alkyl, oxo, and halogen;

p is selected from the group consisting of 0, 1, 2, 3, and 4;

X is NR$_{12}$ or CH$_2$, wherein the hydrogen(s) of CH$_2$ may be substituted with R$_6$;

R$_{12}$ is hydrogen or C$_{1-6}$alkyl;

R$_7$ is selected from the group consisting of:

[structures shown]

and C$_{1-6}$alkyl optionally substituted with one or more substituents each independently selected from the group consisting of: —(O—CH$_2$CH$_2$)$_k$—OR$_{13}$, —OH, —C(O)OR$_{14}$, and C$_{1-6}$alkoxy optionally substituted with C(O)OR$_{14}$;

[structure shown]

is a monosaccharide or disaccharide;

R$_8$ is C$_{1-6}$alkyl substituted with one or more substituents each independently selected from the group consisting of —OH, C$_{1-6}$alkoxy, —C(O)NReRf, —C(O)R$_g$, —C(O)OR$_h$, S(O)$_2$C$_{1-6}$alkyl, and S(O)$_2$NR$_e$R$_f$;

R$_9$ is hydrogen or C$_{1-6}$alkyl;

R$_e$, R$_f$, R$_g$, and R$_h$ are each independently hydrogen or C$_{1-6}$alkyl;

R$_{13}$ is selected from the group consisting of hydrogen, C$_{1-6}$alkyl, 3-7 membered cycloalkyl, and C$_{1-6}$alkylene-(3-7 membered cycloalkyl);

R$_{14}$ is each independently hydrogen or C$_{1-6}$alkyl;

y is selected from the group consisting of 1, 2, and 3;

r is selected from the group consisting of 1, 2, and 3;

k is an integer selected from 1 to 10;

R$_{10}$ is each independently selected from the group consisting of C$_{1-6}$alkyl, C$_{1-6}$alkylene-OH, —OH, C$_{1-6}$alkoxy, and C$_{1-6}$alkylene-C$_{1-6}$alkoxy; and x is selected from the group consisting of 0, 1, 2, 3, and 4;

wherein, the compound is not a compound of:

[structure shown]

[structure shown]

or a pharmaceutically acceptable salt thereof.

In some embodiments of formula (VI), R$_1$ is hydrogen.

In some embodiments of formula (VI), R$_1$ is OH.

In some embodiments of formula (VI), n is 1.

In some embodiments of formula (VI), R$_2$ and R$_3$ are taken together to form

[structure shown]

In some embodiments of formula (VI), R$_2$ and R$_3$ are taken together to form:

[structure shown]

In some embodiments of formula (VI), R$_2$ is hydrogen or C$_{1-6}$alkyl optionally substituted with —OH or C$_{1-6}$alkoxy, and R$_3$ is

[structure shown]

or C$_{1-6}$alkyl substituted with —OH or C$_{1-6}$alkoxy.

In some embodiments of formula (VI), R$_2$ is C$_{1-6}$alkyl substituted with —OH and R$_3$ is C$_{1-6}$alkyl substituted with —OH.

In some embodiments of formula (VI), R$_2$ is —CH$_2$CH$_2$—OH and R$_3$ is —CH$_2$CH$_2$—OH.

In some embodiments of formula (VI), R$_7$ is

[structure shown]

In some embodiments of formula (VI), $R_7$ is

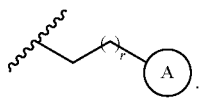

In some embodiments of formula (VI),

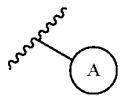

is a monosaccharide.

In some embodiments of formula (VI), is

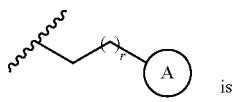 is

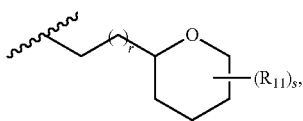

wherein
r is selected from the group consisting of 1, 2, and 3;
$R_{11}$ is selected from the group consisting of $C_{1-6}$alky, $C_{1-6}$alkylene-$OR_{15}$, —$OR_{16}$, and —$NR_{17}R_{18}$;
$R_{15}$ and $R_{16}$ are independently selected from the group consisting of hydrogen, $C_{1-6}$alkyl, $C_{2-6}$alkenyl, $C_{2-6}$alkynyl, phenyl, benzyl, and $C_{3-7}$cycloalkyl;
$R_{17}$ and $R_{18}$ are independently hydrogen or $C_{1-6}$alkyl; and
s is selected from the group consisting of 0, 1, 2, 3, and 4.

In another aspect, the present invention provides a method of treating a ribosomal disorder or ribosomopathy in a subject in need thereof, comprising administering to the subject an effective amount of a disclosed pharmaceutical composition (e.g., a pharmaceutical composition comprising a compound of formula (I), (Ia), (II), (III), (IIIa), (IV), (V), or (VI)).

In another aspect, provided herein is a method of inhibiting Calmodulin to treat a disease or disorder in a subject in need thereof, the method comprising administering to the subject a therapeutically effective amount of a disclosed phenothiazine compound (e.g., a compound of formula (I), (Ia), (II), (III), (IIIa), (IV), (V), or (VI)).

In some embodiments, the compound does not accumulate in the brain of the subject.

In some embodiments, the disease or disorder is selected from the group consisting of: ribosomal disorder or ribosomopathy (e.g., DBA), gastrointestinal disease (e.g., travelers' diarrhea, secretory diarrhea), cardiovascular diseases (e.g., structural heart disease), neurodegenerative diseases (e.g., Alzheimer's disease), and autoimmune disorders (e.g., autoimmune encephalomyelitis and lupus-like disease).

In some embodiments, the disease or disorder is DBA.

In some embodiments, the disease or disorder is travelers' diarrhea.

In some embodiments, the disease or disorder is secretory diarrhea.

In some embodiments, the disease or disorder is structural heart disease.

In some embodiments, the disease or disorder is Alzheimer's disease.

In some embodiments, the disease or disorder is autoimmune encephalomyelitis.

In some embodiments, the disease or disorder is lupus-like disease.

In some embodiments, the compound is selected from the group consisting of:

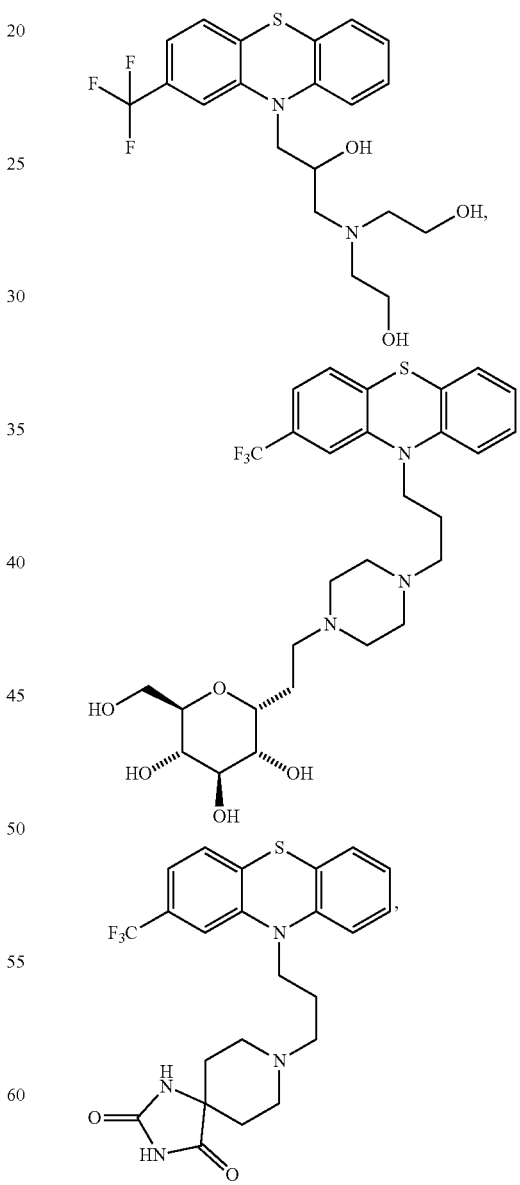

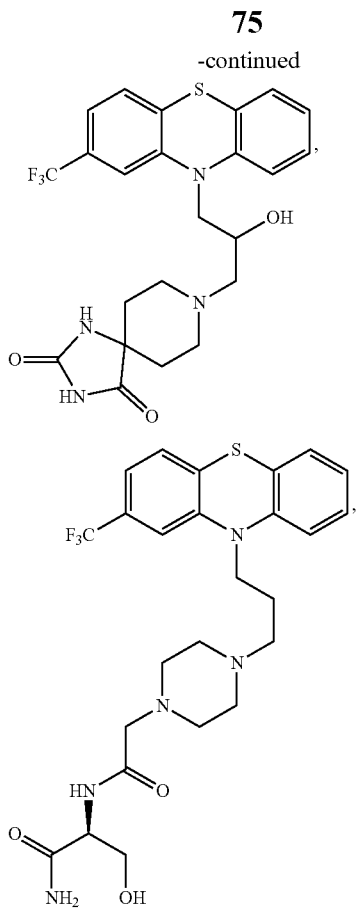

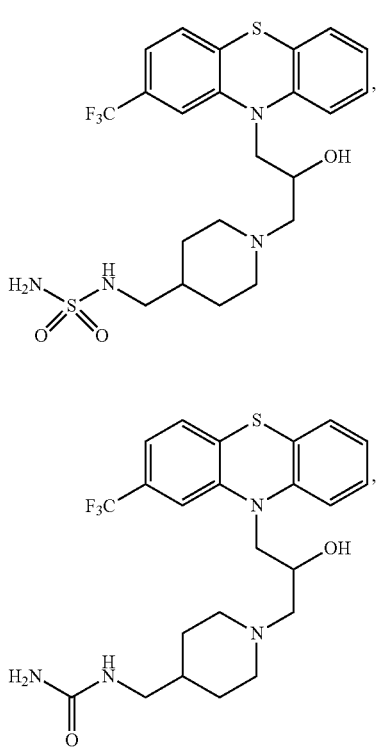

or a pharmaceutically acceptable salt thereof.

Selection of Subjects for Administration with a Pharmaceutical Composition Comprising a Phenothiazine Compound In some embodiments, a subject amenable or suitable for treatment with a composition comprising a phenothiazine compound as disclosed herein (e.g., a compound of formula (I), (Ia), (II), (III), (IIIa), (IV), (V), or (VI)) can be selected based on decreased levels of hematopoietic cells and decreased flk1 expression in CD34+ cells, as compared to normal reference levels of hematapoeitc cells and flk1 expression level from a normal subject. Additionally, a subject amenable or suitable for treatment with a composition comprising a phenothiazine compound as disclosed herein (e.g., a compound of formula (I), (Ia), (II), (III), (IIIa), (IV), (V), or (VI)) can be selected based on increased levels of p21 expression in CD34+ cells as compared to a control reference p21 expression level. In some embodiments, a subject amenable or suitable for treatment with a composition comprising a phenothiazine compound as disclosed herein (e.g., a compound of formula (I), (Ia), (II), (III), (IIIa), (IV), (V), or (VI)) can be selected based on decreased CD71+ expression and decreased glycophorin A (GPA) expression in CD34+ cells as compared to a normal reference CD71+ and GPA expression level, e.g., in a sample from a normal subject not having a ribosomal disorder or ribosomopathy. In some embodiments, the normal reference levels are the based on the level of hematopoetic cells, flk1 expression, CD71+ expression, GPA expression, p21 expression levels in a sample from a normal subject not having a ribosomal disorder or ribosomopathy, or a control cell line, or cells from a normal tissue sample, where in the tissue sample is a biological tissue sample from a tissue matched, and species matched and age matched biological sample.

In some embodiments, the levels of flk1 expression, CD71+ expression, GPA expression, and p21 expression levels are measured in a biological sample comprising hematopoietic cells or erythroid cells or erythroid differentiated cells. In some embodiments, a biological sample obtained from the subject comprises cancer cells, and may be s serum plasma, blood or tissue sample. In alternative embodiments, the biological sample includes, for example blood, plasma, serum, urine, spinal fluid, plural fluid, nipple aspirates, lymph fluid, external secretions of the skin, respiratory, internal and genitoururinary tracts, bile, tears, sweat, saliva, organs, milk cells and primary ascite cells, biopsy tissue sample, an in vitro or ex vivo cultivated biopsy tissue sample.

III. Pharmaceutical Compositions and Formulations

Pharmaceutical Compositions

According to the present invention the compositions may be prepared as pharmaceutical compositions. As used herein the term "pharmaceutical composition" refers to compositions comprising at least one active ingredient (e.g., a phenothiazine compound) and optionally one or more pharmaceutically acceptable excipients. In some embodiments, a pharmaceutical composition of the invention comprises a therapeutically effective amount of at least one phenothiazine compound as disclosed herein (e.g., a compound of formula (I), (Ia), (II), (III), (IIIa), (IV), (V), or (VI)). In some embodiments, a phenothiazine compound is, for example, but not limited to, any one of those listed in Table 1, or an analog or derivative thereof.

As disclosed herein, a pharmaceutical composition comprising an effective amount of at least one phenothiazine compound as described herein (e.g., a compound of formula (I), (Ia), (II), (III), (IIIa), (IV), (V), or (VI)) may be administered to a subject for the therapeutic treatment or prevention (e.g. prophylactic treatment) of ribosomal diseases and disorders or ribosomopathies. In some embodiments, pharmaceutical compositions of the present invention may be used for treatment of ribosomal diseases and disorders or ribosomopathies, such as DBA, myelodysplasia, 5q-myelodysplasia, Shwachman-Diamond syndrome, and Treacher-Collins Syndrome.

In some embodiments, a pharmaceutical composition comprising at least one phenothiazine compound as described herein (e.g., a compound of formula (I), (Ia), (II), (III), (IIIa), (IV), (V), or (VI)) is formulated for ribosomal diseases and/or ribosomopaties, e.g. DBA, myelodysplasia, for example, but not limited to 5q-myelodysplasia, Shwachman-Diamond syndrome and Treacher-Collins Syndrome. In one embodiment, a phenothiazine compound as disclosed herein (e.g., a compound of formula (I), (Ia), (II), (III), (IIIa), (IV), (V), or (VI)) is a derivative, analogue, prodrug, or pharmaceutically acceptable salts thereof.

According to the present invention, in therapeutic applications, an effective amount or effective dose of a pharmaceutical composition comprising a phenothiazine compound as disclosed herein (e.g., a compound of formula (I), (Ia), (II), (III), (IIIa), (IV), (V), or (VI)) may be administered to the subject with a ribosomal disease or disorder and/or ribosomopathy to inhibit or alleviate, or otherwise delay, at least one of the symptoms of such a ribosomal disease. In some embodiments, administration of an effective amount or effective dose of a pharmaceutical composition comprising a phenothiazine compound to a subject with a ribosomal disease or disorder and/or ribosomopathy can inhibit or delay progression of physical abnormalities, symptoms of anemia, and/or other symptoms associated with the ribosomal disease or ribosomopathy.

Accordingly, in prophylactic applications, a pharmaceutical composition (or medicament) comprising a phenothiazine compound as described herein (e.g., a compound of formula (I), (Ia), (II), (III), (IIIa), (IV), (V), or (VI)) may be administered to a subject susceptible to, or otherwise at risk of, a ribosomal disease or disorder and/or ribosomopathy in an effective amount to eliminate or reduce the risk or delay the onset of the disease.

The present invention provides compositions comprising a phenothiazine compound as discussed herein (e.g., a compound of formula (I), (Ia), (II), (III), (IIIa), (IV), (V), or (VI)) for practicing the therapeutic and prophylactic methods described herein. In some embodiments, a pharmaceutical composition comprising at least one phenothiazine compound as described herein (e.g., a compound of formula (I), (Ia), (II), (III), (IIIa), (IV), (V), or (VI)) further comprises a second therapeutic agent. In one embodiment, the second therapeutic agent is a corticosteroid. In one embodiment, the second therapeutic agent is another calmodulin inhibitor such as A-3 and/or W-7, as disclosed herein, or any enantiomers, prodrugs, derivatives or pharmaceutically acceptable salts thereof. In one embodiment, the second therapeutic agent is a calcium channel blocker, as disclosed herein or any enantiomers, prodrugs, derivatives or pharmaceutically acceptable salts thereof.

In some embodiments, combinations of a phenothiazine compound (e.g., a compound of formula (I), (Ia), (II), (III), (IIIa), (IV), (V), or (VI)) and another therapeutic agent can be tailored to be combined in a pharmaceutical composition, where each therapeutics can target a different symptom, a different disease or a different disorder. In further embodiments, a phenothiazine compound (e.g., a compound of formula (I), (Ia), (II), (III), (IIIa), (IV), (V), or (VI)) and another therapeutic can be mixed together in a pharmaceutical composition as disclosed herein. In other embodiments, a phenothiazine compound (e.g., a compound of formula (I), (Ia), (II), (III), (IIIa), (IV), (V), or (VI)) and another therapeutic can be present in a different formulation when combined in a pharmaceutical composition. For example, in one embodiment, a phenothiazine compound (e.g., a compound of formula (I), (Ia), (II), (III), (IIIa), (IV), (V), or (VI)) can be present in a liquid formulation, while another therapeutic can be lypholized into powder. The formulations of different active ingredients in a pharmaceutical composition as disclosed herein (e.g. a phenothiazine compound and/or another therapeutic) can be optimized accordingly by various factors such as physical and chemical properties of a drug, bioavailability, route of administration, and whether it is a sustained or a burst release for the drug. Therapeutic and prophylactic compositions of the present invention may further comprise a physiologically tolerable carrier together with a phenothiazine compound as disclosed herein (e.g., a compound of formula (I), (Ia), (II), (III), (IIIa), (IV), (V), or (VI)), or derivatives, enantiomers, prodrugs or pharmaceutically acceptable salts thereof. In additional embodiments, a phenothiazine compound and another therapeutics can employ different physiologically tolerable carriers when combined in a pharmaceutical composition of the invention as disclosed herein.

In some embodiments, bioavailability of a phenothiazine compound according to the invention (e.g., a compound of formula (I), (Ia), (II), (III), (IIIa), (IV), (V), or (VI)) may also be improved by using conjugation procedures which increase the half-life of a phenothiazine compound in a subject, for example by linking a phenothiazine compound to polyethylene glycol (PEG). PEGylation may be carried out by any known methods, for example as described in WO 92/13095, which is incorporated herein in its entirety by reference.

In some embodiments, bioavailability of a phenothiazine compound according to the invention (e.g., a compound of formula (I), (Ia), (II), (III), (IIIa), (IV), (V), or (VI)) can be also enhanced by encapsulating a phenothiazine compound in biocompatible delivery vehicles which increase the half-life of a phenothiazine compound in a subject. Exemplary biocompatible delivery vehicles include polymeric vehicles such as PEG-based vehicles, or liposome-based vehicles. In other embodiments, a phenothiazine compound may be modified by addition of a polymer, for example, using a covalent attachment.

In another aspect, biodegradable or absorbable polymers can provide extended, often localized, release of a phenothiazine compound as disclosed herein (e.g., a compound of formula (I), (Ia), (II), (III), (IIIa), (IV), (V), or (VI)). The potential benefits of an increased half-life or extended release for a therapeutic agent are clear. A potential benefit of localized release is the ability to achieve much higher localized dosages or concentrations, for greater lengths of time, relative to broader systemic administration, with the potential to avoid possible undesirable side effects that may occur with systemic administration.

Bioabsorbable polymeric matrix suitable for delivery of a phenothiazine compound as disclosed herein (e.g., a compound of formula (I), (Ia), (II), (III), (IIIa), (IV), (V), or (VI)), or variants or fragments or derivatives thereof can be selected from a variety of synthetic bioabsorbable polymers, which are described extensively in the literature. Such synthetic bioabsorbable, biocompatible polymers, which may release proteins over several weeks or months can include but not limited to, poly-hydroxy acids (e.g. polylactides, polyglycolides and their copolymers), poly anhydrides, polyorthoesters, segmented block copolymers of polyethylene glycol and polybutylene terephtalate (POLY ACTIVE™), and tyrosine derivative polymers or poly(ester-amides). Suitable bioabsorbable polymers to be used in manufacturing of drug delivery materials and implants have been described extensively in the art, for example, in U.S. Pat. Nos. 4,968,317, 5,618,563, the contents of which are incorporated herein in their entirety by reference, and in Shalaby S. (Ed.), Designed to Degrade Biomedical Polymers, Carl Hauser Verlag (1994) and in many references cited in the above publications. The particular bioabsorbable polymer that should be selected will depend upon the particular patient that is being treated.

In some embodiments, bioavailability of a phenothiazine compound according to the invention (e.g., a compound of formula (I), (Ia), (II), (III), (IIIa), (IV), (V), or (VI)) can also be enhanced by conjugating polysialic acid to a phenothiazine compound to prolong circulation time in a subject. Polysialic acid conjugates have been shown to have a longer half-life and other improved biological features (e.g., see Greco et al., Polymer Chemistry 4(5):1600-1609 (2013), the content of which is incorporated herein by reference in its entirety).

In some embodiments, a phenothiazine compound (e.g., a compound of formula (I), (Ia), (II), (III), (IIIa), (IV), (V), or (VI)) can be dissolved or dispersed as an active ingredient in the physiologically tolerable carrier to increase the half-life of a phenothiazine compound in a subject.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, rats, birds, including commercially relevant birds such as poultry, chickens, ducks, geese, and/or turkeys.

In some embodiments, compositions are administered to humans, human patients or subjects.

Formulations

Formulations of the present invention can include, without limitation, saline, liposomes, lipid nanoparticles, polymers and combinations thereof.

Formulations of the pharmaceutical compositions described herein may be prepared by any method known or hereafter developed in the art of pharmacology. In general, such preparatory methods include the step of bringing the active ingredient (e.g., a phenothiazine compound) into association with an excipient and/or one or more other accessory ingredients, and then, if necessary and/or desirable, dividing, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

In some embodiments, a pharmaceutical composition as disclosed herein comprises a phenothiazine compound (e.g., a compound of formula (I), (Ia), (II), (III), (IIIa), (IV), (V), or (VI)), in some cases together with other therapeutics, and a pharmaceutically acceptable excipient. Relative amounts of the active ingredient, a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, a pharmacological composition as disclosed herein (e.g., a compound of formula (I), (Ia), (II), (III), (IIIa), (IV), (V), or (VI)) is administered orally, and it can be administered in conventional pill or liquid form. If administered in pill form, they can be administered in conventional formulations with excipients, fillers, preservatives, and other typical ingredients used in pharmaceutical formations in pill form. Typically, the pharmacological compositions are administered in a conventional pharmaceutically acceptable formulation, typically including a carrier. Conventional pharmaceutically acceptable carriers known in the art include alcohols, e.g., ethyl alcohol, serum proteins, human serum albumin, liposomes, buffers such as phosphates, water, sterile saline or other salts, electrolytes, glycerol, hydroxymethylcellulose, propylene glycol, polyethylene glycol, polyoxyethylenesorbitan, other surface active agents, vegetable oils, and conventional anti-bacterial or anti-fungal agents, such as parabens, chlorobutanol, phenol, sorbic acid, thimerosal, and the like. A pharmaceutically-acceptable carrier within the scope of the present invention meets industry standards for sterility, isotonicity, stability, and non-pyrogenicity.

The pharmaceutically acceptable formulation may also be in pill, tablet, or lozenge form as is known in the art, and can include excipients or other ingredients for greater stability or acceptability. For the tablets, the excipients can be inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc, along with the substance for controlling the activity of calmodulin and other ingredients.

The drugs can also be administered in liquid form in conventional formulations, that can include preservatives, stabilizers, coloring, flavoring, and other generally accepted pharmaceutical ingredients. Typically, when the drugs are administered in liquid form, they will be in aqueous solution. The aqueous solution can contain buffers, and can contain alcohols such as ethyl alcohol or other pharmaceutically tolerated compounds.

Alternatively, the drugs can be administered by injection by one of several routes well known in the art. The preparation of a pharmacological composition that contains active ingredients (e.g. a phenothiazine compound) as injectable formulations is well understood in the art and need not be limited based on formulation. Typically, pharmacological compositions containing active ingredients are dissolved or dispersed to form liquid solutions or suspensions, however, solid forms suitable for solution or suspension in liquid prior to use can also be prepared. The preparation can also be emulsified or presented as a liposome composition. In some embodiments, a phenothiazine compound (e.g., a compound of formula (I), (Ia), (II), (III), (IIIa), (IV), (V), or (VI)) can be mixed with excipients which are pharmaceutically acceptable and compatible with the active ingredient and in amounts suitable for use in the therapeutic methods described herein. In addition, if desired, the composition comprising a phenothiazine compound (e.g., a compound of formula (I), (Ia), (II), (III), (IIIa), (IV), (V), or (VI)) can contain minor amounts of auxiliary substances such as wetting or emulsifying agents, pH buffering agents and the like which enhance the effectiveness of the active ingredient.

Suitable carriers for a phenothiazine compound of the invention (e.g., a compound of formula (I), (Ia), (II), (III), (IIIa), (IV), (V), or (VI)), and their formulations, are described in Remington's Pharmaceutical Sciences, 16th ed., 1980, Mack Publishing Co., edited by Oslo et al, incorporated herein by reference in its entirety. Typically an appropriate amount of a pharmaceutically acceptable salt is used in the formulation to render the formulation isotonic. Examples of the carrier include buffers such as saline, Ringer's solution and dextrose solution. Further carriers include sustained release preparations such as semipermeable matrices of solid hydrophobic polymers, which matrices are in the form of shaped articles, e.g. liposomes, films or microparticles. It will be apparent to those of skill in the art that certain carriers can be more preferable depending upon for instance the route of administration and concentration of a phenothiazine compound being administered.

Physiologically tolerable carriers (i.e. physiologically acceptable carriers) are well known in the art. Selection of pharmaceutically acceptable carriers can be accomplished by means of administration by a skilled artisan. For example, if the composition is orally administered, it can be formulated in coated tablets, liquids, caplets and so forth. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. For topical application, the carrier may be in the form of, for example, and not by way of limitation, an ointment, cream, gel, paste, foam, aerosol, suppository, pad or gelled stick. In some embodiments, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249, 1527 (1990) and Hanes, Advanced Drug Delivery Reviews 28, 97-119 (1997)). A phenothiazine compound as disclosed herein (e.g., a compound of formula (I), (Ia), (II), (III), (IIIa), (IV), (V), or (VI)) can be administered in the form of a depot injection or implant preparation which can be formulated in such a manner as to permit a sustained or pulsatile release of the active ingredient.

Additional formulations suitable for other modes of administration include intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. These compositions take the form of solutions, suspensions, tablets, pills, capsules, sustained release formulations or powders and contain 10%-95% of active ingredient, preferably 25%-70%.

A skilled artisan will be able to determine the appropriate way of administering pharmaceutical compositions comprising at least one phenothiazine compound as disclosed herein (e.g., a compound of formula (I), (Ia), (II), (III), (IIIa), (IV), (V), or (VI)) in view of the general knowledge and skill in the art.

Excipients and Diluents

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, M D, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

In some embodiments, pharmaceutical compositions of the present invention are formulated for oral administration. Excipients used in oral formulations may include, but are not limited to, pharmaceutical grades of mannitol, lactose, starch, magnesium stearate, sodium saccharine, cellulose, and magnesium carbonate.

Inactive Ingredients

In some embodiments, the pharmaceutical compositions formulations may comprise at least one inactive ingredient. As used herein, the term "inactive ingredient" refers to one or more agents that do not contribute to the activity of the active ingredient of the pharmaceutical composition included in formulations. In some embodiments, all, none or some of the inactive ingredients which may be used in the formulations of the present invention may be approved by the US Food and Drug Administration (FDA).

In one embodiment, the pharmaceutical compositions comprise at least one inactive ingredient such as, but not limited to, 1,2,6-Hexanetriol; 1,2-Dimyristoyl-Sn-Glycero-3-(Phospho-S-(1-Glycerol)); 1,2-Dimyristoyl-Sn-Glycero-3-Phosphocholine; 1,2-Dioleoyl-Sn-Glycero-3-Phosphocholine; 1,2-Dipalmitoyl-Sn-Glycero-3-(Phospho-Rac-(1-Glycerol)); 1,2-Distearoyl-Sn-Glycero-3-(Phospho-Rac-(1-Glycerol)); 1,2-Distearoyl-Sn-Glycero-3-Phosphocholine; 1-O-Tolylbiguanide; 2-Ethyl-1,6-Hexanediol; Acetic Acid; Acetic Acid, Glacial; Acetic Anhydride; Acetone; Acetone Sodium Bisulfite; Acetylated Lanolin Alcohols; Acetylated Monoglycerides; Acetylcysteine; Acetyltryptophan, DL-; Acrylates Copolymer; Acrylic Acid-Isooctyl Acrylate Copolymer; Acrylic Adhesive 788; Activated Charcoal; Adcote 72A103; Adhesive Tape; Adipic Acid; Aerotex Resin 3730; Alanine; Albumin Aggregated; Albumin Colloidal; Albumin Human; Alcohol; Alcohol, Dehydrated; Alcohol, Denatured; Alcohol, Diluted; Alfadex; Alginic Acid; Alkyl Ammonium Sulfonic Acid Betaine; Alkyl Aryl Sodium Sulfonate; Allantoin; Allyl .Alpha.-Ionone; Almond Oil; Alpha-Terpineol; Alpha-Tocopherol; Alpha-Tocopherol Acetate, Dl-; Alpha-Tocopherol, Dl-; Aluminum Acetate; Aluminum Chlorhydroxy Allantoinate; Aluminum Hydroxide; Aluminum Hydroxide-Sucrose, Hydrated; Aluminum Hydroxide Gel; Aluminum Hydroxide Gel F 500; Aluminum Hydroxide Gel F 5000; Aluminum Monostearate; Aluminum Oxide; Aluminum Polyester; Aluminum Silicate; Aluminum Starch Octenylsuccinate; Aluminum Stearate; Aluminum Subacetate; Aluminum Sulfate Anhydrous; Amerchol C; Amerchol-Cab; Aminomethylpropanol; Ammonia; Ammonia Solution; Ammonia Solution, Strong; Ammonium Acetate; Ammonium Hydroxide; Ammonium Lauryl Sulfate; Ammonium Nonoxynol-4 Sulfate; Ammonium Salt Of C-12-C-15 Linear Primary Alcohol Ethoxylate; Ammonium Sulfate; Ammonyx; Amphoteric-2; Amphoteric-9; Anethole; Anhydrous Citric Acid; Anhydrous Dextrose; Anhydrous Lactose; Anhydrous Trisodium Citrate; Aniseed Oil; Anoxid Sbn; Antifoam; Antipyrine; Apaflurane; Apricot Kernel Oil Peg-6 Esters; Aquaphor; Arginine; Arlacel; Ascorbic Acid; Ascorbyl Palmitate; Aspartic Acid; Balsam Peru; Barium Sulfate; Beeswax; Beeswax, Synthetic; Beheneth-10; Bentonite; Benzalkonium Chloride; Benzenesulfonic Acid; Benzethonium Chloride; Benzododecinium Bromide; Benzoic Acid; Benzyl Alcohol; Benzyl Benzoate; Benzyl Chloride; Betadex; Bibapcitide; Bismuth Subgallate; Boric Acid; Brocrinat; Butane; Butyl Alcohol; Butyl Ester Of Vinyl Methyl Ether/Maleic Anhydride Copolymer (125000 Mw); Butyl Stearate; Butylated Hydroxyanisole; Butylated Hydroxytoluene; Butylene Glycol; Butylparaben; Butyric Acid; $C_{20-40}$ Pareth-24; Caffeine; Calcium; Calcium Carbonate; Calcium Chloride; Calcium Gluceptate; Calcium Hydroxide; Calcium Lactate; Calcobutrol; Caldiamide Sodium; Caloxetate Trisodium; Calteridol Calcium; Canada Balsam; Caprylic/Capric Triglyceride; Caprylic/Capric/Stearic Triglyceride; Captan; Captisol; Caramel; Carbomer 1342; Carbomer 1382; Carbomer 934; Carbomer 934p; Carbomer 940; Carbomer 941; Carbomer 980; Carbomer 981; Carbomer Homopolymer Type B (Allyl Pentaerythritol Crosslinked); Carbomer Homopolymer Type C (Allyl Pentaerythritol Crosslinked); Carbon Dioxide; Carboxy Vinyl Copolymer; Carboxymethylcellulose; Carboxymethylcellulose Sodium; Carboxypolymethylene; Carrageenan; Carrageenan Salt; Castor Oil; Cedar Leaf Oil; Cellulose; Cellulose, Microcrystalline; Cerasynt-Se; Ceresin; Ceteareth-12; Ceteareth-15; Ceteareth-30; Cetearyl Alcohol/Ceteareth-20; Cetearyl Ethylhexanoate; Ceteth-10; Ceteth-2; Ceteth-20; Ceteth-23; Cetostearyl Alcohol; Cetrimonium Chloride; Cetyl Alcohol; Cetyl Esters Wax; Cetyl Palmitate; Cetylpyridinium Chloride; Chlorobutanol; Chlorobutanol Hemihydrate; Chlorobutanol, Anhydrous; Chlorocresol; Chloroxylenol; Cholesterol; Choleth; Choleth-24; Citrate; Citric Acid; Citric Acid Monohydrate; Citric Acid, Hydrous; Cocamide Ether Sulfate; Cocamine Oxide; Coco Betaine; Coco Diethanolamide; Coco Monoethanolamide; Cocoa Butter; Coco-Glycerides; Coconut Oil; Coconut Oil, Hydrogenated; Coconut Oil/Palm Kernel Oil Glycerides, Hydrogenated; Cocoyl Caprylocaprate; *Cola Nitida* Seed Extract; Collagen; Coloring Suspension; Corn Oil; Cottonseed Oil; Cream Base; Creatine; Creatinine; Cresol; Croscarmellose Sodium; Crospovidone; Cupric Sulfate; Cupric Sulfate Anhydrous; Cyclomethicone; Cyclomethicone/Dimethicone Copolyol; Cysteine; Cysteine Hydrochloride; Cysteine Hydrochloride Anhydrous; Cysteine, Dl-; D&C Red No. 28; D&C Red No. 33; D&C Red No. 36; D&C Red No. 39; D&C Yellow No. 10; Dalfampridine; Daubert 1-5 Pestr (Matte) 164z; Decyl Methyl Sulfoxide; Dehydag Wax Sx; Dehydroacetic Acid; Dehymuls E; Denatonium Benzoate; Deoxycholic Acid; Dextran; Dextran 40; Dextrin; Dextrose; Dextrose Monohydrate; Dextrose Solution; Diatrizoic Acid; Diazolidinyl Urea; Dichlorobenzyl Alcohol; Dichlorodifluoromethane; Dichlorotetrafluoroethane; Diethanolamine; Diethyl Pyrocarbonate; Diethyl Sebacate; Diethylene Glycol Monoethyl Ether; Diethylhexyl Phthalate; Dihydroxyaluminum Aminoacetate; Diisopropanolamine; Diisopropyl Adipate; Diisopropyl Dilinoleate; Dimethicone 350; Dimethicone Copolyol; Dimethicone Mdx4-4210; Dimethicone Medical Fluid 360; Dimethyl Isosorbide; Dimethyl Sulfoxide; Dimethylaminoethyl Methacrylate-Butyl Methacrylate-Methyl Methacrylate Copolymer; Dimethyldioctadecylammonium Bentonite; Dimethylsiloxane/Methylvinylsiloxane Copolymer; Dinoseb Ammonium Salt; Dipalmitoylphosphatidylglycerol, Dl-; Dipropylene Glycol; Disodium Cocoamphodiacetate; Disodium Laureth Sulfosuccinate; Disodium Lauryl Sulfosuccinate; Disodium Sulfosalicylate; Disofenin; Divinylbenzene Styrene Copolymer; Dmdm Hydantoin; Docosanol; Docusate Sodium; Duro-Tak 280-2516; Duro-Tak 387-2516; Duro-Tak 80-1196; Duro-Tak 87-2070; Duro-Tak 87-2194; Duro-Tak 87-2287; Duro-Tak 87-2296; Duro-Tak 87-2888; Duro-Tak 87-2979; Edetate Calcium Disodium; Edetate Disodium; Edetate Disodium Anhydrous; Edetate Sodium; Edetic Acid; Egg Phospholipids; Entsufon; Entsufon Sodium; Epilactose; Epitetracycline Hydrochloride; Essence Bouquet 9200; Ethanolamine Hydrochloride; Ethyl Acetate; Ethyl Oleate; Ethylcelluloses; Ethylene Glycol; Ethylene Vinyl Acetate Copolymer; Ethylenediamine; Ethylenediamine Dihydrochloride; Ethylene-Propylene Copolymer; Ethylene-Vinyl Acetate Copolymer (28% Vinyl Acetate); Ethylene-Vinyl Acetate Copolymer (9% Vinylacetate); Ethylhexyl Hydroxystearate; Ethylparaben; Eucalyptol; Exametazime; Fat, Edible; Fat, Hard; Fatty Acid Esters; Fatty Acid Pentaerythriol Ester; Fatty Acids; Fatty Alcohol Citrate; Fatty Alcohols; Fd&C Blue No. 1; Fd&C Green No. 3; Fd&C Red No. 4; Fd&C Red No. 40; Fd&C Yellow No. 10 (Delisted); Fd&C Yellow No. 5; Fd&C Yellow No. 6; Ferric Chloride; Ferric Oxide; Flavor 89-186; Flavor 89-259; Flavor Df-119; Flavor Df-1530; Flavor Enhancer; Flavor Fig. 827118; Flavor Raspberry Pfc-8407; Flavor Rhodia Pharmaceutical No. Rf 451; Fluorochlorohydrocarbons; Formaldehyde; Formaldehyde Solution; Fractionated Coconut Oil; Fragrance 3949-5; Fragrance 520a; Fragrance 6.007; Fragrance 91-122; Fragrance 9128-Y; Fragrance 93498g; Fragrance Balsam Pine No. 5124; Fragrance Bouquet 10328; Fragrance Chemoderm 6401-B; Fragrance Chemoderm 6411; Fragrance Cream No. 73457; Fragrance Cs-28197; Fragrance Felton 066m; Fragrance Firmenich 47373; Fragrance Givaudan Ess 9090/1c; Fragrance H-6540; Fragrance Herbal 10396; Fragrance Nj-1085; Fragrance P O F1-147; Fragrance Pa 52805; Fragrance Pera Derm D; Fragrance Rbd-9819; Fragrance Shaw Mudge U-7776; Fragrance Tf 044078; Fragrance Ungerer Honeysuckle K 2771; Fragrance Ungerer N5195; Fructose; Gadolinium Oxide; Galactose; Gamma Cyclodextrin; Gelatin; Gelatin, Crosslinked; Gelfoam Sponge; Gellan Gum (Low Acyl); Gelva 737; Gentisic Acid; Gentisic Acid Ethanolamide; Gluceptate Sodium; Gluceptate Sodium Dihydrate; Gluconolactone; Glucuronic Acid; Glutamic Acid, Dl-; Glutathione; Glycerin; Glycerol Ester Of Hydrogenated Rosin; Glyceryl Citrate; Glyceryl Isostearate; Glyceryl Laurate; Glyceryl Monostearate; Glyceryl Oleate; Glyceryl Oleate/Propylene Glycol; Glyceryl Palmitate; Glyceryl Ricinoleate; Glyceryl Stearate; Glyceryl Stearate-Laureth-23; Glyceryl Stearate/Peg Stearate; Glyceryl Stearate/Peg-100 Stearate; Glyceryl Stearate/Peg-40 Stearate; Glyceryl Stearate-Stearamidoethyl Diethylamine; Glyceryl Trioleate; Glycine; Glycine Hydrochloride; Glycol Distearate; Glycol Stearate; Guanidine Hydrochloride; Guar Gum; Hair Conditioner (18n195-1m); Heptane; Hetastarch; Hexylene Glycol; High Density Polyethylene; Histidine; Human Albumin Microspheres; Hyaluronate Sodium; Hydrocarbon; Hydrocarbon Gel, Plasticized; Hydrochloric Acid; Hydrochloric Acid, Diluted; Hydrocortisone; Hydrogel Polymer; Hydrogen Peroxide; Hydrogenated Castor Oil; Hydrogenated Palm Oil; Hydrogenated Palm/Palm Kernel Oil Peg-6 Esters; Hydrogenated Polybutene 635-690; Hydroxide Ion; Hydroxyethyl Cellulose; Hydroxyethylpiperazine Ethane Sulfonic Acid; Hydroxymethyl Cellulose; Hydroxyoctacosanyl Hydroxystearate; Hydroxypropyl Cellulose; Hydroxypropyl Methylcellulose 2906; Hydroxypropyl-Beta-cyclodextrin; Hypromellose 2208 (15000 Mpa.S); Hypromellose 2910 (15000 Mpa.S); Hypromelloses; Imidurea; Iodine; Iodoxamic Acid; Iofetamine Hydrochloride; Irish Moss Extract; Isobutane; Isoceteth-20; Isoleucine; Isooctyl Acrylate; Isopropyl Alcohol; Isopropyl Isostearate; Isopropyl Myristate; Isopropyl Myristate-Myristyl Alcohol; Isopropyl Palmitate; Isopropyl Stearate; Isostearic Acid; Isostearyl Alcohol; Isotonic Sodium Chloride Solution; Jelene; Kaolin; Kathon Cg; Kathon Cg II; Lactate; Lactic Acid; Lactic Acid, Dl-; Lactic Acid, L-; Lactobionic Acid; Lactose; Lactose Monohydrate; Lactose, Hydrous; Laneth; Lanolin; Lanolin Alcohol-Mineral Oil; Lanolin Alcohols; Lanolin Anhydrous; Lanolin Cholesterols; Lanolin Nonionic Derivatives; Lanolin, Ethoxylated; Lanolin, Hydrogenated; Lauralkonium Chloride; Lauramine Oxide; Laurdimonium Hydrolyzed Animal Collagen; Laureth Sulfate; Laureth-2; Laureth-23; Laureth-4; Lauric Diethanolamide; Lauric Myristic Diethanolamide; Lauroyl Sarcosine; Lauryl Lactate; Lauryl Sulfate; *Lavandula Angustifolia* Flowering Top; Lecithin; Lecithin Unbleached; Lecithin, Egg; Lecithin, Hydrogenated; Lecithin, Hydrogenated Soy; Lecithin, Soybean; Lemon Oil; Leucine; Levulinic Acid; Lidofenin; Light Mineral Oil; Light Mineral Oil (85 Ssu); Limonene, (+/−)-; Lipocol Sc-15; Lysine; Lysine Acetate; Lysine Monohydrate; Magnesium Aluminum Silicate; Magnesium Aluminum Silicate Hydrate; Magnesium Chloride; Magnesium Nitrate; Magnesium Stearate; Maleic Acid; Mannitol; Maprofix; Mebrofenin; Medical Adhesive Modified S-15; Medical Antiform A-F Emulsion; Medronate Disodium; Medronic Acid; Meglumine; Menthol; Metacresol; Metaphosphoric Acid; Methanesulfonic Acid; Methionine; Methyl Alcohol; Methyl Gluceth-10; Methyl Gluceth-20; Methyl Gluceth-20 Sesquistearate; Methyl Glucose Sesquistearate; Methyl Laurate; Methyl Pyrrolidone; Methyl Salicylate; Methyl Stearate; Methylboronic Acid; Methylcellulose (4000 Mpa.S); Methylcelluloses; Methylchloroisothiazolinone; Methylene Blue; Methylisothiazolinone; Methylparaben; Microcrystalline Wax; Mineral Oil; Mono and Diglyceride; Monostearyl Citrate; Monothioglycerol; Multisterol Extract; Myristyl Alcohol; Myristyl Lactate; Myristyl-.Gamma.-Picolinium Chloride; N-(Carbamoyl-Methoxy Peg-40)-1,2-Distearoyl-Cephalin Sodium; N,N-Dimethylacetamide; Niacinamide; Nioxime; Nitric Acid; Nitrogen; Nonoxynol Iodine; Nonoxynol-15; Nonoxynol-9; Norflurane; Oatmeal; Octadecene-1/Maleic Acid Copolymer; Octanoic Acid; Octisalate; Octoxynol-1; Octoxynol-40; Octoxynol-9; Octyldodecanol; Octylphenol Polymethylene; Oleic Acid; Oleth-10/Oleth-5; Oleth-2; Oleth-20; Oleyl Alcohol; Oleyl Oleate; Olive Oil; Oxidronate Disodium; Oxyquinoline; Palm Kernel Oil; Palmitamine Oxide; Parabens; Paraffin; Paraffin, White Soft; Parfum Creme 45/3; Peanut Oil; Peanut Oil, Refined; Pectin; Peg 6-32 Stearate/Glycol Stearate; Peg Vegetable Oil; Peg-100 Stearate; Peg-12 Glyceryl Laurate; Peg-120 Glyceryl Stearate; Peg-120 Methyl Glucose Dioleate; Peg-15 Cocamine; Peg-150 Distearate; Peg-2 Stearate; Peg-20 Sorbitan Isostearate; Peg-22 Methyl Ether/Dodecyl Glycol Copolymer; Peg-25 Propylene Glycol Stearate; Peg-4 Dilaurate; Peg-4 Laurate; Peg-40 Castor Oil; Peg-40 Sorbitan Diisostearate; Peg-45/Dodecyl Glycol Copolymer; Peg-5 Oleate; Peg-50 Stearate; Peg-54 Hydrogenated Castor Oil; Peg-6 Isostearate; Peg-60 Castor Oil; Peg-60 Hydrogenated Castor Oil; Peg-7 Methyl Ether; Peg-75 Lanolin; Peg-8 Laurate; Peg-8 Stearate; Pegoxol 7 Stearate; Pentadecalactone; Pentaerythritol Cocoate; Pentasodium Pentetate; Pentetate Calcium Trisodium; Pentetic Acid; Peppermint Oil; Perflutren; Perfume 25677; Perfume Bouquet; Perfume E-1991; Perfume Gd 5604; Perfume Tana 90/42 Scba; Perfume W-1952-1; Petrolatum; Petrolatum, White; Petroleum Distillates; Phenol; Phenol, Liquefied; Phenonip; Phenoxyethanol; Phenylalanine; Phenylethyl Alcohol; Phenylmercuric Acetate; Phenylmercuric Nitrate; Phosphatidyl Glycerol, Egg; Phospholipid; Phospholipid, Egg; Phospholipon 90g; Phosphoric Acid; Pine Needle Oil (*Pinus Sylvestris*); Piperazine Hexahydrate; Plastibase-50w; Polacrilin; Polidronium Chloride; Poloxamer 124; Poloxamer 181; Poloxamer 182; Poloxamer 188; Poloxamer 237; Poloxamer 407; Poly(Bis(P-Carboxyphenoxy)Propane Anhydride):Sebacic Acid; Poly(Dimethylsiloxane/Methylvinylsiloxane/Methylhydrogensiloxane) Dimethylvinyl Or Dimethylhydroxy Or Trimethyl Endblocked; Poly(D1-Lactic-Co-Glycolic Acid), (50:50; Poly(D1-Lactic-Co-Glycolic Acid), Ethyl Ester Terminated, (50:50; Polyacrylic Acid (250000 Mw); Polybutene (1400 Mw); Polycarbophil; Polyester; Polyester Polyamine Copolymer; Polyester Rayon; Polyethylene Glycol 1000; Polyethylene Glycol 1450; Polyethylene Glycol 1500; Polyethylene Glycol 1540; Polyethylene Glycol 200; Polyethylene Glycol 300; Polyethylene Glycol 300-1600; Polyethylene Glycol 3350; Polyethylene Glycol 400; Polyethylene Glycol 4000; Polyethylene Glycol 540; Polyethylene Glycol 600; Polyethylene Glycol 6000; Polyethylene Glycol 8000; Polyethylene Glycol 900; Polyethylene High Density Containing Ferric Oxide Black (<1%); Polyethylene Low Density Containing Barium Sulfate (20-24%); Polyethylene T; Polyethylene Terephthalates; Polyglactin; Polyglyceryl-3 Oleate; Polyglyceryl-4 Oleate; Polyhydroxyethyl Methacrylate; Polyisobutylene; Polyisobutylene (1100000 Mw); Polyisobutylene (35000 Mw); Polyisobutylene 178-236; Polyisobutylene 241-294; Polyisobutylene 35-39; Polyisobutylene Low Molecular Weight; Polyisobutylene Medium Molecular Weight; Polyisobutylene/Polybutene Adhesive; Polylactide; Polyols; Polyoxyethylene-Polyoxypropylene 1800; Polyoxyethylene Alcohols; Polyoxyethylene Fatty Acid Esters; Polyoxyethylene Propylene; Polyoxyl 20 Cetostearyl Ether; Polyoxyl 35 Castor Oil; Polyoxyl 40 Hydrogenated Castor Oil; Polyoxyl 40 Stearate; Polyoxyl 400 Stearate; Polyoxyl 6 And Polyoxyl 32 Palmitostearate; Polyoxyl Distearate; Polyoxyl Glyceryl Stearate; Polyoxyl Lanolin; Polyoxyl Palmitate; Polyoxyl Stearate; Polypropylene; Polypropylene Glycol; Polyquaternium-10; Polyquaternium-7 (70/30 Acrylamide/Dadmac; Polysiloxane; Polysorbate 20; Polysorbate 40; Polysorbate 60; Polysorbate 65; Polysorbate 80; Polyurethane; Polyvinyl Acetate; Polyvinyl Alcohol; Polyvinyl Chloride; Polyvinyl Chloride-Polyvinyl Acetate Copolymer; Polyvinylpyridine; Poppy Seed Oil; Potash; Potassium Acetate; Potassium Alum; Potassium Bicarbonate; Potassium Bisulfite; Potassium Chloride; Potassium Citrate; Potassium Hydroxide; Potassium Metabisulfite; Potassium Phosphate, Dibasic; Potassium Phosphate, Monobasic; Potassium Soap; Potassium Sorbate; Povidone Acrylate Copolymer; Povidone Hydrogel; Povidone K17; Povidone K25; Povidone K29/32; Povidone K30; Povidone K90; Povidone K90f; Povidone/Eicosene Copolymer; Povidones; Ppg-12/Smdi Copolymer; Ppg-15 Stearyl Ether; Ppg-20 Methyl Glucose Ether Distearate; Ppg-26 Oleate; Product Wat; Proline; Promulgen D; Promulgen G; Propane; Propellant A-46; Propyl Gallate; Propylene Carbonate; Propylene Glycol; Propylene Glycol Diacetate; Propylene Glycol Dicaprylate; Propylene Glycol Monolaurate; Propylene Glycol Monopalmitostearate; Propylene Glycol Palmitostearate; Propylene Glycol Ricinoleate; Propylene Glycol/Diazolidinyl Urea/Methylparaben/Propylparben; Propylparaben; Protamine Sulfate; Protein Hydrolysate; Pvm/Ma Copolymer; Quaternium-15; Quaternium-15 Cis-Form; Quaternium-52; Ra-2397; Ra-3011; Saccharin; Saccharin Sodium; Saccharin Sodium Anhydrous; Safflower Oil; Sd Alcohol 3a; Sd Alcohol 40; Sd Alcohol 40-2; Sd Alcohol 40b; Sepineo P 600; Serine; Sesame Oil; Shea Butter; Silastic Brand Medical Grade Tubing; Silastic Medical Adhesive,Silicone Type A; Silica, Dental; Silicon; Silicon Dioxide; Silicon Dioxide, Colloidal; Silicone; Silicone Adhesive 4102; Silicone Adhesive 4502; Silicone Adhesive Bio-Psa Q7-4201; Silicone Adhesive Bio-Psa Q7-4301; Silicone Emulsion; Silicone/Polyester Film Strip; Simethicone; Simethicone Emulsion; Sipon Ls 20np; Soda Ash; Sodium Acetate; Sodium Acetate Anhydrous; Sodium Alkyl Sulfate; Sodium Ascorbate; Sodium Benzoate; Sodium Bicarbonate; Sodium Bisulfate; Sodium Bisulfite; Sodium Borate; Sodium Borate Decahydrate; Sodium Carbonate; Sodium Carbonate Decahydrate; Sodium Carbonate Monohydrate; Sodium Cetostearyl Sulfate; Sodium Chlorate; Sodium Chloride; Sodium Chloride Injection; Sodium Chloride Injection, Bacteriostatic; Sodium Cholesteryl Sulfate; Sodium Citrate; Sodium Cocoyl Sarcosinate; Sodium Desoxycholate; Sodium Dithionite; Sodium Dodecylbenzenesulfonate; Sodium Formaldehyde Sulfoxylate; Sodium Gluconate; Sodium Hydroxide; Sodium Hypochlorite; Sodium Iodide; Sodium Lactate; Sodium Lactate, L-; Sodium Laureth-2 Sulfate; Sodium Laureth-3 Sulfate; Sodium Laureth-5 Sulfate; Sodium Lauroyl Sarcosinate; Sodium Lauryl Sulfate; Sodium Lauryl Sulfoacetate; Sodium Metabisulfite; Sodium Nitrate; Sodium Phosphate; Sodium Phosphate Dihydrate; Sodium Phosphate, Dibasic; Sodium Phosphate, Dibasic, Anhydrous; Sodium Phosphate, Dibasic, Dihydrate; Sodium Phosphate, Dibasic, Dodecahydrate; Sodium Phosphate, Dibasic, Heptahydrate; Sodium Phosphate, Monobasic; Sodium Phosphate, Monobasic, Anhydrous; Sodium Phosphate, Monobasic, Dihydrate; Sodium Phosphate, Monobasic, Monohydrate; Sodium Polyacrylate (2500000 Mw); Sodium Pyrophosphate; Sodium Pyrrolidone Carboxylate; Sodium Starch Glycolate; Sodium Succinate Hexahydrate; Sodium Sulfate; Sodium Sulfate Anhydrous; Sodium Sulfate Decahydrate; Sodium Sulfite; Sodium Sulfosuccinated Undecyclenic Monoalkylolamide; Sodium Tartrate; Sodium Thioglycolate; Sodium Thiomalate; Sodium Thiosulfate; Sodium Thiosulfate Anhydrous; Sodium Trimetaphosphate; Sodium Xylenesulfonate; Somay 44; Sorbic Acid; Sorbitan; Sorbitan Isostearate; Sorbitan Monolaurate; Sorbitan Monooleate; Sorbitan Monopalmitate; Sorbitan Monostearate; Sorbitan Sesquioleate; Sorbitan Trioleate; Sorbitan Tristearate; Sorbitol; Sorbitol Solution; Soybean Flour; Soybean Oil; Spearmint Oil; Spermaceti; Squalane; Stabilized Oxychloro Complex; Stannous 2-Ethylhexanoate; Stannous Chloride; Stannous Chloride Anhydrous; Stannous Fluoride; Stannous Tartrate; Starch; Starch 1500, Pregelatinized; Starch, Corn; Stearalkonium Chloride; Stearalkonium Hectorite/Propylene Carbonate; Stearamidoethyl Diethylamine; Steareth-10; Steareth-100; Steareth-2; Steareth-20; Steareth-21; Steareth-40; Stearic Acid; Stearic Diethanolamide; Stearoxytrimethylsilane; Steartrimonium Hydrolyzed Animal Collagen; Stearyl Alcohol; Sterile Water For Inhalation; Styrene/Isoprene/Styrene Block Copolymer; Succimer; Succinic Acid; Sucralose; Sucrose; Sucrose Distearate; Sucrose Polyesters; Sulfacetamide Sodium; Sulfobutylether .Beta.-Cyclodextrin; Sulfur Dioxide; Sulfuric Acid; Sulfurous Acid; Surfactol Qs; Tagatose, D-; Talc; Tall Oil; Tallow Glycerides; Tartaric Acid; Tartaric Acid, Dl-; Tenox; Tenox-2; Tert-Butyl Alcohol; Tert-Butyl Hydroperoxide; Tert-Butylhydroquinone; Tetrakis(2-Methoxyisobutylisocyanide)Copper(I) Tetrafluoroborate; Tetrapropyl Orthosilicate;

Tetrofosmin; Theophylline; Thimerosal; Threonine; Thymol; Tin; Titanium Dioxide; Tocopherol; Tocophersolan; Total parenteral nutrition, lipid emulsion; Triacetin; Tricaprylin; Trichloromonofluoromethane; Trideceth-10; Triethanolamine Lauryl Sulfate; Trifluoroacetic Acid; Triglycerides, Medium Chain; Trihydroxystearin; Trilaneth-4 Phosphate; Trilaureth-4 Phosphate; Trisodium Citrate Dihydrate; Trisodium Hedta; Triton 720; Triton X-200; Trolamine; Tromantadine; Tromethamine (TRIS); Tryptophan; Tyloxapol; Tyrosine; Undecylenic Acid; Union 76 Amsco-Res 6038; Urea; Valine; Vegetable Oil; Vegetable Oil Glyceride, Hydrogenated; Vegetable Oil, Hydrogenated; Versetamide; Viscarin; Viscose/Cotton; Vitamin E; Wax, Emulsifying; Wecobee Fs; White Ceresin Wax; White Wax; Xanthan Gum; Zinc; Zinc Acetate; Zinc Carbonate; Zinc Chloride; and Zinc Oxide.

Pharmaceutical composition formulations disclosed herein may include cations or anions. In one embodiment, the formulations include metal cations such as, but not limited to, $Zn^{2+}$, $Ca^{2+}$, $Cu^{2+}$, $Mn^{2+}$, $Mg^{2+}$ and combinations thereof. As a non-limiting example, formulations may include polymers and complexes with a metal cation (See e.g., U.S. Pat. Nos. 6,265,389 and 6,555,525, each of which is herein incorporated by reference in its entirety).

Formulations of the invention may also include one or more pharmaceutically acceptable salts. Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids.

Solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

IV. Administration and Dosing

Administration

According to the present invention, the pharmaceutical composition containing one or more phenothiazine compounds disclosed herein (e.g., a compound of formula (I), (Ia), (II), (III), (IIIa), (IV), (V), or (VI)) can be administered to an individual by any route known to persons skilled in the art. The routes of administration include enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electroosmosis, endocervical, endosinusial, endotracheal, extracorporeal, hemodialysis, infiltration, interstitial, intraabdominal, intra-amniotic, intra-articular, intrabiliary, intrabronchial, intrabursal, intracartilaginous (within a cartilage), intracaudal (within the cauda equine), intracisternal (within the cisterna *magna* cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis and spinal. Any other therapeutically efficacious route of administration can be used, for example absorption through epithelial or endothelial tissues or systemic administration. In addition, a phenothiazine compound according to the invention (e.g., a compound of formula (I), (Ia), (II), (III), (IIIa), (IV), (V), or (VI)) can be administered together with other components of biologically active agents such as pharmaceutically acceptable surfactants, excipients, carriers, diluents and vehicles.

The phrases "systemic administration," "administered systemically", "peripheral administration" and "administered peripherally" refer to the administration other than directly into a target site, tissue, or organ, such that it enters, instead, the subject's circulatory system and, thus, is subject to metabolism and other like processes.

In some embodiments, the route of administration is oral administration, via either gastrointestinal tract or oral mucosa absorption. For oral administration, the pharmaceutical compositions may be formulated as, for example, a tablet, powder, suspension tablet, chewable tablet, effervescent tablet, capsule, effervescent powder, pellets, granules, or a liquid solution or suspension. In some embodiments, a pharmaceutical composition comprising a phenothiazine compound as disclosed herein (e.g., a compound of formula (I), (Ia), (II), (III), (IIIa), (IV), (V), or (VI)) can be administered as a formulation adapted not to pass through the blood-brain barrier.

Alternative modes of administration include injection. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebro spinal, and intrasternal injection and infusion. In some examples, the route is intravenous.

For parenteral (e.g. intravenous, subcutaneous, intramuscular) administration, a phenothiazine compound can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

In some embodiments, the route of administration is administration by subcutaneous route. Intramuscular administration is another alternative route of administration. Intramuscular injection is most typically performed in the arm or leg muscles. In some embodiments, a pharmaceutical composition comprising a phenothiazine compound can be administered as a formulation adapted for systemic delivery. In some embodiments, the compositions can be administered as a formulation adapted for delivery to specific organs, for example but not limited to the liver.

In further embodiments, topical administration may be used. Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein.

Alternatively, in some embodiments, a pharmaceutical composition can be incorporated in a gel, sponge, or other permeable matrix (e.g., formed as pellets or a disk) and placed in proximity to the liver endothelium for sustained, local release. The composition comprising a phenothiazine compound can be administered in a single dose or in multiple doses, which are administered at different times.

The exact route of administration as well as the optimal dosages can be determined by standard clinical techniques for each specific case, mainly based on the nature of the disease or disorder and on the stage of this disease. Preferably, the medicament according to the present invention is applied locally or systemically, in particular, orally, intravenously, parenterally, epicutaneously, subcutaneously, intrapulmonarily by inhalation or bronchoalveolar lavage, intramuscularily, intracranially, locally into intervertebral discs or other connective tissues.

In various embodiments, a phenothiazine compound as disclosed herein (e.g., a compound of formula (I), (Ia), (II), (III), (IIIa), (IV), (V), or (VI)) can optionally be administered in combination with other agents that are at least partly effective in treatment of ribosomal protein diseases and disorders, such as corticosteroids, blood transfusions, bone marrow transplants and the like. In other embodiments, a phenothiazine compound of the invention can be administered prior to, concurrently, or after administration of another therapeutics that targets another disease or disorder, or a different symptom.

In various embodiments, a phenothiazine compound (e.g., a compound of formula (I), (Ia), (II), (III), (IIIa), (IV), (V), or (VI)) can be a pro-drug, where it is activated by a second agent in vivo. Accordingly, in such embodiments, administration of such the second agent which activates the pro-drug of the phenothiazine compound into its active form can be administered the same time, concurrent with, or prior to, or after the administration of the pharmaceutical composition comprising a phenothiazine compound as disclosed herein (e.g., a compound of formula (I), (Ia), (II), (III), (IIIa), (IV), (V), or (VI)).

Dosing

The term "effective amount" refers to the amount of the active ingredient needed to prevent or alleviate at least one or more signs or symptoms of a specific disease and/or condition, and relates to a sufficient amount of a composition to provide the desired effect. The term "therapeutically effective amount" therefore refers to an amount of active ingredient or a composition comprising the active ingredient that is sufficient to promote a particular effect when administered to a typical subject. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

Work from Dr. Leonard Zon and colleagues has shown that a phenothiazine compound reverses the vascular deformations and morphology in vivo of rps29 −/− zebrafish embryos at a concentration of between 5-50 μg/mL, and that TFP restored the percentage of CD71+ cells in an erythroid cell population at between 5-20 μM in vitro (U.S. Pat. No. 9,827,252). Accordingly, in some embodiments, a phenothiazine compound as disclosed herein (e.g., a compound of formula (I), (Ia), (II), (III), (IIIa), (IV), (V), or (VI)) can be administered to a subject according to the methods as disclosed herein in an effective dose to increase the levels of CD71+ cells in an erythroid cell population obtained from the subject by at least about 1%, at least about 2%, at least about 3%, at least about 5%, at least about 10%, at least about 15%, least about 20%, at least about 30%, at least about 40%, at least about 50%, or more than 50%, as compared to in the absence of the phenothiazine compound.

Work from Dr. Leonard Zon and colleagues also shows the phenothiazine compound A-3, at between 1-50 μM decreased the levels of p21 in CD34+ cells present in an erythroid cell population in vitro (U.S. Pat. No. 9,827,252) Accordingly, in another embodiment, a phenothiazine compound as disclosed herein (e.g., a compound of formula (I), (Ia), (II), (III), (IIIa), (IV), (V), or (VI)) can be administered to a subject according to the methods as disclosed herein in an effective dose to decrease the levels of p21 expression in CD34+ cells present in an erythroid cell population obtained from the subject by at least about 1%, at least about 2%, at least about 3%, at least about 5%, at least about 10%, at least about 15%, least about 20%, at least about 30%, at least about 40%, at least about 50%, at least about 60%, at least about 70%, at least about 80%, at least about 90%, at least about 95%, at least about 98%, at least about 99%, or more than 99%, as compared to in the absence of the phenothiazine compound.

One can use any immunoassay to determine the level of p21 expression in CD34+ cells in a biological sample, such as ELISA or immunohistochemical methods which are commonly known in the art and are encompassed for use in the present invention. A treatment administered to a subject is considered to be effective if the level of expression of p21 in CD34+ cells present in a biological sample obtained from the subject is decreased by at least about 20%, at least about 30%, at least about 40%, at least about 50%, at least about 60%, at least about 70%, at least about 80%, at least about 90%, at least about 95%, at least about 98%, about 99% or about 100% as compared to a reference level, or in the absence of the phenothiazine compound. In such embodiments, the reference level is the measurement of p21 in CD34+ cells present in a biological sample obtained from the subject at a previous time point, e.g., who has not been administered the phenothiazine compounds. Based on the outcome of treatment, the dosage and frequency of administration using the methods and compositions as disclosed herein can be adjusted accordingly by one of skill in the art.

Generally, effective dosages and dosing schedules can be adjusted based on, for example, the outcome of the treatment such as whether the subject has reduced symptoms of anemia, and/or whether at least one of the symptoms associated with the ribosomal protein disorder, such as elevated p21 and/or p53 levels, is reduced. In accordance with the teachings provided herein, the effectiveness of the treatment can be monitored by obtaining a biological sample from a subject, e.g. a blood serum sample, and determining the level of biomarkers for DBA, such as percentage of CD71+ cells in an erythroid cell population and/or level of p21 in CD34+ cells, using methods well known in the art and the diagnostic methods as described herein.

The pharmaceutical, therapeutical, or prophylactic compositions of the present invention (e.g., a pharmaceutical composition comprising a compound of formula (I), (Ia), (II), (III), (IIIa), (IV), (V), or (VI) and a pharmaceutically acceptable salt thereof) may be administered to a subject using any amount and any route of administration effective for preventing, treating, or managing ribosomal protein diseases and disorders. The exact amount required will vary from subject to subject, depending on the species, age, weight and general condition of the subject, the severity of the disease, the particular composition, its mode of administration, its mode of activity, and the like. The subject may be a human, a mammal, or an animal. The interrelationship of dosages for animals of various sizes and species and humans based on mg/m$^3$ of surface area is described by E. J. Freireich et al., Quantitative Comparison of Toxicity of Anticancer Agents in Mouse, Rat, Hamster, Dog, Monkey and Man, Cancer Chemother. Rep. 50: 219-244 (1966). Compositions in accordance with the invention are typically formulated in unit dosage form for ease of administration and uniformity of dosage. It will be understood, however, that the total daily usage of the compositions of the present invention may be decided by the attending physician within the scope of sound medical judgment. The specific therapeutically effective, or prophylactically effective dose level for any particular individual will depend upon a variety of factors including the disorder being treated and the severity of the disorder; the activity of the specific payload employed; the specific composition employed; the age, body weight, general health, sex and diet of the patient; the time of administration, and route of administration; the duration of the treatment; drugs used in combination or coincidental with the active ingredient; and like factors well known in the medical arts.

In certain embodiments, pharmaceutical compositions in accordance with the present invention (e.g., a pharmaceutical composition comprising a compound of formula (I), (Ia), (II), (III), (IIIa), (IV), (V), or (VI) and a pharmaceutically acceptable salt thereof) may be administered at dosage levels sufficient to deliver from about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight of the subject per day, one or more times a day, to obtain the desired therapeutic, or prophylactic, effect. In some embodiments, a phenothiazine compound can be used in an amount of about 0.1 to 1000 g/kg of body weight or about 1 to 100 μg/kg of body weight or about 10 to 50 μg/kg of body weight. In some embodiments, a phenothiazine compound can be administered at a concentration of about 0.001 mg/ml or 0.1 mg/ml or a higher concentration of 0.1 mg/ml. In alternative embodiments, a pharmaceutical composition comprises at least one phenothiazine compound at a concentration of about 0.01 μM to 300 μM, or about 0.1 μM to 150 μM, or about 1 μM to 50 μM, or about 1 μM to 25 μM. The dosage may vary within this range depending upon the dosage form employed and the route of administration utilized.

The pharmaceutical compositions (e.g., a pharmaceutical composition comprising a compound of formula (I), (Ia), (II), (III), (IIIa), (IV), (V), or (VI) and a pharmaceutically acceptable salt thereof) may be administered from once per day to up to at least five times per day, depending on the severity of the disease, the total dosage to be administered, and the judgment of the treating physician. In some cases, the pharmaceutical compositions need not be administered on a daily basis, but can be administered every other day, every third day, or on other such schedules. The desired dosage of the composition present invention may be delivered only once, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of "single unit dose" or total daily dose into two or more doses, e.g., two or more administrations of the "single unit dose". As used herein, a "single unit dose" is a dose of any therapeutic administered in one dose/at one time/single route/single point of contact, i.e., single administration event.

In some embodiments, the daily dose administered to a subject in a form of a bolus composition comprising a phenothiazine compound can be given in a single dose, in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease. It is also within the skill of the art to start doses at levels lower than required to achieve the desired therapeutic effect and to gradually increase the dosage until the desired effect is achieved.

Depending on routes of administration and the dosage form employed, one of ordinary skill in the art can determine and adjust an effective dosage of a phenothiazine compound disclosed herein to a subject such as a human subject accordingly, by determining pharmacokinetics and bioavailability of a phenothiazine compound and analyzing dose-response relationship specific to a phenothiazine compound in animal models such as a mouse.

Toxicity and therapeutic efficacy can be determined by standard pharmaceutical procedures in cell cultures or experimental animals, e.g., for determining the $LD_{50}$ (i.e., the dose lethal to 50% of the population) and $ED_{50}$ (i.e., the dose therapeutically effective in 50% of the population). The dose ratio between toxic and therapeutic effects is the therapeutic index and it can be expressed as the ratio $LD_{50}/ED_{50}$. Compositions that exhibit large therapeutic indices, are preferred.

The data obtained from the cell culture assays and animal studies can be used in formulating a range of dosage for use in humans. The therapeutically effective dose can be determined by one of ordinary skill in the art, e.g. using cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture by methods described herein. An effective dose of a phenothiazine compound can be determined in an animal model by measuring the levels of hemoglobin over the course of treatment with a phenothiazine compound as compared to no treatment. In some embodiments, a dosage comprising a phenothiazine compound is considered to be effective if the dosage increases hemoglobin levels, red cell number, and/or reduces expression of p21 in CD34+ cells by at least about 15%, at least about 20%, at least about 30%, at least about 40%, at least about 50%, at least about 60%, at least about 70%, at least about 80%, at least about 90%, 95%, 99% or even 100%, as compared to a control (e.g. in the absence of a phenothiazine compound). In some embodiments, a therapeutically effective amount of a phenothiazine compound administered to a subject is dependent upon factors known to a person skilled in the art, including bioactivity and bioavailability of a phenothiazine compound (e.g. half-life and stability of a phenothiazine compound in the body), chemical properties of a phenothiazine compound (e.g. molecular weight, hydrophobicity and solubility); route and frequency of administration, time of administration (e.g. before or after a meal), and the like. Further, it will be understood that the specific dose of the pharmaceutical composition comprising a phenothiazine compound as disclosed herein (e.g., a compound of formula (I), (Ia), (II), (III), (IIIa), (IV), (V), or (VI)) to provide the therapeutic or prophylactic benefits can depend on a variety of factors including physical condition of the subject (e.g. age, gender, weight), medical history of the subject (e.g. medications being taken, other diseases or disorders) and clinical condition of the subject (e.g. health condition, stage of the disease). The precise dose of a pharmaceutical composition comprising a phenothiazine compound (e.g., a pharmaceutical composition comprising a compound of formula (I), (Ia), (II), (III), (IIIa), (IV), (V), or (VI) and a pharmaceutically acceptable salt thereof) can be determined by methods known to a skilled artisan such as pharmacologists and physicians.

In therapeutic applications, a relatively high dosage in relatively short intervals is sometimes required until progression of the disease is reduced or terminated, or until the subject shows partial or complete amelioration of symptoms of disease. Thereafter, the subject can be administered a prophylactic regime. For example, subjects with DBA can be treated with a phenothiazine compound as disclosed herein (e.g., a compound of formula (I), (Ia), (II), (III), (IIIa), (IV), (V), or (VI)) at an effective dose in a therapeutic regimen accordingly to decrease the p21 levels and or p53 levels back to a normal level, and then be administered a maintenance dose, e.g., prophylactically. In some embodiments, a phenothiazine compound as disclosed herein (e.g., a compound of formula (I), (Ia), (II), (III), (IIIa), (IV), (V), or (VI)) can be administered to subjects prior to, concurrently with, or sequentially to treatment with a corticosteroid, and/or when the subject us undergoing an adjuvant therapy, such as a blood transfusion and/or bone marrow transplant. In some embodiments for example, a DBA subject which is selected for other therapeutic procedures or surgeries, such as blood transfusions and/or bone marrow transplant, can be subjected to a treatment with a phenothiazine compound as disclosed herein (e.g., a compound of formula (I), (Ia), (II), (III), (IIIa), (IV), (V), or (VI)). For example, a pharmaceutical composition of the invention can be administered prior to, during or after therapeutic procedures. Route of administration can vary with therapeutic procedures or surgeries and can be determined by a skilled artisan. In yet another embodiment, compositions and methods of the invention can be used as an adjuvant therapy.

According to the invention, a phenothiazine compound as disclosed herein (e.g., a compound of formula (I), (Ia), (II), (III), (IIIa), (IV), (V), or (VI) and a pharmaceutically acceptable salt thereof) can be administered prophylactically or therapeutically to a subject prior to, simultaneously or sequentially with other therapeutic regimens or agents (e.g., multiple drug regimens), in a therapeutically effective amount. In some embodiments, a phenothiazine compound administered concurrently with other therapeutic agents can be administered in the same or different compositions. Additional therapeutic agents or regimens include, but are not limited to, steroids, corticosteroids, blood transfusions and bone marrow transplants.

V. Kits

The present invention provides a variety of kits for conveniently and/or effectively carrying out methods of the present invention. According to the present invention, a kit may comprise at least one pharmaceutical composition comprising one or more phenothiazine compound as disclosed herein (e.g., a pharmaceutical composition comprising a compound of formula (I), (Ia), (II), (III), (IIIa), (IV), (V), or (VI) and a pharmaceutically acceptable salt thereof), and optionally reagents, instructions, and/or devices for carrying out a method as disclosed herein.

In some embodiments, a kit can optionally additionally comprise reagents or agents for measuring the level of p21 expression in a biological sample (e.g., a blood sample) from the subject to identify the efficacy of treatment with the phenothiazine compound as disclosed herein (e.g., a compound of formula (I), (Ia), (II), (III), (IIIa), (IV), (V), or (VI)). Such agents are well known in the art, and include without limitation, labeled antibodies that specifically bind to p21 protein and/or oligonucleotides specifically detect p21 mRNA and the like. In some embodiments, the labeled antibodies or oligonucleotides may be fluorescently labeled, or labeled with magnetic beads and the like. In further embodiments, a kit as disclosed herein may comprise at least one or more reagents for profiling and annotating a biological sample (e.g., a blood sample) from the subject in a high through-put assay.

In some embodiments, the kit can further comprise instructions for administering a composition comprising a phenothiazine compound to a subject in need thereof, e.g., with a ribosomal protein disease or disorder, e.g., DBA and instructions for doses and the like.

In some embodiments, the kit can further comprise devices which may incorporate a phenothiazine compound of the present invention. These devices may contain a stable formulation available to be immediately delivered to a subject in need thereof, such as a human patient. The devices may be employed to deliver a phenothiazine compound of the present invention according to single, multi- or split-dosing regiments.

In addition to the above-mentioned component(s), the kit can also include informational material. The informational material can be descriptive, instructional, marketing or other material that relates to the methods described herein and/or the use of the components for the assays, methods and systems described herein.

In some embodiments, the methods and kits comprising a phenothiazine compound as disclosed herein (e.g., a compound of formula (I), (Ia), (II), (III), (IIIa), (IV), (V), or (VI)) can be performed by a service provider. For example, an investigator or physician can send the biological sample (e.g., a blood sample) from a subject to a diagnostic laboratory service provider to measure the level of p21 expression in CD34+ cells, and/or the level of CD71+ cells in an erythroid cell population present in the sample. After performing such measurements, the service provider can provide the investigator or physician a report of the efficacy of the phenothiazine compound and/or report if the subject is a suitable or amenable to be treated with a phenothiazine compound according to the methods and composition as disclosed herein (e.g., a compound of formula (I), (Ia), (II), (III), (IIIa), (IV), (V), or (VI)).

In alternative embodiments, a service provider can provide the investigator with the raw data of the levels of p21 or p53 expression in CD34+ cells, and/or the levels of CD71+ cells in an erythroid cell population present in the biological sample from the subject and leave the analysis to be performed by the investigator or physician. In some embodiments, the report is communicated or sent to the investigator via electronic means, e.g., uploaded on a secure web-site, or sent via e-mail or other electronic communication means. In some embodiments, the investigator can send the samples to the service provider via any means (e.g., via mail, express mail, etc.), or alternatively, the service provider can provide a service to collect the samples from the investigator and transport them to the diagnostic laboratories of the service provider. In some embodiments, the investigator can deposit the samples to be analyzed at the location of the service provider diagnostic laboratories. In alternative embodiments, the service provider provides a stop-by service, where the service provider send personnel to the laboratories of the investigator and also provides the kits, apparatus, and reagents for performing the assays to measure the levels of p21 expression in CD34+ cells, and/or the level of CD71+ cells in a erythroid cell population present in the biological subject from the subject as disclosed herein in the investigators laboratories, and analyses the result and provides a report to the investigator for each subject, and leaves the physician to make appropriate recommendations of treatment, and dose to administer the subject with a composition comprising a phenothiazine compound according to the methods as disclosed herein.

VI. Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Car-*

*bon Compounds* (McGraw-Hill, N Y, 1962); and Wilen, Tables of Resolving Agents and Optical Resolutions p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

The following terms are intended to have the meanings presented therewith below and are useful in understanding the description and intended scope of the present invention. When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

When a range of values is listed, it is intended to encompass each value and sub-range within the range. For example, "$C_{1-6}$alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_1$-2, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group, e.g., having 1 to 20 carbon atoms ("$C_{1-20}$alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

As used herein, "alkylene" refers to a divalent radical of an alkyl group. When a range or number of carbons is provided for a particular "alkylene," it is understood that the range or number refers to the range or number of carbons in the linear carbon divalent chain. "Alkylene" groups may be substituted or unsubstituted with one or more substituents as described herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more cycloalkyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

As used herein, "heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more cycloalkyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

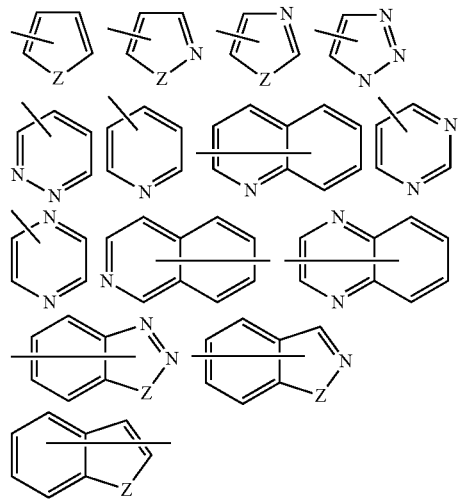

wherein each Z is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

As used herein, "cycloalkyl" refers to a radical of a non-aromatic cyclic hydrocarbon group having from 3 to 10 ring carbon atoms ("C$_{3-10}$ cycloalkyl") and zero heteroatoms in the non-aromatic ring system. In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-s}$ cycloalkyl"). In some embodiments, a cycloalkyl group has 5 to 10 ring carbon atoms ("C$_{5-10}$ cycloalkyl"). Exemplary C$_{3-6}$ cycloalkyl groups include, without limitation, cyclopropyl (C$_3$), cyclobutyl (C$_4$), cyclobutenyl (C$_4$), cyclopentyl (C), cyclopentenyl (C$_5$), cyclohexyl (C), cyclohexenyl (C), cyclohexadienyl (C), and the like. Exemplary C$_{3-8}$ cycloalkyl groups include, without limitation, the aforementioned C$_{3-6}$ cycloalkyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ cycloalkyl groups include, without limitation, the aforementioned C$_{3-8}$ cycloalkyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl or heteroaryl groups wherein the point of attachment is on the cycloalkyl ring, and in such instances, the number of carbons continue to designate the number of carbons in the carbocyclic ring system.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

As used herein, "heterocyclylene" refers to a divalent radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl").

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl; cycloalkyl, e.g., heterocyclyl; aryl, e.g., heteroaryl; and the like having from 1 to 5, and particularly from 1 to 3 heteroatoms.

As used herein, "benzyl" refers to —$CH_2C_6H_5$ substituent.

As used herein, "halo" or "halogen" refers to fluoro (F), chloro (Cl), bromo (Br) and iodo (I). In certain embodiments, the halo group is either fluoro or chloro.

As used herein, "haloalkyl" refers to an alkyl group substituted with one or more halogen atoms.

As used herein, "oxo" refers to —C═O.

As used herein, "monosaccharide" refers to a carbohydrate that is not decomposable into simpler sugars by hydrolysis. For example, a "monosaccharide" may be a glucose, fructose, or ribose.

As used herein, "disaccharide" refers to a carbohydrate formed by two monosaccharides.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(═O)R$^{aa}$, —C(═O)N(R$^{cc}$)$_2$, —CO$_2$R$^{aa}$, —SO$_2$R$^{aa}$, —C(═NR$^{bb}$)R—, —C(═NR$^{cc}$)OR$^{aa}$, —C(═NR$^{cc}$)N(R$^{cc}$)$_2$, —SO$_2$N(R$^{cc}$)$_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$—$P(=O)_2R$, —$P(=O)(R^{aa})_2$, —$P(=O)_2N(R^{cc})_2$, —$P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and Claims. The invention is not intended to be limited in any manner by the above exemplary listing of substituents.

Other Definitions

As used herein, the term "analog" (or "analogue") refers to an agent that retains the same, or a substantially similar biological function (i.e., inhibition of calmodulin) and/or structure as the molecule or chemical or polypeptide it is an analogue of. Examples of analogs include peptidomimetics (a peptide analog), peptide nucleic acids (a nucleic acid analog), small and large organic or inorganic compounds, as well as derivatives and variants of a polypeptide or nucleic acid herein.

As used herein, the term "bind" refers to any physical attachment or close association, which may be permanent or temporary, between two molecules. The binding can result from, for example, hydrogen bonding, hydrophobic forces, van der Waals forces, covalent, or ionic bonding.

As used herein, the term "calmodulin inhibitor", generally refers to an agent or molecule that inhibits the activity or expression of calmodulin. In the context of this invention, the term "calmodulin inhibitor" is used as a synonym for "calmodulin antagonist."

As used herein, the term "compound(s) of the present invention" and similar terms refers to a compound provided in the present disclosure, a pharmaceutically acceptable salt, solvate, clathrate, hydrate, polymorph, prodrug, metabolite, analog or derivative thereof.

As used herein, the term "derivative" refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

As used herein, the term "inactive ingredient" refers to one or more agents that do not contribute to the activity of the active ingredient of the pharmaceutical composition included in formulations.

As used herein, the term "permeability", as used herein, refers to a measure of the ability of a compound or an agent to pass through a barrier (e.g., a membrane, a layer of cells, blood-brain barrier).

As used herein, the terms "prevent," "preventing" and "prevention" refer to the avoidance or delay in manifestation of one or more symptoms or measurable markers of a disease or disorder.

As used herein, the term "ribosomal disorder" or "ribosomal protein disorder" refers to a disease or disorder linked to a mutated and/or abnormal function of a ribosome protein.

As used herein, the term "stereoisomers" refers to isomers which differ only in configuration and/or conformation.

As used herein, the term "subject" includes human and other mammalian subjects that receive either prophylactic or therapeutic treatment. The terms "subject", "individual", and "patient" are used interchangeably herein, and refer to an animal, for example a human, to whom treatment, including prophylactic treatment, with the cells according to the present invention, is provided. The "non-human animals" of the invention include mammals such as rats, mice, rabbits, sheep, cats, dogs, cows, pigs, and non-human primates.

As used herein, the term "substantially similar," when used to define the biological activity of a derivative or analogue of a phenothiazine compound as compared to the biological activity of phenothiazine compound to which it is a derivative or analogue of, means that a particular derivative or analogue differs from the initial phenothiazine compound in chemical structure, by one or more groups or elements, including substitutions, deletions, or additions of groups of elements, the net effect of which is to retain at least some of the biological activity found in the initial calmodulin inhibitor with respect to inhibition of calmodulin activity and/or expression.

As used herein, the terms "treat," "treating" or "treatment" when used with reference to treatment of a disease or disorder, refer to the mitigation and/or elimination of one or more symptoms of the disease, and/or a reduction in the rate of onset or severity of one or more symptoms of the disease, and/or the prevention of the disease. The terms encompass both therapeutic and prophylactic treatments.

As used herein, the term "prophylactic" or "therapeutic" treatment refers to administration to a subject of one or more of the pharmaceutical compositions. If it is administered prior to clinical manifestation of the unwanted condition (e.g., disease or other unwanted state of the subject) then the treatment is prophylactic, i.e., it protects the subject against developing the unwanted condition, whereas if administered after manifestation of the unwanted condition, the treatment is therapeutic (i.e., it is intended to diminish, ameliorate or maintain the existing unwanted condition or side effects therefrom).

As used herein, the terms "up-regulate", "increase" or "activate" are all used herein to generally mean an increase by a statically significant amount, preferably an increase of at least about 10% versus control.

As used herein, the terms "lower," "reduced", "reduction" or "decrease", "down-regulate" or "inhibit" are all used herein generally to mean a decrease by a statistically significant amount, preferably a decrease of at least about 10% versus control.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

The present invention is further illustrated by the following non-limiting examples.

EXAMPLES

Compound Design and Synthesis

The objective of this study was to develop phenothiazine compounds that retain CaM antagonist activity but do not cross blood-brain barrier. A set of candidate compounds (see Table 1) were designed to increase its total polar surface area (TPSA) compared to tifluoperazine. Expansion of compound TPSA increases the probability of CNS exclusion by reducing passive permeability and increasing the chances of being actively pumped out by the efflux transporter, p-glycoprotein. Candidate compounds were synthesized at ChemPartner (Shanghai, China). Identity of the compounds was confirmed via HNMR and LCMS. Purity of the compounds measured by HPLC is higher than 95%.

General information: All evaporations were carried out in vacuo with a rotary evaporator. Analytical samples were dried in vacuo (1-5 mm Hg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

LCMS Conditions:
Column; Waters XBridge-C18 (50 mm×4.6 mm, 3.5 μm)
Mobile Phase: A: Water (0.05% TFA) B: ACN (0.05% TFA);
Gradient: B from 5% to 100% for 1.6 min and hold 100% for 1.4 min;
Flow Rate: 2 mL/min;
Column Temperature: 40° C.

LIST OF ABBREVIATION

EtOAc ethyl acetate
MeCN acetonitrile
ACN acetonitrile
TFA trifluoroacetic acid
MeOH methanol
EtOH ethanol
TsCl 4-toluenesulfonyl chloride
MsCl methanesulfonyl chloride
Et$_3$N triethylamine
DMF dimethylformamide
HATU 1-[bis(dimethylamino)methylene]-1H-1,2,3-triazolo[4,5-b]pyridinium 3-oxid hexafluorophosphate
DIPEA N,N-diisopropylethylamine
TMSOTf trimethylsilyl trifluoromethanesulfonate
NMP N-methyl-2-pyrrolidone
Boc tert-butyloxycarbonyl
PE petroleum ether
DCM dichloromethane
DMSO dimethyl sulfoxide
THF tetrahydrofuran Example 1. Synthesis of Compound MT-001 [2-(4-(3-(2-(trifluoromethyl)-10H-phenothiazin-10-yl)propyl)piperazin-1-yl)acetic acid trihydrochloride]

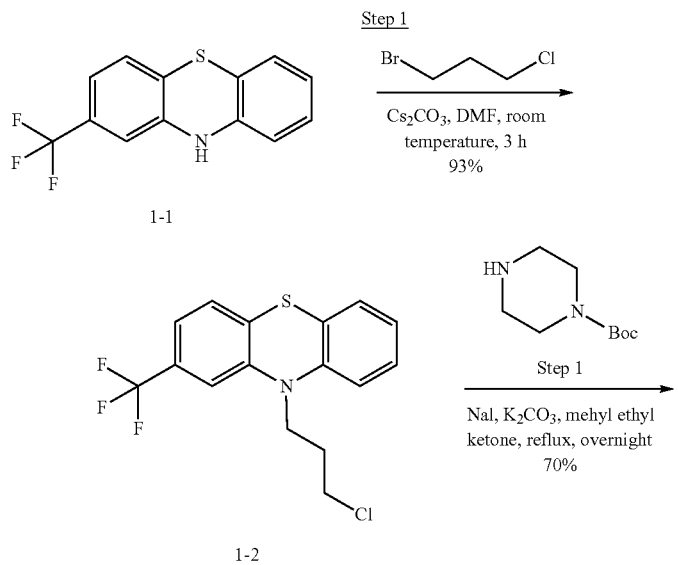

-continued
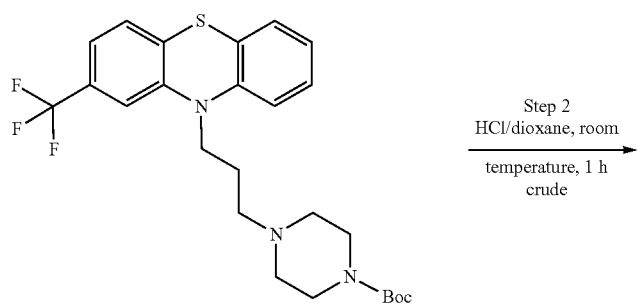
1-3
Step 2
HCl/dioxane, room
temperature, 1 h
crude
1-4
Step 3
K₂CO₃, CH₃CN, room
temperature, 3 h
83%
1-5
Step 4
HCl/dioxane, room
temperature, 6 h
54%
MT-001

A mixture of 1-2 [10-(3-chloropropyl)-2-(trifluoromethyl)-10H-phenothiazine] (see Example 19 for the synthesis of 1-2; 600 mg, 1.75 mmol), tert-butyl piperazine-1-carboxylate (488 mg, 2.62 mmol), NaI (262 mg, 1.75 mmol) and $K_2CO_3$ (482 mg, 3.49 mmol) in methyl ethyl ketone (10 mL) was refluxed overnight. After being cooled to rt, the mixture was diluted with water (20 mL) and extracted with EtOAc (60 mL×3). The combined organic layers were washed with brine (50 mL×2), dried over sodium sulfate, and concentrated to dryness. The residue was purified by column chromatography on silica gel (petrol ether: EtOAc=1:1) to provide a brown solid (600 mg, 70% yield).
LC-MS: Rt=1.87 min; ESI, m/z 494 [M+1]$^+$

Step 2 [10-(3-(piperazin-1-yl)propyl)-2-(trifluoromethyl)-10H-phenothiazine]

A mixture of 1-3 [tert-butyl 4-(3-(2-(trifluoromethyl)-10H-phenothiazin-10-yl)propyl)piperazine-1-carboxylate] (400 mg, 0.81 mmol) in 4M HCl/dioxane (5 mL) was stirred at rt for 1 h. Then the reaction mixture was concentrated to an oil which was used for next step directly.
LC-MS): Rt=1.57 min; ESI, m/z394 [M+1]$^+$.

Step 3: [tert-butyl 2-(4-(3-(2-(trifluoromethyl)-10H-phenothiazin-10-yl)propyl)piperazin-1-yl) acetate]

A mixture of 1-4 [10-(3-(piperazin-1-yl)propyl)-2-(trifluoromethyl)-10H-phenothiazine] (319 mg, 0.81 mmol), tert-butyl 2-bromoacetate (158 mg, 0.81 mmol) and $K_2CO_3$ (224 mg, 1.62 mmol) in MeCN (10 mL) was stirred at rt for 3 h. The mixture was diluted with water (20 mL) and extracted with EtOAc (50 mL×3). The combined organic layers were washed with brine (60 mL×2), dried over sodium sulfate and concentrated to dryness. The residue was purified by column chromatography on silica gel (petrol ether:EtOAc=2:1) to provide yellow oil (340 mg, 83% yield).
LC-MS: Rt=1.87 min; ESI, m/z 508 [M+1]$^+$

Step 4

A mixture of 1-5 [tert-butyl 2-(4-(3-(2-(trifluoromethyl)-10H-phenothiazin-10-yl)propyl)piperazin-1-yl) acetate] (50 mg, 0.099 mmol) in HCl/dioxane (4 N, 5 mL) was stirred at rt for 6 h and then concentrated to dryness. The residue was purified by prep-HPLC (Boston Green ODS (150 mm×30 mm, 5 mm); A=$H_2O$ (0.075% TFA) and B=$CH_3CN$; 33-63% B over 7 min) to provide a white solid (30 mg, 3HCl salt, 54% yield).
MT-001
$^1$H NMR (400 MHz, CDCl$_3$) δ 7.22-7.11 (m, 4H), 7.03 (s, 1H), 6.99-6.93 (m, 1H), 6.92-6.87 (m, 1H), 3.98 (t, J=6.4 Hz, 2H), 3.27 (s, 2H), 2.91 (s, 4H), 2.69-2.51 (m, 6H), 2.00-1.91 (m, 3H); LC-MS: Rt=2.26 min; ESI, m/z: 452 [M+1]$^+$

Example 2. Synthesis of Compound MT-002

10-(3-(piperidin-1-yl)propyl)-2-(trifluoromethyl)-10H-phenothiazine

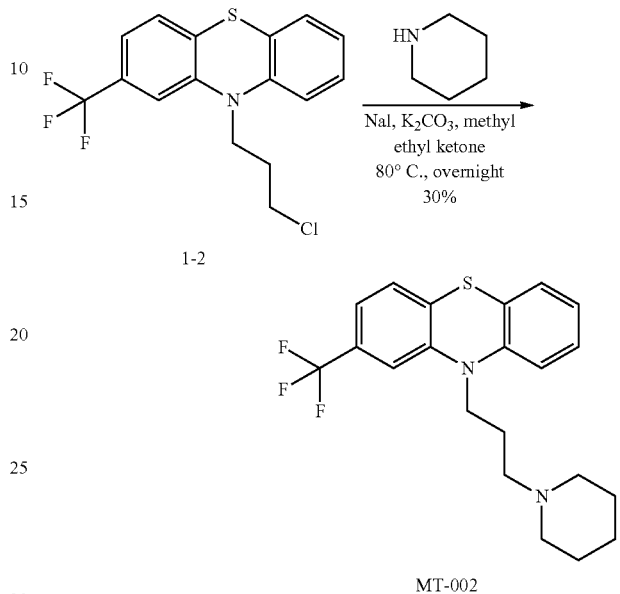

A mixture of 1-2 [10-(3-chloropropyl)-2-(trifluoromethyl)-10H-phenothiazine] (63 mg, 0.183 mmol), piperidine (18.8 mg, 0.22 mmol), $K_2CO_3$ (50 mg, 0.366 mmol) and NaI (27 mg, 0.183 mmol) in methyl ethyl ketone (5 mL) was stirred at 80° C. overnight. After cooling to rt, the mixture was diluted with water (20 mL) and extracted with EtOAc (15 mL×3). The combined organic extracts were washed with brine, dried over $Na_2SO_4$, filtered and concentrated under reduced pressure. The residue was purified by column chromatography ($CH_2Cl_2$:MeOH=20:1) to provide a faint yellow solid (21 mg, 30% yield).
MT-002
$^1$H NMR (400 MHz, CDCl$_3$) δ 7.20-7.10 (m, 4H), 7.04 (s, 1H), 6.96-6.92 (m, 2H), 3.95 (t, J=6.8 Hz, 2H), 2.48 (t, J=7.2 Hz, 2H), 2.42-2.38 (m, 4H), 2.03-1.98 (m, 2H), 1.60-1.55 (m, 2H), 1.44-1.40 (m, 2H), 1.27-1.25 (m, 2H); LC-MS: Rt=2.49 min; ESI, m/z: 393 [M+1]$^+$.

Example 3. Synthesis of Compound MT-003

3 [1-(3-(2-(trifluoromethyl)-10H-phenothiazin-10-yl)propyl)piperidin-4-ol]

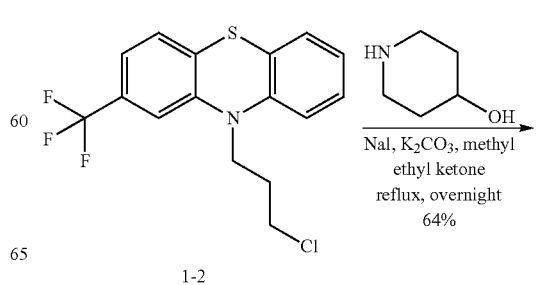

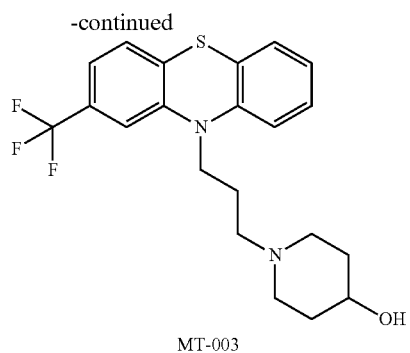

MT-003

A mixture of 1-2 [10-(3-chloropropyl)-2-(trifluoromethyl)-10H-phenothiazine] (50 mg, 0.146 mmol), piperidin-4-ol (18 mg, 0.175 mmol), K$_2$CO$_3$ (40 mg, 0.290 mmol) and NaI (22 mg, 0.145 mmol) in methyl ethyl ketone (5 mL) was stirred at 80° C. (reflux) overnight. After cooling to rt, the mixture was poured into cool water (10 mL) and extracted with EtOAc (10 mL×3). The combined organic extracts were washed with brine, dried over Na$_2$SO$_4$, filtered and concentrated under reduced pressure. The residue was purified by column chromatography on silica gel (CH$_2$Cl$_2$: MeOH=20:1) to provide a yellow solid (38 mg, 64% yield). MT-003

$^1$H NMR (400 MHz, CDCl$_3$) δ 7.20-7.11 (m, 4H), 7.04 (s, 1H), 6.97-6.91 (m, 2H), 3.96 (t, J=7.0 Hz, 2H), 3.72-3.50 (m, 1H), 2.74-2.71 (m, 2H), 2.49 (t, J=7.0 Hz, 2H), 2.16-2.13 (m, 2H), 1.99-1.91 (m, 2H), 1.89-1.84 (m, 2H), 1.63-1.60 (m, 1H), 1.57-1.51 (m, 2H); LC-MS Rt=2.30 min; ESI, m/z): 409 [M+1]$^+$ Example 4. Synthesis of Compound MT-004

4-hydroxy-1-(3-(2-(trifluoromethyl)-10H-phenothiazin-10-yl)propyl)piperidine-4-carboxylic acid

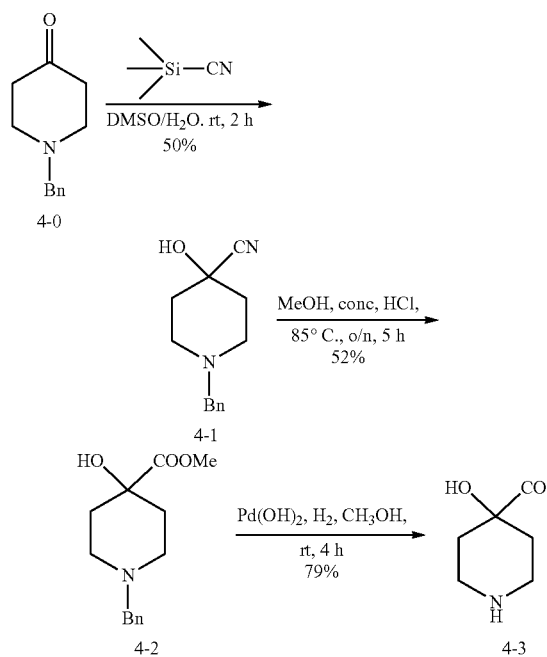

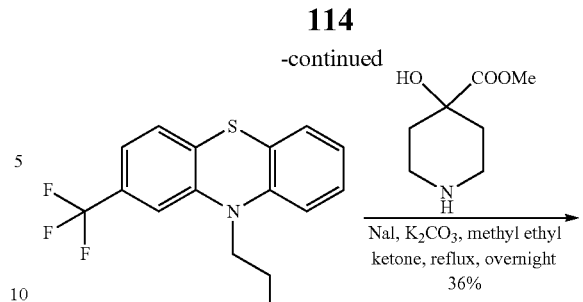

Step 1: Synthesis of 4-1 [1-benzyl-4-hydroxypiperidine-4-carbonitrile]

A mixture of 1-benzylpiperidin-4-one (1.0 g, 5.3 mmol) and trimethylsilyl cyanide (530 mg, 5.3 mmol) in water (2 mL) and DMSO (10 mL) was stirred at rt for 1 h. The mixture was diluted with water (10 mL) and extracted with EtOAc (20 mL×3). The combined organic layers were washed with brine (10 mL×2), dried over sodium sulfate, and concentrated to dryness. The residue was purified by column chromatography on silica gel (petrol ether: EtOAc=4:1) to provide a white solid (150 mg, 50% yield). LC-MS: Rt=1.13 min; ESI, m/z: 217 [M+1]$^+$ Step 2: Synthesis of 4-2 [methyl 1-benzyl-4-hydroxypiperidine-4-carboxylate]

To a solution of 4-1 [1-benzyl-4-hydroxypiperidine-4-carbonitrile] (2 g, 9.2 mmol) in MeOH (50 mL) was added under nitrogen atmosphere conc. HCl (2 mL). The reaction mixture was stirred at 85° C. for 5 h. After being cooled to rt, the mixture was diluted with water (20 mE), basified with sat. NaHCO$_3$ solution and extracted with EtOAc (10 mL×3). The combined organic layers were washed with brine (10 mL×2), dried over sodium sulfate, and concentrated to dryness. The residue was purified by column chromatography (petrol ether:EtOAc=5:1) to provide colorless oil (1.2 g, 52% yield).

LC-MS: Rt=1.12 min; ESI, m/z: 250 [M+1]+

Step 3: Synthesis of 4-3 [methyl 4-hydroxypiperidine-4-carboxylate]

To a solution of 4-2 [methyl 1-benzyl-4-hydroxypiperidine-4-carboxylate] (1 g, 4 mmol) in MeOH (10 mE), Pd(OH)$_2$/C (1.12 g, 20%) was added at rt. The reaction mixture was hydrogenated under hydrogen atmosphere at rt for 4 h. The insoluble solids in the mixture were filtered out, and then the filtrate was concentrated under reduced pressure. The residue was purified by column chromatography (petrol ether:EtOAc=4:1) to provide colorless oil (0.5 g, 79% yield).

LC-MS: Rt=0.81 min; ESI, m/z: 160 [M+1]+

Step 4: Synthesis of 4-4 [methyl 4-hydroxy-1-(3-(2-(trifluoromethyl)-10H-phenothiazin-10-yl)propyl) piperidine-4-carboxylate]

A mixture of 1-2 [10-(3-chloropropyl)-2-(trifluoromethyl)-10H-phenothiazine] (600 mg, 1.7 mmol), methyl 4-hydroxypiperidine-4-carboxylate (270 mg, 1.7 mmol), NaI (134 mg, 0.9 mmol), K$_2$CO$_3$ (703 mg, 5.1 mmol) in methyl ethyl ketone (20 mL) was stirred at 85° C. for 16 h. After being cooled to rt, the insoluble solids in the mixture were filtered out, then the filtrate was diluted with water (20 mL) and extracted with EtOAc (30 mL×3). The combined organic layers were washed with brine (10 mL×2), dried over sodium sulfate, and concentrated to dryness. The residue was purified by column chromatography on silica gel (petrol ether EtOAc=5:1) to provide a yellow solid (300 mg, 36% yield).

LC-MS: Rt=1.75 min; ESI, m/z: 467 [M+1]+

Step 5

A mixture of 4-4 [methyl 4-hydroxy-1-(3-(2-(trifluoromethyl)-10H-phenothiazin-10-yl)propyl) piperidi-ne-4-carboxylate] (200 mg, 0.43 mmol) and NaOH (35 mg, 0.86 mmol) in MeOH (10 mL) was stirred at rt under nitrogen for 3 h. The mixture was diluted with water (10 mL), then adjusted to pH=4 with diluted hydrochloric acid and extracted with EtOAc (20 mL×3). The combined organic layers were washed with brine (20 mL×2), dried over sodium sulfate, and concentrated to dryness. The residue was purified by column chromatography on silica gel (CH$_2$Cl$_2$:MeOH=10:1) to provide a white solid (27 mg, 10% yield).

MT-004

$^1$H NMR (400 MHz, CDCl$_3$) δ 7.26-7.24 (m, 1H), 7.19-7.17 (m, 3H), 7.05 (s, 1H), 6.99-6.98 (m, 1H), 6.93-6.91 (m, 1H), 4.03 (t, J=6.0 Hz, 2H), 3.16-3.13 (m, 2H), 3.05-3.04 (m, 2H), 2.92-2.73 (m, 2H), 2.50-2.41 (m, 2H), 2.41-2.30 (m, 2H), 1.42-1.53 (m, 2H); LC-MS: Rt=2.28 min; ESI, m/z: 453 [M+1]+

Example 5. Synthesis of Compound MT-005

2,2'-(3-(2-(trifluoromethyl)-10H-phenothiazin-10-yl) propylazanediyl)diethanol

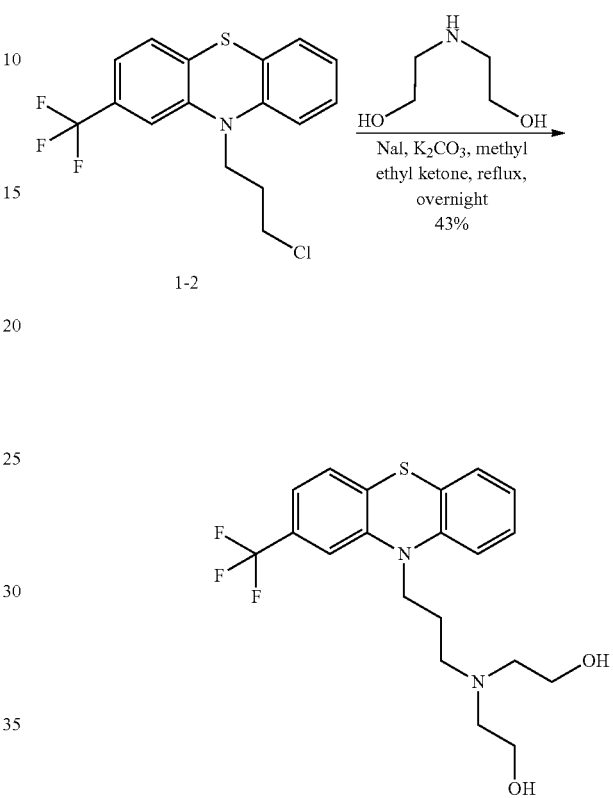

A mixture of 1-2 [10-(3-chloropropyl)-2-(trifluoromethyl)-10H-phenothiazine] (60 mg, 0.174 mmol), 2,2'-azanediyldiethanol (49 mg, 0.465 mmol), K$_2$CO$_3$ (64 mg, 0.465 mmol) and NaI (43 mg, 0.290 mmol) in methyl ethyl ketone (5 mL) was stirred at 80° C. overnight. After being cooled to rt, the mixture was diluted with water (20 mL) and extracted with EtOAc (15 mL×3). The combined organic extracts were washed with brine, dried over Na$_2$SO$_4$, filtered and concentrated under reduced pressure. The residue was purified by column chromatography (CH$_2$Cl$_2$:MeOH=20:1) to provide yellow oil (31 mg, 43% yield).

MT-005

$^1$H NMR (400 MHz, CDCl$_3$) δ 7.24-7.15 (m, 4H), 7.06 (s, 1H), 6.99-6.93 (m, 2H), 4.01 (t, J=6.4 Hz, 2H), 3.54 (t, J=5.2 Hz, 4H), 2.69 (t, J=6.8 Hz, 2H), 2.59 (t, J=5.4 Hz, 4H), 2.08-2.06 (m, 2H), 1.96-1.93 (m, 2H); LC-MS: Rt=2.24 min; ESI, m/z: 413 [M+1]+

Example 6. Synthesis of Compound MT-006

2-hydroxy-3-(4-(3-(2-(trifluoromethyl)-10H-phenothiazin-10-yl)propyl)piperazin-1-yl)propanoic acid

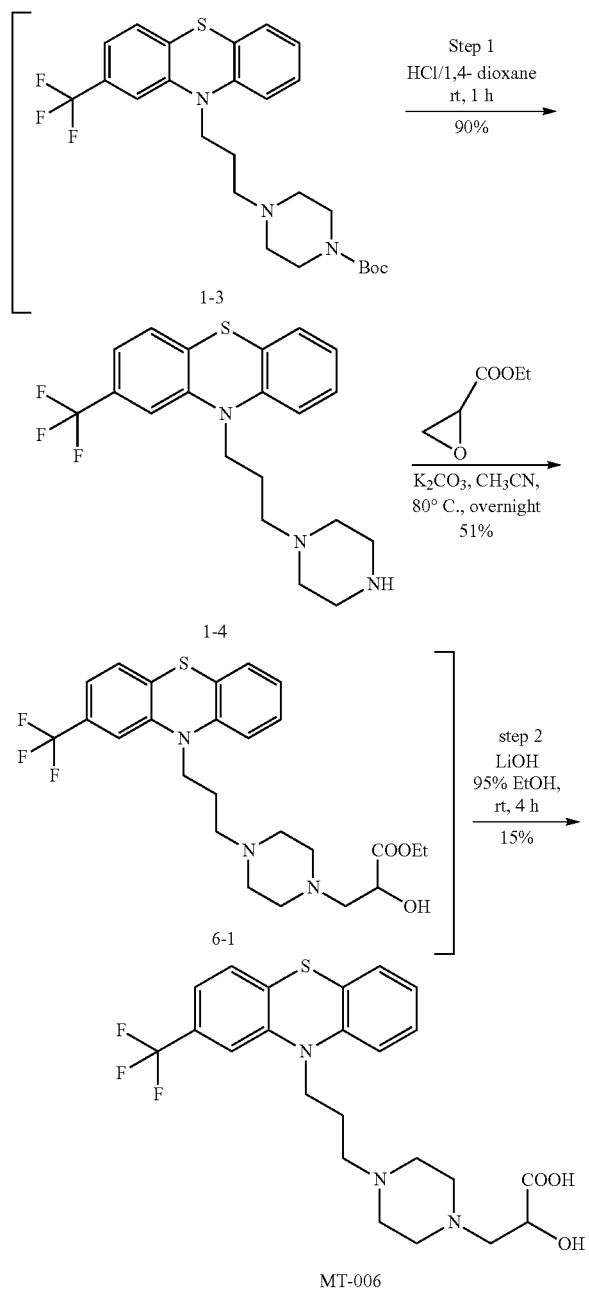

Step 1: Synthesis of 6-1 ethyl 2-hydroxy-3-(4-(3-(2-(trifluoromethyl)-10H-phenothiazin-10-yl)propyl)piperazin-1-yl)propanoate A mixture of 1-3 [tert-butyl 4-(3-(2-(trifluoromethyl)-10H-phenothiazin-10-yl)propyl)piperazine-1-carboxylate] (150 mg, 0.382 mmol) in HCl/1,4-dioxane (4 N, 5 mL) was stirred at rt for 1 h. After the reaction was complete, the solvent was removed under reduced pressure. The residue was dissolved in $CH_3CN$ (5 mL) and then ethyl oxirane-2-carboxylate (53 mg, 0.458 mmol) and $K_2CO_3$ (316 mg, 2.29 mmol) was added in turn. The resulting mixture was stirred at 80° C. overnight. After being cooled to rt, the mixture was filtered. The filtrate was diluted with water (15 mL) and extracted with EtOAc (5 mL×3). The combined organic extracts were washed with brine, dried over $Na_2SO_4$, filtered and concentrated under reduced pressure. The residue was purified by column chromatography ($CH_2Cl_2$:MeOH=20:1) to provide a yellow solid (100 mg, 51% yield).
LC-MS: Rt=2.37 min; ESI, m/z: 510 $[M+1]^+$

Step 2

A mixture of 6-1 ethyl 2-hydroxy-3-(4-(3-(2-(trifluoromethyl)-10H-phenothiazin-10-yl)propyl)piperazin-1-yl)propanoate (100 mg, 0.478 mmol) and LiOH $H_2O$ (32 mg, 0.763 mmol) in 95% EtOH (5 mL) was stirred at rt for 4 h. After being acidified to pH=4-5, the mixture was purified by prep-HPLC (Boston Green ODS (150 mm×30 mm, 5 mm); A=$H_2O$ (0.075% TFA) and B=$CH_3CN$; 33-63% B over 7 min) to provide a white solid (28 mg, 15% yield).

MT-006

$^1$H NMR (400 MHz, $CDCl_3$) δ 7.21-7.11 (m, 4H), 7.03 (s, 1H), 6.97-6.88 (m, 2H), 4.13 (t, J=4.6 Hz, 1H), 3.98 (d, J=6.4 Hz, 2H), 3.23-2.99 (m, 6H), 2.69-2.65 (m, 4H), 2.55 (t, J=6.6 Hz, 2H), 1.93-1.88 (m, J=, 2H); LC-MS: Rt=2.21 min; ESI, m/z: 482 [M+1]

Example 7. Synthesis of Compound MT-007

2-(2-(2-(4-(3-(2-(trifluoromethyl)-10H-phenothiazin-10-yl)propyl)piperazin-1-yl) ethoxy)ethoxy)ethanol

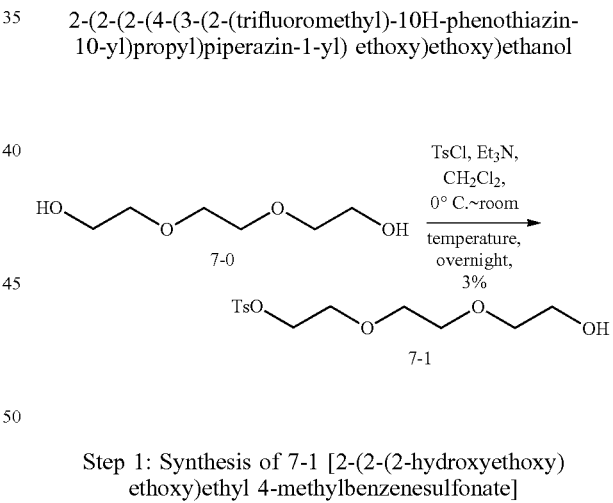

Step 1: Synthesis of 7-1 [2-(2-(2-hydroxyethoxy)ethoxy)ethyl 4-methylbenzenesulfonate]

To a solution of 7-0 [2,2'-(ethane-1,2-diylbis(oxy))diethanol] (5.0 g, 33.29 mmol) and $Et_3N$ (674 mg, 6.66 mmol) in $CH_2Cl_2$ (20 mL) was added TsCl (635 mg, 3.33 mmol) in a nitrogen atmosphere and the temperature was maintained at 0° C. Then the temperature was slowly warmed to rt and the reaction solution was stirred at rt overnight. The mixture was diluted with water (50 mL) and extracted with $CH_2Cl_2$ (40 mL×3). The combined organic layers were washed with brine (60 mL×2), dried over sodium sulfate, and concentrated to dryness. The residue was purified by column chromatography on silica gel (petrol ether:EtOAc=1:10) to provide brown oil (300 mg, 3% yield). LC-MS: Rt=1.52 min; ESI, m/z: 305 $[M+1]^+$

Step 2

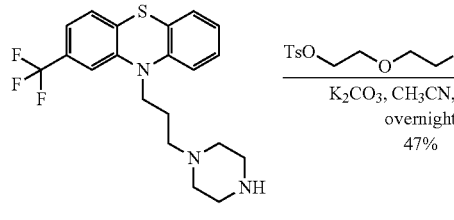

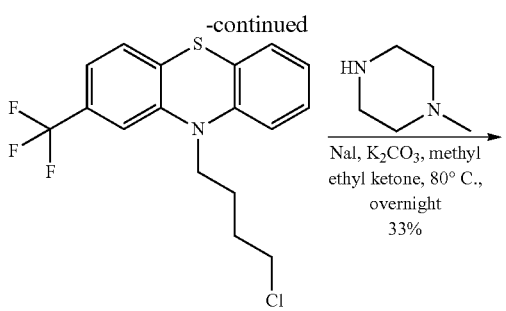

A mixture of 1-4 [10-(3-(piperazin-1-yl)propyl)-2-(trifluoromethyl)-10H-phenothiazine] (64 mg, 0.16 mmol), 7-1 [2-(2-(2-hydroxyethoxy)ethoxy)ethyl 4-methylbenzenesulfonate] (50 mg, 0.16 mmol) and $K_2CO_3$ (45 mg, 0.33 mmol) in acetonitrile (10 mL) was stirred at 80° C. overnight. After being cooled to rt, the mixture was diluted with water (30 mL) and extracted with EtOAc (20 mL×3). The combined organic layers were washed with brine (30 mL×2), dried over sodium sulfate, and concentrated to dryness. The residue was purified by column chromatography ($CH_2Cl_2$ MeOH=20:1) to provide yellow oil (40 mg, 47% yield).

MT-007

$^1$H NMR (400 MHz, $CDCl_3$) δ 7.22-7.07 (m, 4H), 7.03 (s, 1H), 6.97-6.88 (m, 2H), 3.95 (t, J=6.8 Hz, 2H), 3.74-3.68 (m, 2H), 3.68-3.63 (m, 2H), 3.63-3.53 (m, 6H), 2.57 (t, J=5.6 Hz, 3H), 2.52-2.44 (m, 7H), 2.40-2.30 (m, 3H), 1.99-1.86 (m, 2H); LC-MS: Rt=2.16; ESI, m/z: 526 [M+1]$^+$

Example 8. Synthesis of Compound MT-008

10-(4-(4-methylpiperazin-1-yl)butyl)-2-(trifluoromethyl)-10H-phenothiazine

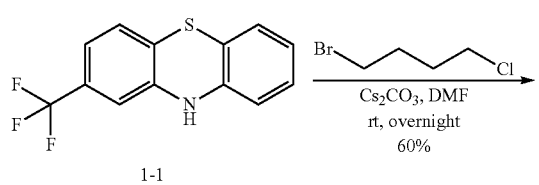

Step 1: Synthesis of 8-1 [10-(4-chlorobutyl)-2-(trifluoromethyl)-10H-phenothiazine]

A mixture of 1-1 [2-(trifluoromethyl)-10H-phenothiazine] (300 mg, 1.12 mmol), 1-bromo-4-chlorobutane (391 mg, 2.28 mmol) and $Cs_2CO_3$ (1.04 g, 3.19 mmol) in DMF (15 mL) was stirred at rt overnight. The mixture was poured into cool water (20 mL) and extracted with EtOAc (15 mL×3). The combined organic extracts were washed with brine, dried over $Na_2SO_4$, filtered and concentrated under reduced pressure. The residue was purified by column chromatography (petrol ether:EtOAc=10:1) to provide a yellow solid (240 mg, 60% yield).

LC-MS: Rt=2.30 min; ESI, m/z: 358 [M+1]$^+$

Step 2

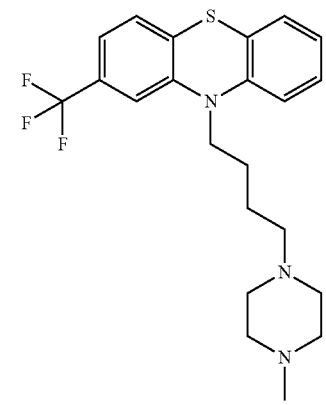

A mixture of 8-1 [10-(4-chlorobutyl)-2-(trifluoromethyl)-10H-phenothiazine] (70 mg, 0.196 mmol), 1-methylpiperazine (77 mg, 0.767 mmol) $K_2CO_3$ (128 mg, 0.924 mmol) and NaI (109 mg, 0.728 mmol) in methyl ethyl ketone (20 mL) was stirred at 80° C. overnight. After being cooled to rt, the mixture was diluted with water (20 mL) and extracted with EtOAc (15 mL×3). The combined organic extracts were washed with brine, dried over $Na_2SO_4$, filtered and concentrated under reduced pressure. The residue was purified by column chromatography ($CH_2Cl_2$:MeOH=15:1) to provide yellow oil (27 mg, 33% yield).

MT-008

$^1$H NMR (400 MHz, $CDCl_3$) δ 7.21-7.11 (m, 4H), 7.02 (s, 1H), 6.97-6.89 (m, 2H), 3.91 (t, J=7.0 Hz, 2H), 2.45-2.35 (m, 8H), 2.12 (s, 3H), 1.86 (brs, 2H), 1.83 (m, 2H), 1.64 (m, 2H); LC-MS: Rt=2.21 min; ESI, m/z: 422 [M+1]$^+$

Example 9. Synthesis of Compound MT-009

10-(4-(piperidin-1-yl)butyl)-2-(trifluoromethyl)-10H-phenothiazine

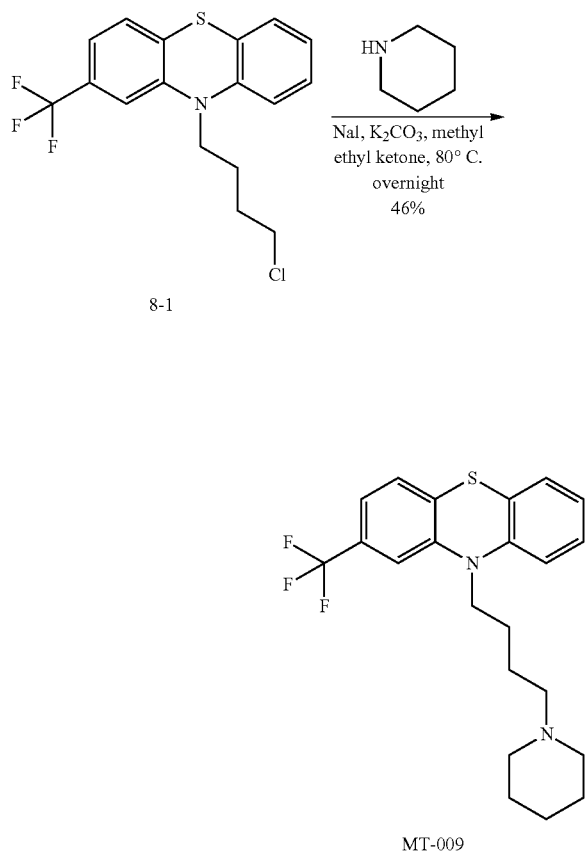

A mixture of 8-1 [10-(4-chlorobutyl)-2-(trifluoromethyl)-10H-phenothiazine] (50 mg, 0.140 mmol), piperidine (23 mg, 0.274 mmol), $K_2CO_3$ (55 mg, 0.395 mmol) and NaI (37 mg, 0.240 mmol) in methyl ethyl ketone (3 mL) was stirred at 80° C. overnight. After being cooled to rt, the mixture was diluted with water (5 mL) and extracted with EtOAc (5 mL×3). The combined organic extracts were washed with brine, dried over $Na_2SO_4$, filtered and concentrated under reduced pressure. The residue was purified by column chromatography ($CH_2Cl_2$:MeOH=15:1) to provide yellow oil (26 mg, 46% yield).

MT-009

$^1$H NMR (400 MHz, $CDCl_3$) δ 7.21-7.12 (m, 4H), 7.02 (s, 1H), 6.98-6.89 (m, 2H), 3.92 (t, J=6.8 Hz, 2H), 2.49-2.46 (m, 4H), 1.86-1.75 (m, 3H), 1.77-1.73 (m, 3H), 1.72-1.65 (m, 4H), 1.48-1.45 (m, 2H); LC-MS; Rt=2.56 min; ESI, m/z: 407 [M+1]$^+$

Example 10. Synthesis of Compound MT-010

N-(methylsulfonyl)-2-(4-(3-(2-(trifluoromethyl)-10H-phenothiazin-10-yl)propyl)piperazin-1-yl)acetamide

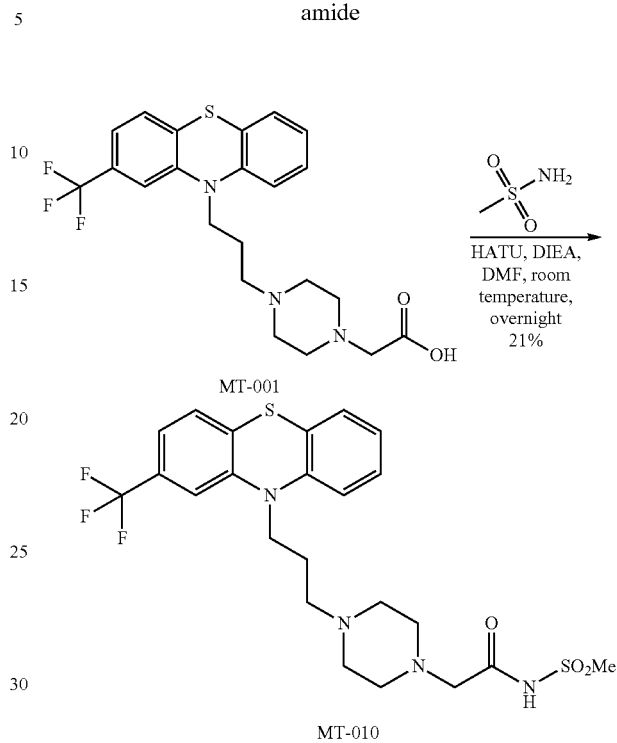

A mixture of MT-001 [2-(4-(3-(2-(trifluoromethyl)-10H-phenothiazin-10-yl)propyl)piperazin-1-yl)acetic acid trihydrochloride] (180 mg, 0.40 mmol), HATU (304 mg, 0.80 mmol), DIPEA (206 mg, 1.59 mmol) and methanesulfonamide (76 mg, 0.80 mmol) in DMF (4 mL) was stirred at rt under nitrogen overnight. The mixture was diluted with water (20 mL) and extracted with EtOAc (20 mL×3). The combined organic layers were washed with brine (20 mL×2), dried over sodium sulfate, and concentrated to dryness. The residue was purified by column chromatography ($CH_2Cl_2$:MeOH=15:1) to provide a white solid (28 mg, 21% yield).

MT-010

$^1$H NMR (400 MHz, $CDCl_3$) δ 7.23-7.08 (m, 4H), 7.04 (s, 1H), 6.98-6.87 (m, 2H), 3.97 (t, J=6.4 Hz, 2H), 3.26 (s, 3H), 3.12 (s, 2H), 2.70-2.38 (m, 10H), 2.00-1.84 (m, 2H); LC-MS; RT 2.40 min; ESI, m/z: 429 [M+1]$^+$

Example 11. Synthesis of Compound MT-011

1-(4-methylpiperazin-1-yl)-3-(2-(trifluoromethyl)-10H-phenothiazin-10-yl)propan-2-ol

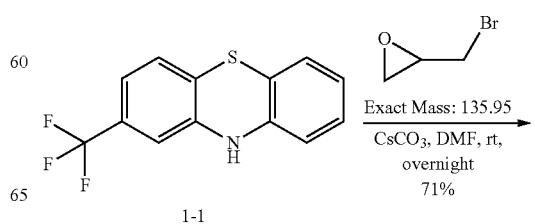

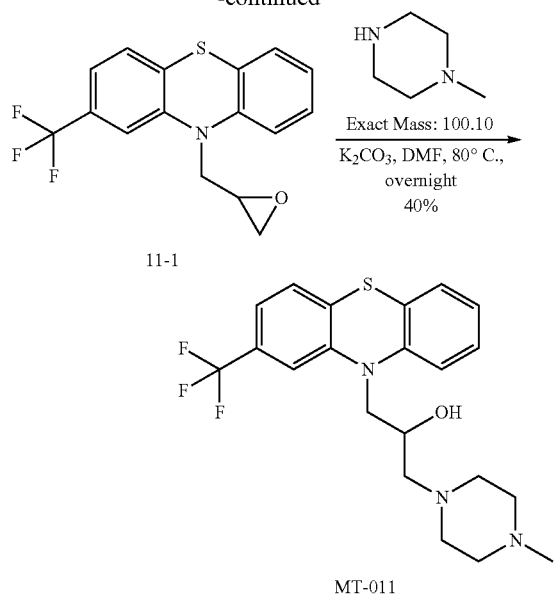

MT-011

Step 1: Synthesis of 11-1 [10-(oxiran-2-ylmethyl)-2-(trifluoromethyl)-10H-phenothiazine]

To a solution of compound 1-1 [2-(trifluoromethyl)-10H-phenothiazine] (2.0 g, 7.49 mmol) in DMF (50 mL) was added 2-(bromomethyl)oxirane (3.0 g, 22.47 mmol) and Cs$_2$CO$_3$ (9.8 g, 29.96 mmol) and the reaction mixture was stirred at rt overnight. Then the mixture was added to water (50 mL) and extracted with EtOAc (50 mL×3). The combined organic layers were washed with brine (30 mL), dried over sodium sulfate, and concentrated to dryness. The residue was purified by column chromatography on silica gel (petrol ether:EtOAc=10:1) to provide a light yellow solid (1.72 g, 71% yield).

$^1$H NMR (400 MHz, CDCl$_3$) δ 7.21-7.14 (m, 4H), 7.11 (dd, J=7.8, 1.4 Hz, 1H), 7.00-6.94 (m, 2H), 4.23 (dd, J=15.6, 2.8 Hz, 1H), 3.86 (dd, J=15.6, 5.2 Hz, 1H), 3.31-3.27 (m, 1H), 2.95 (t, J=4.4 Hz, 1H), 2.79 (q, J=2.4 Hz, 1H).

Step 2

To a solution of compound 11-1 10-(oxiran-2-ylmethyl)-2-(trifluoromethyl)-10H-phenothiazine (77 mg, 0.24 mmol) in DMF (4 mL) was added 1-methylpiperazine (48 mg, 0.48 mmol) and K$_2$CO$_3$ (132 mg, 0.95 mmol), and the reaction mixture was stirred at 80° C. overnight. After being cooled to rt, the mixture was diluted with water (5 mL) and extracted with EtOAc (5 mL×3). The combined organic layers were washed with brine (5 mL), dried over sodium sulfate, and concentrated to dryness, the residue was purified by column chromatography (CH$_2$Cl$_2$:MeOH=15:1) to provide a light yellow solid (40.1 mg, 40% yield).
MT-011

$^1$H NMR (400 MHz, CDCl$_3$) δ 7.24 (d, J=8.0 Hz, 1H), 7.22-7.15 (m, 4H), 7.00-6.96 (m, 2H), 4.14-4.02 (m, 2H), 3.96 (dd, J=13.8, 5.4 Hz, 1H), 2.65-2.55 (m, 3H), 2.55-2.30 (m, 6H), 2.27 (s, 3H), 1.67 (brs, 2H); LC-MS: Rt=2.14 min; ESI, m/z: 424 [M+1]$^+$ Example 12. Synthesis of Compound MT-012

1-(4-(2-hydroxyethyl)piperazin-1-yl)-3-(2-(trifluoromethyl)-10H-phenothiazin-10-yl)-propan-2-ol

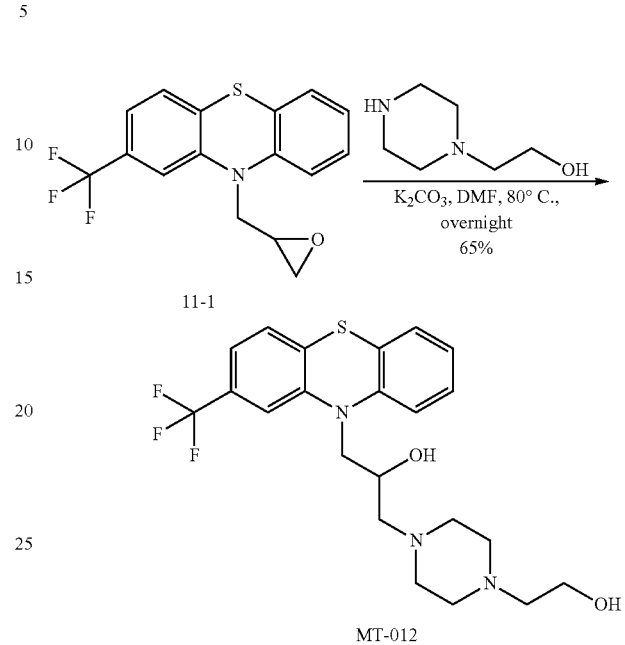

MT-012

To a solution of compound 11-1 10-(oxiran-2-ylmethyl)-2-(trifluoromethyl)-10H-phenothiazine (60 mg, 0.19 mmol) in DMF (4 mL) was added 2-(piperazin-1-yl)ethanol (48 mg, 0.37 mmol) and K$_2$CO$_3$ (103 mg, 0.74 mmol), and the reaction mixture was stirred at 80° C. overnight. After being cooled to rt, the mixture was diluted with water (5 mL) and extracted with EtOAc (5 mL×3). The combined organic layers were washed with brine (5 mL), dried over sodium sulfate, and concentrated to dryness. The residue was purified by column chromatography (CH$_2$Cl$_2$:MeOH=15:1) to provide a light yellow solid (54.3 mg, 65% yield).
MT-012

$^1$H NMR (400 MHz, CDCl$_3$) δ 7.24 (d, J=8.0 Hz, 1H), 7.22-7.15 (m, 4H), 7.01-6.96 (m, 2H), 4.15-4.03 (m, 2H), 3.96 (dd, J=13.8, 5.4 Hz, 1H), 3.60 (t, J=5.4 Hz, 2H), 2.62-2.32 (m, 12H), 1.78 (brs, 2H); LC-MS: Rt=2.68 min; ESI, m/z: 454 [M+1]$^+$ Example 13. Synthesis of Compound MT-013

2-(4-(2-hydroxy-3-(2-(trifluoromethyl)-10H-phenothiazin-10-yl)propyl)piperazin-1-yl) acetic acid

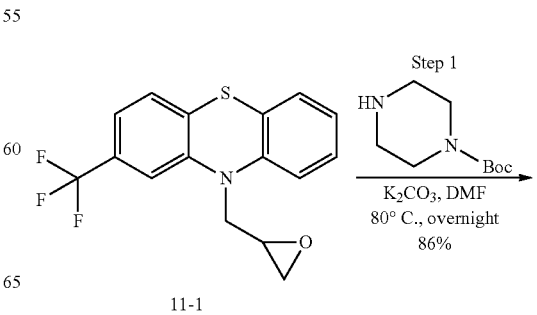

11-1

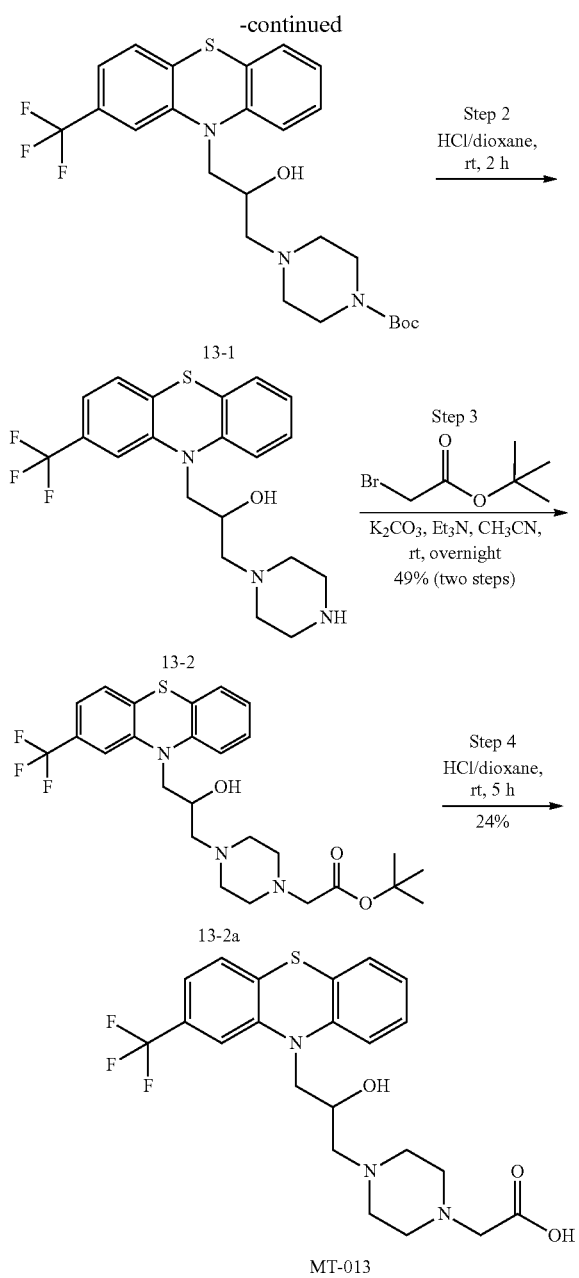

Step 1: Synthesis of 13-1 tert-butyl 4-(2-hydroxy-3-(2-(trifluoromethyl)-10H-phenothiazin-10-yl)propyl)-piperazine-1-carboxylate To a solution of compound 11-1 10-(oxiran-2-ylmethyl)-2-(trifluoromethyl)-10H-phenothiazine (0.88 g, 2.72 mmol) in dry DMF (30 mL) was added tert-butyl piperazine-1-carboxylate (1.01 g, 5.45 mmol) and $K_2CO_3$ (1.50 g, 10.90 mmol), and then the reaction mixture was stirred at 80° C. overnight. The mixture was added to water (50 mL) and extracted with EtOAc (30 mL×3). The combined organic layers were washed with brine (30 mL), dried over sodium sulfate, and concentrated to dryness. The residue was purified by column chromatography (petrol ether:EtOAc=10: 1~1:1) to afford an off-white solid (1.20 g, 86% yield).

$^1$H NMR (400 MHz, CDCl$_3$) δ 7.24 (d, J=8.0 Hz, 1H), 7.23-7.15 (m, 4H), 7.01-6.96 (m, 2H), 4.15-4.03 (m, 2H), 3.97 (dd, J=13.4, 5.4 Hz, 1H), 3.41-3.37 (m, 4H), 2.58 (dd, J=12.8, 3.6 Hz, 1H), 2.52-2.42 (m, 3H), 2.37-2.31 (m, 2H), 1.65 (brs, 1H), 1.44 (s, 9H); LC-MS: Rt=1.85 min; ESI, m/z: 510.1 [M+1]$^+$

Step 2: Synthesis of 13-2 1-(piperazin-1-yl)-3-(2-(trifluoromethyl)-10H-phenothiazin-10-yl)propan-2-ol trihydrochloride To a solution of compound 13-1 tert-butyl 4-(2-hydroxy-3-(2-(trifluoromethyl)-10H-phenothiazin-10-yl)propyl)piperazine-1-carboxylate (240 mg, 0.47 mmol) in 1,4-dioxane (5 mL) was added HCl (5 mL, 4M in dioxane), the reaction mixture was stirred at room temperature for 2 h. Then the mixture was concentrated in vacuo and the residue was used for the next step without further purification.

LC-MS: Rt=0.56 min; ESI, m/z: 374 [M+23]+

Step 3: Synthesis of 13-2a tert-butyl 2-(4-(2-hydroxy-3-(2-(trifluoromethyl)-10H-phenothiazin-10-yl)propyl)-piperazin-1-yl) acetate To above solution of compound 13-2 1-(piperazin-1-yl)-3-(2-(trifluoromethyl)-10H-phenothiazin-10-yl)propan-2-ol trihydrochloride and Et$_3$N (143 mg, 1.41 mmol) in CH$_3$CN (8 mL) was added tert-butyl 2-bromoacetate (184 mg, 0.94 mmol) and K$_2$CO$_3$ (195 mg, 1.41 mmol), and then the reaction mixture was stirred at rt overnight. The mixture was added to water (8 mL) and extracted with EtOAc (8 mL×3). The combined organic layers were washed with brine (5 mL), dried over sodium sulfate, and concentrated to dryness, the residue was purified by column chromatography (CH$_2$Cl$_2$:MeOH=20:1-15:1) to afford a light yellow solid (150 mg, 49% yield (two steps)).

LC-MS: Rt=1.82; ESI, m/z: 524 [M+1]$^+$

Step 4

A mixture of compound 13-2a tert-butyl 2-(4-(2-hydroxy-3-(2-(trifluoromethyl)-10H-phenothiazin-10-yl)propyl)-piperazin-1-yl) acetate (252 mg, 0.48 mmol) in HCl/dioxane (10 mL, 4 N) was stirred at rt for 5 h. The reaction mixture was concentrated to dryness. The residue was diluted with water (10 mL), basified with sat. Na$_2$CO$_3$ solution to pH=9, then re-acidified to pH=4 with 1 N HCl and extracted with EtOAc (8 mL×3). The combined organic layers were dried over Na$_2$SO$_4$, filtered and evaporated to dryness. The residue was purified by prep-HPLC (Boston Green ODS (150 mm×30 mm, 5 mm); A=H$_2$O (0.075% TFA) and B=CH$_3$CN; 33-63% B over 7 min) to afford an off-white solid (55 mg, 24% yield).

MT-013

$^1$H NMR (400 MHz, CDCl$_3$) δ 7.28-7.14 (m, 5H), 7.04-6.99 (m, 2H), 4.54-4.48 (m, 1H), 4.23 (dd, J=13.8, 4.2 Hz, 1H), 3.82 (dd, J=13.8, 10.2 Hz, 1H), 3.33 (s, 2H), 3.12 (d, J=12.8 Hz, 1H), 2.93-2.29 (m, 7H), 2.30-1.25 (m, 4H); LC-MS=Rt=2.26; ESI, m/z: 468.2 [M+1]$^+$

Example 14. Synthesis of Compound MT-014

2,2'-(2-hydroxy-3-(2-(trifluoromethyl)-10H-phenothiazin-10-yl)propylazanediyl)-diethanol

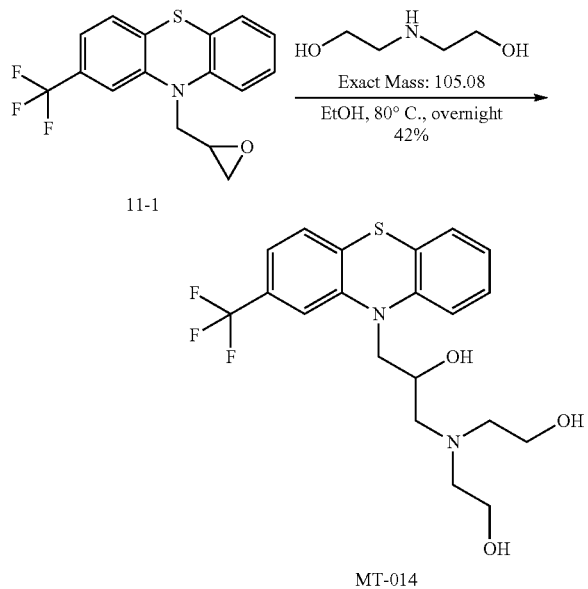

To a solution of compound 11-1 10-(oxiran-2-ylmethyl)-2-(trifluoromethyl)-10H-phenothiazine (100 mg, 0.31 mmol) in EtOH (5 mL) was added 2,2'-azanediyldiethanol (325 mg, 3.10 mmol), and the reaction mixture was stirred at 80° C. overnight. After being cooled to rt, the mixture was concentrated to dryness. The residue was purified by column chromatography (CH$_2$Cl$_2$:MeOH=15:1) to provide a light yellow solid (55.8 mg, 42% yield).
MT-014
$^1$H NMR (400 MHz, CDCl$_3$) δ 7.40-7.33 (m, 2H), 7.24 (q, J=8.0 Hz, 2H), 7.16 (t, J=9.2 Hz, 2H), 6.99 (t, J=7.2 Hz, 1H), 4.81 (s, 1H), 4.35 (brs, 2H), 4.03-3.98 (m, 1H), 3.89-3.84 (m, 2H), 3.50-3.35 (m, 4H), 2.66-2.62 (m, 1H), 2.54 (t, J=5.6 Hz, 5H); LC-MS: Rt=2.72 min; ESI, m/z: 429 [M+1]$^+$

Example 15. Synthesis of Compound MT-015

2-hydroxy-3-(4-(2-hydroxy-3-(2-(trifluoromethyl)-10H-phenothiazin-10-yl)propyl)-piperazin-1-yl)propanoic acid

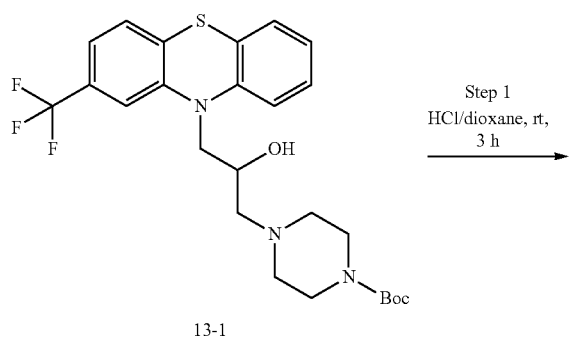

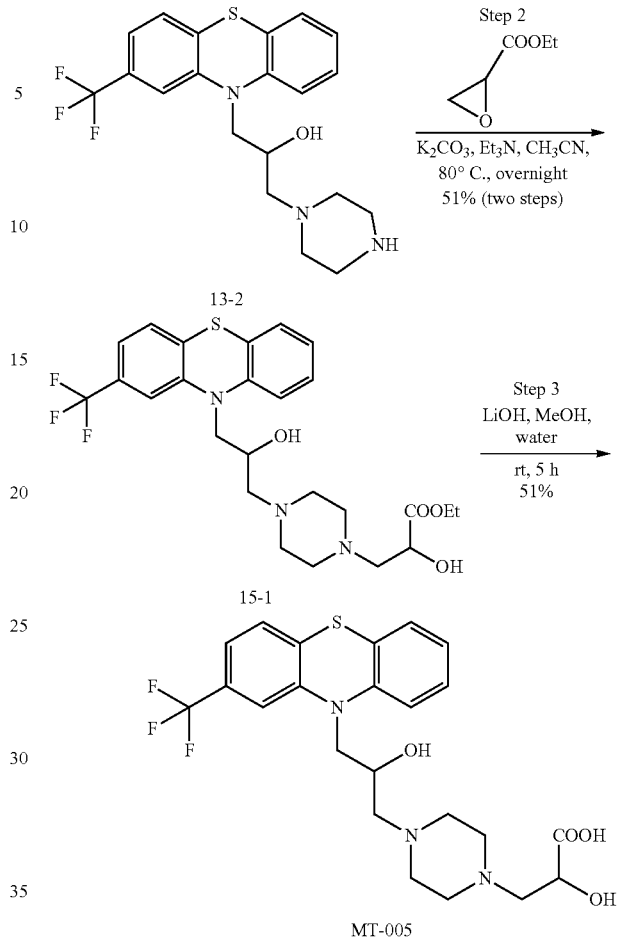

Step 1: Synthesis of 13-2 1-(piperazin-1-yl)-3-(2-(trifluoromethyl)-10H-phenothiazin-10-yl)propan-2-ol trihydrochloride To a solution of compound 13-1 tert-butyl 4-(2-hydroxy-3-(2-(trifluoromethyl)-10H-phenothiazin-10-yl)propyl)piperazine-1-carboxylate (200 mg, 0.39 mmol) was dissolved in HCl/dioxane (16 mL, 4 M), and then the reaction mixture was stirred at rt for 2 h. The mixture was concentrated in vacuo, and the residue was used to the next step without further purification.
LC-MS: Rt=0.056 min; ESI, m/z: 374 [M+23]+

Step 2: Synthesis of 15-1 ethyl 2-hydroxy-3-(4-(2-hydroxy-3-(2-(trifluoromethyl)-10H-phenothiazin-10-yl)-propyl)

To the solution of 13-2 1-(piperazin-1-yl)-3-(2-(trifluoromethyl)-10H-phenothiazin-10-yl)propan-2-ol trihydrochloride and Et$_3$N (119 mg, 1.18 mmol) in CH$_3$CN (20 mL) was added ethyl oxirane-2-carboxylate (92 mg, 0.79 mmol) and K$_2$CO$_3$ (163 mg, 1.18 mmol), and then the reaction mixture was stirred at 80° C. overnight. The mixture was filtered, and the filtrate was concentrated to dryness. The residue was purified by column chromatography (CH$_2$Cl$_2$:MeOH=20:1~15:1) to afford a light yellow solid (106 mg, 51% yield (two steps)).
LC-MS: Rt=1.71 min; ESI, m/z: 526 [M+1]$^+$ Step 3

To a solution of compound 15-1 ethyl 2-hydroxy-3-(4-(2-hydroxy-3-(2-(trifluoromethyl)-10H-phenothiazin-10-yl)-propyl) piperazin-1-yl)propanoate (106 mg, 0.20 mmol) in MeOH (5 mL) and water (5 mL) was added LiOH H$_2$O (85 mg, 2.03 mmol), and then the reaction mixture was stirred at rt for 5 h. The mixture was adjusted to pH=4 with 2 N HCl and extracted with EtOAc (8 mL×3). The combined organic layers were washed with brine (5 mL), dried over sodium sulfate, and concentrated to dryness. The residue was purified by prep-HPLC (Boston Green ODS (150 mm×30 mm, 5 mm); A=H$_2$O (0.075% TFA) and B=CH$_3$CN; 33-63% B over 7 min) to afford an off-white solid (51 mg, 51% yield).
MT-015

$^1$H NMR (400 MHz, CDCl$_3$) δ 7.28-7.14 (m, 5H), 7.03-6.97 (m, 2H), 4.29 (brs, 1H), 4.16-4.08 (m, 2H), 3.97-3.91 (m, 1H), 3.13-2.60 (m, 15H); LC-MS: Rt=2.14 min; ESI, m/z: 498 [M+1]$^+$ Example 16. Synthesis of Compound MT-016

1-(4-(2-(2-(2-hydroxyethoxy)ethoxy)ethyl)piperazin-1-yl)-3-(2-(trifluoromethyl)-10H-phenothiazin-10-yl)propan-2-ol

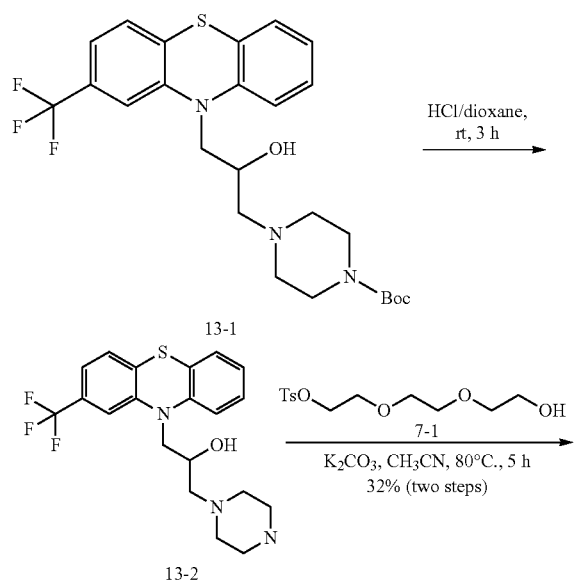

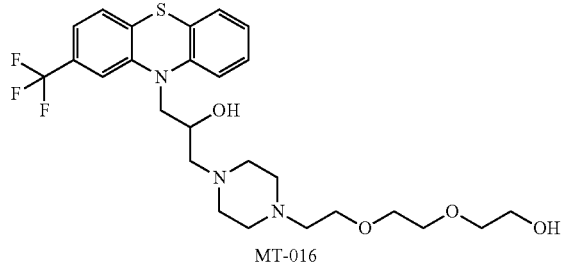

MT-016

To above solution of compound 13-2 1-(piperazin-1-yl)-3-(2-(trifluoromethyl)-10H-phenothiazin-10-yl)propan-2-ol trihydrochloride and Et$_3$N (83 mg, 0.83 mmol) in CH$_3$CN (10 mL) was added compound 7-1 2-(2-(2-hydroxyethoxy)ethoxy)ethyl 4-methylbenzenesulfonate (167 mg, 0.55 mmol) and K$_2$CO$_3$ (115 mg, 0.83 mmol), and then the reaction mixture was stirred at 80° C. for 5 h. Then the mixture was diluted with water (10 mL) and extracted with EtOAc (10 mL×3). The combined organic layers were washed with brine (5 mL), dried over sodium sulfate, and concentrated to dryness, the residue was purified by column chromatography (CH$_2$Cl$_2$:MeOH=15:1) to afford a light yellow oil (48 mg, 32% yield (two steps)).

MT-016

$^1$H NMR (400 MHz, CDCl$_3$) δ 7.23 (d, J=7.6 Hz, 1H), 7.22-7.14 (m, 4H), 7.00-6.95 (m, 2H), 4.14-4.01 (m, 2H), 3.94 (dd, J=13.6, 5.2 Hz, 1H), 3.73-3.70 (m, 2H), 3.67-3.64 (m, 2H), 3.61-3.57 (m, 6H), 2.61-2.27 (m, 14H); LC-MS: Rt=2.78 min; ESI, m/z: 542.2 [M+1]$^+$ Example 17. Synthesis of Compound MT-017

2-(2-(4-(3-(2-(trifluoromethyl)-10H-phenothiazin-10-yl)propyl)piperazin-1-yl)ethoxy) acetic acid tri-hydrochloride

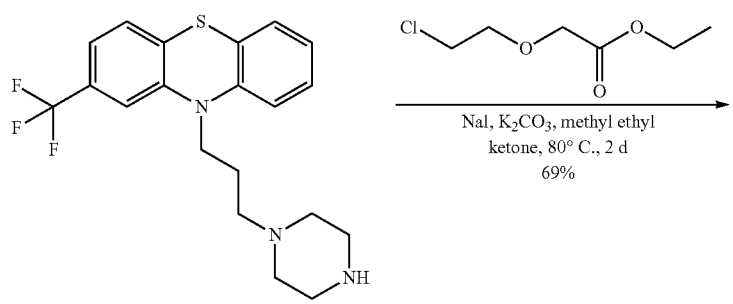

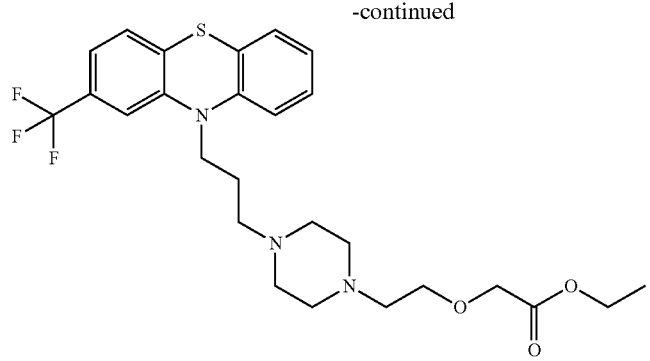

17-2

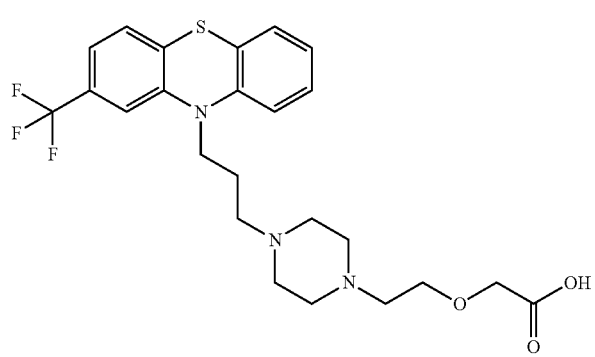

MT-017

Step 1: Synthesis of 17-2 [ethyl 2-(2-(4-(3-(2-(trifluoromethyl)-10H-phenothiazin-10-yl)propyl)piperazin-1-yl)ethoxy)acetate]

A mixture of 1-4 [10-(3-(piperazin-1-yl)propyl)-2-(trifluoromethyl)-10H-phenothiazine] (175 mg, 0.44 mmol), ethyl 2-(2-chloroethoxy)acetate (222 mg, 1.33 mmol), NaI (200 mg, 1.33 mmol) and $K_2CO_3$ (369 mg, 2.67 mmol) in methyl ethyl ketone (10 mL) was stirred at 80° C. for 2 days. After being cooled to rt, the mixture was diluted with water (20 mL) and extracted with EtOAc (60 mL×3). The combined organic layers were washed with brine (50 mL×2), dried over sodium sulfate, and concentrated to dryness. The residue was purified by column chromatography on silica gel (petrol ether:EtOAc=1:1) to provide a brown solid (160 mg, 69% yield).
LC-MS: Rt=2.43 min; ESI, m/z: 524 [M+1]$^+$

Step 2

To a solution of 17-2 [ethyl 2-(2-(4-(3-(2-(trifluoromethyl)-10H-phenothiazin-10-yl)propyl)piperazin-1-yl)ethoxy)acetate] (160 mg, 0.31 mmol) in MeOH (6 mL) was added NaOH (2 N, 0.93 mL, 1.86 mmol) and the reaction mixture was stirred at rt for 1 h. The mixture was diluted with water (20 mL) and then the pH was adjusted to pH=2-3 with dilute hydrochloric acid. The solution was lyophilized to dryness. The residue was purified by prep-HPLC (Boston Green ODS (150 mm×30 mm, 5 mm); A=$H_2O$ (0.075% TFA) and B=$CH_3CN$; 33-63% B over 7 min) to provide a white solid (28 mg, 3HCl salt, 15% yield).

MT-017
$^1$H NMR (400 MHz, $CDCl_3$) δ 7.35 (d, J=8.0 Hz, 1H), 7.31-7.20 (m, 3H), 7.17 (dd, J=7.6, 1.2 Hz, 1H), 7.09 (d, J=8.0 Hz, 1H), 6.99 (dd, J=7.2, 7.2 Hz, 1H), 4.00 (t, J=6.6 Hz, 2H), 3.85 (s, 2H), 3.63 (t, J=5.4 Hz, 2H), 2.84-2.55 (m, 6H), 2.49-2.24 (m, 6H), 1.94-1.58 (m, 2H); LC-MS: Rt=2.20 min; ESI, m/z: 496 [M+1]$^+$

Example 18. Synthesis of Compound MT-018

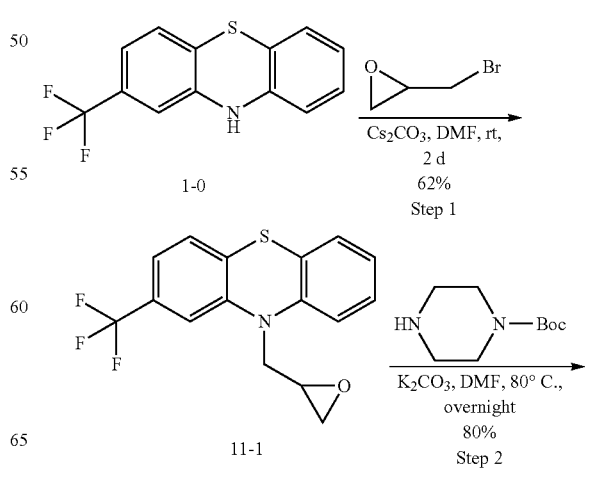

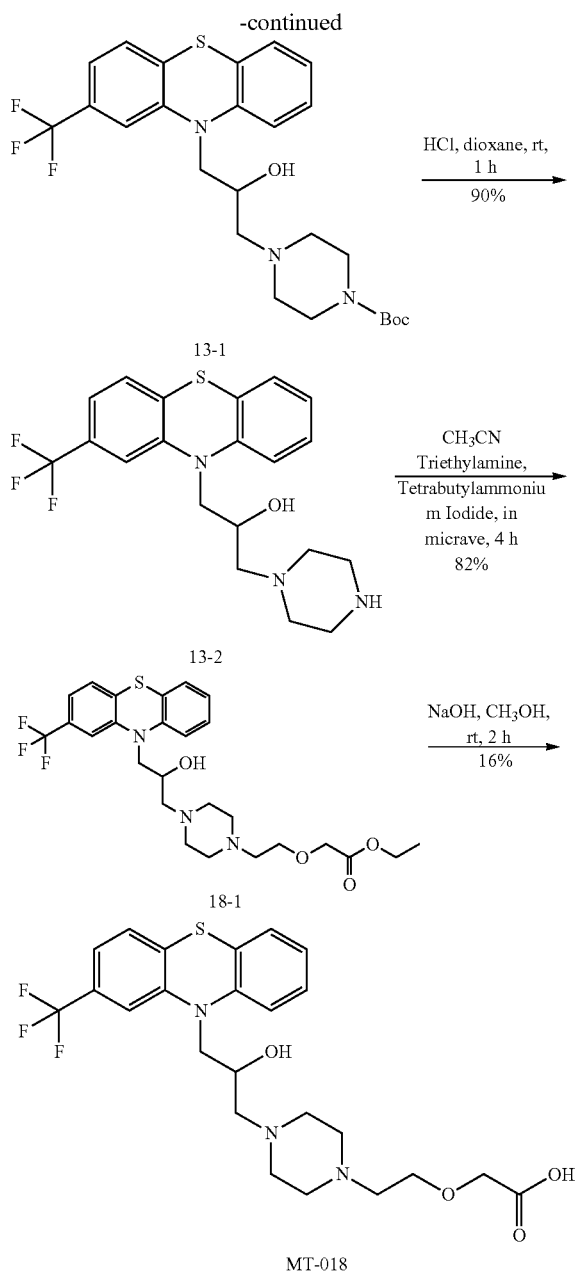

Step 1: Synthesis of 18-1 ethyl 2-(2-(4-(2-hydroxy-3-(2-(trifluoromethyl)-10H-phenothiazin-10-yl)propyl)piperazin-1-yl) ethoxy)acetate A mixture of 13-2 1-(piperazin-1-yl)-3-(2-(trifluoromethyl)-10H-phenothiazin-10-yl)propan-2-ol (500 mg, 1.2 mmol), ethyl 2-(2-chloroethoxy)acetate (0.25 g, 1.5 mmol) and tetrabutylammonium iodide (40 mg, 0.12 mmol) in triethylamine (5 mL) and CH₃CN (1 mL) was irradiated with microwave radiation at 135° C. for 4 h. The mixture was concentrated under reduced pressure. The residue was diluted with water (10 mL) and extracted with ethyl acetate (10 mL×3). The combined organic layers were washed with brine (10 mL×2), dried over sodium sulfate, and concentrated to dryness. The residue was purified by column chromatography (CH$_2$Cl$_2$:MeOH=20:1) to afford a yellow solid (510 mg, 82% yield). LC-MS: Rt=1.75 min; ESI, m/z: 540 [M+1]$^+$ Step 2

A mixture of 18-1 ethyl 2-(2-(4-(2-hydroxy-3-(2-(trifluoromethyl)-10H-phenothiazin-10-yl)propyl)piperazin-1-yl) ethoxy)acetate (200 mg, 0.37 mmol) and NaOH (33 mg, 0.82 mmol) in MeOH (5 mL) was stirred at rt for 2 h. The mixture was diluted with water (20 mL), then adjusted to pH=4 with diluted hydrochloric acid and extracted with ethyl acetate (20 mL×3). The combined organic layers were washed with brine (20 mL×2), dried over sodium sulfate, and concentrated to dryness. The residue was purified by column chromatography (CH$_2$Cl$_2$:MeOH=8:1) to afford a yellow oil (30 mg, 16% yield).

MT-018

$^1$H NMR (400 MHz, CDCl$_3$) δ 7.26-7.15 (m, 5H), 7.01-6.95 (m, 2H), 4.15-4.12 (m, 1H), 4.04-3.97 (m, 4H), 3.73-3.70 (m, 2H), 2.85-2.81 (m, 4H), 2.79-2.60 (m, 11H), 2.56-2.50 (m, 1H); LC-MS: Rt=2.40 min; ESI, m/z: 511[M+1]$^+$.

Example 19. Synthesis of Compound MT-019

The synthesis of A-1 [(2R,3R,4R,5S,6R)-2-allyl-6-(hydroxymethyl)tetrahydro-2H-pyran-3,4,5-triol]

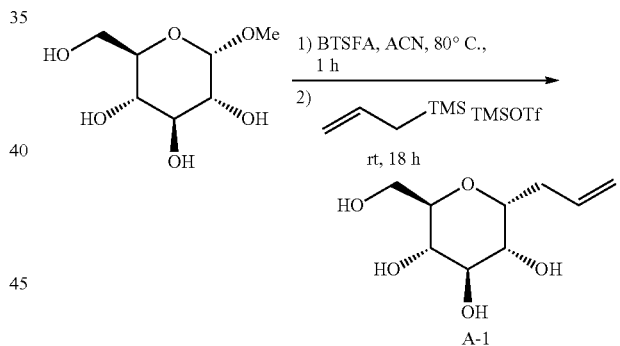

Bis(trimethylsilyl)trifluoroacetamide (38.55 g, 150 mmol) was added to (2R,3S,4S,5R,6S)-2-(hydroxymethyl)-6-methoxytetrahydro-2H-pyran-3,4,5-triol (9.7 g, 50 mmol) in ACN (50 mL) under argon. The mixture was heated to 80° C. for 1 h. When the solution became clear it was cooled to 0° C. and allyltrimethylsilane (8.56 g, 75 mmol) and TMSOTf (5.55 g, 25 mmol) were added warmed to rt. The mixture was stirred at rt for 24 h. The mixture was then slowly added to ice-cold water and stirred for another 30 min. IRN78 resin was added to adjust the pH=7 and the mixture was filtrated through Celite. The filtrate was concentrated in vacuo and lyophilized. The residue was purified by column chromatography (EtOAc:MeOH=20:1) to provide a white solid (5.5 g, 53.9%).

$^1$H NMR (400 MHz, MeOD) δ ppm 5.89-5.86 (m, 1H), 5.16-5.05 (m, 2H), 3.99-3.94 (m, 1H), 3.78-3.74 (m, 1H), 3.69-3.53 (m, 3H), 3.49-3.45 (m, 1H), 3.29 (m, 1H), 2.49-2.43 (m, 2H);

Intermediate Synthesis of A [(3aR,5R,6S,7S,7aR)-5-(hydroxymethyl)hexahydro-2H-furo[3,2-b]pyran-2,6,7-triol]

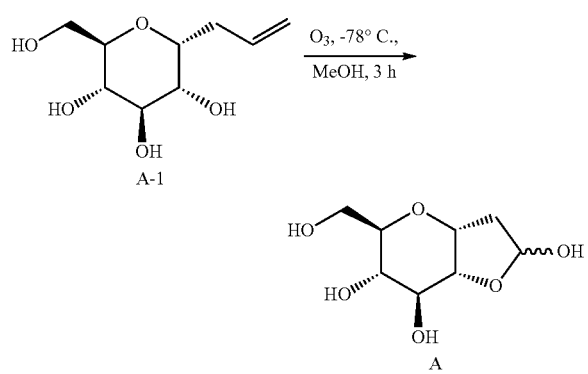

A-1 [(2R,3R,4R,5S,6R)-2-allyl-6-(hydroxymethyl)tetrahydro-2H-pyran-3,4,5-triol] (2.0 g, 10 mmol) was dissolved in acetone (200 mL) and H$_2$O (10 mL). O3 was bubbled into the mixture at −78° C. for 2 h. When the solution became blue, O$_2$ was bubbled through the solution for 30 min and then N$_2$ bubbled through the solution for 30 min. Me$_2$S (5 mL) was added and the solution was stirred for another 30 min. The mixture was concentrated in vacuo (below 20° C. water bath). The residue was lyophilized to a colorless oil which was used without purification. Intermediate synthesis of 1-1 (10-(3-chloropropyl)-2-(trifluoromethyl)-10H-phenothiazine)

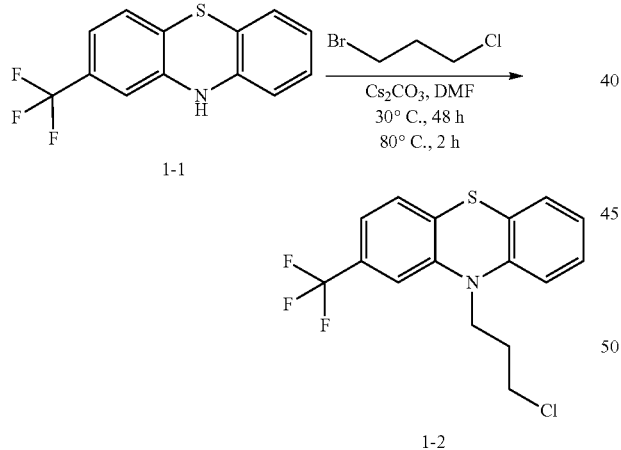

1-Bromo-3-chloropropane (37.68 g, 200 mmol) was added to 2-(trifluoromethyl)-10H-phenothiazine (26.7 g, 100 mmol) and Cs$_2$CO$_3$ (65.6 g, 200 mmol) in DMF (130 mL). The mixture was stirred at 30° C. for 48 h and then heated to 80° C. for 2 h. The mixture was cooled to rt then H$_2$O was added. The mixture was extracted with PE three times (200 mL×3). The combined organic phase was washed with brine, dried over Na$_2$SO$_4$, and concentrated in vacuo. The residue was purified by column chromatography (PE 100%, PE:EtOAc=60:1) to get 10.8 g pure and 19 g crude. LC-MS: Rt=2.29 min; ESI, m/z 344 [M+1]$^+$.

Compound MT-019

(2R,3S,4R,5R,6R)-2-(hydroxymethyl)-6-(2-(4-(3-(2-(trifluoromethyl)-10H-phenothiazin-10-yl)propyl)piperazin-1-yl)ethyl)tetrahydro-2H-pyran-3,4,5-triol Step 1

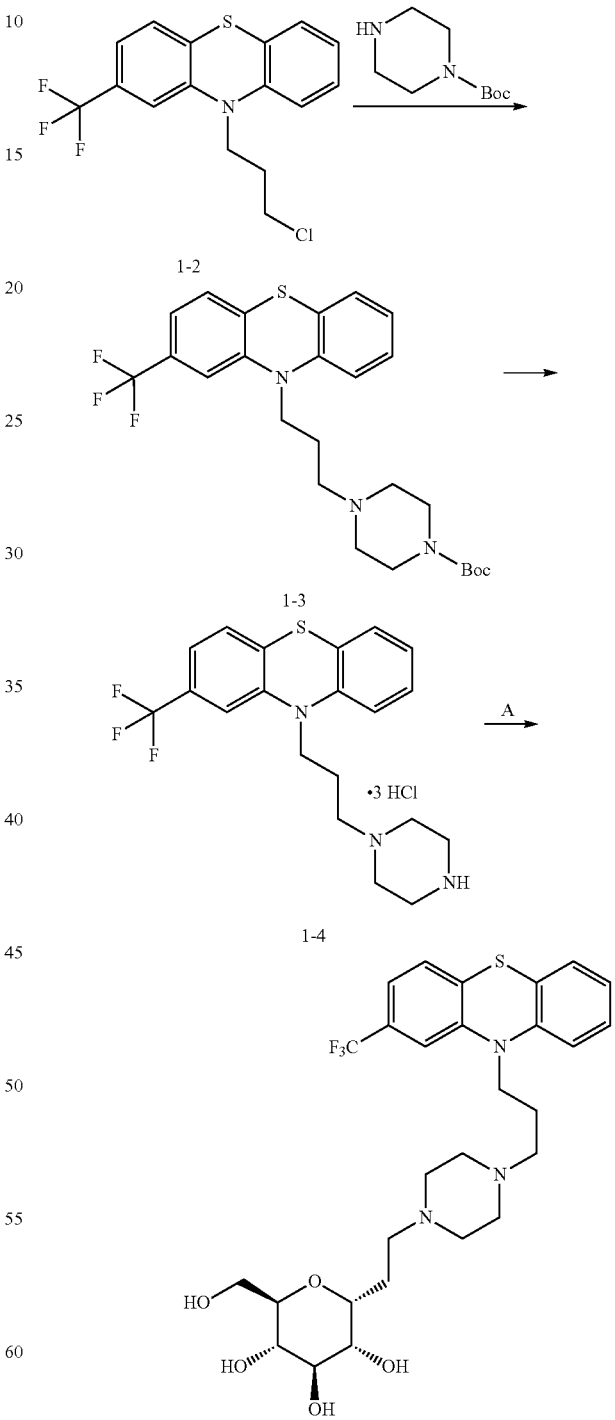

Triethyl amine (2.4 g, 24 mmol) was added to 1-1[10-(3-chloropropyl)-2-(trifluoromethyl)-10H-phenothiazine]

(2.744 g, 8 mmol) and tert-butyl piperazine-1-carboxylate (2.232 g, 12 mmol) in NMP (15 mL). The mixture was heated to 80° C. for 18 h. H₂O was added, extracted with EtOAc (20 mL×3). The combined organic phase was washed with brine, dried over Na₂SO₄, and concentrated in vacuo. The residue was purified by column chromatography (PE:EtOAc=10:1, 3:1) to get a light brown solid (3 g, 76%).

LC-MS: Rt=1.88 min; ESI m/z 494 [M+1]⁺.

Step 2

HCl in MeOH (1.0 N, 50 mL) was added to 1-2 [tert-butyl 4-(3-(2-(trifluoromethyl)-10H-phenothiazin-10-yl)propyl) piperazine-1-carboxylate] (2.8 g, 5.7 mmol). The mixture was stirred at rt for 18 h. The mixture was concentrated in vacuo to get a light brown solid (2.8 g, 98%) which was used directly for the next step.

LC-MS: Rt=2.29 min; ESI m/z 394 [M+1]⁺.

Step 3

CH₃COOH (200 mg, 3 mmol) was added to 1-3 [10-(3-(piperazin-1-yl)propyl)-2-(trifluoromethyl)-10H-phenothiazine HCl] (150 mg, 0.3 mmol) and A [(3aR,5R,6S,7S,7aR)-5-(hydroxymethyl)hexahydro-2H-furo[3,2-b]pyran-2,6,7-triol] (225 mg crude, 0.72 mmol) in C₂H₅OH (8 mL). The mixture was stirred at 60° C. for 20 min. NaBH₃CN (200 mg, 3 mmol) was added and the mixture was stirred at 60° C. for an additional 1 h. The mixture was concentrated in vacuo. The residue was purified by prep-HPLC (Waters XBridge C18 (50 mm×4.6 mm, 3.5 μm); A=H₂O (0.01 mol/L NH₄HCO₃) and B=CH₃CN; 15-85% B over 8 min) to get a white solid (20 mg, 4%).

MT-019

¹H NMR (400 MHz, d⁶-DMSO) δ ppm 7.32-7.29 (m, 1H), 7.24-7.19 (m, 3H), 7.15-7.13 (m, 1H), 7.08-7.06 (m, 1H), 6.96 (t, J=7.6 Hz, 1H), 4.95-4.94 (m, 1H), 4.76-4.73 (m, 2H), 4.39 (t, J=6.0 Hz, 1H), 3.97 (t, J=6.0 Hz, 2H), 3.73-3.70 (m, 1H), 3.57-3.53 (m, 1H), 3.37-3.35 (m, 1H), 3.28-3.24 (m, 2H), 3.18-3.14 (m, 1H), 2.98-2.96 (m, 1H), 2.36-2.14 (m, 12H), 1.76-1.57 (m, 4H); LC-MS: Rt=1.96 min; ESI m/z 584 [M+1]⁺.

Example 20. Synthesis of Compound MT-020

(2R,3R,4R,5S,6R)-2-(2-(4-(2-hydroxy-3-(2-(trifluoromethyl)-10H-phenothiazin-10-yl)propyl)piperazin-1-yl)ethyl)-6-(hydroxymethyl)tetrahydro-2H-pyran-3,4,5-triol

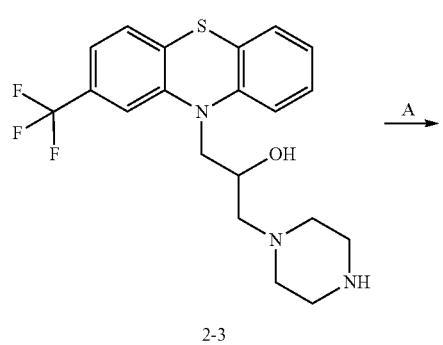

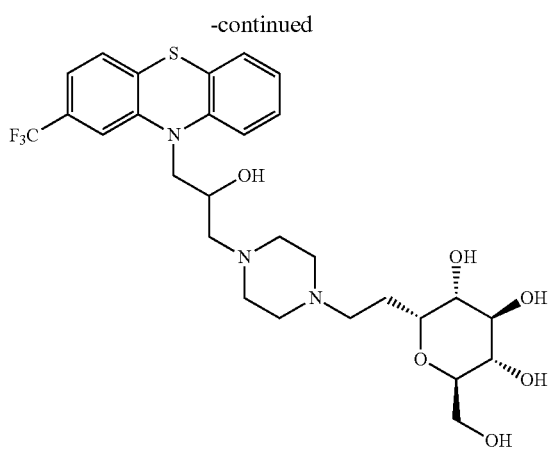

MT-020

Acetic acid (300 mg, 5 mmol) was added to 2-3 [1-(piperazin-1-yl)-3-(2-(trifluoromethyl)-10H-phenothiazin-10-yl)propan-2-ol HCl] (409 mg, 1 mmol) and A (406 mg crude, 2 mmol) in C₂H₅OH (20 mL). The mixture was stirred at rt for 20 min and then NaBH₃CN (300 mg, 5 mmol) was added. The mixture was stirred at rt for 18 h. The mixture was concentrated in vacuo. The residue was purified by the reverse phase column chromatography (C18 spherical 20-35 μm 100A 80 g; A=H₂O (0.01 mol/L NH₄HCO₃) and B=CH₃CN; 10-95% B over 30 min) to get a white solid (70 mg, 11%).

MT-020

¹H NMR (400 MHz, d⁶-DMSO) δ ppm 7.35-7.33 (m, 2H), 7.26-7.22 (m, 2H), 7.20 (m, 2H), 6.99 (t, J=7.6 Hz, 1H), 4.97 (brs., 1H), 4.88 (d, J=4.4 Hz, 1H), 4.78-4.76 (m, 2H), 4.41 (t, J=6.0 Hz, 1H), 4.09-4.07 (m, 1H), 3.89-3.87 (m, 2H), 3.76-3.72 (m, 1H), 3.60-3.56 (m, 1H), 3.40-3.38 (m, 1H), 3.31-3.25 (m, 2H), 3.21-3.18 (m, 1H), 3.03-2.99 (m, 1H), 2.45-2.18 (m, 12H), 1.70-1.60 (m, 2H); LC-MS: Rt=1.86 min; ESI m/z 600 [M+1]⁺.

Example 21. Synthesis of Compound MT-021

(2R,3S,4R,5R,6R)-2-(hydroxymethyl)-6-(2-(methyl (3-(2-(trifluoromethyl)-10H-phenothiazin-10-yl) propyl)amino)ethyl)tetrahydro-2H-pyran-3,4,5-triol Step 1

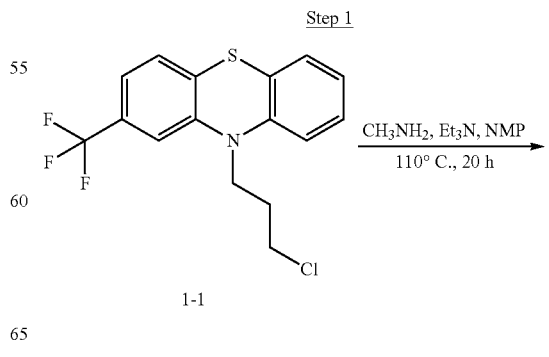

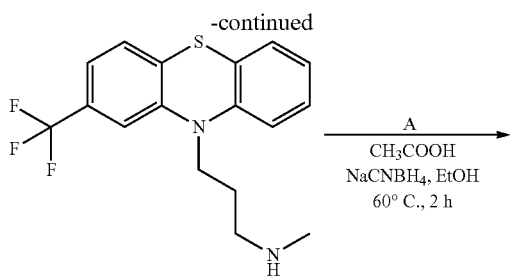

3-1

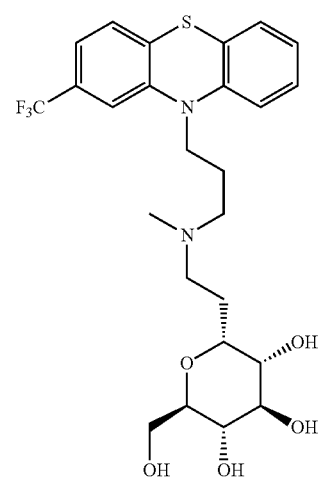

MT-021

Methylamine (2.0 N in ACN, 6 mL, 12 mmol) was added to Et$_3$N (909 mg, 9 mmol) and 1-1(10-(3-chloropropyl)-2-(trifluoromethyl)-10H-phenothiazine) (1.029 g, 3 mmol) in NMP (10 mL). The mixture was heated to 110° C. for 18 h in a sealed tube. The mixture was cooled to rt and H$_2$O was added. The mixture was extracted with EtOAc (20 mL×3). The combined organic phase was washed with brine, dried over Na$_2$SO$_4$, and concentrated in vacuo. The residue was purified by column chromatography (EtOAc:MeOH=4:1) to get a light yellow oil (760 mg, yield: 74.9%). LC-MS: Rt=1.69 min; ESI m/z 339 [M+1]$^+$.

Step 2

NaBH$_3$CN (540 mg, 8 mmol) was added to 3-1[(N-methyl-3-(2-(trifluoromethyl)-10H-phenothiazin-10-yl)propan-1-amine)] (670 mg, 2 mmol) and A [(3aR,5R,6S,7S,7aR)-5-(hydroxymethyl)hexahydro-2H-furo[3,2-b]pyran-2,6,7-triol] (600 mg, 2 mmol) in EtOH (60 mL) and CH$_3$COOH (500 mg, 8 mol). The mixture was heated to 60° C. for 3 h under N$_2$. The mixture was concentrated in vacuo. The residue was purified by the reverse phase column chromatography (C18 spherical 20-35 μm 100A 120 g; A=H$_2$O (0.01 mol/L NH$_4$HCO$_3$) and B=CH$_3$CN; 5-95% B over 25 min and then prep-HPLC (Waters XBridge C18 OBD (100 mm×30 mm, 5 μm); A=H$_2$O (0.01 mol/L NH$_4$HCO$_3$) and B=CH$_3$CN; 15-85% B over 10 min) to get a white solid (150 mg, 14%).

MT-021

$^1$H NMR (400 MHz, d$^6$-DMSO) δ ppm 7.33-7.31 (m, 1H), 7.24-7.20 (m, 3H), 7.16-7.14 (m, 1H), 7.06 (d, J=7.6 Hz, 1H), 6.96 (t, J=7.6 Hz, 1H), 4.90 (s, 1H), 4.77-4.75 (m, 2H), 4.35 (t, J=6.0 Hz, 1H), 3.95 (m, 2H), 3.70-3.66 (m, 1H), 3.56-3.52 (m, 1H), 3.38-3.35 (m, 1H), 3.28-3.20 (m, 2H), 3.16-3.13 (m, 1H), 3.01-2.97 (m, 1H), 2.42-2.26 (m, 4H), 2.07 (s, 3H), 1.75 (t, J=6.8 Hz, 2H), 1.66-1.56 (m, 2H); LC-MS: Rt=1.94 min; ESI m/z 529 [M+1]$^+$.

Example 22. Synthesis of Compound MT-022

(2R,3R,4R,5S,6R)-2-(2-((2-hydroxy-3-(2-(trifluoromethyl)-10H-phenothiazin-10-yl)propyl)(methyl)amino)ethyl)-6-(hydroxymethyl)tetrahydro-2H-pyran-3,4,5-triol Step 1

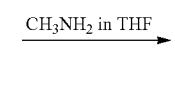

2-1

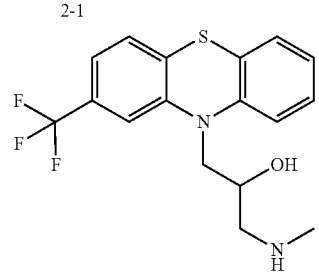

4-1

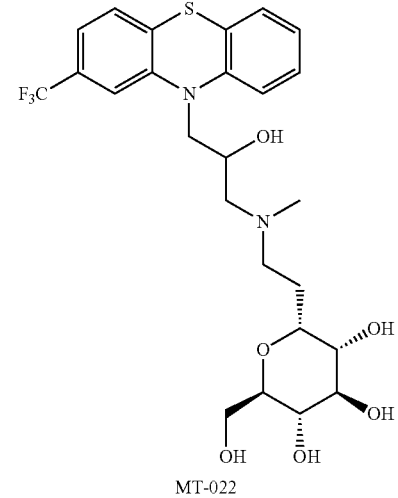

MT-022

2-1 [10-(oxiran-2-ylmethyl)-2-(trifluoromethyl)-10H-phenothiazine] (640 mg, 2 mmol) and K$_2$CO$_3$ (552 mg, 4 mmol) were added to CH$_3$NH$_2$ in THF (2.0 N, 10 mL). The mixture was stirred at 90° C. in a sealed tube for 18 h. The mixture was cooled to rt then H$_2$O was added and then it was extracted with EtOAc (20 mL×3). The combined organic phase was washed with brine, dried over Na$_2$SO$_4$, and concentrated in vacuo. The residue was purified by column chromatography (PE:EtOAc=10:1, 1:1) to get a light brown solid (520 mg, 73%). LC-MS: Rt=1.72 min; ESI m/z 355 [M+1]$^+$.

Step 2

CH$_3$COOH (300 mg, 5 mmol) was added to 4-1[1-(methylamino)-3-(2-(trifluoromethyl)-10H-phenothiazin-10-yl)propan-2-ol] (354 mg, 1 mmol) and A [(3aR,5R,6S,7S,7aR)-5-(hydroxymethyl)hexahydro-2H-furo[3,2-b]

pyran-2,6,7-triol] (412 mg crude, 2 mmol) in C₂H₅OH (20 mL). The mixture was stirred at rt for 20 min. NaBH₃CN (300 mg, 5 mmol) was added and the mixture was stirred at rt for 18 h. The mixture was concentrated in vacuo and the residue was purified by the reverse phase column chromatography (C18 spherical 20-35 μm 100A 120 g; A=H₂O (0.01 mol/L NH₄HCO₃) and B=CH₃CN; 10-95% B over 30 min) to get a white solid (50 mg, 9%).

MT-022

¹H NMR (400 MHz, d⁶-DMSO) δ ppm 7.37-7.26 (m, 2H), 7.24-7.20 (m, 2H), 7.17-7.13 (m, 2H), 6.98 (t, J=7.6 Hz, 1H), 4.91 (dd, J=6.8 Hz, J=4.4 Hz, 1H), 4.82-4.78 (m, 3H), 4.39-4.37 (m, 1H), 4.04-4.01 (m, 1H), 3.87-3.84 (m, 2H), 3.75-3.73 (m, 1H), 3.59-3.55 (m, 1H), 3.41-3.37 (m, 1H), 3.29-3.28 (m, 1H), 3.21-3.19 (m, 1H), 3.02-3.00 (m, 1H), 2.45-2.33 (m, 4H), 2.16 (d, J=6.0 Hz, 3H), 1.69-1.67 (m, 2H), 0.93 (t, J=6.8 Hz, 1H); LC-MS: Rt=1.88 min; ESI m/z 545 [M+1]⁺.

Example 23. Synthesis of Compound MT-023

(2R,3S,4R,5R,6R)-2-(hydroxymethyl)-6-(2-((3-(2-(trifluoromethyl)-10H-phenothiazin-10-yl)propyl)amino)ethyl)tetrahydro-2H-pyran-3,4,5-triol]

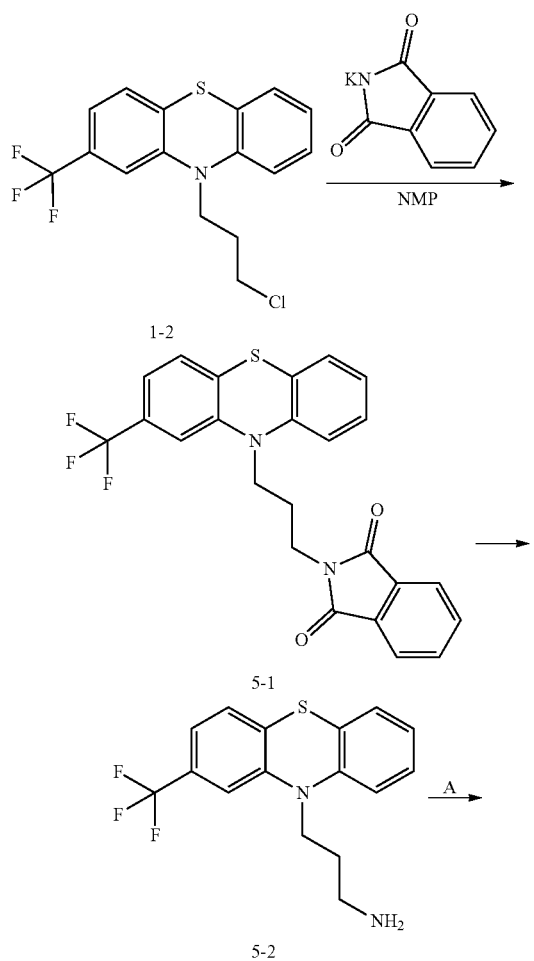

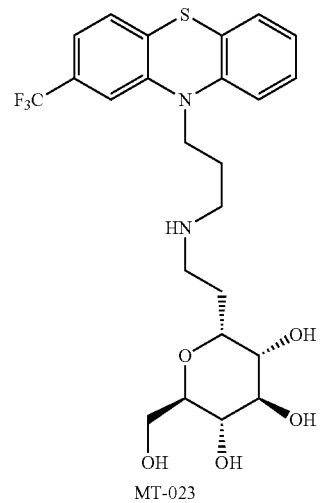

1-(10-(3-chloropropyl)-2-(trifluoromethyl)-10H-phenothiazine) (510 mg, 1.5 mmol) and potassium 1,3-dioxoisoindolin-2-ide (320 mg, 1.7 mmol) in NMP (5 mL) were heated to 80° C. for 18 h. After cooling to rt, 95% EtOH (4 mL) and hydrazine hydrate (4 mL) were added. The mixture was heated to 80° C. for 5 h. The mixture was cooled to rt and the mixture was concentrated in vacuo. H₂O was added, extracted with EtOAc (10 mL×3). The combined organic phase was washed with brine, dried over Na₂SO₄, and concentrated in vacuo. The residue was purified by column chromatography (EtOAc:MeOH=60:1) to get a brown solid (350 mg, 73%).

LC-MS: Rt=1.70 min; ESI m/z 325 [M+1]⁺.

Step 2

CH₃COOH (300 mg, 5 mmol) was added to 5-2 (3-(2-(trifluoromethyl)-10H-phenothiazin-10-yl)propan-1-amine) (324 mg, 1 mmol) and A [(3aR,5R,6S,7S,7aR)-5-(hydroxymethyl)hexahydro-2H-furo[3,2-b]pyran-2,6,7-triol] (313 mg, 1.5 mmol) in ethanol (8 mL). The mixture was stirred at rt for 20 min and then NaBH₃CN (300 mg, 5 mmol) was added. The mixture was stirred at rt for 18 h and then concentrated in vacuo. The residue was purified by the reverse phase column chromatography (C18 spherical 20-35 μm 100A 80 g; A=H₂O (0.01 mol/L NH₄HCO₃) and B=CH₃CN; 5-95% B over 15 min) and prep-HPLC (Waters XBridge C18 OBD (100 mm×19 mm, 5 μm); A=H₂O (0.01 mol/L NH₄HCO₃) and B=CH₃CN; 15-85% B over 12 min) to get a white solid (20 mg, 3%).

MT-023

¹H NMR (400 MHz, MeOD) δ ppm 7.22-7.20 (m, 1H), 7.17-7.12 (m, 3H), 7.08-7.05 (m, 1H), 7.97 (d, J=8.0 Hz, 1H), 6.90 (t, J=7.2 Hz, 1H), 3.97 (t, J=6.4 Hz, 2H), 3.84-3.79 (m, 1H), 3.68-3.65 (m, 1H), 3.51-3.29 (m, 4H), 3.09 (t, J=8.8 Hz, 1H), 2.74-2.67 (m, 3H), 2.64-2.59 (m, 1H), 1.96-1.90 (m, 2H), 1.79-1.75 (m, 2H), 1.20-1.19 (m, 2H).

¹H NMR (400 MHz, d⁶-DMSO) δ ppm 7.35-7.18 (m, 5H), 7.16 (m, 1H), 7.10-6.97 (m, 1H), 6.08 (s, 1H), 4.84-4.78 (m, 2H), 4.00-3.92 (m, 2H), 3.77-3.54 (m, 3H), 3.40-3.38 (m, 1H), 3.25-3.21 (m, 2H), 3.16-2.97 (m, 2H), 2.68-2.54 (m, 3H), 2.33 (s, 1H), 1.82-1.90 (m, 1H), 1.80-1.63 (m, 4H); LC-MS: Rt=1.58 min; ESI m/z 515 [M+1]⁺.

Example 24. Synthesis of Compound MT-024

(2R,3R,4R,5S,6R)-2-(2-((2-hydroxy-3-(2-(trifluoromethyl)-10H-phenothiazin-10-yl)propyl)amino)ethyl)-6-(hydroxymethyl)tetrahydro-2H-pyran-3,4,5-triol

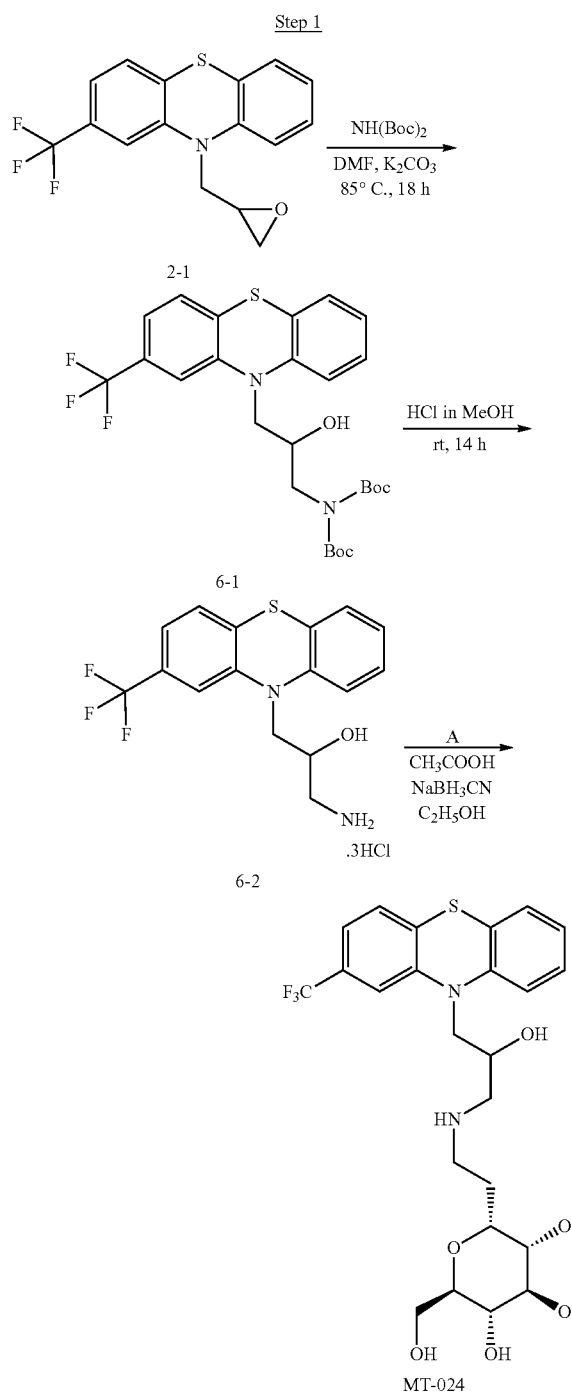

2-1 [10-(oxiran-2-ylmethyl)-2-(trifluoromethyl)-10H-phenothiazine] (600 mg, 1.86 mmol) and $K_2CO_3$ (800 mg, 5.79 mmol) were added to $NH(Boc)_2$ (600 mg, 2.79 mmol) in DMF (15 mL). The mixture was stirred at 80° C. for 18 h. $H_2O$ was added, and mixture was extracted with EtOAc (10 mL×3) The combined organic phase was washed with brine, dried over $Na_2SO_4$, and concentrated in vacuo. The residue was purified by column chromatography (PE:EtOAc=5:1, 3:1) to get a white solid (580 mg, 57.7%).
LC-MS: Rt=2.71 min; ESI m/z 541 [M+1]$^+$.

Step 2

HCl in MeOH (1.0 N, 10 mL) was added to 6-1 [tert-butyl (tert-butoxycarbonyl)(2-hydroxy-3-(2-(trifluoromethyl)-10H-phenothiazin-10-yl)propyl)carbamate] (580 mg, 1.0 mmol). The mixture was stirred at rt for 18 h. The mixture was concentrated in vacuo to get a white solid (440 mg, 90%) which was used directly for the next step.

Step 3

6-2 [1-amino-3-(2-(trifluoromethyl)-10H-phenothiazin-10-yl)propan-2-ol·HCl] (440 mg, 1 mmol) and $Et_3N$ (101 mg, 1 mmol) were stirred in EtOH (20 mL) at rt for 5 min. $CH_3COOH$ (300 mg, 5 mmol) and A [(3aR,5R,6S,7S,7aR)-5-(hydroxymethyl)hexahydro-2H-furo[3,2-b]pyran-2,6,7-triol] (306 mg, 1.5 mmol) were then added, and the mixture was stirred for another 15 min then $NaBH_3CN$ (300 mg, 5 mmol) was added. The mixture was stirred at rt for 18 h. The mixture was concentrated in vacuo. The residue was purified by reverse phase column chromatography (C18 spherical 20-35 μm 100A 80 g; $A=H_2O$ (0.01 mol/L $NH_4HCO_3$) and $B=CH_3CN$; 10-95% B over 30 min) to get a white solid (27 mg, 4%).

MT-024

$^1$H NMR (400 MHz, MeOD) δ ppm 7.34-7.31 (m, 2H), 7.29-7.24 (m, 2H), 7.20-7.18 (m, 1H), 7.14-7.12 (m, 1H), 7.03 (t, J=7.6 Hz, 1H), 4.17-4.07 (m, 2H), 4.00-3.92 (m, 2H), 3.78-3.75 (m, 1H), 3.64-3.62 (m, 1H), 3.61-3.45 (m, 2H), 3.43-3.40 (m, 1H), 3.32-3.20 (m, 1H), 2.97-2.94 (m, 1H), 2.71-2.66 (m, 3H), 1.89-1.83 (m, 2H);

$^1$H NMR (400 MHz, d$^6$-DMSO) δ ppm 7.47-7.34 (m, 2H), 7.27-7.21 (m, 2H), 7.18-7.12 (q, 2H), 6.99 (t, J=7.2 Hz, 1H), 4.96-4.93 (m, 2H), 4.80-4.77 (m, 2H), 4.40-4.39 (m, 1H), 4.02-3.98 (m, 1H), 3.90-3.86 (m, 2H), 3.78-3.75 (m, 1H), 3.58-3.55 (m, 1H), 3.40-3.36 (m, 1H), 3.31-3.19 (m, 3H), 3.03-3.00 (m, 1H), 2.58-2.53 (m, 2H), 2.33 (s, 1H), 1.68-1.62 (m, 3H); LC-MS: Rt=1.53 min; ESI m/z 531 [M+1]$^+$.

Example 25. Synthesis of Compound MT-025

1-(4-(2-(2-(2-methoxyethoxy)ethoxy)ethyl)piperazin-1-yl)-3-(2-(trifluoromethyl)-10H-phenothiazin-10-yl)propan-2-ol

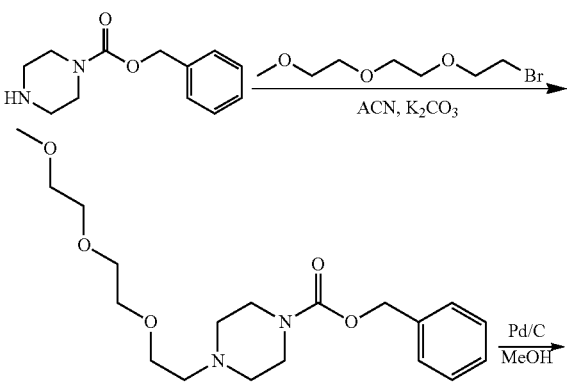

145

-continued

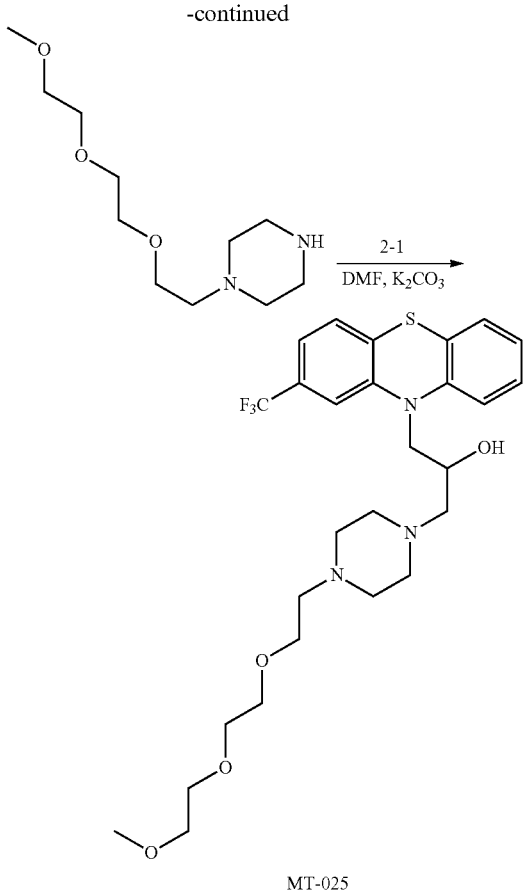

MT-025

Step 1 Synthesis of benzyl 4-(2-(2-(2-methoxyethoxy)ethoxy)ethyl)piperazine-1-carboxylate A mixture of benzyl piperazine-1-carboxylate (400 mg, 1.818 mmol), 1-bromo-2-(2-(2-methoxyethoxy)ethoxy)ethane (620 mg, 2.727 mmol) and K$_2$CO$_3$ (501 mg, 3.636 mmol) in ACN (20 mL) was stirred at 70° C. overnight under a N$_2$ atmosphere. The mixture was cooled to rt, then concentrated in vacuo, and water (10 mL) was added to the residue and the mixture was extracted with EtOAc (15 mL×3), the combined organic phases were washed with brine (50 mL). The organic layer was dried over anhydrous Na$_2$SO$_4$ and then concentrated in vacuo. The residue was purified by column chromatography on silica gel (PE: EtOAc=10:1-6:1) to give a colorless oil (500 mg, 82%).

Step 2 Synthesis of 1-(2-(2-(2-methoxyethoxy)ethoxy)ethyl)piperazine

A mixture of benzyl 4-(2-(2-(2-methoxyethoxy)ethoxy)ethyl)piperazine-1-carboxylate (500 mg, 1.36 mmol) and Pd/C (30 mg) in MeOH (50 mL) was stirred at room temperature overnight under H$_2$. The mixture was filtered through Celite and the pad was washed with MeOH. The filtrate was concentrated to get crude compound which was used without purification in the next step.

Step 3

To a solution of 1-(2-(2-(2-methoxyethoxy)ethoxy)ethyl)piperazine (400 mg, 1.23 mmol) in DMF (4 mL) was added

146

2-1 [10-(oxiran-2-ylmethyl)-2-(trifluoromethyl)-10H-phenothiazine] (900 mg, 2.476 mmol) and K$_2$CO$_3$ (103 mg, 0.74 mmol), and the reaction mixture was stirred at 80° C. overnight. The mixture was cooled to rt, and then it was added to water (10 mL) and extracted with EtOAc (10 mL×3). The combined organic layers were washed with brine (10 mL), dried over sodium sulfate, and concentrated to dryness. The residue was purified by prep-HPLC (Waters XBridge C18 (50 mm×4.6 mm, 3.5 μm); A=H$_2$O (0.01 mol/L NH$_4$HCO$_3$) and B=CH$_3$CN; 15-85% B over 8 min) to afford a light-yellow oil (50 mg, 7.2% yield).

MT-025

$^1$H NMR (400 MHz, d$^6$-DMSO) δ ppm 7.32-7.12 (m, 6H), 6.98-6.94 (m, 1H), 4.85 (d, J=4.4 Hz, 1H), 4.06-4.04 (m, 1H), 3.87-3.84 (m, 2H), 3.49-3.38 (m, 10H), 3.21 (s, 3H), 2.42-2.29 (m, 11H); LC-MS: Rt=2.21 min; ESI m/z 556 [M+1]$^+$.

Example 26. Synthesis of Compound MT-026

(S)-3-(4-(3-(2-(trifluoromethyl)-10H-phenothiazin-10-yl)propyl)piperazin-1-yl)propane-1,2-diol

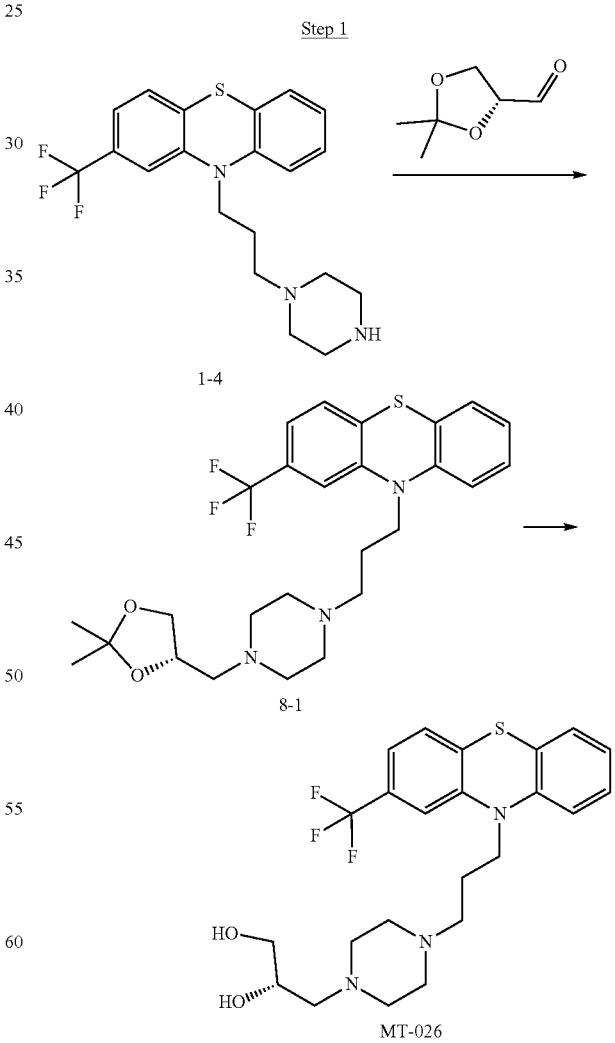

NaBH(CH$_3$COO)$_3$ (840 mg, 4 mmol) was added to 1-4 [10-(3-(piperazin-1-yl)propyl)-2-(trifluoromethyl)-10H- phenothiazine] (400 mg, 1 mmol) and (R)-2,2-dimethyl-1,3-dioxolane-4-carbaldehyde (400 mg, 3 mmol) in CH₂Cl₂ (10 mL) and MeOH (5 mL). The reaction was stirred at rt for 8 h. The mixture was concentrated in vacuo. The residue was purified by column chromatography (PE:EtOAc=10:1-3:1) to get a light brown oil (330 mg, 69.6%).

LC-MS: Rt=2.69 min; ESI m/z 508 [M+1]⁺.

Step 2

1.3 N HCl (8 mL) was added to 8-1 [(S)-10-(3-(4-((2,2-dimethyl-1,3-dioxolan-4-yl)methyl)piperazin-1-yl)propyl)-2-(trifluoromethyl)-10H-phenothiazine] (200 mg, 0.39 mmol) in THF (8 mL). The mixture was stirred at rt for 4 h. NaHCO₃ was added to adjust pH=9. The mixture was extracted with EtOAc (10 mL×3). The combined organic phase was washed with brine, dried over Na₂SO₄, and concentrated in vacuo. The residue was purified by reverse phase column chromatography (C18 spherical 20-35 μm 100A 120 g; A=H₂O (0.01 mol/L NH₄HCO₃) and B=CH₃CN; 10-95% B over 40 min) to get a yellow paste (22 mg, 12%).

MT-026

¹H NMR (400 MHz, d⁶-DMSO) δ ppm 7.35-7.33 (m, 1H), 7.26-7.21 (m, 3H), 7.17-7.15 (m, 1H), 7.10-7.08 (m, 1H), 6.98 (t, J=7.6 Hz, 1H), 4.53 (m, 1H), 4.35 (d, J=4.0 Hz, 1H), 4.99 (t, J=6.4 Hz, 2H), 3.56-3.54 (m, 1H), 3.31-3.27 (m, 2H), 2.78-2.14 (m, 12H), 1.78-1.75 (m, 2H); LC-MS: Rt=2.16 min; ESI m/z 468 [M+1]⁺.

Example 27. Synthesis of Compound MT-027

(2S)-3-(4-(2-hydroxy-3-(2-(trifluoromethyl)-10H-phenothiazin-10-yl)propyl)piperazin-1-yl)propane-1,2-diol Step 1 Synthesis of 1-(4-(((S)-2,2-dimethyl-1,3-dioxolan-4-yl)methyl)piperazin-1-yl)-3-(2-(trifluoromethyl)-10H-phenothiazin-10-yl)propan-2-ol

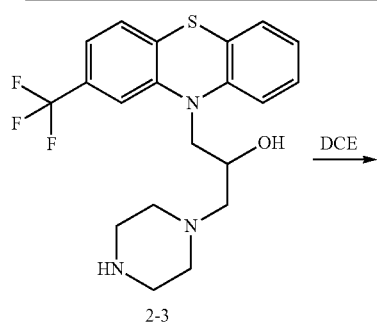

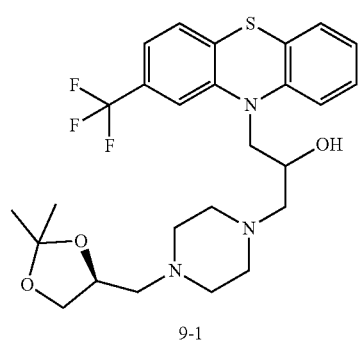

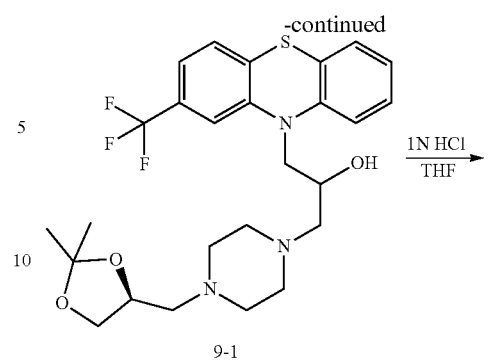

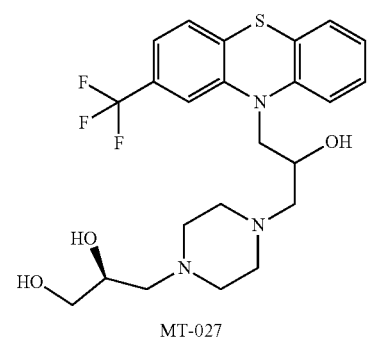

To a solution of 2-3 [1-(piperazin-1-yl)-3-(2-(trifluoromethyl)-10H-phenothiazin-10-yl)propan-2-ol HCl] (200 mg, 0.489 mmol) and (S)-2,2-dimethyl-1,3-dioxolane-4-carbaldehyde (95 mg, 0.7335) in DCE (10 mL) was added NaHB(OAc)₃ (207 mg, 0.978 mmol), and the reaction mixture was stirred at rt overnight. Then the mixture was added to water (20 mL) and extracted with DCM (10 mL×3). The combined organic layers were washed with brine (20 mL), dried over sodium sulfate and concentrated to dryness. The residue was purified by prep-HPLC (Waters XBridge C18 OBD (250 mm×19 mm, 5 μm); A=H₂O (0.01 mol/L NH₄HCO₃) and B=CH₃CN; 15-85% B over 8 min) to afford a white solid (150 mg, 53% yield).

Step 2

A solution of 9-1 [1-(4-(((S)-2,2-dimethyl-1,3-dioxolan-4-yl)methyl)piperazin-1-yl)-3-(2-(trifluoromethyl)-10H-phenothiazin-10-yl)propan-2-ol] (300 mg, 0.59 mmol) in 1 N HCl (10 mL) and THF (10 mL) was stirred at rt. The solvent was removed under reduced pressure and the residue was purified by prep-HPLC (Waters X-Bridge C18 OBD 5 μm 30*100 mm); A=H₂O (0.01 mol/L NH₄HCO₃) and B=CH₃CN; 10-70% B over 7 min) to get 80 mg white solid (58% yield).

MT-027

¹H NMR (400 MHz, d⁶-DMSO) δ ppm 7.31-7.12 (m, 6H), 6.98-6.94 (m, 1H), 4.87 (s, 1H), 4.50 (s, 1H), 4.33 (s, 1H), 4.06-4.02 (m, 1H), 3.87-3.83 (m, 2H), 3.55-3.53 (m, 1H), 3.28 (m, 2H), 2.42-2.12 (m, 12H); LC-MS: Rt=1.98 min; ESI m/z 484 [M+1]⁺.

Example 28. Synthesis of Compound MT-028

(S)—N-(2,3-dihydroxypropyl)-2-(4-(3-(2-(trifluoromethyl)-10H-phenothiazin-10-yl)propyl)piperazin-1-yl)acetamide

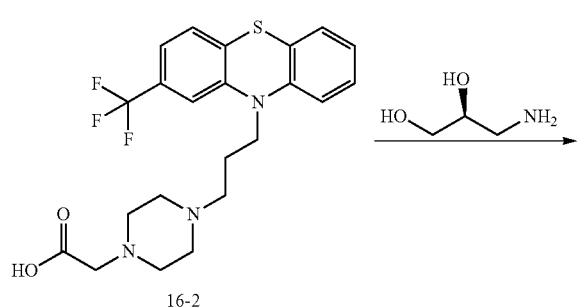

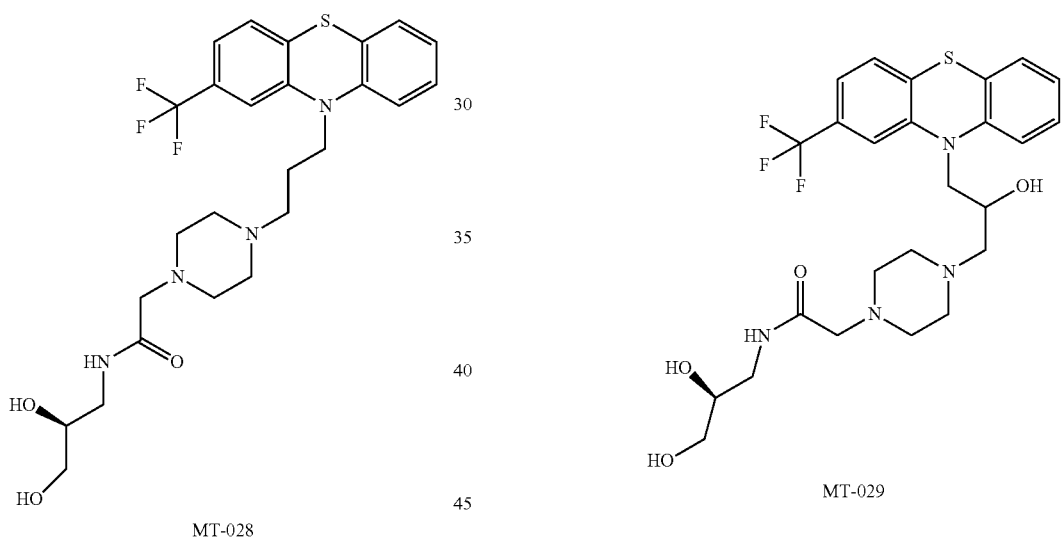

Compound 16-2 salt [2-(4-(3-(2-(trifluoromethyl)-10H-phenothiazin-10-yl)propyl)piperazin-1-yl)acetic acid] (400 mg, 0.51 mol), Et$_3$N (505 mg, 5 mmol) and HATU (570 mg, 1.5 mol) were stirred in DMF for 5 min and then (S)-3-aminopropane-1,2-dio (91 mg, 1 mmol) was added. The mixture was stirred at rt for 18 h. The mixture was purified by reverse phase column chromatography (C18 spherical 20-35 μm 100A 120 g; A=H$_2$O (0.01 mol/L NH$_4$HCO$_3$) and B=CH$_3$CN; 10-95% B over 35 min) to provide a white solid (100 mg, 32%).
MT-028
$^1$H NMR (400 MHz, d$^6$-DMSO) δ ppm 7.58 (t, J=6 Hz, 1H), 7.35-7.33 (m, 1H), 7.26-7.21 (m, 3H), 7.18-7.15 (m, 1H), 7.10-7.08 (m, 1H), 6.99 (t, J=7.2 Hz, 1H), 4.80 (d, J=4.8 Hz, 1H), 4.58 (t, J=6.0 Hz, 1H), 4.00 (t, J=6.5 Hz, 2H), 3.47-3.46 (m, 1H), 3.31-3.21 (m, 4H), 3.03 (m, 1H), 2.84 (s, 2H), 2.41-2.33 (m, 9H), 1.77 (t, J=6.4 Hz, 2H); LC-MS: Rt=2.10 min; ESI m/z 525 [M+1]$^+$.

Example 29. Synthesis of Compound MT-029

N—((S)-2,3-dihydroxypropyl)-2-(4-(2-hydroxy-3-(2-(trifluoromethyl)-10H-phenothiazin-10-yl)propyl)piperazin-1-yl)acetamide

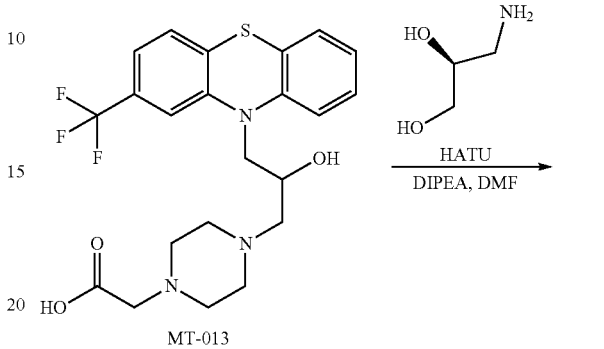

To a solution of MT-013 [2-(4-(2-hydroxy-3-(2-(trifluoromethyl)-10H-phenothiazin-10-yl)propyl)piperazin-1-yl) acetic acid](150 mg, 0.32 mmol), DIPEA (123.84 mg, 0.96 mmol) and (S)-3-aminopropane-1,2-diol (58 mg, 0.64 mmol) in DCM (200 mL) was added HATU (304 mg, 0.8 mmol), and the reaction mixture was stirred at rt overnight. Then the mixture was added to water (30 mL) and extracted with DCM (200 mL×3). The combined organic layers were washed with brine (30 mL), dried over sodium sulfate, and concentrated to dryness. The residue was purified by prep-HPLC (Waters XBridge C18 OBD (250 m×19 mm, 5 μm); A=H$_2$O (0.01 mol/L NH$_4$HCO$_3$) and B=CH$_3$CN; 15-85% B over 8 min) to afford a white solid (80 mg, 46.2% yield).
MT-029
$^1$H NMR (400 MHz, d$^6$-DMSO) δ ppm 7.59 (t, J=6.0 Hz, 1H), 7.35-7.15 (m, 6H), 7.01-6.97 (m, 1H), 4.91-4.82 (m, 2H), 4.60 (m, 1H), 4.10-4.07 (m, 1H), 3.91-3.88 (m, 2H), 3.49-3.48 (m, 1H), 3.32-3.24 (m, 3H), 3.04 (m, 1H), 2.87-2.85 (m, 2H), 2.48-2.35 (m, 9H); LC-MS: Rt=1.84 min; ESI m/z 541 [M+1]$^+$.

151

Example 30. Synthesis of Compound MT-030

8-(3-(2-(trifluoromethyl)-10H-phenothiazin-10-yl) propyl)-1,3,8-triazaspiro[4.5]decane-2,4-dione

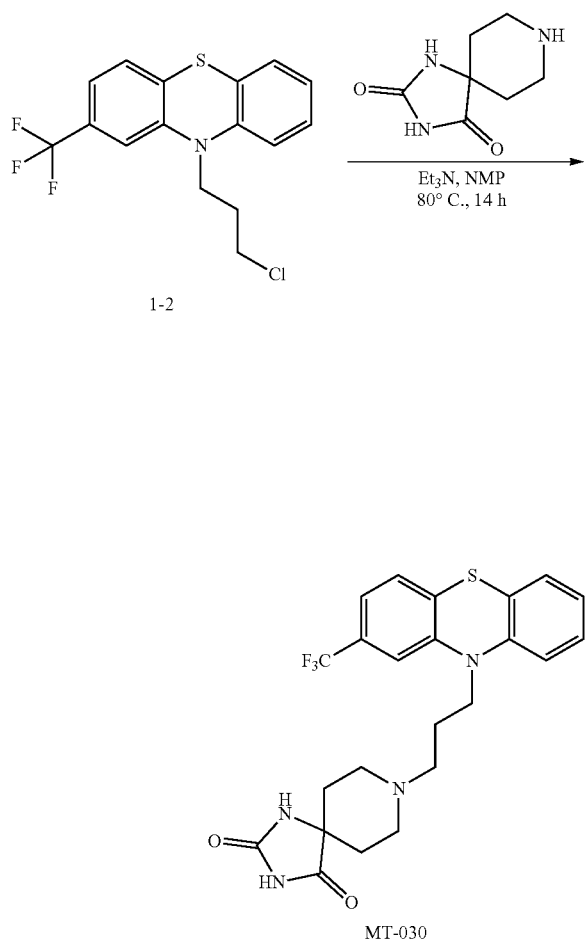

MT-030

Et₃N (180 mg, 1.8 mmol) was added to 1-1 (200 mg, 0.58 mmol) and 1,3,8-triazaspiro[4.5]decane-2,4-dione (100 mg, 0.6 mmol) in NMP (5 mL). The mixture was heated to 80° C. for 14 h. The mixture was cooled to rt, filtered and the filtrate was concentrated. The residue was purified by prep-HPLC, (Waters XBridge C18 (50 mm×4.6 mm, 3.5 μm); A=H₂O (0.01 mol/L NH₄HCO₃) and B=CH₃CN; 15-85% B over 12 min) to get a white solid (40 mg, 14.5%).

MT-030

¹H NMR (400 MHz, d⁶-DMSO) δ ppm 10.54 (s, 1H), 8.39 (s, 1H), 7.36-7.34 (m, 1H), 7.26-7.22 (m, 3H), 7.18-7.16 (m, 1H), 7.11-7.09 (m, 1H), 7.01-6.97 (m, 1H), 4.00 (t, J=6.4 Hz, 2H), 2.67-2.64 (m, 2H), 2.43 (t, J=6.8 Hz, 2H), 2.22 (t, J=9.6 Hz, 2H), 1.82-1.70 (m, 4H), 1.45 (d, J=12.8 Hz, 2H); LC-MS: Rt=2.61 min; ESI m/z 477 [M+1]⁺.

152

Example 30a. Synthesis of Compound MT-030a 3-(3-(2-(trifluoromethyl)-10H-phenothiazin-10-yl) propyl)-1,3,8-triazaspiro[4.5]decane-2,4-dione Step 1

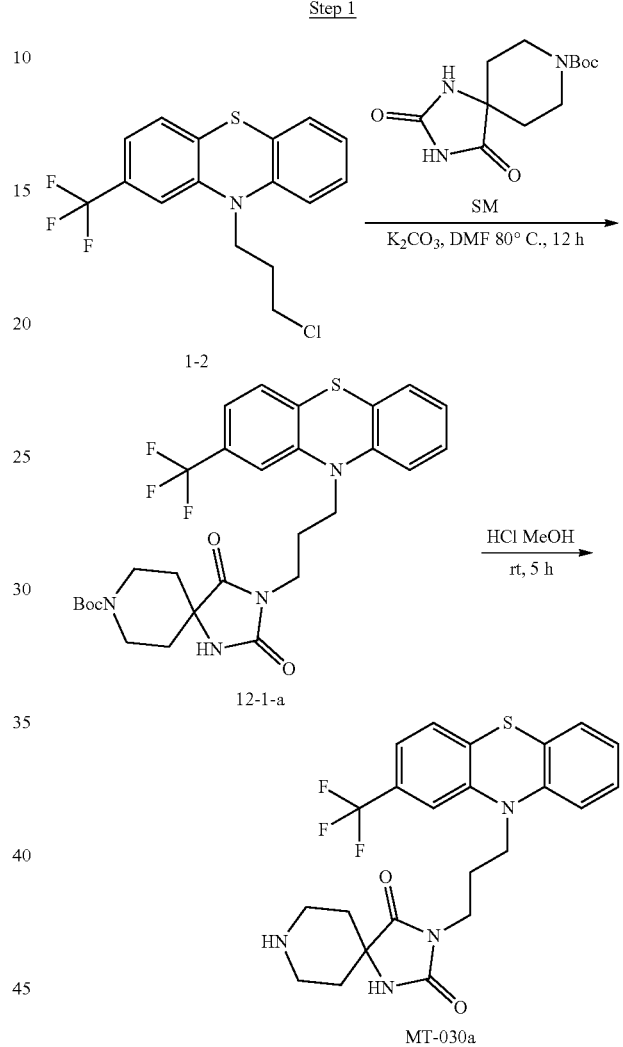

MT-030a

To a solution of 1-2 10-(3-chloropropyl)-2-(trifluoromethyl)-10H-phenothiazine (400 mg, 1.17 mmol) and K₂CO₃ (480 mg, 3.50 mmol) in DMF (10 mL) was added tert-butyl 2,4-dioxo-1,3,8-triazaspiro[4.5]decane-8-carboxylate (333 mg, 1.24 mmol), and the reaction mixture was stirred at 80° C. overnight. Then the mixture was concentrated to dryness. The residue was purified by prep-HPLC (Waters XBridge C18 (50 mm×4.6 mm, 3.5 μm); A=H₂O (0.01 mol/L NH₄HCO₃) and B=CH₃CN; 15-95% B over 8 min) to afford a white solid (410 mg, 60.8% yield).

LC-MS: Rt=2.51 min; ESI m/z 577 [M+1]⁺.

Step 2

HCl in MeOH (1.0 N, 20 mL) was added to 12-1-a tert-butyl 2,4-dioxo-3-(3-(2-(trifluoromethyl)-10H-phenothiazin-10-yl)propyl)-1,3,8-triazaspiro[4.5]decane-8-carboxylate (280 mg, 0.49 mmol). The mixture was stirred at rt for 18 h. The mixture was concentrated in vacuo. The residue was dissolved in EtOAc (30 mL) and MeOH (5 mL).

The organic phase was washed with Na₂CO₃ (2.0 N, 20 mL), dried over Na₂SO₄, and concentrated in vacuo to get a white solid (200 mg, 85.7%) MT-030a ¹H NMR (400 MHz, d⁶-DMSO) δ ppm 8.74 (s, 1H), 7.37 (d, J=6 Hz, 1H), 7.27-7.18 (m, 4H), 7.04-6.99 (m, 2H) 3.93 (q, J=6.8 Hz, 2H), 3.47 (q, J=6.8 Hz, 2H), 2.83-2.79 (m, 2H), 2.69-2.64 (m, 2H), 1.95-1.92 (m, 2H), 1.67-1.62 (m, 2H); 1.35-1.32 (m, 2H), 1.23 (s, 1H); LC-MS: Rt=2.13 min; ESI m/z 477 [M+1]⁺.

Example 31. Synthesis of Compound MT-031

8-(2-hydroxy-3-(2-(trifluoromethyl)-10H-phenothi-azin-10-yl)propyl)-1,3,8-triazaspiro[4.5]decane-2,4-

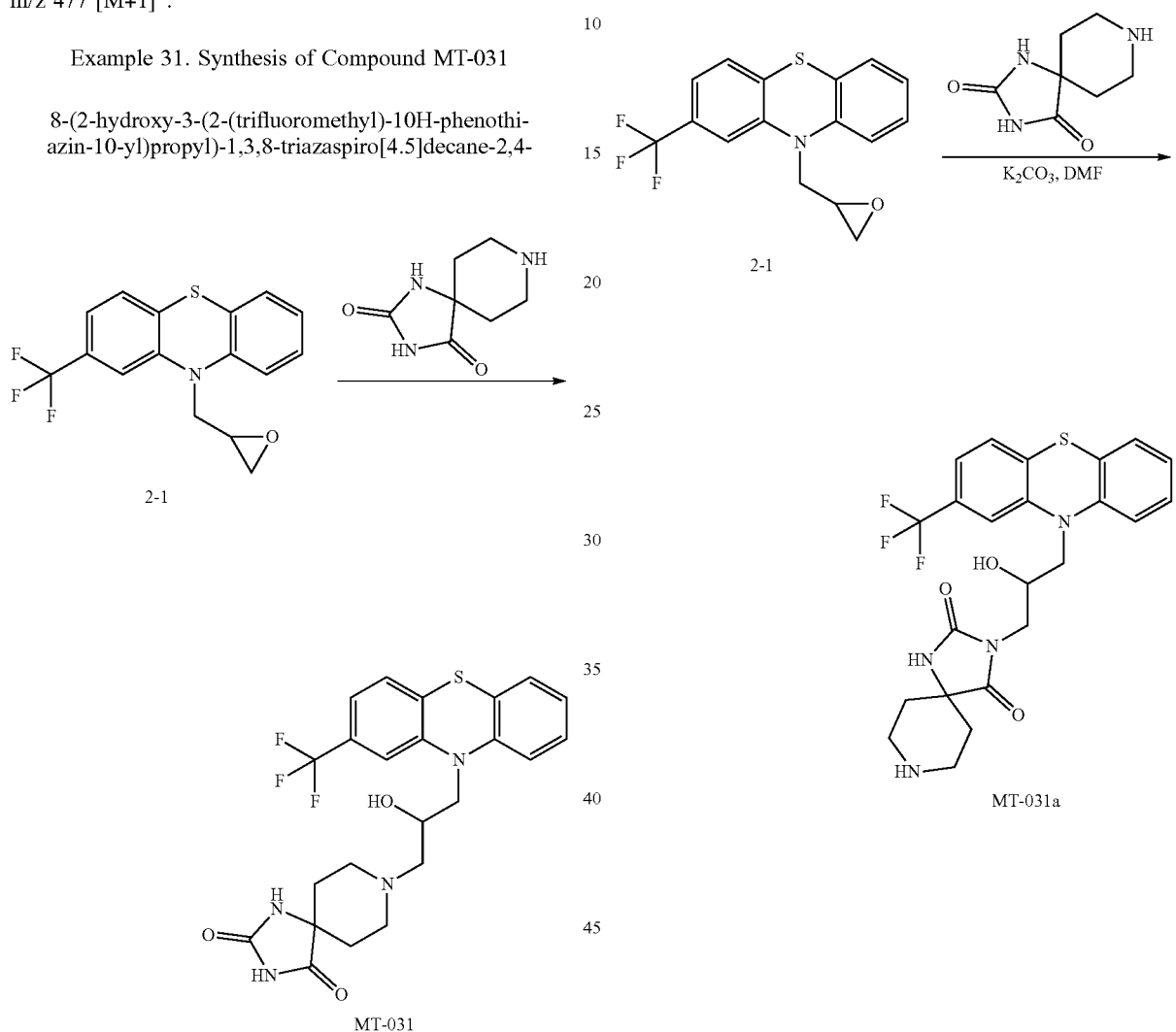

MT-031

To a solution of 2-1 10-(oxiran-2-ylmethyl)-2-(trifluoromethyl)-10H-phenothiazine (100 mg, 0.31 mmol) in DMF (10 mL) was added 1,3,8-triazaspiro[4.5]decane-2,4-dione (210 mg, 1.24 mmol), and the reaction mixture was stirred at 80° C. overnight. Then the mixture was concentrated to dryness. The residue was purified by prep-HPLC (Waters XBridge C18 (50 mm×4.6 mm, 3.5 μm); A=H₂O (0.01 mol/L NH₄HCO₃) and B=CH₃CN; 15-85% B over 8 min) to afford a white solid (25 mg, 21% yield).
MT-031

¹H NMR (400 MHz, d⁶-DMSO) δ ppm 10.59 (s, 1H), 8.38 (s, 1H), 7.35-7.33 (m, 2H), 7.26-7.16 (m, 4H), 7.01-6.97 (m, 1H), 4.87 (d, J=4.0 Hz, 1H), 4.10-4.07 (m, 1H), 3.89-3.87 (m, 2H), 2.74-2.68 (m, 2H), 2.46-2.31 (m, 4H), 1.79-1.75 (m, 2H), 1.44 (d, J=12.8 Hz, 2H); LC-MS: Rt=2.04 min; ESI m/z 493 [M+1]⁺.

Example 31a. Synthesis of Compound MT-031a 3-(2-hydroxy-3-(2-(trifluoromethyl)-10H-phenothi-azin-10-yl)propyl)-1,3,8-triazaspiro[4.5]decane-2,4-dione

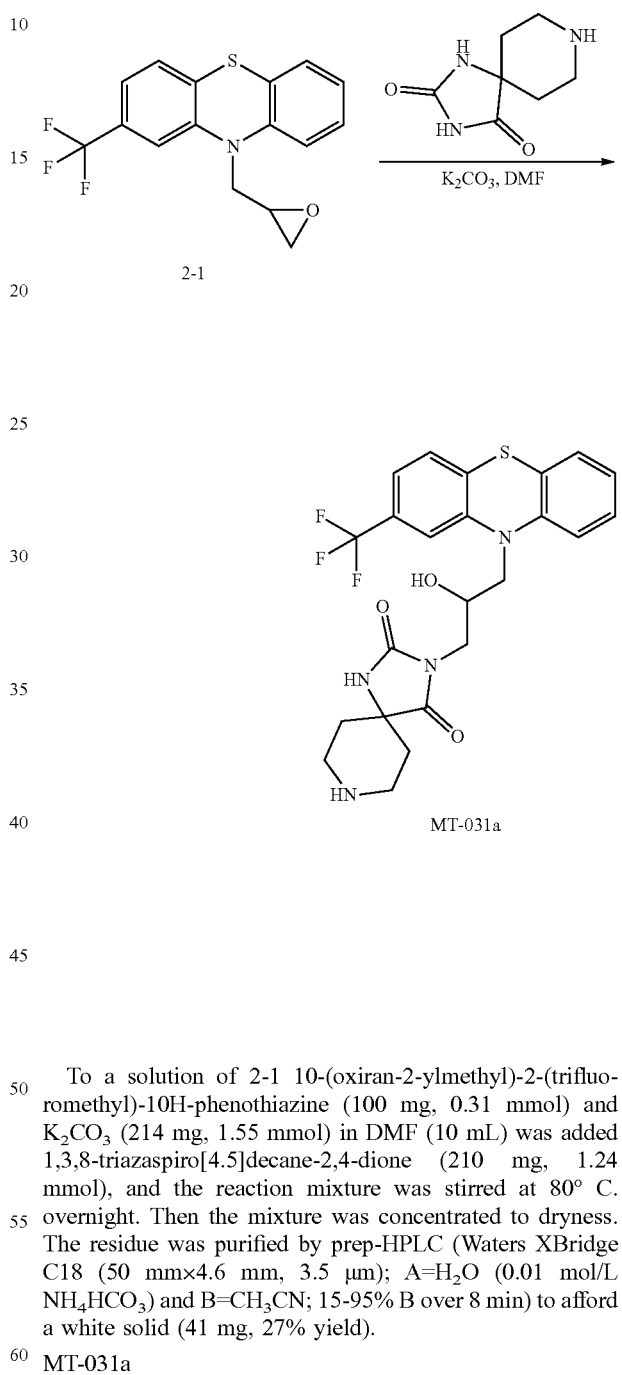

MT-031a

To a solution of 2-1 10-(oxiran-2-ylmethyl)-2-(trifluoromethyl)-10H-phenothiazine (100 mg, 0.31 mmol) and K₂CO₃ (214 mg, 1.55 mmol) in DMF (10 mL) was added 1,3,8-triazaspiro[4.5]decane-2,4-dione (210 mg, 1.24 mmol), and the reaction mixture was stirred at 80° C. overnight. Then the mixture was concentrated to dryness. The residue was purified by prep-HPLC (Waters XBridge C18 (50 mm×4.6 mm, 3.5 μm); A=H₂O (0.01 mol/L NH₄HCO₃) and B=CH₃CN; 15-95% B over 8 min) to afford a white solid (41 mg, 27% yield).
MT-031a ¹H NMR (400 MHz, d⁶-DMSO) δ ppm 8.69 (s, 1H), 7.36-7.34 (d, J=7.6 Hz, 1H), 7.28-7.17 (m, 4H), 7.05-6.98 (m, 2H), 5.26-5.25 (d, J=6.0 Hz, 1H), 4.12-4.10 (m, 1H), 3.97-3.92 (m, 2H), 3.45-3.43 (m, J=6.4 Hz, 2H), 2.84-2.64 (m, 4H), 1.95 (s, 1H), 1.67-1.63 (m, 2H); 1.40-1.32 (m, 2H); LC-MS: Rt=1.63 min; ESI m/z 493 [M+1]⁺.

Example 32. Synthesis of Compound MT-032

8-(2-hydroxy-3-(2-(trifluoromethyl)-10H-phenothi-azin-10-yl)propyl)-1,3,8-triazaspiro[4.5]decan-4-one

Example 33. Synthesis of Compound MT-033

8-(2-hydroxy-3-(2-(trifluoromethyl)-10H-phenothi-azin-10-yl)propyl)-1,3,8-triazaspiro[4.5]decan-2-one

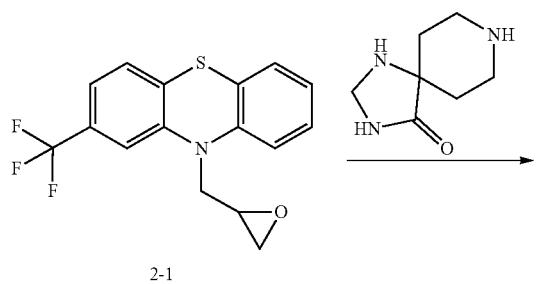

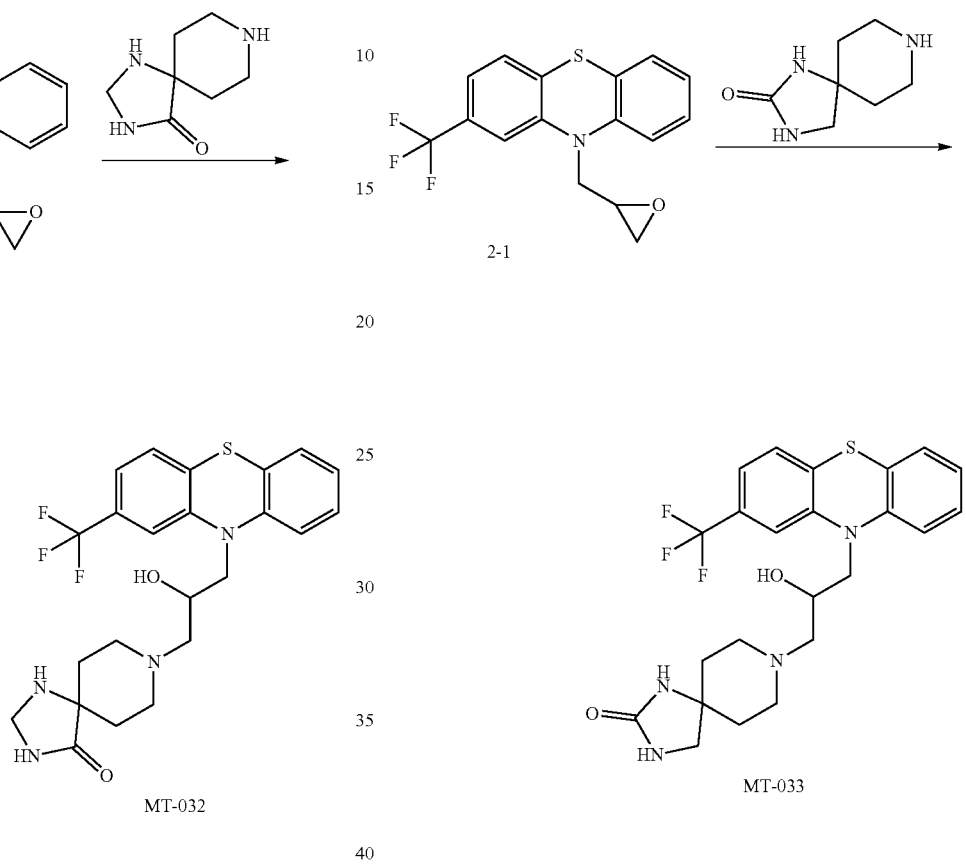

To a solution of compound 2-1 [10-(oxiran-2-ylmethyl)-2-(trifluoromethyl)-10H-phenothiazine] (100 mg, 0.31 mmol) in DMF (10 mL) was added 1,3,8-triazaspiro[4.5]decan-4-one (72 mg, 0.464 mmol) and $K_2CO_3$ (90 mg, 0.62 mmol), and the reaction mixture was stirred at 80° C. overnight. The mixture was cooled to rt. Then the mixture was added to water (10 mL) and extracted with EtOAc (10 mL×3). The combined organic layers were washed with brine (20 mL), dried over sodium sulfate, and concentrated to dryness. The residue was purified by prep-HPLC (Waters XBridge C18 (50 mm×4.6 mm, 3.5 μm); A=$H_2O$ (0.01 mol/L $NH_4HCO_3$) and B=$CH_3CN$; 10-85% B over 8 min) to afford a white solid (30 mg, 20% yield).

MT-032

$^1$H NMR (400 MHz, $d^6$-DMSO) δ ppm 7.95 (s, 1H), 7.35-7.33 (m, 2H), 7.26-7.16 (m, 4H), 7.01-6.97 (m, 1H), 4.85 (s, 1H), 4.09-4.05 (m, 3H), 3.88-3.83 (m, 2H), 2.98 (t, J=8.4 Hz, 1H), 2.67-2.64 (m, 2H), 2.46-2.32 (m, 2H), 2.26-2.19 (m, 2H), 1.66-1.60 (m, 2H), 1.33 (d, J=13.2 Hz, 2H); LC-MS: Rt=1.97 min; ESI m/z 479 [M+1]$^+$.

To a solution of compound 2-1 [10-(oxiran-2-ylmethyl)-2-(trifluoromethyl)-10H-phenothiazine] (200 mg, 0.62 mmol) in DMF (10 mL) was added 1,3,8-triazaspiro[4.5]decan-2-one (144 mg, 0.928 mmol) and $K_2CO_3$ (171 mg, 1.24 mmol), and the reaction mixture was stirred at 80° C. overnight. Then the mixture was cooled to rt. The mixture was added to water (10 mL) and extracted with EtOAc (10 mL×3). The combined organic layers were washed with brine (10 mL), dried over sodium sulfate, and concentrated to dryness. The residue was purified by prep-HPLC (Waters XBridge C18 (50 mm×4.6 mm, 3.5 μm); A=$H_2O$ (0.01 mol/L $NH_4HCO_3$) and B=$CH_3CN$; 15-80% B over 8 min) to afford a white solid (40 mg, 13.5% yield).

MT-033

$^1$H NMR (400 MHz, $d^6$-DMSO) δ ppm 7.35-7.33 (m, 2H), 7.26-7.15 (m, 4H), 7.01-6.97 (m, 1H), 6.53 (s, 1H), 6.09 (s, 1H), 4.86 (d, J=4.8 Hz, 1H), 4.08-4.05 (m, 1H), 3.87-3.85 (m, 2H), 3.03 (s, 2H), 2.53-2.51 (m, 2H), 2.43-2.41 (m, 1H), 2.36-2.33 (m, 1H), 2.25 (brs., 2H), 1.55-1.48 (m, 4H); LC-MS: Rt=1.96 min; ESI m/z 479 [M+1]$^+$.

Example 34. Synthesis of Compound MT-034

(S)-3-hydroxy-2-(2-(4-(3-(2-(trifluoromethyl)-10H-phenothiazin-10-yl)propyl)piperazin-1-yl)acetamido)propenamide

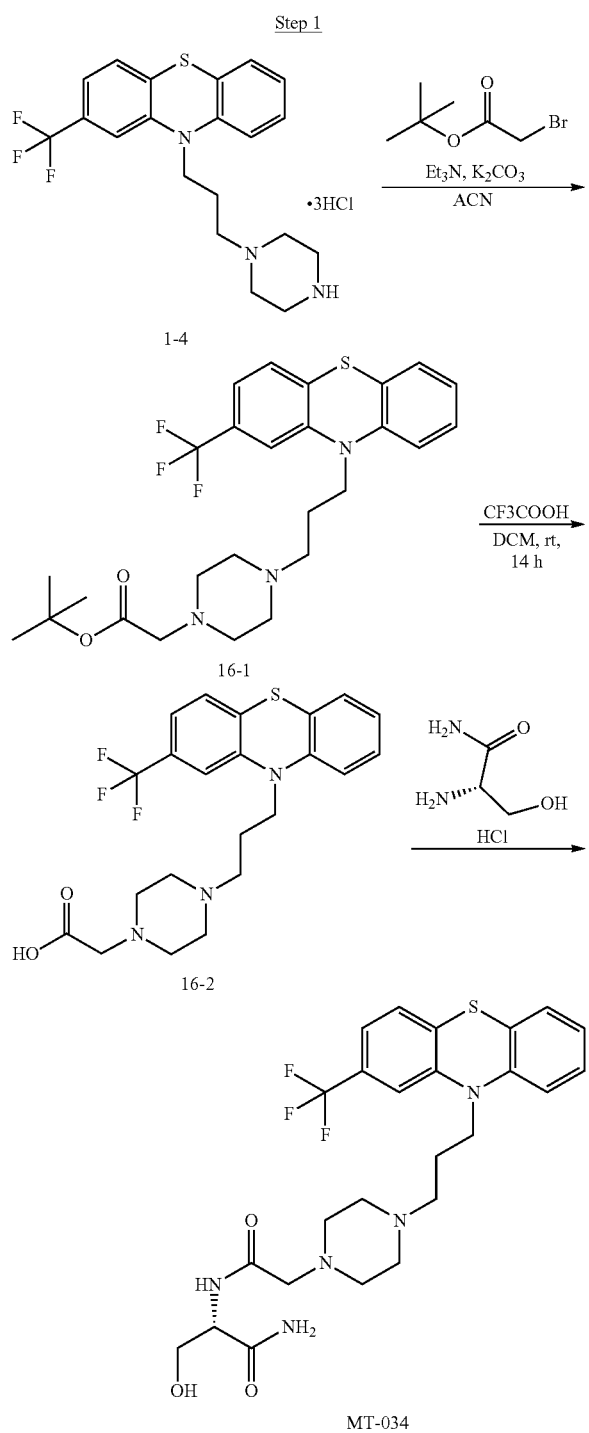

Et$_3$N (2.8 g, 27.7 mmol) was added to 1-3 [10-(3-(piperazin-1-yl)propyl)-2-(trifluoromethyl)-10H-phenothiazine tris HCl] (2.8 g, 5.57 mmol), K$_2$CO$_3$ (2.8 g, 20 mmol) and tert-butyl 2-bromoacetate (2.8 g, 14.4 mmol) in ACN (10 mL). The mixture was stirred at rt for 18 h. The mixture was filtrated and the filtrate was concentrated in vacuo and purified by column chromatography (PE:EtOAc=5:1) to get a light yellow oil (2.8 g, 98%).

LC-MS: Rt=2.81 min; ESI m/z 508 [M+1]$^+$.

Step 2

Compound 16-1 [tert-butyl 2-(4-(3-(2-(trifluoromethyl)-10H-phenothiazin-10-yl)propyl)piperazin-1-yl)acetate] (2.8 g, 5.5 mmol) was added to CF$_3$COOH (12 mL) in DCM (12 mL). The mixture was stirred at rt for 18 h and then concentrated in vacuo. The residue was purified by the reverse phase column chromatography (C18 spherical 20-35 μm 100A 330 g; A=H$_2$O (0.01 mol/L NH$_4$HCO$_3$) and B=CH$_3$CN; 5-95% B over 30 min) to get a white solid (2.0 g, 45.5%). LC-MS: Rt=1.86 min; ESI m/z 452 [M+1]$^+$.

Step 3

Compound 16-2 [2-(4-(3-(2-(trifluoromethyl)-10H-phenothiazin-10-yl)propyl)piperazin-1-yl)acetic acid] (400 mg, 0.51 mol), Et$_3$N (505 mg, 5 mmol) and HATU (570 mg, 1.5 mol) were stirred in DMF for 5 min, and then (S)-2-amino-3-hydroxypropanamide HCl (146 mg, 1 mmol) was added. The mixture was stirred at rt for 18 h. The mixture was then purified by the reverse phase column chromatography (C18 spherical 20-35 μm 100A 120 g; A=H$_2$O (0.01 mol/L NH$_4$HCO$_3$) and B=CH$_3$CN; 5-95% B over 25 min) to get a white solid (70 mg, 29%).

MT-034

$^1$H NMR (400 MHz, d$^6$-DMSO) δ ppm 7.66 (d, J=8.0 Hz, 1H), 7.38-7.33 (m, 2H), 7.26-7.22 (m, 3H), 7.18-7.15 (m, 1H), 7.10-7.08 (m, 2H), 6.99 (t, J=7.6 Hz, 1H), 4.93 (t, J=5.6 Hz, 1H), 4.20-4.17 (m, 1H), 4.00 (t, J=7.2 Hz, 2H), 3.64-3.60 (m, 1H), 3.55-3.52 (m, 1H), 2.87 (s, 2H), 2.46-2.27 (m, 9H), 1.78 (t, J=6.4 Hz, 2H), 0.93 (t, J=6.8 Hz, 1H); LC-MS: Rt=2.06 min; ESI m/z 538 [M+1]$^+$.

Example 35. Synthesis of Compound MT-035

(1-(3-(2-(trifluoromethyl)-10H-phenothiazin-10-yl)propyl)piperidin-4-yl)methyl)aminosulfonamide

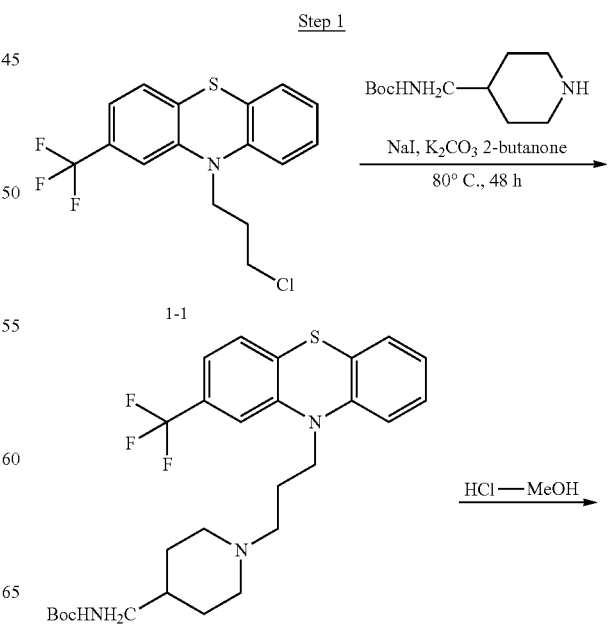

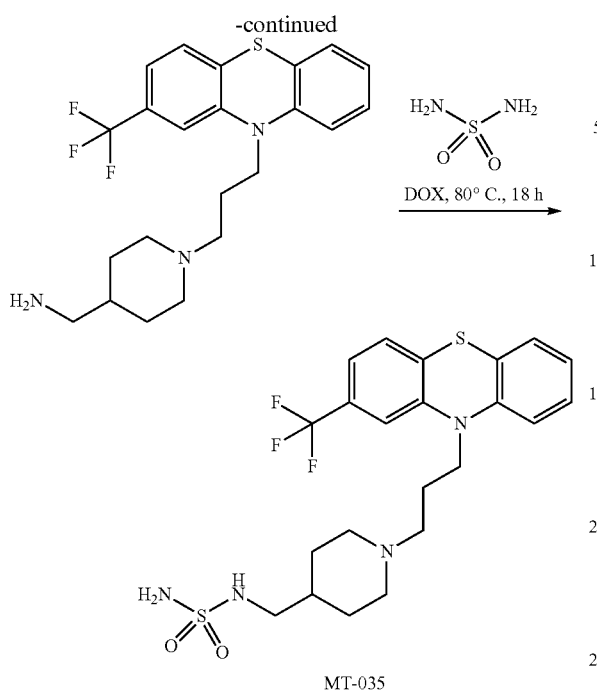

MT-035

NaI (225 mg, 1.5 mmol) and K2CO3 (414 mg, 3 mmol) were added to 1-1 [10-(3-chloropropyl)-2-(trifluoromethyl)-10H-phenothiazine] (515 mg, 1.5 mmol) and tert-butyl piperidin-4-ylmethylcarbamate (479 mg, 2.25 mmol) in 2-butanone (8 mL). The mixture was heated to 80° C. for 48 h. The mixture was cooled to rt and concentrated in vacuo. The residue was purified by column chromatography (PE: EtOAc=50%-100%) to get a yellow solid (750 mg, 95.9%). LC-MS: Rt=1.88 min; ESI m/z 522 [M+1]+.

Step 2

HCl in MeOH (1.0 N, 10 mL) was added to 17-1 [tert-butyl ((1-(3-(2-(trifluoromethyl)-10H-phenothiazin-10-yl)propyl)piperidin-4-yl)methyl)carbamate] (520 mg, 1 mmol). The mixture was stirred at rt for 18 h. The mixture was concentrated in vacuo to get a yellow solid (350 mg, 72%) which was used directly for the next step.

LC-MS: Rt=1.53 min; ESI m/z 422 [M+1]+.

Step 3

Et3N (500 mg, 5 mmol) was added to 17-2 [(1-(3-(2-(trifluoromethyl)-10H-phenothiazin-10-yl)propyl)piperidin-4-yl)methanamine] HCl (250 mg, 0.64 mmol) and sulfuric diamide (300 mg, 3.1 mmol) in 1,4-dioxane (10 mL). The mixture was heated to 80° C. for 18 h. The mixture was cooled to rt and concentrated in vacuo. The residue was purified by prep-HPLC, (Waters XBridge C18 OBD (250 mm×19 mm, 5 µm); A=H2O (0.01 mol/L NH4HCO3) and B=CH3CN; 15-85% B over 12 min) to get a yellow solid (36 mg, 11%).

MT-035

1H NMR (400 MHz, d6-DMSO) δ ppm 7.33-7.31 (m, 1H), 7.23-7.13 (m, 4H), 7.08-7.06 (m, 1H), 6.96 (t, J=7.2 Hz, 1H), 6.45-6.40 (m, 2H), 3.96 (t, J=6.4 Hz, 2H), 2.73-2.61 (m, 4H), 2.34 (m, 2H), 1.80-1.75 (m, 4H), 1.61-1.55 (m, 2H), 1.34 (m, 1H), 1.00-0.92 (m, 2H); LC-MS: Rt=2.28 min; ESI m/z 501 [M+1]+.

Example 36. Synthesis of Compound MT-036

Intermediate Synthesis: Synthesis of 2-1 10-(oxiran-2-ylmethyl)-2-(trifluoromethyl)-10H-phenothiazine

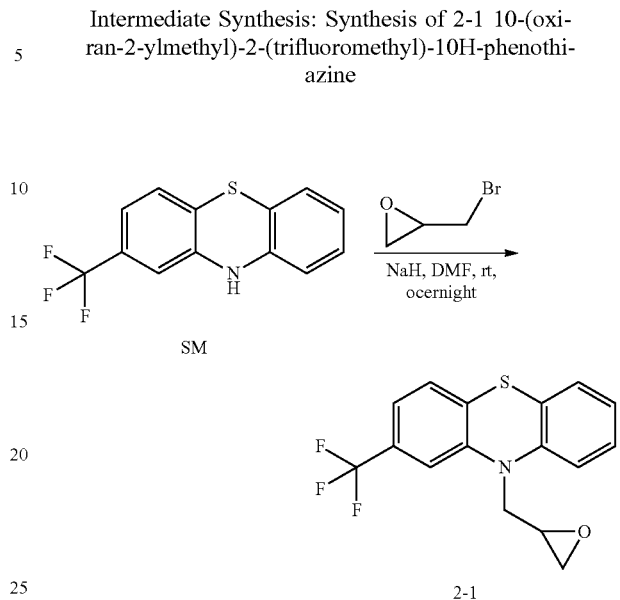

To a mixture of 2-(trifluoromethyl)-10H-phenothiazine (5.0 g, 18.726 mmol) and NaH (0.674 g, 28.09 mmol) in DMF (50 mL) was added 2-(bromomethyl)oxirane (3.8 g, 28.09 mmol) at 0° C. The mixture was allowed to slowly warm to rt and was stirred at room temperature overnight. Then the mixture was added to water (100 mL) and extracted with EtOAc (100 mL×3). The combined organic layers were washed with brine (30 mL), dried over sodium sulfate, and concentrated to dryness. The residue was purified by column chromatography on silica gel (PE/EtOAc=8/1) to afford compound 2-1 (4.5 g, 75% yield) as a white solid. 1H NMR (400 MHz, d6-DMSO) δ ppm 7.40-7.34 (m, 2H), 7.29-7.22 (m, 2H), 7.19-7.17 (m, 1H), 7.13-7.18 (d, J=7.6 Hz, 1H), 7.03-6.99 (m, 1H), 4.44-4.40 (m, 1H), 3.83-3.78 (m, 1H), 3.28-3.24 (m, 1H), 2.89-2.87 (t, J=4.8 Hz, 1H), 2.79-2.77 (m, 1H).

Intermediate Synthesis: Synthesis of 13-2-(piperazin-1-yl)-3-(2-(trifluoromethyl)-10H-phenothiazin-10-yl)propan-2-ol Step 1

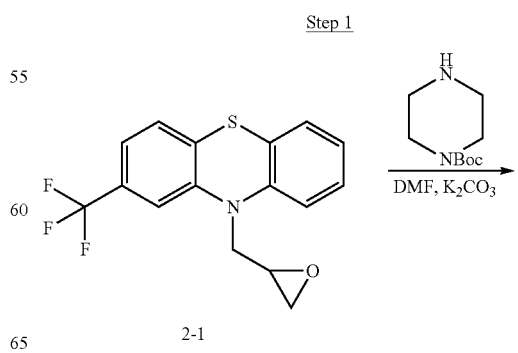

2-1

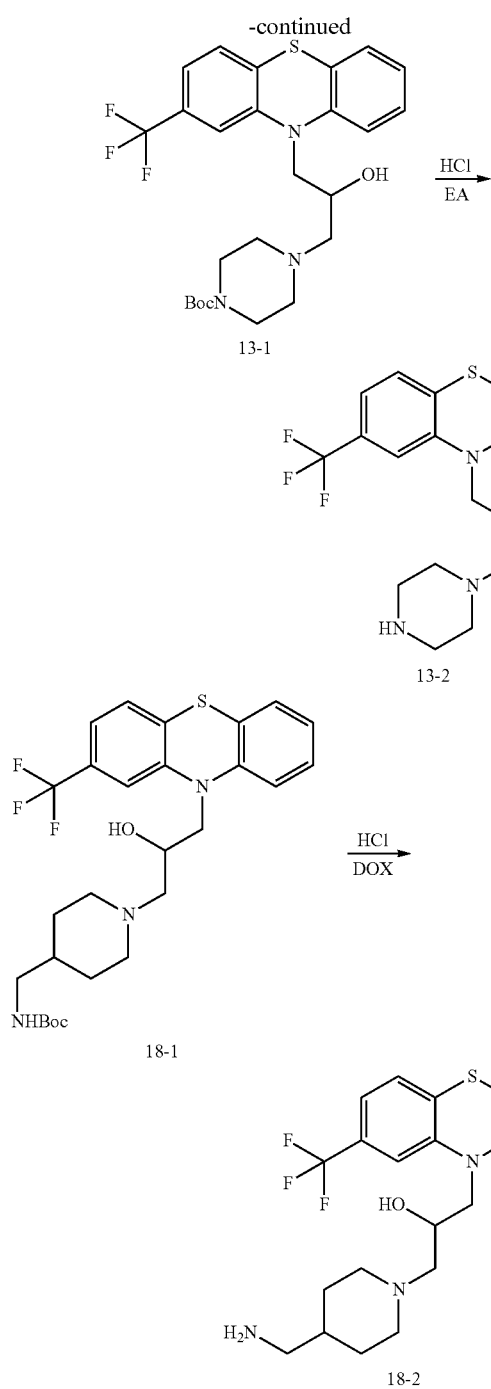

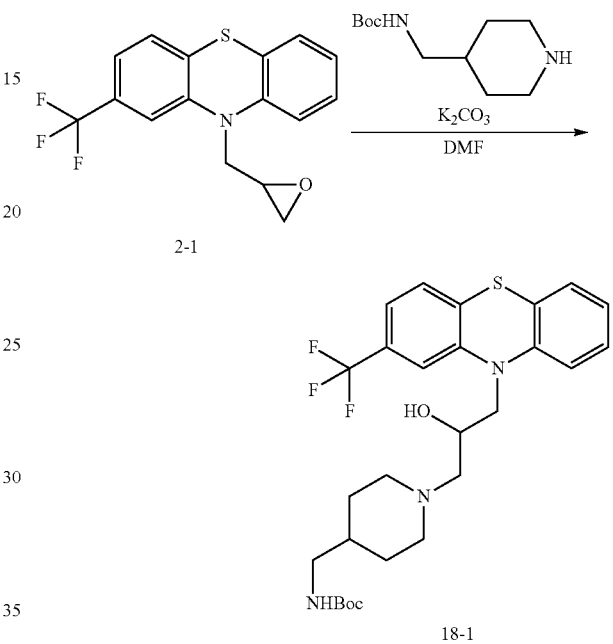

A mixture of tert-butyl piperazine-1-carboxylate (3.5 g, 18.6 mmol), 2-1 (3 g, 9.3 mmol) and K₂CO₃ (5.13 g, 37.15 mmol) in DMF (80 mL) was stirred at 80° C. overnight. The mixture was cooled to rt, and water (100 mL) was added and the mixture was then extracted with EtOAc (50 mL×3). The combine organic phase was dried over Na₂SO₄, filtered, and concentrated under reduced pressure to get crude compound, purified column chromatography (DCM/PE=2/1) to get a white solid (1.5 g, 33% yield).

Step 2

A solution of 13-1 [tert-butyl 4-(2-hydroxy-3-(2-(trifluoromethyl)-10H-phenothiazin-10-yl)propyl)piperazine-1-carboxylate] (0.3 g, 0.59 mmol) in 4N HCl in EtOAc (40 mL) was stirred at rt overnight and the solvent was removed under reduced pressure to get crude product. The crude product was purified by prep-HPLC (Waters XBridge C18 OBD (250 mm×19 mm, 5 μm); A=H₂O (0.01 mol/L NH₄HCO₃) and B=CH₃CN; 15-85% B over 8 min) to get a white solid (200 mg, 83% yield).

Intermediate synthesis 18-2 1-(4-(aminomethyl)piperidin-1-yl)-3-(2-(trifluoromethyl)-10H-phenothiazin-10-yl)propan-2-ol

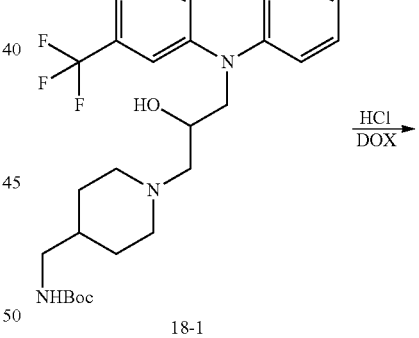

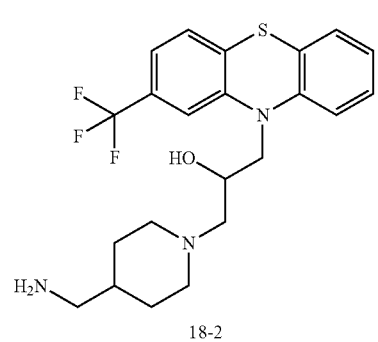

Step 1 Synthesis of 18-1 tert-butyl ((1-(2-hydroxy-3-(2-(trifluoromethyl)-10H-phenothiazin-10-yl)propyl)piperidin-4-yl)methyl)carbamate To a solution of compound 2-1 (2 g, 0.62 mmol) and tert-butylpiperidin-4-ylmethylcarbamate (3.5 g, 24.76 mmol) in DMF (10 mL) was added K$_2$CO$_3$ (2.65 g, 12.4 mmol), and the reaction mixture was stirred at 80° C. overnight. Then the mixture was added to water (50 mL) and extracted with EtOAc (50 mL×3). The combined organic layers were washed with brine (100 mL), dried over sodium sulfate, and concentrated to dryness. The residue was purified by prep-HPLC (Waters XBridge C18 OBD (250 mm×19 mm, 5 μm); A=H$_2$O (0.01 mol/L NH$_4$HCO$_3$) and B=CH$_3$CN; 15-95% B over 8 min) to afford a white solid (2.5 g, 80% yield).

Step 2 Synthesis of 18-2 1-(4-(aminomethyl)piperidin-1-yl)-3-(2-(trifluoromethyl)-10H-phenothiazin-10-yl)propan-2-ol A solution of 18-1 (800 mg, 1.49 mmol) in 4N HCl in 1,4-dioxane (30 mL) was stirred at room temperature overnight, and the solvent was removed in vacuo. The residue was purified by prep-HPLC (Waters XBridge C18 OBD (250 mm×19 mm, 5 μm); A=H$_2$O (0.01 mol/L NH$_4$HCO$_3$) and B=CH$_3$CN; 10-95% B over 10 min) to get a white solid (600 mg, 92.16% yield).

Synthesis of Compound MT-036

N-((1-(2-hydroxy-3-(2-(trifluoromethyl)-10H-phenothiazin-10-yl)propyl)piperidin-4-yl)methyl)methanesulfonamide

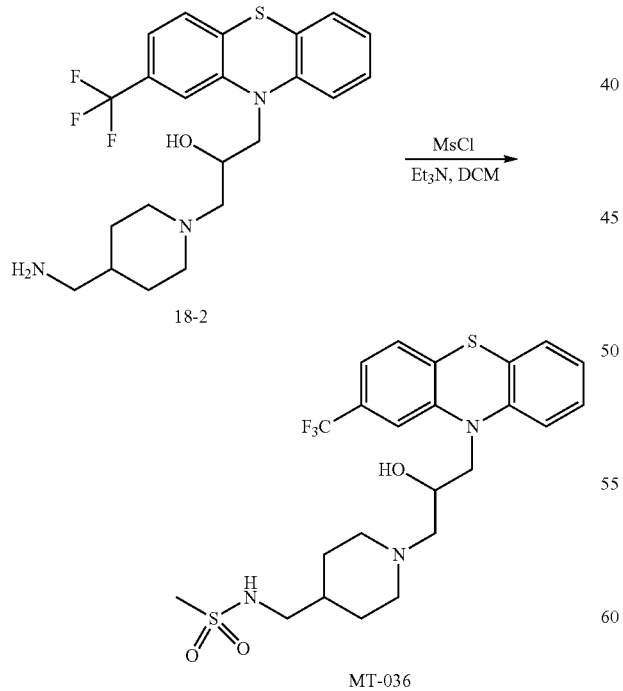

MT-036

To a solution of compound 18-2 1-(4-(aminomethyl)piperidin-1-yl)-3-(2-(trifluoromethyl)-10H-phenothiazin-10-yl)propan-2-ol] (200 mg, 0.4576 mmol) and Et$_3$N (116 mg, 1.144 mmol) in DCM (20 mL) was added MsCl (63 mg, 0.55 mmol), and the reaction solution was stirred at rt overnight. Then the solution was added to water (20 mL) and extracted with DCM (20 mL×3). The combined organic layers were washed with brine (20 mL), dried over sodium sulfate, and concentrated to dryness. The residue was purified by prep-HPLC (Waters XBridge C18 (50 mm×4.6 mm, 3.5 μm); A=H$_2$O (0.01 mol/L NH$_4$HCO$_3$) and B=CH$_3$CN; 15-85% B over 8 min) to afford a white solid (55 mg, 23.4% yield).

MT-036

$^1$H NMR (400 MHz, d$^6$-DMSO) δ ppm 7.34-7.33 (m, 2H), 7.26-7.15 (m, 4H), 7.00-6.95 (m, 2H), 4.85 (d, J=4.0 Hz, 1H), 4.06 (m, 1H), 3.88-3.85 (m, 2H), 2.86 (s, 3H), 2.82-2.74 (m, 4H), 2.41-2.34 (m, 2H), 1.95-1.91 (m, 2H), 1.60 (d, J=12.0 Hz, 2H), 1.34-1.32 (t, J=12.0 Hz, 1H), 1.07-1.00 (m, 2H).

$^1$H NMR (400 MHz, d$^6$-DMSO and D$_2$O) δ ppm 7.36-7.33 (m, 2H), 7.27-7.15 (m, 4H), 7.02-6.98 (m, 1H), 4.07-4.05 (m, 1H), 3.89-3.85 (m, 2H), 2.87 (s, 3H), 2.81-2.75 (m, 4H), 2.46-2.32 (m, 2H), 1.97-1.89 (q, 2H), 1.60 (d, J=12.4 Hz, 2H), 1.34-1.32 (m, 1H), 1.07-1.01 (m, 2H); LC-MS: Rt=2.20 min; ESI m/z 516 [M+1]$^+$.

Example 37. Synthesis of Compound MT-037

(1-(3-(2-(trifluoromethyl)-10H-phenothiazin-10-yl)propyl)piperidin-4-yl)methyl)aminosulfonamide

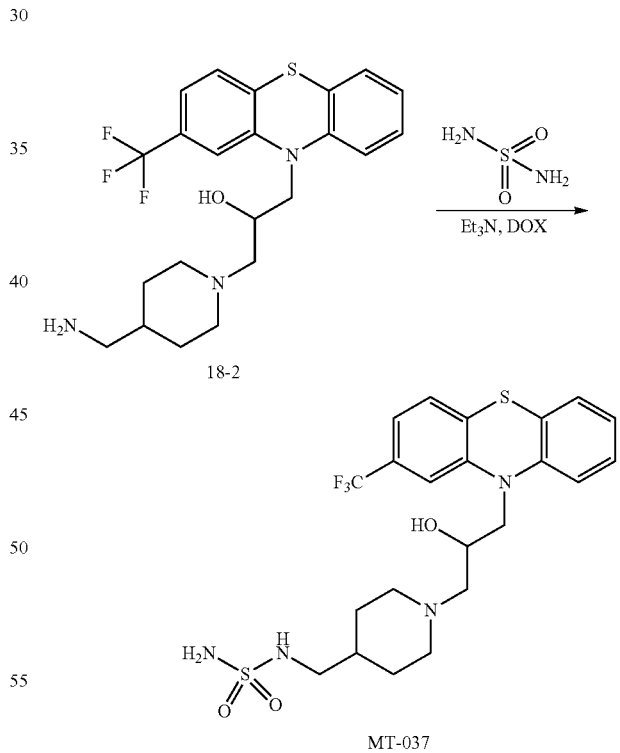

MT-037

To a solution of compound 18-2 [1-(4-(aminomethyl)piperidin-1-yl)-3-(2-(trifluoromethyl)-10H-phenothiazin-10-yl)propan-2-ol] (200 mg, 0.4576 mmol) and Et$_3$N (116 mg, 1.144 mmol) in 1,4-dioxane (20 mL) was added sulfuric diamide (220 mg, 2.29 mmol), and the reaction solution was stirred at 90° C. overnight. Then the solution was added to water (20 mL) and extracted with EtOAc (20 mL×3). The combined organic layers were washed with brine (20 mL), dried over sodium sulfate, and concentrated to dryness. The residue was purified by prep-HPLC (Waters XBridge C18 (50 mm×4.6 mm, 3.5 μm); A=H$_2$O (0.01 mol/L NH$_4$HCO$_3$) and B=CH$_3$CN; 15-95% B over 8 min) to afford a white solid (35 mg, 14.8% yield).

MT-037

$^1$H NMR (400 MHz, d$^6$-DMSO) δ ppm 7.32-7.13 (m, 6H), 6.98-6.94 (m, 1H), 6.46-6.41 (m, 3H), 4.83 (s, 1H), 4.05-4.03 (m, 1H), 3.86-3.81 (m, 2H), 2.78-2.65 (m, 4H), 2.42-2.28 (m, 2H), 1.95-1.86 (q, 2H), 1.60 (d, J=12.4 Hz, 2H), 1.36-1.34 (m, 1H), 1.03-0.97 (m, 2H); LC-MS: Rt=2.10 min; ESI m/z): 517 [M+1]$^+$.

Example 38. Synthesis of Compound MT-038

1-((1-(2-hydroxy-3-(2-(trifluoromethyl)-10H-phenothiazin-10-yl)propyl)piperidin-4-yl)methyl)urea

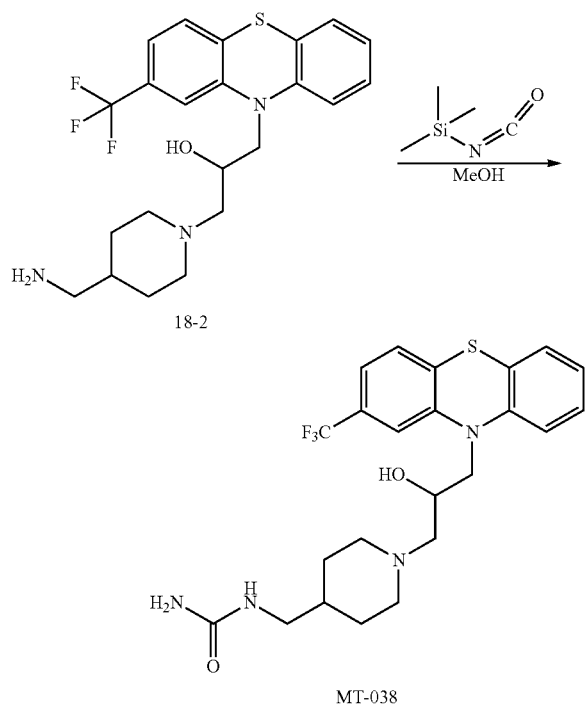

A solution of compound 18-2 [1-(4-(aminomethyl)piperidin-1-yl)-3-(2-(trifluoromethyl)-10H-phenothiazin-10-yl) propan-2-ol] (200 mg, 0.4576 mmol) in isocyanatotrimethylsilane (5 mL) was stirred at rt overnight. Then the solution was added to MeOH (10 mL) and stirred at rt for 2 h. Then the solution was added to water and extracted with EtOAc (20 mL×3). The combined organic layers were washed with brine (20 mL), dried over sodium sulfate, and concentrated to dryness. The residue was purified by prep-HPLC (Waters XBridge C18 (50 mm×4.6 mm, 3.5 μm); A=H$_2$O (0.01 mol/L NH$_4$HCO$_3$) and B=CH$_3$CN; 15-95% B over 8 min) to afford a white solid (30 mg, 13.6% yield).

MT-038

$^1$H NMR (400 MHz, d$^6$-DMSO) δ ppm 7.35-7.15 (m, 6H), 7.01-6.97 (m, 1H), 5.96 (t, J=5.6 Hz, 1H), 5.35 (s, 2H), 4.86 (d, J=4.4 Hz, 1H), 4.08-4.05 (m, 1H), 3.91-3.84 (m, 2H), 2.81-2.78 (m, 4H), 2.44-2.30 (m, 2H), 1.96-1.87 (q, 2H), 1.52 (d, J=11.6 Hz, 2H), 1.25-1.22 (m, 1H), 1.06-0.98 (m, 2H); LC-MS: Rt=2.02 min; ESI m/z 481 [M+1]$^+$.

Example 39: Experimental Procedures

Fluorescence Polarization Assay

A competition-based fluorescence polarization assay was developed to evaluate calmodulin (CaM) binding. The assay measures changes in fluorescence polarization (FP) of a given fluorescent peptide probe (16B05 ortho isomer or 17F07 ortho isomer, characterized previously in Dagher et al., Biochim Biophys Acta. 2006 November; 1763(11): 1250-5) upon binding of a competitive test compound to CaM. Fluorescence polarization is calculated from the relative intensity of emitted light in the planes normal and orthogonal to the plane of the incident polarized light. The CaM-bound probe gives a higher fluorescence polarization value than the CaM-free probe. When there is no competitor (e.g., a CaM inhibitor) present, the fluorescent probe remains bound to CaM and displays a high fluorescence polarization value. In the presence of a competitor, the fluorescent probe is displaced from CaM, resulting in a decrease in the fluorescence polarization signal. Thus, by measuring the difference in fluorescence polarization, the extent of binding of a test compound to CaM can be calculated.

Fluorescent peptide probes were designed according to Dagher et al. 2006 and synthesized by ChemPartner (Shanghai, China). All peptides displayed positive spectrum in liquid chromatography-mass spectrometry (LC-MS) analysis and showed >99% purity in high-performance liquid chromatography (HPLC) analysis. 16B05 was tested for binding with serial dilutions (1-500 nM) of full-length recombinant human calmodulin (Millipore, Cat. No. 208670) in an assay buffer containing 50 mM HEPES pH 7.5, 0.01% (w/v) Triton X-100 and 100 μM CaCl$_2$) at room temperature for 0 min, 15 min, and 30 min, and 60 min. The binding affinity of the fluorescent peptide probe to CaM, reported as the equilibrium dissociation constant (Kd), measured in all four sets of experiments was between 80-100 nM, in agreement with previously reported Kd of 67 nM (Dagher et al., Biochim Biophys Acta. 2006 November; 1763(11):1250-5). The result was stable within 1 hour.

The competition binding assay was performed in a 384-well plate format and in 20 μl reactions. Serial dilutions (0.001-100 μM) of a test compound were incubated with CaM in the presence of 16B05 at room temperature for 30 min. The final binding reagent contained 50 nM of CaM and 5 nM of 16B05 in the assay buffer (50 mM HEPES pH 7.5, 0.01% (w/v) Triton X-100 and 100 μM CaCl$_2$). Each plate contained two types of control wells, containing either 5 nM fluorescent probe bound to 50 nM CaM (bound state, maximum read) or 5 nM unbound probe alone (free state, minimum read) in the assay buffer. Reference compounds Trifluoperazine (CP-Chengdu, Barcode 20008599), A-3 hydrochloride (Sigma, Cat. No. A1980), and A-7 (Tocris Bioscience, Cat. No. 0378) were also included. Upon completion of the incubation, fluorescence polarization degrees (excitation at 531 nm, emission at 595 nm) were measured on the EnVision Microplate Reader (PerkinElmer). Data analysis was performed according to Audran et al., Biochim Biophys Acta. 1833 (2013) 1720-1731. Fluorescence decay was plotted against log concentration of the compound and half maximal inhibitory concentration (IC$_{50}$) was calculated by XLfit version 4.3.1 (ID Business Solutions) with a 4-parameter logistic model or sigmoidal dose-response model.

The suitability of the assay for high-throughput screening applications can be evaluated by analyzing the statistical quality parameter Z' factor (Iversen et al., J. Biomol.

Screen., 11 (2006), pp. 247-252). The value of Z' factor was calculated using the equation:

$$Z' = 1 - (3SD_{bound} + 3SD_{free})/(MP_{bound} - mP_{free}),$$

where SD is the standard deviation and mP is the fluorescence polarization expressed as P×1000, where P stands for the polarization degree. The "bound state" is represented by the fluorescent probe bound to the CaM and the "free state" is represented by the unbound fluorescent probe prepared in the assay buffer.

Cell Permeability Assays

A Caco-2 cell permeability assay was used to screen compounds for intestinal absorption and identify P-glycoprotein (P-gp) or breast cancer resistance protein (BCRP) substrates. Caco-2 cells are a human colon epithelial cancer cell line used as a model of human intestinal absorption of drugs and other compounds (van Breemen and Li, Expert Opin Drug Metab Toxicol. 2005 August; 1(2):175-85). The cells have characteristics that resemble intestinal epithelial cells such as the formation of a polarized monolayer, well-defined brush border on the apical surface and intercellular junctions. Prior to the experiment, Caco-2 cells were seeded on a Millipore Millicell plate and allowed to form a confluent monolayer over 20 days. On day 20, a test compound was added to either the apical side (toward the intestinal lumen, for A→B transport) of the cell monolayer or the basolateral side (toward the blood stream, for B→A transport) of the cell monolayer. The transport of the compound across the monolayer was monitored over a 2-hour time period. After incubation, the assay was stopped after by separating apical insert from basolateral well. Both apical and basolateral samples were collected and the the concentration of the compounds in each sample was determined using LC-MS/MS. Integrity of the cells was monitored during incubation by inclusion of a non-permeable probe, Lucifer Yellow.

A MDCK-MDR1 cell permeability assay was used to evaluate blood brain barrier permeability and identify P-gp substrates. MDCK-MDR1 cells orinigate from transfection of Madin Darby canine kidney (MDCK) cells with the MDR1 gene, the gene encoding for the efflux protein, P-gp (Pastan et al., Proc Natl Acad Sci USA. 1988 June;85(12): 4486-90). The MDCK-MDR1 cell line can be used to identify intestinal or CNS permeability, characterize P-gp substrates or investigate P-gp efflux. Prior to the experiment, MDCK-MDR1 cells were seeded on a MULTISCREEN™ plate (Millipore, MA, USA) and allowed to form a confluent monolayer over 4 days. Monolayer integrity is checked with TEER (Transepithelial Electrical Resistance) measurement. On day 4, after washing with with HBSS buffer, a test compound was added to either the apical side (toward the blood stream, for A→B transport) of the membrane or the basolateral side (toward the brain side, for B→A transport) of the membrane. The transport of the compound across the monolayer was monitored over a 60-min time period at 37° C. After incubation, the assay was stopped after by separating apical insert from basolateral well. Both apical and basolateral samples were collected and the the concentration of the compounds in each sample was determined using LC-MS/MS. Integrity of cells was monitored during incubation by inclusion of a non-permeable probe, Lucifer Yellow.

The permeability coefficient ($P_{app}$) was calculated from the following equation $$P_{app} = \left(\frac{dQ/dt}{C_0 \times A}\right)$$

where dQ/dt is the rate of permeation of the drug across the cells, Co is the donor compartment concentration at time zero, and A is the area of the cell monolayer.

Assessing compound transport in both directions (apical to basolateral (A-B) and basolateral to apical (B-A)) across the cell monolayer enables an efflux ratio to be determined which provides an indicator of whether a compound undergoes active efflux. An efflux ratio was calculated from the mean apical to basolateral (A-B) Papp data and basolateral to apical (B-A) $P_{app}$ data. Compounds with efflux ratios higher than 4 are generally considered P-gp substrates.

$$\text{Efflux Ratio} = \frac{P_{app}(B-A)}{P_{app}(A-B)}$$

Four reference compounds were used, including Atenolol, Erythromycin, Metoprolol and Quinidine. Atenolol has low cell permeability and limited brain penetrance. Metoprolol has high cell permeability. Both Erythromycin and Quinidine are efflux substrates.

For Caco-2 cell permeability assay, the following reference standard was considered: a) $P_{app} < 5 \times 10^{-6}$ cm/s indicates low permeability; b) $P_{app}$ from 5 to $10 \times 10^{-6}$ cm/s indicates moderate permeability; and c) $P_{app} > 10 \times 10^{-6}$ cm/s indicates high permeability. An efflux ratio of >2.5 correlates with compounds not active in brain.

Zebra Fish Assay

Rps29 heterozygote fish (separated based on the gender by the separator) were allowed to sit in a breeding tank overnight. The separator was removed the following morning and the fish were allowed to breed for 3-5 hours. Embryos were collected in a petri dish with E3 medium and stored at 28° C. At 24 hours post fertilization, the embryos were dechlorinated with pronase and then washed multiple times with E3 medium. The dechlorinated embryos were randomly separated (about 50-150 per dish) for different treatments. The E3 medium in the dishes was removed and replaced with 15 mL of E3 medium treated with either DMSO or a phenothiazine compound (10 μM of the compound).

The embryos were incubated at 28° C. for 2 days. After 48 hours of treatment, the embryos were subjected to o-diansidine staining. Once the embryos were stained, the embryos were classified into four groups: Wild type (WT), Mutant Not Anemic (MNA), Mutant Partial Anemic (MPA), and Mutant Anemic (MA). Details for the classification are provided below. The stained samples were then stored at 4° C. in 4% PFA in the dark for a long term.

TABLE 2

Traits of 4 groups

| group | tail mutation | levels of anemia |
|---|---|---|
| WT | no mutation | not anemic/normal blood level |
| MNA | mutation present | not anemic/normal blood level |
| MPA | mutation present | partially anemic/much lower blood level |
| MA | mutation present | anemic/trance amount of blood or no blood |

Tail Mutation:

As shown in the first row of FIG. 1, when there is no tail mutation (WT), the tail stays straight. When there is a tail mutation, the tail curves downward. A noticeable bend is present in an MNA embryo (the second row of FIG. 1), and a bend is observed in an MPA embryo (the third row of FIG. 1) and an MA embryo (the fourth row of FIG. 1).

Levels of Anemia:

When the embryo is not anemic, majority of blood (roughly 75%) is dark red/orange and is found in and around the heart cavity. In a WT embryo, the blood is dark red due to high density of red blood cells. In an MNA embryo, majority of the blood is dark red, but can have some low density areas that appear pale orange (roughly 75% dark red/25% pale orange). When the embryo is partially anemic, the blood is mostly pale orange (roughly 75%) and located outside the heart cavity (e.g., small amounts of blood in the head or tail area). In an MPA embryo, majority of the blood is pale orange due to low density of blood cells or there are small clusters of dark red blood (typically under 25% dark red). In an MA embryo, majority of anemic embryos contain no blood but some contain a trace amount of blood. In an embryo with a trace amount of blood, the blood appears pale orange and is located outside the heart cavity.

Example 40. Calmodulin Binding Assay

Binding affinity of the compounds to Calmodulin was determined using a competition-based fluorescence polarization assay as described in Example 39. Known CaM inhibitors Trifluoperazine, A-3 hydrochloride, and A-7 were used as references in the assay. $IC_{50}$ values of the compounds are presented in Tables 2-4.

TABLE 3

Results from Calmodulin binding assay

| Compounds | Calmodulin binding IC50 (µM) |
|---|---|
| Trifluoperazine (reference) | 1.11 |
| A-3 (reference) | 24.05 |
| A-7 (reference) | 0.47 |
| MT-001 | 32.1 |
| MT-002 | 1.41 |
| MT-003 | 1.73 |
| MT-004 | 94.86 |
| MT-005 | 3.17 |
| MT-006 | 75.76 |
| MT-007 | 2.97 |
| MT-008 | 0.9 |
| MT-009 | 0.86 |
| MT-010 | >100 |
| MT-011 | 4.47 |
| MT-012 | 5.65 |
| MT-013 | >100 |
| MT-014 | 9.6 |
| MT-015 | >100 |
| MT-016 | 7.82 |
| MT-017 | 55.08 |
| MT-018 | >100 |

TABLE 4

Results from Calmodulin binding assay

| Compounds | Calmodulin binding IC50 (µM) |
|---|---|
| Trifluoperazine (reference) | 1.36 |
| MT-019 | 2.83 |
| MT-020 | 13.91 |
| MT-021 | 8.13 |
| MT-022 | 15.30 |
| MT-023 | 3.96 |
| MT-024 | 7.02 |
| MT-025 | 6.70 |
| MT-026 | 2.03 |
| MT-027 | 9.03 |
| MT-028 | 4.83 |
| MT-029 | 13.91 |
| MT-030 | 1.65 |
| MT-030a | 1.01 |
| MT-031 | 8.93 |
| MT-031a | 2.97 |

TABLE 5

Results from Calmodulin binding assay

| Compounds | Calmodulin binding IC50 (µM) |
|---|---|
| Trifluoperazine (reference) | 1.06 |
| MT-032 | 7.43 |
| MT-033 | 4.99 |
| MT-034 | 4.10 |
| MT-035 | 0.24 |
| MT-036 | 2.99 |
| MT-037 | 0.85 |
| MT-038 | 3.90 |

The performance of the assay was evaluated by analyzing the statistical quality parameter Z' factor. The Z' factor quantifies the difference that separates the signals corresponding to the polarization degree of the bound ligand and the free ligand in the FP-screening assay and accounts for the observed variability. Typically, an assay with a Z' factor between 0.5-1 is considered excellent (Audran et al., Biochim Biophys Acta. 1833 (2013) 1720-1731). The Z' value calculated from this data was between 0.61-0.75.

Example 41. Membrane Permeability Assay

Compounds were screened for membrane permeability in two cell-based assays: Caco-2 cell permeability assay and MDCK-MDR1 cell permeability assay. The two assays were performed as described in Example 40.

The efflux ratios and permeability coefficients (unit: $10^{-6}$ cm/s) of the compounds in each assay are shown in Tables 5-8. Ideal compound should have relatively low Caco-2 cells efflux (high intestinal absorption) and high MDCK-MDR1 cell efflux (limited brain penetration). Trifluoperazine displayed a moderate permeability across membranes and is likely not a P-gp substrate. In the tables, "*" indicates that real concentration of receiver was below the limit of quantification, and data is presented with respect to minimum concentration of standard.

TABLE 6

Efflux ratio

| Compounds | Caco-2 cells | MDCK-MDR1 cells |
|---|---|---|
| Metoprolol | 0.89 | 0.81 |
| Atenolol | 2.69 | 1.15 |
| Quinidine/Erythromycin | 106.55 | 4.37 |
| MT-001 | 3.57 | 2.80 |
| MT-002 | 0.27 | 0.31 |
| MT-003 | 0.30 | 1.08 |
| MT-004 | 78.12 | 13.79 |
| MT-005 | 0.31 | 0.55 |
| MT-006 | 15.74 | 8.67 |
| MT-007 | 0.52 | >2.05 |
| MT-008 | 0.65 | 0 |
| MT-009 | 0.68 | 0 |
| MT-010 | 9.84 | 5.25 |
| MT-011 | 0.48 | 1.70 |
| MT-012 | 0.53 | 1.63 |
| MT-013 | 27.05 | 24.83 |
| MT-014 | 1.17 | 2.58 |
| MT-015 | 46.15 | 5.11 |
| MT-016 | 1.33 | >9.83 |
| MT-017 | 8.47 | 13.71 |
| MT-018 | 28.00 | 4.16 |
| trifluoperazine | 0.72 | N/A* |

TABLE 7

Permeability coefficient ($P_{app}$) × $10^6$ cm/s

| Compounds | Caco-2 cells (A -> B) | Caco-2 cells (B -> A) | MDCK-MDR1 cells (A -> B) | MDCK-MDR1 cells (B -> A) |
|---|---|---|---|---|
| Metoprolol | 33.80 | 30.21 | 35.85 | 29.16 |
| Atenolol | 0.62 | 1.66 | 0.50 | 0.58 |
| Erythromycin | 0.21 | 21.86 | n.d. | n.d. |
| Quinidine | n.d. | n.d. | 10.06 | 44.00 |
| MT-001 | 9.42 | 33.68 | 16.41 | 46.02 |
| MT-002 | 9.33 | 2.56 | <2.11 | 0.66 |
| MT-003 | 10.93 | 3.30 | <0.98 | 1.06 |
| MT-004 | 0.27 | 21.25 | <1.45 | 19.99 |
| MT-005 | 15.79 | 4.95 | <2.25 | 1.23 |
| MT-006 | 2.09 | 32.83 | 5.12 | 44.37 |
| MT-007 | 16.65 | 8.71 | <1.31 | 2.68 |
| MT-008 | 3.88 | 2.52 | <1.44 | 0 |
| MT-009 | 3.81 | 2.61 | <1.42 | 0 |
| MT-010 | 3.91 | 38.41 | 10.31 | 54.13 |
| MT-011 | 16.83 | 8.01 | 1.34 | 2.28 |
| MT-012 | 22.50 | 11.99 | 2.55 | 4.15 |
| MT-013 | 0.64 | 17.26 | <0.41 | 10.18 |
| MT-014 | 14.06 | 16.40 | 4.13 | 10.66 |
| MT-015 | 0.17 | 7.95 | <0.46 | 2.35 |
| MT-016 | 12.49 | 16.57 | 1.05 | 10.32 |
| MT-017 | 3.66 | 31.00 | 3.13 | 42.95 |
| MT-018 | 0.37 | 10.22 | <0.92 | 3.83 |
| Trifluoperazine | 5.05 | 3.62 | <0.87* | <0.31* |

TABLE 8

Efflux ratio

| Compounds | Caco-2 cells | MDCK-MDR1 cells |
|---|---|---|
| Erythromycin | >172.65 | 0.96 |
| Metoprolol | 1.11 | 0.85 |
| Atenolol | 3.22 | 7.03 |
| 10H-phenothiazine | 0.88 | 0.71 |
| Prochloperazine | 0.35 | N/A |
| Thioproperazine Dimesilate | 0.86 | 1.06 |
| MT-019 | 111.33 | >38.06 |
| MT-020 | >65.00 | 5.30 |
| MT-021 | 113.81 | 37.54 |
| MT-022 | >64.30 | 6.06 |
| MT-023 | >43.89 | 7.62 |
| MT-024 | >7.68 | 2.08 |
| MT-025 | 0.53 | 0.62 |
| MT-026 | 0.68 | >0.71 |
| MT-027 | 0.95 | 2.46 |
| MT-028 | 1.31 | 4.27 |
| MT-029 | 25.01 | 49.59 |
| MT-030 | 1.08 | 3.24 |
| MT-030a | 30.37 | 27.01 |
| MT-031 | 3.37 | 16.65 |
| MT-031a | >159.90 | 70.08 |
| MT-032 | 8.59 | 8.25 |
| MT-033 | 8.42 | 10.02 |
| MT-034 | 14.75 | 16.45 |
| MT-035 | 1.80 | 4.19 |
| MT-036 | 1.86 | 4.89 |
| MT-037 | 14.17 | 26.16 |
| MT-038 | 35.78 | 47.10 |
| Trifluoperazine Dihydrochloride | 1.27 | N/A* |

TABLE 9

Permeability coefficient ($P_{app}$) × $10^6$ cm/s

| Compounds | Caco-2 cells (A -> B) | Caco-2 cells (B -> A) | MDCK-MDR1 cells (A -> B) | MDCK-MDR1 cells (B -> A) |
|---|---|---|---|---|
| Erythromycin | <0.17 | 29.35 | 31.86 | 30.55 |
| Metoprolol | 34.62 | 38.28 | 1.05 | 0.89 |
| Atenolol | 0.51 | 1.65 | 6.88 | 48.36 |
| 10H-phenothiazine | 42.68 | 37.72 | 53.84 | 38.02 |
| Prochloroperazine | 1.29 | 0.46 | <1.28 | <0.59 |
| Triproperazine Dimesilate | 4.07 | 3.51 | 3.35 | 3.56 |
| MT-019 | 0.21 | 23.54 | <0.67 | 25.50 |
| MT-020 | <0.18 | 11.70 | 0.39 | 2.09 |
| MT-021 | 0.23 | 26.56 | 0.59 | 22.14 |
| MT-022 | <0.20 | 12.86 | 0.66 | 3.99 |
| MT-023 | <0.19 | 8.34 | 0.43 | 3.31 |
| MT-024 | <0.34 | 2.61 | 0.40 | 0.83 |
| MT-025 | 30.15 | 16.06 | 18.19 | 11.23 |
| MT-026 | 1.33 | 0.91 | <0.77 | 0.55 |
| MT-027 | 18.56 | 17.64 | 6.40 | 15.76 |

TABLE 9-continued

| Compounds | Permeability coefficient ($P_{app}$) × $10^6$ cm/s | | | |
|---|---|---|---|---|
| | Caco-2 cells (A -> B) | Caco-2 cells (B -> A) | MDCK-MDR1 cells (A -> B) | MDCK-MDR1 cells (B -> A) |
| MT-028 | 13.75 | 18.07 | 3.78 | 16.16 |
| MT-029 | 1.69 | 42.35 | 0.91 | 44.90 |
| MT-030 | 3.88 | 4.19 | 0.70 | 2.26 |
| MT-030a | 0.45 | 13.57 | 0.54 | 14.55 |
| MT-031 | 7.66 | 25.82 | 2.27 | 37.79 |
| MT-031a | <0.20 | 31.98 | 0.48 | 33.56 |
| MT-032 | 4.86 | 41.72 | 3.96 | 32.70 |
| MT-033 | 4.10 | 34.51 | 3.04 | 30.45 |
| MT-034 | 1.99 | 29.32 | 1.67 | 27.51 |
| MT-035 | 5.92 | 10.67 | 1.76 | 7.39 |
| MT-036 | 8.55 | 15.93 | 2.85 | 13.91 |
| MT-037 | 2.97 | 42.06 | 1.47 | 38.47 |
| MT-038 | 1.18 | 42.18 | 0.98 | 46.35 |
| Trifluoperazine Dihydrochloride | 1.01 | 1.28 | <1.32 | <0.74 |

Example 42. Zebra Fish Assay

Compounds MT-001, 007, 014, and 016 were tested in the zebra fish assay as described in Example 40. The number of embryos in each of the 4 groups was counted and the ratio was determined and presented as % in the below tables. The experiment was performed once for MT-001 and MT-007 and three times for each of MT-014 and MT-016. The embryos treated with Compound MT-014 displayed less severe tail and anemia phenotypes compared to the ones treated with DMSO, showing a trend of less MA and more MPA/MNA.

TABLE 10

| Assay result of MT-001 | | |
|---|---|---|
| | DMSO (n = 89) | MT-001 (n = 79) |
| WT | 80% | 81% |
| MNA | 8% | 8% |
| MPA | 10% | 9% |
| MA | 2% | 3% |

TABLE 11

| Assay result of MT-007 | | |
|---|---|---|
| | DMSO (n = 138) | MT-007 (n = 132) |
| WT | 79% | 79% |
| MNA | 8% | 8% |
| MPA | 11% | 10% |
| MA | 2% | 3% |

TABLE 12

| Assay result of MT-014 | | | | | | |
|---|---|---|---|---|---|---|
| | DMSO (n = 44) | MT-014 (n = 54) | DMSO (n = 14) | MT-014 (n = 139) | DMSO (n = 70) | MT-014 (n = 61) |
| WT | 77% | 73% | 79% | 78% | 76% | 79% |
| MNA | 7% | 16% | 8% | 12% | 9% | 13% |
| MPA | 15% | 10% | 9% | 9% | 13% | 7% |
| MA | 6% | 2% | 4% | 1% | 3% | 2% |

TABLE 13

| Assay result of MT-016 | | | | | | |
|---|---|---|---|---|---|---|
| | DMSO (n = 21) | MT-016 (n = 29) | DMSO (n = 88) | MT-016 (n = 94) | DMSO (n = 115) | MT-016 (n = 115) |
| WT | 85% | 69% | 74% | 74% | 76% | 72% |
| MNA | 0% | 7% | 8% | 7% | 6% | 8% |
| MPA | 5% | 17% | 11% | 10% | 13% | 15% |
| MA | 10% | 7% | 7% | 9% | 5% | 5% |

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

The invention claimed is:
1. A compound of formula (II):

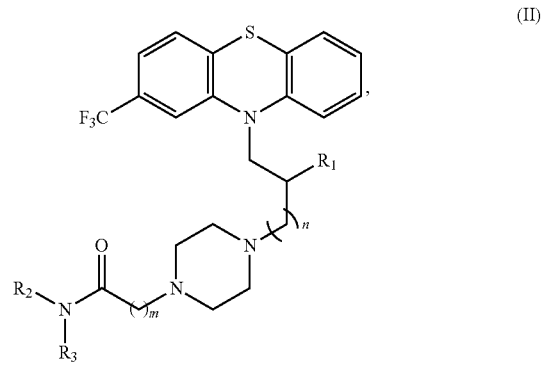

(II)

or a pharmaceutically acceptable salt thereof, wherein
R$_1$ is selected from the group consisting of hydrogen, —OH, and C$_{1-6}$alkoxy;
R$_2$ is C$_{1-6}$alkyl substituted with one or more substituents each independently selected from the group consisting of —OH, C$_{1-6}$alkoxy, —C(O)NR$_a$R$_b$, —C(O)R$_c$, —C(O)OR$_d$, S(O)$_2$C$_{1-6}$alkyl, and S(O)$_2$NR$_a$R$_b$;
R$_3$ is hydrogen or C$_{1-6}$alkyl;
R$_a$, R$_b$, R$_c$, and R$_d$ are each independently hydrogen or C$_{1-6}$alkyl;
n is 1 or 2; and
m is selected from the group consisting of 1, 2, or 3.

* * * * *